(12) United States Patent
Srivastava et al.

(10) Patent No.: US 7,915,245 B2
(45) Date of Patent: Mar. 29, 2011

(54) METHODS AND COMPOSITIONS OF TRAIL-DEATH RECEPTOR AGONISTS/ACTIVATORS

(75) Inventors: Rakesh Srivastava, Tyler, TX (US); Sharmila Shankar, Tyler, TX (US); Alexander D. Mackerell, Jr., Baltimore, MD (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 11/866,162

(22) Filed: Oct. 2, 2007

(65) Prior Publication Data

US 2008/0214547 A1 Sep. 4, 2008

Related U.S. Application Data

(60) Provisional application No. 60/887,783, filed on Feb. 1, 2007.

(51) Int. Cl.
| | | |
|---|---|---|
| *A01N 43/48* | (2006.01) | |
| *A01N 43/90* | (2006.01) | |
| *A01N 43/64* | (2006.01) | |
| *A01N 33/02* | (2006.01) | |
| *A61K 31/50* | (2006.01) | |
| *A61K 31/415* | (2006.01) | |

(52) U.S. Cl. ............ 514/183; 514/255.05; 514/262.1; 514/359; 514/404; 514/638; 514/248

(58) Field of Classification Search .................. None
See application file for complete search history.

(56) References Cited

U.S. PATENT DOCUMENTS

| | | | |
|---|---|---|---|
| 4,325,959 A | 4/1982 | Matthews | 514/363 |
| 6,897,240 B2 | 5/2005 | Cohen et al. | 514/582 |
| 7,078,493 B1 | 7/2006 | Greene et al. | 530/389.2 |
| 7,109,298 B2 | 9/2006 | Browning et al. | 530/350 |
| 7,115,717 B2 | 10/2006 | Mori et al. | 530/388.22 |
| 7,164,004 B2 | 1/2007 | Ruben et al. | 530/350 |
| 2002/0091148 A1 | 7/2002 | BaMaung et al. | 514/414 |
| 2004/0133012 A1* | 7/2004 | Brown | 548/317.1 |

FOREIGN PATENT DOCUMENTS

| | | |
|---|---|---|
| EP | 1 693 369 | 8/2006 |
| WO | WO 01/81315 | 11/2001 |
| WO | WO 02/079377 | 10/2002 |
| WO | WO 03/073999 | 9/2003 |
| WO | WO 03/084475 | 10/2003 |
| WO | WO 2004/093803 | 11/2004 |
| WO | WO 2005/007141 | 1/2005 |
| WO | WO 2005/070024 | 8/2005 |
| WO | WO 2006/044402 | 4/2006 |
| WO | WO 2006/105237 | 10/2006 |

OTHER PUBLICATIONS

Rosenberg. Immunotherapy and Gene Therapy of Cancer. Cancer Research, 51, 5074s-5079s, 1991.*

Nillson et al. Phase II study of single agent gemcitabine in patients with hormone refractory prostate cancer. Journal of CAncer, 2004 ASCO Annual Meetings Proceedings (Post-Meeting Edition). vol. 22, No. 14S (Jul. 15 Supplement): 4705.*

Goodman et al. [Editors] "Chapter 198: Principles of Cancer Therapy." Cecil's Textbook of Medicine (Twenty-First Edition, vol. 1). W.B. Saunders Company, 2000. pp. 1060-1074.*

International Search Report and Written Opinion issued in Application No. PCT/US2007/080211, dated Jan. 5, 2009.

"Benzoic acid, 3-[ [ (2, 3-dibromo-5-ethoxy-6-hydroxyphenyl)methylene]amino]-," Database Chemcats Chemical Abstract, Sep. 6, 2007.

Bakhite et al., "Synthesis and some reactions of new Thieno[2, 3-c]pyridazine derivatives," *Bull. Korean Chem. Soc.*, 23:1715-1718, 2002.

Li et al., "A small molecule Smac minic potentiates TRAIL- and TNFalpha—mediated cell death," *Science*, 305:1471-1474, 2004.

Radwan, "Synthesis and reactions of some new heterocyclic compounds containing thieno {2, 3-c]pyridazine moiety," Chemical Abstract accession No. 2000:813677, 2000.

Alnemri et al., "Human ICE/CED-3 protease nomenclature," *Cell*, 87:171, 1996.

Ashkenazi and Dixit, "Death receptors: signaling and modulation," *Science*, 281:1305-1308, 1998.

Ashkenazi et al., "Apoptosis control by death and decoy receptors," *Curr. Opin. Cell. Biol.*, 11:255-260, 1999.

Ashkenzai et al., "Safety and antitumor activity of recombinant soluble Apo2 ligand," *J. Clin. Invest.*, 104:155-162, 1999.

Butler et al., "Suberoylanilide hydroxamic acid, an inhibitor of histone deacetylase, suppresses the growth of prostate cancer cells in vitro and in vivo," *Cancer Res.*,60: 5165-5170, 2000.

Cal et al., "Resveratrol and cancer: chemoprevention, apoptosis, and chemo-immunosensitizing activities," *Curr. Med. Chem. Anti-Cancer Agents*, 3:77-93(Abstract), 2003.

Chen et al., "Constitutively active Akt is an important regulator of TRAIL sensitivity in prostate cancer," Oncogene, 20:6073-6083, 2001.

Chinnaiyan et al., "Combined effect of tumor necrosis factor-related apoptosis-inducing ligand and ionizing radiation in breast cancer therapy," *Proc. Natl. Acad. Sci. USA*, 97:1754-1759, 2000.

(Continued)

*Primary Examiner* — Brandon J Fetterolf
*Assistant Examiner* — Anna Pagonakis
(74) *Attorney, Agent, or Firm* — Fulbright & Jaworski LLP

(57) ABSTRACT

This invention describes a series of methods and compositions for prevention and treatment of diseases such as cancer. One aspect of the invention describes small molecule-based drugs that can be used to bind to death receptors TRAIL-R1/DR4 and/or TRAIL-R2/DR5 and induce apoptosis in cancer cells, while sparing normal cells. The invention also describes TRAIL Death Receptor Agonists/Activators (DRAs) and their uses, such as the induction of apoptosis through caspase-8 and caspase-3 activation. The present invention also describes the methods of treating cancers, such as breast, prostate, colon, pancreatic, ovarian, lung, and brain cancers, leukemia, lymphoma, multiple myeloma, and mesothelioma, using DRAs either as single-agent treatments, or in combination with other therapies.

8 Claims, 62 Drawing Sheets

OTHER PUBLICATIONS

Coffey et al., "The histone deacetylase inhibitor, CBHA, inhibits growth of human neuroblastoma xenografts in vivo, alone and synergistically with all-trans retinoic acid," *Cancer Res.*, 61:3591-3594, 2001.

Coffey et al., "Histone deacetylase inhibitors and retinoic acids inhibit growth of human neuroblastoma in vitro," *Med. Pediatr. Oncol.*, 35:577-581, 2000.

Cress and Seto, "Histone deacetylases, transcriptional control, and cancer," *J. Cell. Physiol.*, 184:1-16, 2000.

Culver et al., "In vivo gene transfer with retroviral vector-producer cells for treatment of experimental brain tumors," *Science*, 256:1550-2(Abstract), 1992.

Deckert and Struhl, "Histone acetylation at promoters is differentially affected by specific activators and repressors," *Mol. Cell. Biol.*, 21:2726-2735, 2001.

Deeb et al., "Curcumin (diferuloyl-methane) enhances tumor necrosis factor-related apoptosis-inducing ligand-induced apoptosis in LNCaP prostate cancer cells," *Mol. Cancer Ther.*, 2:95-103, 2003.

Degli-Esposti et al., "The novel receptor TRAIL-R4 induces NF-kappaB and protects against TRAIL-mediated apoptosis, yet retains an incomplete death domain," *Immunity*, 7:813-820, 1997.

Degli-Esposti et al., "Cloning and characterization of TRAIL-R3, a novel member of the emerging TRAIL receptor family," *J. Exp. Med.*, 186:1165-1170, 1997.

Desagher and Martinou, "Mitochondria as the central control point of apoptosis," *Trends Cell. Bio.*, 10:369-377, 2000.

Droin et al., "Egr family members regulate nonlymphoid expression of Fas ligand, TRAIL, and tumor necrosis factor during immune responses," *Mol. Cell. Biol.*, 23:7638-7647, 2003.

Du et al., "Smac, a mitochondrial protein that promotes cytochrome c-dependent caspase activation by eliminating IAP inhibition," *Cell*, 102:33-42, 2000.

Emery et al., "Osteoprotegerin is a receptor for the cytotoxic ligand TRAIL," *J. Biol. Chem.*, 273:14363-14367, 1998.

French and Tschopp, "Protein-based therapeutic approaches targeting death receptors," *Cell Death Differ.*, 10:117-123, 2003.

Fulda and Debatin, "Sensitization for tumor necrosis factor-related apoptosis-inducing ligand-induced apoptosis by the chemopreventive agent resveratrol," *Cancer Res.*, 64:337-346, 2004.

Fulda and Debatin, "Apoptosis pathways: turned on their heads?," *Drug Resist.*, 6:1-3, 2003.

Gibson et al., "Increased expression of death receptors 4 and 5 synergizes the apoptosis response to combined treatment with etoposide and TRAIL," *Mol. Cell. Biol.*, 20:205-212, 2000.

Gliniak and Le, "Tumor necrosis factor-related apoptosis-inducing ligand's antitumor activity in vivo is enhanced by the chemotherapeutic agent CPT-11," *Cancer Res.*, 59:6153-6158, 1999.

Gong et al., "Ionizing radiation-induced, Bax-mediated cell death is dependent on activation of cysteine and serine proteases," *Cell Growth Differ.*, 10:491-502, 1999.

Gopee et al., "Sodium selenite-induced apoptosis in murine B-lymphoma cells is associated with inhibition of protein kinase C-delta, nuclear factor kappaB, and inhibitor of apoptosis protein," *Toxicol. Sci.* 78:204-214, 2004.

Gray and Teh, "Histone acetylation/deacetylation and cancer: an "open" and "shut" case?," *Curr. Mol. Med.*, 1:401-29(Abstract), 2001.

Green and Reed, "Mitochondria and apoptosis," *Science*, 281:1309-1312, 1998.

Green, "Apoptotic pathways: the roads to ruin," *Cell*, 94:695-698, 1998.

Gregory et al., "Histone acetylation and chromatin remodeling," *Exp. Cell Res.*, 265:195-202, 2001.

Griffith et al., "Monocyte-mediated tumoricidal activity via the tumor necrosis factor-related cytokine, TRAIL," *J. Exp. Med.*, 189:1343-1354, 1999.

Grinberg et al., "tBID Homooligomerizes in the mitochondrial membrane to induce apoptosis," *J. Biol. Chem.*, 277:12237-12245, 2002.

Gross et al., "Caspase cleaved BID targets mitochondria and is required for cytochrome c release, while BCL-XL prevents this release but not tumor necrosis factor-R1/Fas death," *J. Biol. Chem.*, 274:1156-1163, 1999.

Gusman et al., "A reappraisal of the potential chemopreventive and chemotherapeutic properties of resveratrol," *Carcinogenesis*, 22:1111-1117, 2001.

He et al., "Apo2L/TRAIL differentially modulates the apoptotic effects of sulindac and a COX-2 selective non-steroidal anti-inflammatory agent in Bax-deficient cells.," *Oncogene*, 21:6032-6040, 2002.

Hegde et al., "Identification of Omi/HtrA2 as a mitochondrial apoptotic serine protease that disrupts inhibitor of apoptosis protein-caspase interaction," *J. Biol. Chem.*, 277:432-438, 2002.

Hotta et al., "Chemotherapeutic agents sensitize sarcoma cell lines to tumor necrosis factor-related apoptosis-inducing ligand-induced caspase-8 activation, apoptosis and loss of mitochondrial membrane potential," *J. Orthop. Res.*, 21:949-57 (Abstract), 2003.

Hymowitz et al., "Triggering cell death: the crystal structure of Apo2L/TRAIL in a complex with death receptor 5," *Mol. Cell.*, 4:563-571, 1999.

Igney and Krammer, "Death and anti-death: tumour resistance to apoptosis," *Nat. Rev. Cancer*, 2:277-288, 2002.

Kandasamy and Srivastava, "Role of the phosphatidylinositol 3'-kinase/PTEN/Akt kinase pathway in tumor necrosis factor-related apoptosis-inducing ligand-induced apoptosis in non-small cell lung cancer cells," *Cancer Res.*, 62:4929-4937, 2002.

Kandasamy et al., "Involvement of proapoptotic molecules Bax and Bak in tumor necrosis factor-related apoptosis-inducing ligand (TRAIL)-induced mitochondrial disruption and apoptosis: differential regulation of cytochrome c and Smac/DIABLO release," *Cancer Res.*, 63:1712-1721, 2003.

Kayagaki et al., "Type I interferons (IFNs) regulate tumor necrosis factor-related apoptosis-inducing ligand (TRAIL) expression on human T cells: A novel mechanism for the antitumor effects of type I IFNs," *J. Exp. Med.*, 189:1451-1460, 1999.

Kayagaki et al., "Expression and function of TNF-related apoptosis-inducing ligand on murine activated NK cells," *J. Immunol.*, 163:1906-1913, 1999.

Keane et al., "Chemotherapy augments TRAIL-induced apoptosis in breast cell lines," *Cancer Res.*, 59:734-741, 1999.

Keogh et al., "Failure of Bcl-2 to block cytochrome c redistribution during TRAIL-induced apoptosis," *FEBS Lett.*, 471:93-98, 2000.

Khochbin et al., "Functional significance of histone deacetylase diversity," *Curr. Opin. Genet. Dev.*, 11:162-166,2001.

Kim and Gupta, "Expression of TRAIL (Apo2L), DR4 (TRAIL receptor 1), DR5 (TRAIL receptor 2) and TRID (TRAIL receptor 3) genes in multidrug resistant human acute myeloid leukemia cell lines that overexpress MDR 1 (HL60/Tax) or MRP (HL60/AR).," *Int. J. Oncol.*, 16:1137-9 (Abstract), 2000.

Kim et al., "Failure of Bcl-2 to block mitochondrial dysfunction during TRAIL-induced apoptosis. Tumor necrosis-related apoptosis-inducing ligand," *Int. J. Oncol.*, 18:187-94 (Abstract), 2001.

Klein, "Selenium: epidemiology and basic science," *J. Urol.*, 171:S50-3 (Abstract), 2004.

Krammer, "CD95(APO-1/Fas)-mediated apoptosis: live and let die," *Adv. Immunol.*, 71:163-210 (Abstract), 1999.

Kroemer et al., "The mitochondrial death/life regulator in apoptosis and necrosis," *Ann. Rev. Physiol.*, 60:619-642, 1998.

LeBlanc and Ashkenazi, "Apo2L/TRAIL and its death and decoy receptors," *Cell Death Differ.*, 10:66-75, 2003.

Lee et al., "Involvement of histone hyperacetylation in triggering DNA fragmentation of rat thymocytes undergoing apoptosis," *FEBS Lett.*, 395:183-187, 1996.

Li et al., "Cleavage of BID by caspase 8 mediates the mitochondrial damage in the Fas pathway of apoptosis," *Cell*, 94:491-501, 1998.

Luo et al., "Bid, a Bc12 interacting protein, mediates cytochrome c release from mitochondria in response to activation of cell surface death receptors.," *Cell*, 94:481-490, 1998.

Mahlknecht and Hoelzer, "Histone acetylation modifiers in the pathogenesis of malignant disease," *Mol. Med.*, 6:623-644, 2000.

Marini et al., "Molecular requirements for the combined effects of TRAIL and ionising radiation," *Radiother. Oncol.*, 68:189-198, 2003.

Marks et al., "The role of three-dimensional information in health care and medical education: the implications for anatomy and dissection," *Curr. Opin. Oncol.*, 13:477-483, 2000.

Marks et al., "Histone deacetylase inhibitors: inducers of differentiation or apoptosis of transformed cells," *J. Natl. Cancer Inst.*, 92:1210-1216, 2000.

Marks et al., "Histone deacetylases and cancer: causes and therapies," *Nat. Rev. Cancer*, 1:194-202, 2001.

Marsters et al., "A novel receptor for Apo2L/TRAIL contains a truncated death domain," *Curr. Biol.*, 7:1003-1006, 1997.

Medina et al., "Induction of caspase-3 protease activity and apoptosis by butyrate and trichostatin A (inhibitors of histone deacetylase): dependence on protein synthesis and synergy with a mitochondrial/cytochrome c-dependent pathway," *Cancer Res.*, 57:3697-3707, 1997.

Neuzil et al., "Sensitization of mesothelioma to TRAIL apoptosis by inhibition of histone deacetylase: role of Bcl-xL down-regulation," *Biochem. Biophys. Res. Commun.*, 314:186-191, 2004.

Ortiz et al., "Retinoids in combination therapies for the treatment of cancer: mechanisms and perspectives," *Drug Resist.*, 5:162-175, 2002.

Pan et al., "TRUNDD, a new member of the TRAIL receptor family that antagonizes TRAIL signalling," *FEBS Lett.*, 424:41-45, 1998.

Pan et al., "The receptor for the cytotoxic ligand TRAIL," *Science*, 276:111-113, 1997.

Pan et al., "An antagonist decoy receptor and a death domain-containing receptor for TRAIL," *Science*, 277:815-818, 1997.

Ratan et al., "Resveratrol—a prostate cancer chemopreventive agent?," *Urol. Oncol.*, 7:223-227, 2002.

Ray and Almasan, "Apoptosis induction in prostate cancer cells and xenografts by combined treatment with Apo2 ligand/tumor necrosis factor-related apoptosis-inducing ligand and CPT-11," *Cancer Res.*, 63:4713-4723, 2003.

Rosato et al., "Simultaneous activation of the intrinsic and extrinsic pathways by histone deacetylase (HDAC) inhibitors and tumor necrosis factor-related apoptosis-inducing ligand (TRAIL) synergistically induces mitochondrial damage and apoptosis in human leukemia cells," *Mol. Cancer Ther.*, 2:1273-1284, 2003.

Schneider et al., "Characterization of two receptors for TRAIL," *FEBS Lett.*, 416:329-334, 1997.

Screaton et al., "TRICK2, a new alternatively spliced receptor that transduces the cytotoxic signal from TRAIL," *Curr. Biol.*, 7:693-696, 1997.

Shanker and Srivastava, "Enhancement of therapeutic potential of TRAIL by cancer chemotherapy and irradiation: mechanisms and clinical implications," *Drug Resist. Updat.*, 7:139-56, 2004.

Shankar et al., "The sequential treatment with ionizing radiation followed by TRAIL/Apo-2L reduces tumor growth and induces apoptosis of breast tumor xenografts in nude mice," *Int. J. Oncol.*, 24:1133-40 (Abstract), 2004.

Shankar et al., "Ionizing radiation enhances the therapeutic potential of TRAIL in prostate cancer in vitro and in vivo: Intracellular mechanisms," *Prostate*, 61:35-49, 2004.

Sheridan et al., "Control of TRAIL-induced apoptosis by a family of signaling and decoy receptors," *Science*, 277:818-821, 1997.

Singh et al., "Synergistic interactions of chemotherapeutic drugs and tumor necrosis factor-related apoptosis-inducing ligand/Apo-2 ligand on apoptosis and on regression of breast carcinoma in vivo," *Cancer Res.*, 63:5390-5400, 2003.

Sinha and El-Bayoumy, "Apoptosis is a critical cellular event in cancer chemoprevention and chemotherapy by selenium compounds," *Curr. Cancer Drug Targets*, 4:13-28 (Abstract), 2004.

Srinivasula et al., "Autoactivation of procaspase-9 by Apaf-1-mediated oligomerization," *Mol. Cell.*, 1:949-957, 1998.

Srivastava, "TRAIL/Apo-2L: mechanisms and clinical applications in cancer," *Neoplasia*, 3:535-546, 2001.

Struhl, "Histone acetylation and transcriptional regulatory mechanisms," *Genes Dev.*, 12:599-606, 1998.

Suliman et al., "Intracellular mechanisms of TRAIL: apoptosis through mitochondrial-dependent and -independent pathways," *Oncogene*, 20:2122-2133, 2001.

Sun et al., "Augmentation of tumor necrosis factor-related apoptosis-inducing ligand (TRAIL)-induced apoptosis by the synthetic retinoid 6-[3-(1-adamantyl)-4-hydroxyphenyl]-2-naphthalene carboxylic acid (CD437) through up-regulation of TRAIL receptors in human lung cancer cells," *Cancer Res.*, 60:7149-7155, 2000.

Sun et al., "Implication of multiple mechanisms in apoptosis induced by the synthetic retinoid CD437 in human prostate carcinoma cells," *Oncogene*, 19:4513-4522, 2000.

Susin et al., "Molecular characterization of mitochondrial apoptosis-inducing factor," *Nature*, 397:441-446, 1999.

Suzuki et al., "A serine protease, HtrA2, is released from the mitochondria and interacts with XIAP, inducing cell death," *Mol. Cell.*, 8:613-621, 2001.

Thomas and Hersey, "TNF-related apoptosis-inducing ligand (TRAIL) induces apoptosis in Fas ligand-resistant melanoma cells and mediates CD4 T cell killing of target cells," *J. Immunol.*, 161:2195-2200, 1998.

Schulze-Ostoff et al., "Apoptosis signaling by death receptors," 254:439-59 (Abstract), 1998.

Timmermann et al., "Histone acetylation and disease," *Cell Mol. Life Sci.*, 58:728-736 (Abstract), 2001.

Van Lint et al., "The expression of a small fraction of cellular genes is changed in response to histone hyperacetylation," *Gene Exp.*, 5:245-253 (Abstract), 1996.

Verhagen et al., "Identification of DIABLO, a mammalian protein that promotes apoptosis by binding to and antagonizing IAP proteins," *Cell*, 102:43-53, 2000.

Wajant et al., "TNF-related apoptosis inducing ligand (TRAIL) and its receptors in tumor surveillance and cancer therapy," *Apoptosis*, 7:449-459, 2002.

Walczak et al., "TRAIL-R2: a novel apoptosis-mediating receptor for Trail," *EMBO J.*, 16:5386-5397, 1997.

Walczak et al., "Tumoricidal activity of tumor necrosis factor-related apoptosis-inducing ligand in vivo," *Nat. Med.*, 5:157-163, 1999.

Wang et al., "BID: a novel BH3 domain-only death agonist," *Genes Dev.*, 10:2859-2869, 1996.

Wei et al., "tBID, a membrane-targeted death ligand, oligomerizes BAK to release cytochrome c," *Genes Dev.*, 14:2060-2071, 2000.

Whanger, "Selenium and its relationship to cancer: an update," *Br. J. Nutr.*, 91:11-28 (Abstract), 2004.

Wiley et al., "Identification and characterization of a new member of the TNF family that induces apoptosis," *Immunity*, 3:673-682 (Abstract), 1995.

Wolf and Green, "Suicidal tendencies: apoptotic cell death by caspase family proteinases," *J. Biol. Chem.*, 274:20049-20052, 1999.

Wu et al., "KILLER/DR5 is a DNA damage-inducible p53-regulated death receptor gene," *Nat. Genet.*, 17:141-143, 1997.

Zhang et al., "The histone deacetylase inhibitor suberic bishydroxamate: a potential sensitizer of melanoma to TNF-related apoptosis-inducing ligand (TRAIL) induced apoptosis," *Biochem. Pharmacol.*, 66:1537-1545, 2003.

Zou et al., "Apaf-1, a human protein homologous to C. elegans CED-4, participates in cytochrome c-dependent activation of caspase-3," *Cell*, 90:405-413, 1997.

U.S. Appl. No. 60/705,695, Aug. 5, 2006, Srivastava et al.

Office Communication, issued in International Application No. PCT/US2007/080211, dated Aug. 12, 2008.

"Benzoic acid, 3-[[(2, 3-dibromo-5-ethoxy-6-hydroxphenyl)methylene]amino]-," Chemical Abstracts, published Sep. 6, 2007.

Billman et al., "Preparation and antitumor activity of some Schiff bases of 2'-amino-4' , 5'- dichlorobenzenesulfonanilid and 2'-amino-p-toluenesulfonanilide," Chemical Abstracts, Accession No. 1970:487582, 1970.

LaVallee et al., "2-methoxyestradiol up-regulates death receptor 5 and induces apoptosis through activation of the extrinsic pathway," *Cancer Research*, 63:468-475, 2003.

Li et al., "Activation of the proapoptotic death receptor DR5 by oligomeric peptide and antibody agonists," *J. Mol. Biol.*, 361:522-536, 2006.

Shankar et al., "Interactive effects of histone deacetylase inhibitors and TRAIL on apoptosis in human leukemia cells: involvement of both death receptor and mitochondrial pathways," *International Journal of Molecular Medicine*, 16:1125-1138, 2005.

Song et al., "Synthesis and antitumor activit of Antineoplaston A10 and analogs," Chemical Abstracts, Accession No. 2000:517152, 2000.

Tani et al., "Anticancer studies. XXXV. Preparation and antitumor effect 4-arylmethyleneamino 6-n-octylresorcinol analogs," Chemical Abstracts, Accession No. 1969:86088, 1969.

Xie et al., "Studies on synthesis and antitumor activity of phenol substituted bisphosphonate Schiff base," Chemical Abstracts, Accession No. 2000:564324, 2000.

* cited by examiner

METHODS AND COMPOSITIONS OF TRAIL-DEATH RECEPTOR AGONISTS/ACTIVATORS

The present application claims benefit of priority to U.S. Provisional Application Ser. No. 60/887,783, filed Feb. 1, 2007, the entire content of this application being incorporated by reference herein.

The U.S. Government owns rights in the application pursuant to funding from the Department of Defense through U.S. Army grants DAMD17-03-1-0242, X81XWH-04-1-0021, and PC060782.

BACKGROUND OF THE INVENTION

I. Field of the Invention

The present invention relates generally to the treatment and prevention of cancer. The methods and compositions of this invention comprise the use of small molecules as ligands for binding to TRAIL-R1/DR4 and/or TRAIL-R2/DR5 death receptors, the recruitment of FADD (Fas-associated death domain protein), the activation of the death-inducing signaling complex (DISC), the activating of caspase-8, and the induction apoptosis in malignant cells. The methods and compositions of this invention may be used for the treatment and/or prevention of a variety of diseases, such as those where excess cell growth is a problem.

II. Description of Related Art

Apoptosis is a genetically programmed cell death that is required for morphogenesis during embryogenic development and for tissue homeostasis in adult organisms. Failure to undergo apoptosis has been implicated in tumor development and resistance to cancer therapy. Dysregulation of the apoptotic machinery plays a role in the pathogenesis of various diseases and molecules involved in cell death pathways are potential therapeutic targets in immunologic, neurologic, cancer, infectious and inflammatory diseases. Strategies for overcoming resistance to apoptosis include direct targeting of antiapoptotic molecules expressed in tumors, re-sensitization of previously resistant tumor cells by counteracting survival pathways and inducing expression or activity of proapoptotic molecules.

Most chemotherapeutic drugs can induce tumor cell death by apoptosis. Analysis of the molecular mechanisms that regulate apoptosis indicates that anticancer agents simultaneously activate several pathways that either positively or negatively regulate the death process. The main pathway of apoptosis induced by drugs involves activation of caspases in the cytosol by pro-apoptotic molecules. At least in some cell types, anticancer drugs also upregulate the expression of death receptors and sensitize tumor cells to their cognate ligands (Singh et al., 2003). In some cases, the Fas-mediated pathway contributes to the early steps of drug-induced apoptosis while sensitization to the cytokine TRAIL can be used to amplify the response to cytotoxic drugs.

The Bcl-2 family of proteins, that includes anti- and pro-apoptotic molecules, regulates cell sensitivity mainly at the mitochondrial level (Green and Reed, 1998; Singh et al., 2003). Anticancer drugs modulate their expression (e.g. through p53-dependent gene transcription), their activity (e.g. by phosphorylating Bcl-2) and their subcellular localization (e.g. by inducing translocation of pro-apoptotic proteins). Very early after interacting with tumor cells, anticancer drugs also activate lipid-dependent signaling pathways that increase or decrease apoptosis. In addition, cytotoxic agents can activate protective pathways that involve activation of NFκB transcription factor, Akt protein kinase and proteins involved in cell cycle regulation (e.g. cyclin D1), and accumulation of heat shock proteins such as Hsp27.

TNF-related apoptosis-inducing ligand (TRAIL) is a ligand molecule which induces the process of cell death called apoptosis. It is a type II transmembrane protein with homology to other members of the tumor necrosis factor (TNF) family. There are a number of ligand-receptor families that are involved in apoptosis. Some of the members of this family are TNF-α, CD95L/FasL/APO-1L, and TRAIL/APO-2L (TRAIL=TNF related apoptosis inducing ligand.). They regulate many biological functions including cell metabolism, proliferation, cytokine production and apoptosis (Krammer, 1999; Pitti et al., 1996; Wiley et al., 1995). TRAIL/APO-2L specifically kills transformed and cancer cells via binding with specific cell-surface death receptors (TRAIL-R1/DR4 and TRAIL-R2/DR5). Most normal cells appear to be resistant to TRAIL activation (Ashkenazi and Dixit, 1999; Chen et al., 2001; Singh et al., 2003; Walczak et al., 1999), suggesting a higher activity of TRAIL with its receptors on tumor cells. Binding of DR4 or DR5 with TRAIL results in a caspase-activating signal leading to apoptosis (French and Tschopp, 2003; LeBlanc and Ashkenazi, 2003; Srivastava, 2001). Recent studies have shown that systemic administration of TRAIL in 60 mice is physiologically safe, effective in killing human breast, prostate and colon tumor xenografts, and prolongs survival of tumor-bearing mice (French and Tschopp, 1999; Ray and Almasan, 2003; Shankar et al., 2004a,b; Singh et al., 2003). TRAIL participates in cytotoxicity mediated by activated NK cells (Kayagaki et al., 1999a), monocytes (Griffith et al., 1999) and some cytotoxic T cells (Kayagaki et al., 1999b; Thomas and Hersey, 1998).

Current approaches for the development of TRAIL-R1 and/or TRAIL-R2 agonists as anticancer agents include the use of monoclonal antibodies, as discussed in WO/2079377, and targeting of the receptor(s) using a soluble form of TRAIL. Given the drawback of monoclonal antibodies and polypeptide therapeutics, new strategies for treating cancer by targeting death receptor pathway are desirable.

SUMMARY OF THE INVENTION

Thus, in order to overcome deficiencies in the prior art, this invention provides compositions and methods of treating cancer and other diseases using small molecule TRAIL-death receptor activator/agonists (DRAs). Also provided are methods and compositions to induce cell death (apoptosis and autophagy) in cells expressing death receptor TRAIL-R1/DR4 and TRAIL-R2/DR5. It is further provided that the methods and compositions of the present invention may be used for the treatment of a variety of cancers, including breast, prostate, colon, pancreatic, ovarian, lung, and brain cancers, leukemia, lymphoma, multiple myeloma, and mesothelioma.

In one aspect, the invention provides methods of treating an individual comprising administering to said individual a therapeutically effective amount of a compound having the general formula:

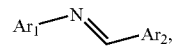

wherein $Ar_1$ and $Ar_2$ are each independently heteroatom-substituted or heteroatom-unsubstituted $C_6$-$C_{35}$-aryl, and pharmaceutically acceptable salts, hydrates, amine-N-oxides, imine-N-oxides, tautomers, and optical isomers thereof. The terms DRAs and DRA-compounds include compounds defined by this formula. In some embodiments, $Ar_1$ and $Ar_2$ are each independently heteroatom-substituted or heteroatom-unsubstituted $C_7$-$C_{10}$-aryl. In other embodiments, $Ar_1$ is a heteroatom-substituted $C_7$-$C_8$-aryl and $Ar_2$ is a heteroatom-substituted $C_8$-aryl. In yet other embodiments, $Ar_1$ and $Ar_2$ are each independently heteroatom-substituted or heteroatom-unsubstituted $C_n$-aryl groups, wherein n is 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35.

The further embodiments, the compound is further defined by the formula:

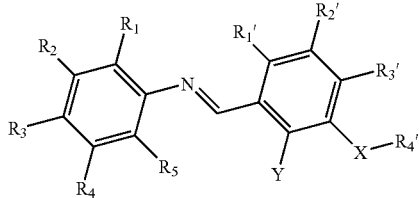

wherein: $R_1$, $R_2$, $R_3$, $R_4$, $R_5$, $R_{1'}$, $R_{2'}$, and $R_{3'}$ are each independently —H, hydroxy, amino, cyano, halo, nitro, mercapto, —OPO(OH)$_2$, —PO(OH)$_2$, —OSO$_2$OH, —SO$_2$OH, or a heteroatom-substituted or heteroatom-unsubstituted $C_1$-$C_3$-alkyl, $C_2$-$C_3$-alkenyl, $C_2$-$C_3$-alkynyl, $C_1$-$C_3$-acyl, $C_1$-$C_3$-alkoxy, $C_1$-$C_3$-acyloxy, $C_1$-$C_3$-alkylamino, or $C_1$-$C_3$-amido; $R_{4'}$ is —H or a heteroatom-substituted or heteroatom-unsubstituted $C_1$-$C_{10}$-alkyl, $C_1$-$C_{10}$-aryl, $C_2$-$C_{10}$-aralkyl, $C_2$-$C_{10}$-alkenyl, $C_2$-$C_{10}$-alkynyl, or $C_1$-$C_{10}$-acyl; X is selected from the group consisting of —O—, —S—, and —NH—, and Y is selected from the groups consisting of hydroxy, amino, and mercapto.

In still further embodiments, the compounds are further defined by the formula:

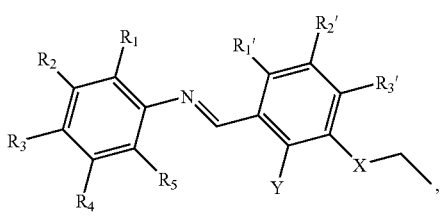

wherein $R_1$, $R_2$, $R_3$, $R_4$, $R_5$, $R_{1'}$, $R_{2'}$, and $R_{3'}$ are each independently —H, hydroxy, amino, cyano, halo, nitro, mercapto, —OPO(OH)$_2$, —PO(OH)$_2$, —OSO$_2$OH, or —SO$_2$OH; X is selected from the group consisting of —O—, —S—, and —NH—, and Y is selected from the groups consisting of hydroxy, amino, and mercapto.

In further embodiments, the compounds are further defined by the formula:

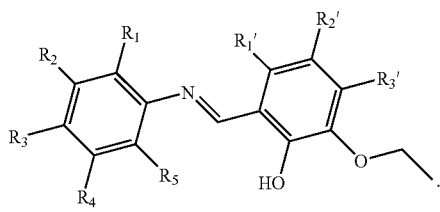

In still further embodiments, a compound is selected from one of the compounds shown below:

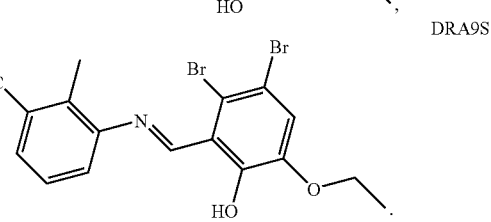

DRA9

DRA9S

In another aspect, the invention provides methods of treating an individual comprising administering to said individual a therapeutically effective amount of a compound having the general formula:

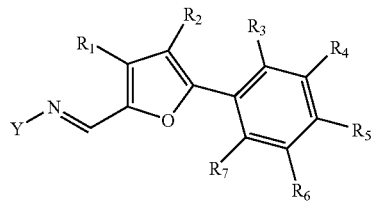

wherein: $R_1$, $R_2$, $R_3$, $R_4$, $R_5$, $R_6$ and $R_7$, are each independently —H, hydroxy, amino, cyano, halo, nitro, mercapto, —OPO(OH)$_2$, —PO(OH)$_2$, —OSO$_2$OH, —SO$_2$OH, or a heteroatom-substituted or heteroatom-unsubstituted $C_1$-$C_8$-alkyl, $C_2$-$C_8$-alkenyl, $C_2$-$C_8$-alkynyl, $C_1$-$C_8$-aryl, $C_2$-$C_8$-aralkyl, $C_1$-$C_8$-acyl, $C_1$-$C_8$-alkoxy, $C_1$-$C_8$-aryloxy, $C_2$-$C_8$-aralkoxy, $C_1$-$C_8$-acyloxy, $C_1$-$C_8$-alkylamino, $C_1$-$C_8$-arylamino, $C_2$-$C_8$-aralkylamino, or $C_1$-$C_8$-amido; Y is selected from the groups consisting of heteroatom-substituted or heteroatom-unsubstituted $C_1$-$C_{15}$-alkylamino, $C_1$-$C_{15}$-alkenylamino, $C_1$-$C_{15}$-alkynylamino, $C_1$-$C_{15}$-arylamino, $C_2$-$C_{15}$-aralkylamino, and $C_1$-$C_{15}$-amido; and pharmaceutically acceptable salts, hydrates, tautomers, and optical isomers thereof. The terms DRAs and DRA-compounds include compounds defined by this formula.

In certain embodiments, $R_3$, $R_4$, $R_5$, $R_6$ and $R_7$, are each independently —H, hydroxy, amino, cyano, halo, nitro, mercapto, —OPO(OH)$_2$, —PO(OH)$_2$, —OSO$_2$OH, —SO$_2$OH, or a heteroatom-substituted or heteroatom-unsubstituted $C_1$-$C_3$-alkyl, $C_2$-$C_3$-alkenyl, $C_2$-$C_3$-alkynyl, $C_1$-$C_3$-acyl, $C_1$-$C_3$-alkoxy, $C_1$-$C_3$-acyloxy, $C_1$-$C_3$-alkylamino, or $C_1$-$C_3$-amido. In some embodiments, Y is —NC(S)NH$_2$ or —NC(O)NH$_2$.

In some embodiments, the compounds are further defined by the formula:

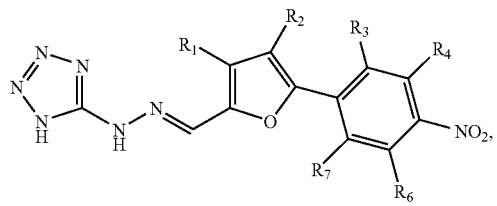

and pharmaceutically acceptable salts, hydrates, tautomers, and optical isomers thereof.

In still further embodiments, the compound is:

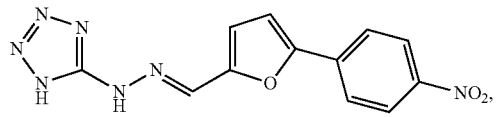

or pharmaceutically acceptable salts, hydrates, and tautomers thereof.

In another aspect, the invention provides methods of treating an individual comprising administering to said individual a therapeutically effective amount of a compound from Group A, B or C, shown in the detailed description of the invention section below, or pharmaceutically acceptable salts, hydrates, tautomers, or optical isomers thereof.

In a further aspect, the invention provides methods of treating an individual comprising administering to said individual a therapeutically effective amount of a compound, having a molecular weight ranging from 200-500 g/mol, wherein the mechanism of treatment comprises binding between the compound and a TRAIL-R1/DR4 and/or a TRAIL-R2/DR5 death receptor to form a complex, binding between a Fas-associated death domain protein and the complex to form a death-inducing signaling complex (DISC), and activating caspase-8 to induce apoptosis in a cell.

In certain embodiments, the individual has cancer, such as brain, lung, liver, spleen, kidney, lymph node, small intestine, pancreas, blood cell, bone, colon, stomach, breast, endometrium, prostate, testicle, ovary, central nervous system, skin, head and neck, esophagus, or bone marrow cancer. In some embodiments, the cancer is mesothelioma. In other embodiments said cancer is leukemia. In still other embodiments, the cancer is epithelial cancer. In still further embodiments, the bone marrow cancer is multiple myeloma. In still further embodiments, the individual has been identified as having a high risk for the development of cancer.

The invention also discloses methods of treating a patient having cancer comprising administering a therapeutically effective amount of a compound of this invention, such as those described above or throughout this specification. In some of these embodiments, the cancer is brain, lung, liver, spleen, kidney, lymph node, small intestine, pancreas, blood cell, bone, colon, stomach, bread, endometrium, prostate, testicle, ovary, central nervous system, skin, head and neck, esophagus, or bone marrow cancer. For example, in some embodiments, the cancer is epithelial cancer. In other embodiments, the cancer is lung, colon, breast or prostate cancer. In other embodiments, the cancer is colon cancer. In further embodiments, the patient has been identified as having a high risk for the development of cancer of any type.

In another aspect, the invention provides methods for inducing cytotoxicity in a cell comprising contacting the cell with a compound of the present invention, such as those described above or throughout this specification, wherein the compound is provided in an amount effective to induce cytotoxicity in said cell. In embodiments, method for inducing cytotoxicity in a cell comprises contacting the cell with a compound of the present invention, such as those described above or throughout this specification, and a treatment selected from the group consisting of chemotherapy using a chemotherapeutic agent, radiotherapy, gene therapy, and surgery, wherein the compound and the treatment are provided in a combined amount effective to induce cytotoxicity in said cell.

In certain embodiments, a compound of this invention is contacted with the cell prior to contacting the cell with the chemotherapeutic agent. In other embodiments, a chemotherapeutic agent is contacted with the cell prior to contacting said cell with the compound.

In some embodiments, the cell is a cancer cell. In some of these embodiments, said cancer cell is a leukemic cell. In further of these embodiments, the leukemic cell is a blood cancer cell, a myeloid leukemia cell, a monocytic leukemia cell, a myelocytic leukemia cell, a promyelocytic leukemia cell, a myeloblastic leukemia cell, a lymphocytic leukemia cell, an acute myelogenous leukemic cell, a chronic myelogenous leukemic cell, a lymphoblastic leukemia cell, or a hairy cell leukemia cell.

In other embodiments, the cancer cell is a solid tumor cell. In certain of these embodiments, the solid tumor cell is a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, or a soft tissue cancer cell.

In some embodiments, the cell being cytotoxically induced is located in a human subject. In some of these embodiments, the compound of this invention is administered locally. In further of these embodiments, the compound is administered by direct intratumoral injection, wherein the compound is administered by injection into tumor vasculature. In other embodiments, the compound is administered systemically. In some of these embodiments, the compound is administered intravenously. In other embodiments, the compound is administered intra-arterially. In further embodiments, the compound is administered intra-peritoneally. In still further embodiments, the compound is administered orally. In certain embodiments, the compound is administered by contacting a cell during ex vivo purging.

For example, in some aspects, the chemotherapeutic agent used in combination with a compound of this invention is doxorubicin, decitabine, daunorubicin, dactinomycin, mitoxantrone, cisplatin, procarbazine, mitomycin, carboplatin, bleomycin, etoposide, teniposide, mechlroethamine, cyclophosphamide, ifosfamide, melphalan, chlorambucil, ifosfamide, melphalan, hexamethylmelamine, thiopeta, busulfan, carmustine, lomustine, semustine, streptozocin, dacarbazine, adriamycin, 5-fluorouracil (5FU), camptothecin, actinomycin-D, hydrogen peroxide, nitrosurea, plicomycin, tamoxifen, taxol, transplatinum, vincristin, vinblastin, TRAIL, dolastatin-10, bryostatin, annamycin, mylotarg, sodium phenylacetate, methotrexate, a cortocosteroid, tacrolimus, or histone deacetylase inhibitors, such as sodium butyrate, MS-275, Trichostatin A, M344, M360, LBH589, D85, SW55, SW187, valproic acid, 4-phenylbutyric acid, suberoylanilide hydroxamic acid, PXD-101, and LBH-589. However, one of ordinary skill in the art will appreciate that the invention is not limited to these chemotherapeutic agents and may involve the use of other DNA damaging agents as well.

In other aspects, the chemotherapeutic agent is a retinoid. In some of these embodiments, the retinoid is selected from the group comprising all-trans-retinoic acid, 9-cis-retinoic acid, LG100268, LGD1069, fenretinide, CD437, a RAR-specific retinoic acid, and a RXR-specific retinoic acid. In some of these embodiments, the RXR-specific retinoic acid is LG100268.

In some embodiments, the cell being cytotoxically induced is contacted with a compound of this invention a second time. In further embodiments, the cell is contacted with the chemotherapeutic agent a second time. In certain embodiments, the compound of this invention and the chemotherapeutic agent are contacted with the cell at the same time.

In another aspect, the invention provides methods of killing a tumor cell comprising contacting said tumor cell with a compound of this invention, wherein the compound of this invention is provided in an amount effective to kill said tumor cell. In certain embodiments, the invention provides methods of killing a tumor cell comprising contacting said tumor cell with a compound of this invention and a chemotherapeutic agent, wherein the compound of this invention and said chemotherapeutic agent are provided in a combined amount effective to kill said tumor cell.

In yet another aspect, the invention provides methods of inducing apoptosis in a tumor cell comprising contacting said tumor cell with a compound of this invention, wherein the compound is provided in an amount effective to induce apoptosis of said tumor cell. In some embodiments, the invention provides methods of inducing apoptosis in a tumor cell comprising contacting said tumor cell with a compound of this invention and a chemotherapeutic agent wherein, the compound of this invention and said chemotherapeutic agent are provided in a combined amount effective to induce apoptosis of said tumor cell.

In still another aspect, the invention provides methods of inducing differentiation in a tumor cell, comprising contacting said tumor cell with a compound of this invention, wherein the compound of this invention is provided in an amount effective to induce the differentiation of the tumor cell. In certain embodiments, the invention provides methods of inducing differentiation in a tumor cell comprising contacting said tumor cell with a compound of this invention and a chemotherapeutic agent, wherein the compound and the chemotherapeutic agent are provided in a combined amount effective to induce the differentiation of the tumor cell.

In a further aspect, the invention provides methods of treating cancer in a human patient, comprising administering a compound of this invention to said human patient, are provided. In some embodiments, the compound of this invention is provided in an amount effective to treat the cancer. In other embodiments, the method comprises administering a compound of this invention and a chemotherapeutic agent, wherein the compound and the chemotherapeutic agent are provided in a combined amount effective to treat the cancer.

In another aspect of the invention, methods of potentiating the effect of a chemotherapeutic agent on a tumor cell are provided, comprising contacting said tumor cell with a compound of this invention and a chemotherapeutic agent.

In a further aspect of the invention, methods of inhibiting growth of a tumor cell are disclosed, comprising contacting said tumor cell with a compound of this invention, wherein the compound is provided in an amount effective to inhibit growth of said tumor cell. In certain embodiments, the methods of inhibiting growth of a tumor cell, comprise contacting the tumor cell with a compound of this invention and a chemotherapeutic agent wherein the compound and the chemotherapeutic agent are provided in a combined amount effective to inhibit growth of said tumor cell.

The invention further discloses methods of inducing apoptosis in a lymphoid cell that expresses Bcl-2 comprising contacting said lymphoid cell with a compound of this invention either as a single agent treatment or together with an immunosupressive agent. In some of these embodiments, the Bcl-2 is endogenous. In other of these embodiments, the Bcl-2 is exogenous. In certain embodiments, the Bcl-2 is expressed by an expression vector that comprises a nucleic acid that encodes Bcl-2 under the control of a promoter active in the lymphoid cell. In some embodiments, the lymphoid cell is a T-cell. In further embodiments, the lymphoid cell is a cancer cell. In some of these embodiments, the lymphoid cell is located in a human. In certain aspects, the immunosupressive agent is a corticosteroid. In certain embodiments, the immunosupressive agent is a tacrolimus. The invention further provides in some embodiments, that the lymphoid cell is further contacted with a chemotherapeutic agent.

Therefore, provided in the invention are methods for inducing cytotoxicity in a cell comprising contacting the cell with a DRA-compound and a chemotherapeutic agent, wherein the combination of the DRA-compound with the chemotherapeutic agent is effective in inducing cytotoxicity in the cell.

In one embodiment of the methods, the DRA-compound is contacted with the cell prior to contacting the cell with the chemotherapeutic agent. In another embodiment of the method, the chemotherapeutic agent is contacted with the cell prior to contacting the cell with the DRA-compound.

In other embodiments of the methods, the cell is a cancer cell. In some aspects the cancer cell is a leukemic cell. In more specific aspects, the leukemic cell is a blood cancer cell, a myeloid leukemia cell, a monocytic leukemia cell, a myelocytic leukemia cell, a promyelocytic leukemia cell, a myeloblastic leukemia cell, a lymphocytic leukemia cell, an acute myelogenous leukemic cell, a chronic myelogenous leukemic cell, a lymphoblastic leukemia cell, a hairy cell leukemia cell.

In yet other embodiments, the cancer cell is a solid tumor cell. In specific aspects, the solid tumor cell is a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, a soft tissue cancer cell.

In one embodiment of the methods, the cell is located in a human subject. In one embodiment, the DRA-compound may be administered locally. Therefore, the compound may be administered by intratumoral injection and/or by injection into tumor vasculature.

In another embodiment of the methods, the DRA-compound may be administered systemically. In other specific aspects of this embodiment, the DRA-compounds may be administered intravenously, intra-arterially, intra-peritoneally and/or orally. DRA may be administered at dosages in the range of 5-30 mg/kg intravenously (i.v.) or 5-100 mg/kg orally. Thus, 5, 10, 15, 20, 25, or 30 mg/kg of DRA may be administered by i.v. or 5, 10, 15, 20, 25, 30, 35, 40, 45, 50, 55, 60, 65, 70, 75, 80, 85, 90, 95, or 100 mg/kg DRA may be administered orally. DRA may be administered in the range of 5-100 mg/kg intravenously or 5-100 mg/kg orally for 3-30 days. Thus, 5, 10, 15, 20, 25, 30, 35, 40, 45, 50, 55, 60, 65, 70, 75, 80, 85, 90, 95, or 100 mg/kg of DRA may be administered by i.v. or, 5, 10, 15, 20, 25, 30, 35, 40, 45, 50, 55, 60, 65, 70, 75, 80, 85, 90, 95, or 100 mg/kg of DRA may be administered orally. The skilled artisan will appreciate that these dosages are only guidelines and a physician will determine exact dosages at the time of administration factoring in other conditions such as age, sex, disease, etc. of the patient.

In some embodiments, the retinoids may be administered as liposomal formulations. These liposomal formulations may be administered intravenously or through other routes as well, for example a liposomal formulation of ATRA is administered a range of 10-100 mg/m$^2$/day intravenously. Thus, one may administer 10, 20, 25, 30, 35, 40, 45, 50, 55, 60, 65, 70, 75, 80, 85, 90, 95, or 100 mg/m$^2$/day of a liposomal formulation of ATRA. In one specific embodiment, 90 mg/m$^2$/day of ATRA as a liposomal formulation is intravenously. In other embodiments, the retinoids may be administered orally. For example, ATRA may be administered in the range of 10-100 mg/m$^2$/day. Thus, one may administer 10, 20, 25, 30, 35, 40, 45, 50, 55, 60, 65, 70, 75, 80, 85, 90, 95, or 100 mg/m$^2$/day of ATRA. In one specific embodiment, ATRA may be administered at 45 mg/m$^2$/day orally daily. In another example, 9-cis-Retinoid acid may be administered in the range of 20-150 mg/m$^2$ twice a day orally. Thus, one may administer 20, 25, 30, 35, 40, 45, 50, 55, 60, 65, 70, 75, 80, 85, 90, 95, 100, 105, 110, 115, 120, 125, 130, 135, 140, 145, or 150 mg/m$^2$ of 9-cis-retinoid. LG100268 may be effective in a dose range of 5-50 mg/kg. Thus, 5, 10, 15, 20, 25, 30, 35, 40, 45, to 50 mg/kg of LG100268 may be administered. LGD1069 (Targretin, bexarotene) capsules are contemplated for the topical treatment of cutaneous lesions in patients with cutaneous T-cell lymphoma (CTCL) who have refractory or resistant disease after other therapies. The dose ranges of these capsules are 300-400 mg/m$^2$/day orally. Thus, 300, 350, 400 mg/m$^2$/day may be used. LGD1069 gel at 1% may also be used for the topical treatment of cutaneous lesions in patients with CTCL (Stage (1A and 1B) who have refractory or resistant disease after other therapies; two to four times daily. Fenretinide [N-(4-hydroxyphenyl)retinamide, 4-HPR] is contemplated useful at 25-600 mg daily and the administration in some embodiments may be continuous. Thus, 25, 30, 35, 40, 45, 50, 55, 60, 65, 70, 75, 80, 85, 90, 95, 100, 120, 140, 160, 180, 200, 220, 240, 260, 280, 300, 320, 340, 360, 380, 400, 420, 440, 460, 480, 500, 520, 540, 560, 580, 600 mg may be administered daily. Of course, the skilled artisan will understand that while these dosage ranges provide useful guidelines appropriate adjustments in the dosage depending on the needs of an individual patient factoring in disease, gender, age and other general health conditions will be made at the time of administration to a patient by a trained physician.

In some embodiments of the methods, the cell is contacted with the DRA-compound a second time. In yet other embodiments of the methods, the cell may be contacted with the chemotherapeutic agent a second time. In still other aspects of this method, the DRA-compound and the chemotherapeutic agent can be contacted with the cell at the same time.

One embodiment of the methods, further comprising tumor resection in conjunction with the DRA-compound based combination therapy. The tumor resection may occurs prior to the contacting. Thus, the contacting can comprises treating a resected tumor bed with the DRA-compound and the chemotherapeutic agent. In other aspects, the tumor resection occurs after the contacting. In still other aspects, the contacting occurs both before and after the tumor resection.

The invention also provides methods of killing a tumor cell comprising contacting the tumor cell with a DRA-compound and a chemotherapeutic agent, wherein the combination of said DRA-compound with said chemotherapeutic agent, induces killing of said tumor cell. The invention also provides methods of inducing apoptosis in a tumor cell comprising contacting said tumor cell with a DRA-compound and a chemotherapeutic agent, wherein the combination of said DRA-compound with said chemotherapeutic agent, induces apoptosis of said tumor cell. In some embodiments of this method, the chemotherapeutic agent is a retinoid.

Also provided are methods for inducing differentiation in a tumor cell comprising contacting the tumor cell with a DRA-compound and a chemotherapeutic agent, wherein the combination of the DRA-compound with the chemotherapeutic agent, induces the differentiation of the tumor cell. Further provided are methods for treating cancer in a human patient comprising administering a DRA-compound and a chemotherapeutic agent to the human patient, wherein the combination of the DRA-compound with the chemotherapeutic agent, is effective to treat the cancer. The invention also describes methods of potentiating the effect of a chemotherapeutic agent on a tumor cell comprising contacting the tumor cell with a DRA-compound and the chemotherapeutic agent. In addition, the invention provides methods of inhibiting growth of a tumor cell comprising contacting the tumor cell with a DRA-compound and a chemotherapeutic agent.

In some embodiments, the compound is optically pure. For example, in some embodiments, the compound is predominantly the (+) enantiomer. In other embodiments, the compound is predominantly the (−) enantiomer. In other embodiments, the compound is a racemic mixture. In certain embodiments, the compound is administered with an aqueous solution. In some embodiments, the therapeutically effective amount is 0.1-1000 mg/kg. In further embodiments, an additional agent is administered to said patient.

BRIEF DESCRIPTION OF THE DRAWINGS

The following drawings form part of the present specification and are included to further demonstrate certain aspects of the present invention. The invention may be better understood by reference to one of these drawings in combination with the detailed description of specific embodiments presented herein.

FIG. 24A: Pancreatic cancer AsPC-1 cells were treated with either DRA11 (10 μM) for 0, 0.5, 1 and 2 h or TRAIL (50 ng/ml) for 1 h. Cell lysates were prepared, immunoprecipitated with anti-DR5 antibody, and immunoblotted with anti-FADD antibody, and anti-caspase-8 antibody. The same blot was reprobed with anti-DR5 antibody as a loading control.

DESCRIPTION OF ILLUSTRATIVE EMBODIMENTS

I. The Present Invention

Figure 1:
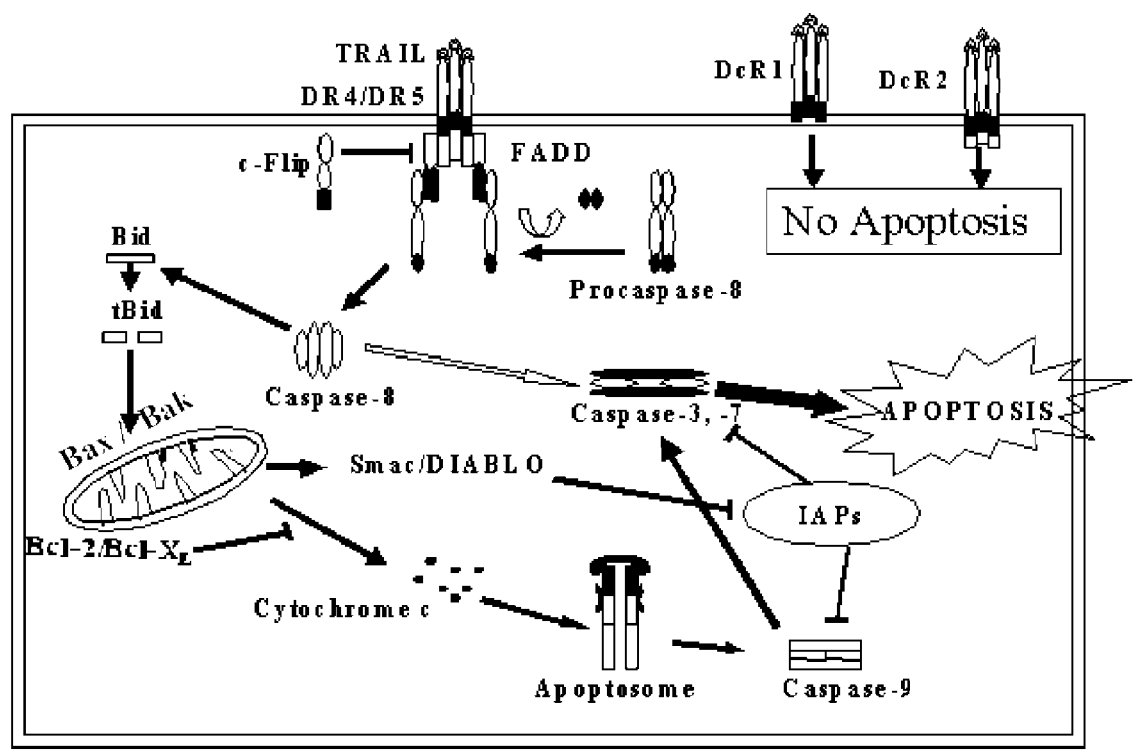
FIG. 1. Schematic representation of TRAIL receptors and the components of TRAIL DISC. Trimerization of TRAIL receptors (TRAIL-R1/DR4 and TRAIL-R2/DR5) initiates recruitment of adaptor protein FADD. FADD contains a death effector domain that promotes recruitment of procaspase-8 or procaspase-10 to the death-inducing complex (DISC). The induced proximity of pro-caspase molecules is postulated to cause their activation by autocatalytic processes. Decoy receptors DcR1 and DcR2 do not induce apoptosis due to complete or partial loss of cytoplasmic death domain, respectively.

The approach described herein involves novel methods for treating individuals have diseases such as cancer using TRAIL-death receptor activators/agonists (DRAs). Methods are provided for the use of DRAs to treat a wide variety of human diseases, such as those where excess cell growth is a problem. For example, DRAs may be used to selectively kill cancer cells, sparing normal cells.

II. Definitions

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an," when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the term "amino" means —$NH_2$; the term "nitro" means —$NO_2$; the term "halo" designates —F, —Cl, —Br or —I; the term "mercapto" means —SH; the term "cyano" means —CN; the term "azido" means —$N_3$; the term "silyl" means —$SiH_3$, and the term "hydroxy" means —OH.

The term "alkyl" includes straight-chain alkyl, branched-chain alkyl, cycloalkyl (alicyclic), cyclic alkyl, heteroatom-unsubstituted alkyl, heteroatom-substituted alkyl, heteroatom-unsubstituted $C_n$-alkyl, and heteroatom-substituted $C_n$-alkyl. The term "heteroatom-unsubstituted $C_n$-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted $C_1$-$C_{10}$-alkyl has 1 to 10 carbon atoms. The groups, —$CH_3$ (Me), —$CH_2CH_3$ (Et), —$CH_2CH_2CH_3$ (n-Pr), —$CH(CH_3)_2$ (iso-Pr), —$CH(CH_2)_2$ (cyclopropyl), —$CH_2CH_2CH_2CH_3$ (n-Bu), —$CH(CH_3)CH_2CH_3$ (sec-butyl), —$CH_2CH(CH_3)_2$ (iso-butyl), —$C(CH_3)_3$ (tert-butyl), —$CH_2C(CH_3)_3$ (neopentyl), cyclobutyl, cyclopentyl, and cyclohexyl, are all non-limiting examples of heteroatom-unsubstituted alkyl groups. The term "heteroatom-substituted $C_n$-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkyl has 1 to 10 carbon atoms. The following groups are all non-limiting examples of heteroatom-substituted alkyl groups: trifluoromethyl, —$CH_2F$, —$CH_2Cl$, —$CH_2Br$, —$CH_2OH$, —$CH_2OCH_3$, —$CH_2OCH_2CF_3$, —$CH_2OC(O)CH_3$, —$CH_2NH_2$, —$CH_2NHCH_3$, —$CH_2N(CH_3)_2$, —$CH_2CH_2Cl$, —$CH_2CH_2OH$, $CH_2CH_2OC(O)CH_3$, —$CH_2CH_2NHCO_2C(CH_3)_3$, and —$CH_2Si(CH_3)_3$.

The term "alkanediyl" includes straight-chain alkanediyl, branched-chain alkanediyl, cycloalkanediyl, cyclic alkanediyl, heteroatom-unsubstituted alkanediyl, heteroatom-substituted alkanediyl, heteroatom-unsubstituted $C_n$-alkanediyl, and heteroatom-substituted $C_n$-alkanediyl. The term "heteroatom-unsubstituted $C_n$-alkanediyl" refers to a diradical, having a linear or branched, cyclic or acyclic structure, further having no carbon-carbon double or triple bonds, further having a total of n carbon atoms, all of which are nonaromatic, 2 or more hydrogen atoms, and no heteroatoms. For example, a heteroatom-unsubstituted $C_1$-$C_{10}$-alkanediyl has 1 to 10 carbon atoms. The groups, —$CH_2$— (methylene), —$CH_2CH_2$—, and —$CH_2CH_2CH_2$—, are all non-limiting examples of heteroatom-unsubstituted alkanediyl groups. The term "heteroatom-substituted $C_n$-alkanediyl" refers to a radical, having two points of attachment to one or two saturated carbon atoms, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkanediyl has 1 to 10 carbon atoms. The following groups are all non-limiting examples of heteroatom-substituted alkanediyl groups: —CH(F)—, —$CF_2$—, —CH(Cl)—, —CH(OH)—, —$CH(OCH_3)$—, and —$CH_2CH(Cl)$—.

The term "alkenyl" includes straight-chain alkenyl, branched-chain alkenyl, cycloalkenyl, cyclic alkenyl, heteroatom-unsubstituted alkenyl, heteroatom-substituted alkenyl, heteroatom-unsubstituted $C_n$-alkenyl, and heteroatom-substituted $C_n$-alkenyl. The term "heteroatom-unsubstituted $C_n$-alkenyl" refers to a radical, having a linear or branched, cyclic or acyclic structure, further having at least one nonaromatic carbon-carbon double bond, but no carbon-carbon triple bonds, a total of n carbon atoms, three or more hydrogen atoms, and no heteroatoms. For example, a heteroatom-unsubstituted $C_2$-$C_{10}$-alkenyl has 2 to 10 carbon atoms. Heteroatom-unsubstituted alkenyl groups include: —CH=$CH_2$ (vinyl), —CH=$CHCH_3$, —CH=$CHCH_2CH_3$, —$CH_2CH$=$CH_2$ (allyl), —$CH_2CH$=$CHCH_3$, and —CH=CH—$C_6H_5$. The term "heteroatom-substituted $C_n$-alkenyl" refers to a radical, having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkenyl has 2 to 10 carbon atoms. The groups, —CH=CHF, —CH=CHCl and —CH=CHBr, are non-limiting examples of heteroatom-substituted alkenyl groups.

The term "alkynyl" includes straight-chain alkynyl, branched-chain alkynyl, cycloalkynyl, cyclic alkynyl, heteroatom-unsubstituted alkynyl, heteroatom-substituted alkynyl, heteroatom-unsubstituted $C_n$-alkynyl, and heteroatom-substituted $C_n$-alkynyl. The term "heteroatom-unsubstituted $C_n$-alkynyl" refers to a radical, having a linear or branched, cyclic or acyclic structure, further having at least one carbon-carbon triple bond, a total of n carbon atoms, at least one hydrogen atom, and no heteroatoms. For example, a heteroatom-unsubstituted $C_2$-$C_{10}$-alkynyl has 2 to 10 carbon atoms. The groups, —C≡CH, —C≡$CCH_3$, and —C≡$CC_6H_5$ are non-limiting examples of heteroatom-unsubstituted alkynyl groups. The term "heteroatom-substituted $C_n$-alkynyl" refers to a radical, having a single nonaromatic carbon atom as the point of attachment and at least one carbon-carbon triple bond, further having a linear or branched, cyclic or acyclic structure, and having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkynyl has 2 to 10 carbon atoms. The group, —C≡$CSi(CH_3)_3$, is a non-limiting example of a heteroatom-substituted alkynyl group.

The term "aryl" includes heteroatom-unsubstituted aryl, heteroatom-substituted aryl, heteroatom-unsubstituted $C_n$-aryl, heteroatom-substituted $C_n$-aryl, heteroaryl, heterocyclic aryl groups, carbocyclic aryl groups, biaryl groups, and single-valent radicals derived from polycyclic fused hydrocarbons (PAHs). The term "heteroatom-unsubstituted $C_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted $C_6$-$C_{10}$-aryl has 6 to 10 carbon atoms. Non-limiting examples of heteroatom-unsubstituted aryl groups include phenyl (Ph), methylphenyl, (dimethyl)phenyl, —$C_6H_4CH_2CH_3$, —$C_6H_4CH_2CH_2CH_3$, —$C_6H_4CH(CH_3)_2$, —$C_6H_4CH(CH_2)_2$, —$C_6H_3(CH_3)CH_2CH_3$, —$C_6H_4CH=CH_2$, —$C_6H_4CH=CHCH_3$, —$C_6H_4C\equiv CH$, —$C_6H_4C\equiv CCH_3$, naphthyl, and the radical derived from biphenyl. The term "heteroatom-substituted $C_n$-aryl" refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted $C_1$-$C_{10}$-heteroaryl has 1 to 10 carbon atoms. Non-limiting examples of heteroatom-substituted aryl groups include the groups: —$C_6H_4F$, —$C_6H_4Cl$, —$C_6H_4Br$, —$C_6H_4I$, —$C_6H_4OH$, —$C_6H_4OCH_3$, —$C_6H_4OCH_2CH_3$, —$C_6H_4OC(O)CH_3$, —$C_6H_4NH_2$, —$C_6H_4NHCH_3$, —$C_6H_4N(CH_3)_2$, —$C_6H_4CH_2OH$, —$C_6H_4CH_2OC(O)CH_3$, —$C_6H_4CH_2NH_2$, —$C_6H_4CF_3$, —$C_6H_4CN$, —$C_6H_4CHO$, —$C_6H_4CHO$, —$C_6H_4C(O)CH_3$, —$C_6H_4C(O)C_6H_5$, —$C_6H_4CO_2H$, —$C_6H_4CO_2CH_3$, —$C_6H_4CONH_2$, —$C_6H_4CONHCH_3$, —$C_6H_4CON(CH_3)_2$, furanyl, thienyl, pyridyl, pyrrolyl, pyrimidyl, pyrazinyl, quinolyl, indolyl, and imidazoyl.

The term "aralkyl" includes heteroatom-unsubstituted aralkyl, heteroatom-substituted aralkyl, heteroatom-unsubstituted $C_n$-aralkyl, heteroatom-substituted $C_n$-aralkyl, heteroaralkyl, and heterocyclic aralkyl groups. The term "heteroatom-unsubstituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted $C_7$-$C_{10}$-aralkyl has 7 to 10 carbon atoms. Non-limiting examples of heteroatom-unsubstituted aralkyls are: phenylmethyl (benzyl, Bn) and phenylethyl. The term "heteroatom-substituted $C_n$-aralkyl" refers to a radical, having a single saturated carbon atom as the point of attachment, further having a total of n carbon atoms, 0, 1, or more than one hydrogen atoms, and at least one heteroatom, wherein at least one of the carbon atoms is incorporated an aromatic ring structures, further wherein each heteroatom is independently selected from the group consisting of N, O, F, Cl, Br, I, Si, P, and S. For example, a heteroatom-substituted $C_2$-$C_{10}$-heteroaralkyl has 2 to 10 carbon atoms.

The term "acyl" includes straight-chain acyl, branched-chain acyl, cycloacyl, cyclic acyl, heteroatom-unsubstituted acyl, heteroatom-substituted acyl, heteroatom-unsubstituted $C_n$-acyl, heteroatom-substituted $C_n$-acyl, alkylcarbonyl, alkoxycarbonyl and aminocarbonyl groups. The term "heteroatom-unsubstituted $C_n$-acyl" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted $C_1$-$C_{10}$-acyl has 1 to 10 carbon atoms. The groups, —CHO, —C(O)$CH_3$, —C(O)$CH_2CH_3$, —C(O)$CH_2CH_2CH_3$, —C(O)CH($CH_3$)$_2$, —C(O)CH($CH_2$)$_2$, —C(O)$C_6H_5$, —C(O)$C_6H_4CH_3$, —C(O)$C_6H_4CH_2CH_3$, and —CO$C_6H_3(CH_3)_2$, are non-limiting examples of heteroatom-unsubstituted acyl groups. The term "heteroatom-substituted $C_n$-acyl" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom, in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-acyl has 1 to 10 carbon atoms. The groups, —C(O)$CH_2CF_3$, —$CO_2H$, —$CO_2CH_3$, —$CO_2CH_2CH_3$, —$CO_2CH_2CH_2CH_3$, —$CO_2CH(CH_3)_2$, —$CO_2CH(CH_2)_2$, —C(O)$NH_2$ (carbamoyl), —C(O)NH$CH_3$, —C(O)NH$CH_2CH_3$, —CONHCH($CH_3$)$_2$, —CONHCH($CH_2$)$_2$, —CON($CH_3$)$_2$, and —CONH$CH_2CF_3$, are non-limiting examples of heteroatom-substituted acyl groups.

The term "alkoxy" includes straight-chain alkoxy, branched-chain alkoxy, cycloalkoxy, cyclic alkoxy, heteroatom-unsubstituted alkoxy, heteroatom-substituted alkoxy, heteroatom-unsubstituted $C_n$-alkoxy, and heteroatom-substituted $C_n$-alkoxy. The term "heteroatom-unsubstituted $C_n$-alkoxy" refers to a group, having the structure —OR, in which R is a heteroatom-unsubstituted $C_n$-alkyl, as that term is defined above. Heteroatom-unsubstituted alkoxy groups include: —OCH$_3$, —OCH$_2$CH$_3$, —OCH$_2$CH$_2$CH$_3$, —OCH(CH$_3$)$_2$, and —OCH(CH$_2$)$_2$. The term "heteroatom-substituted $C_n$-alkoxy" refers to a group, having the structure —OR, in which R is a heteroatom-substituted $C_n$-alkyl, as that term is defined above. For example, —OCH$_2$CF$_3$ is a heteroatom-substituted alkoxy group.

The term "alkenyloxy" includes straight-chain alkenyloxy, branched-chain alkenyloxy, cycloalkenyloxy, cyclic alkenyloxy, heteroatom-unsubstituted alkenyloxy, heteroatom-substituted alkenyloxy, heteroatom-unsubstituted $C_n$-alkenyloxy, and heteroatom-substituted $C_n$-alkenyloxy. The term "heteroatom-unsubstituted $C_n$-alkenyloxy" refers to a group, having the structure —OR, in which R is a heteroatom-unsubstituted $C_n$-alkenyl, as that term is defined above. The term "heteroatom-substituted $C_n$-alkenyloxy" refers to a group, having the structure —OR, in which R is a heteroatom-substituted $C_n$-alkenyl, as that term is defined above.

The term "alkynyloxy" includes straight-chain alkynyloxy, branched-chain alkynyloxy, cycloalkynyloxy, cyclic alkynyloxy, heteroatom-unsubstituted alkynyloxy, heteroatom-substituted alkynyloxy, heteroatom-unsubstituted $C_n$-alkynyloxy, and heteroatom-substituted $C_n$-alkynyloxy. The term "heteroatom-unsubstituted $C_n$-alkynyloxy" refers to a group, having the structure —OR, in which R is a heteroatom-unsubstituted $C_n$-alkynyl, as that term is defined above. The term "heteroatom-substituted $C_n$-alkynyloxy" refers to a group, having the structure —OR, in which R is a heteroatom-substituted $C_n$-alkynyl, as that term is defined above.

The term "aryloxy" includes heteroatom-unsubstituted aryloxy, heteroatom-substituted aryloxy, heteroatom-unsubstituted $C_n$-aryloxy, heteroatom-substituted $C_n$-aryloxy, heteroaryloxy, and heterocyclic aryloxy groups. The term "heteroatom-unsubstituted $C_n$-aryloxy" refers to a group, having the structure —OAr, in which Ar is a heteroatom-unsubstituted $C_n$-aryl, as that term is defined above. A non-limiting example of a heteroatom-unsubstituted aryloxy group is —OC$_6$H$_5$. The term "heteroatom-substituted $C_n$-aryloxy" refers to a group, having the structure —OAr, in which Ar is a heteroatom-substituted $C_n$-aryl, as that term is defined above.

The term "aralkyloxy" includes heteroatom-unsubstituted aralkyloxy, heteroatom-substituted aralkyloxy, heteroatom-unsubstituted $C_n$-aralkyloxy, heteroatom-substituted $C_n$-aralkyloxy, heteroaralkyloxy, and heterocyclic aralkyloxy groups. The term "heteroatom-unsubstituted $C_n$-aralkyloxy" refers to a group, having the structure —OAr, in which Ar is a heteroatom-unsubstituted $C_n$-aralkyl, as that term is defined above. The term "heteroatom-substituted $C_n$-aralkyloxy" refers to a group, having the structure —OAr, in which Ar is a heteroatom-substituted $C_n$-aralkyl, as that term is defined above.

The term "acyloxy" includes straight-chain acyloxy, branched-chain acyloxy, cycloacyloxy, cyclic acyloxy, heteroatom-unsubstituted acyloxy, heteroatom-substituted acyloxy, heteroatom-unsubstituted $C_n$-acyloxy, heteroatom-substituted $C_n$-acyloxy, alkylcarbonyloxy, arylcarbonyloxy, alkoxycarbonyloxy, aryloxycarbonyloxy, and carboxylate groups. The term "heteroatom-unsubstituted $C_n$-acyloxy" refers to a group, having the structure —OAc, in which Ac is a heteroatom-unsubstituted $C_n$-acyl, as that term is defined above. For example, —OC(O)CH$_3$ is a non-limiting example of a heteroatom-unsubstituted acyloxy group. The term "heteroatom-substituted $C_n$-acyloxy" refers to a group, having the structure —OAc, in which Ac is a heteroatom-substituted $C_n$-acyl, as that term is defined above. For example, —OC(O)OCH$_3$ and —OC(O)NHCH$_3$ are non-limiting examples of heteroatom-unsubstituted acyloxy groups.

The term "alkylamino" includes straight-chain alkylamino, branched-chain alkylamino, cycloalkylamino, cyclic alkylamino, heteroatom-unsubstituted alkylamino, heteroatom-substituted alkylamino, heteroatom-unsubstituted $C_n$-alkylamino, and heteroatom-substituted $C_n$-alkylamino. The term "heteroatom-unsubstituted $C_n$-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted $C_1$-$C_{10}$-alkylamino has 1 to 10 carbon atoms. The term "heteroatom-unsubstituted $C_n$-alkylamino" includes groups, having the structure —NHR, in which R is a heteroatom-unsubstituted $C_n$-alkyl, as that term is defined above. A heteroatom-unsubstituted alkylamino group would include —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —N(CH$_3$)$_2$, —N(CH$_3$)CH$_2$CH$_3$, —N(CH$_2$CH$_3$)$_2$, N-pyrrolidinyl, and N-piperidinyl. The term "heteroatom-substituted $C_n$-alkylamino" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_1$-$C_{10}$-alkylamino has 1 to 10 carbon atoms. The term "heteroatom-substituted $C_n$-alkylamino" includes groups, having the structure —NHR, in which R is a heteroatom-substituted $C_n$-alkyl, as that term is defined above.

The term "alkenylamino" includes straight-chain alkenylamino, branched-chain alkenylamino, cycloalkenylamino, cyclic alkenylamino, heteroatom-unsubstituted alkenylamino, heteroatom-substituted alkenylamino, heteroatom-unsubstituted $C_n$-alkenylamino, heteroatom-substituted $C_n$-alkenylamino, dialkenylamino, and alkyl(alkenyl)amino groups. The term "heteroatom-unsubstituted $C_n$-alkenylamino" refers to a radical, having a single nitrogen atom as the point of attachment, further having one or two carbon atoms attached to the nitrogen atom, further having a linear or branched, cyclic or acyclic structure, containing at least one nonaromatic carbon-carbon double bond, a total of n carbon atoms, 4 or more hydrogen atoms, a total of one nitrogen atom, and no additional heteroatoms. For example, a heteroatom-unsubstituted $C_2$-$C_{10}$-alkenylamino has 2 to 10 carbon atoms. The term "heteroatom-unsubstituted $C_n$-alkenylamino" includes groups, having the structure —NHR, in which R is a heteroatom-unsubstituted $C_n$-alkenyl, as that term is defined above. The term "heteroatom-substituted $C_n$-alkenylamino" refers to a radical, having a single nitrogen atom as the point of attachment and at least one nonaromatic carbon-carbon double bond, but no carbon-carbon triple bonds, further having one or two carbon atoms attached to the nitrogen atom, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkenylamino has 2 to 10 carbon atoms. The term "heteroatom-substituted $C_n$-alkenylamino" includes groups, having the structure —NHR, in which R is a heteroatom-substituted $C_n$-alkenyl, as that term is defined above.

The term "alkynylamino" includes straight-chain alkynylamino, branched-chain alkynylamino, cycloalkynylamino, cyclic alkynylamino, heteroatom-unsubstituted alkynylamino, heteroatom-substituted alkynylamino, heteroatom-unsubstituted $C_n$-alkynylamino, heteroatom-substituted $C_n$-alkynylamino, dialkynylamino, alkyl(alkynyl)amino, and alkenyl(alkynyl)amino groups. The term "heteroatom-unsubstituted $C_n$-alkynylamino" refers to a radical, having a single nitrogen atom as the point of attachment, further having one or two carbon atoms attached to the nitrogen atom, further having a linear or branched, cyclic or acyclic structure, containing at least one carbon-carbon triple bond, a total of n carbon atoms, at least one hydrogen atoms, a total of one nitrogen atom, and no additional heteroatoms. For example, a heteroatom-unsubstituted $C_2$-$C_{10}$-alkynylamino has 2 to 10 carbon atoms. The term "heteroatom-unsubstituted $C_n$-alkynylamino" includes groups, having the structure —NHR, in which R is a heteroatom-unsubstituted $C_n$-alkynyl, as that term is defined above. The term "heteroatom-substituted $C_n$-alkynylamino" refers to a radical, having a single nitrogen atom as the point of attachment, further having one or two carbon atoms attached to the nitrogen atom, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkynylamino has 2 to 10 carbon atoms. The term "heteroatom-substituted $C_n$-alkynylamino" includes groups, having the structure —NHR, in which R is a heteroatom-substituted $C_n$-alkynyl, as that term is defined above.

The term "arylamino" includes heteroatom-unsubstituted arylamino, heteroatom-substituted arylamino, heteroatom-unsubstituted $C_n$-arylamino, heteroatom-substituted $C_n$-arylamino, heteroarylamino, heterocyclic arylamino, and alkyl(aryl)amino groups. The term "heteroatom-unsubstituted $C_n$-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, a heteroatom-unsubstituted $C_6$-$C_{10}$-arylamino has 6 to 10 carbon atoms. The term "heteroatom-unsubstituted $C_n$-arylamino" includes groups, having the structure —NHR, in which R is a heteroatom-unsubstituted $C_n$-aryl, as that term is defined above. The term "heteroatom-substituted $C_n$-arylamino" refers to a radical, having a single nitrogen atom as the point of attachment, further having a total of n carbon atoms, at least one hydrogen atom, at least one additional heteroatoms, that is, in addition to the nitrogen atom at the point of attachment, wherein at least one of the carbon atoms is incorporated into one or more aromatic ring structures, further wherein each additional heteroatom is independently selected from the group consisting of N, O, F, Cl, Br, I, Si, P, and S. For example, a heteroatom-substituted $C_6$-$C_{10}$-arylamino has 6 to 10 carbon atoms. The term "heteroatom-substituted $C_n$-arylamino" includes groups, having the structure —NHR, in which R is a heteroatom-substituted $C_n$-aryl, as that term is defined above.

The term "aralkylamino" includes heteroatom-unsubstituted aralkylamino, heteroatom-substituted aralkylamino, heteroatom-unsubstituted $C_n$-aralkylamino, heteroatom-substituted $C_n$-aralkylamino, heteroaralkylamino, heterocyclic aralkylamino groups, and diaralkylamino groups. The term "heteroatom-unsubstituted $C_n$-aralkylamino" refers to a radical, having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, a heteroatom-unsubstituted $C_7$-$C_{10}$-aralkylamino has 7 to 10 carbon atoms. The term "heteroatom-unsubstituted $C_n$-aralkylamino" includes groups, having the structure —NHR, in which R is a heteroatom-unsubstituted $C_n$-aralkyl, as that term is defined above. The term "heteroatom-substituted $C_n$-aralkylamino" refers to a radical, having a single nitrogen atom as the point of attachment, further having at least one or two saturated carbon atoms attached to the nitrogen atom, further having a total of n carbon atoms, 0, 1, or more than one hydrogen atom, at least one additional heteroatom, that is, in addition to the nitrogen atom at the point of attachment, wherein at least one of the carbon atom incorporated into an aromatic ring, further wherein each heteroatom is independently selected from the group consisting of N, O, F, Cl, Br, I, Si, P, and S. For example, a heteroatom-substituted $C_7$-$C_{10}$-aralkylamino has 7 to 10 carbon atoms. The term "heteroatom-substituted $C_n$-aralkylamino" includes groups, having the structure —NHR, in which R is a heteroatom-substituted $C_n$-aralkyl, as that term is defined above.

The term "amido" includes straight-chain amido, branched-chain amido, cycloamido, cyclic amido, heteroatom-unsubstituted amido, heteroatom-substituted amido, heteroatom-unsubstituted $C_n$-amido, heteroatom-substituted $C_n$-amido, alkylcarbonylamino, arylcarbonylamino, alkoxycarbonylamino, aryloxycarbonylamino, acylamino, alkylaminocarbonylamino, arylaminocarbonylamino, and ureido groups. The term "heteroatom-unsubstituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted $C_1$-$C_{10}$-amido has 1 to 10 carbon atoms. The term "heteroatom-unsubstituted $C_n$-amido" includes groups, having the structure —NHR, in which R is a heteroatom-unsubstituted $C_n$-acyl, as that term is defined above. The group, —NHC(O)CH$_3$, is a non-limiting example of a heteroatom-unsubstituted amido group. The term "heteroatom-substituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-amido has 1 to 10 carbon atoms. The term "heteroatom-substituted $C_n$-amido" includes groups, having the structure —NHR, in which R is a heteroatom-unsubstituted $C_n$-acyl, as that term is defined above. The group, —NHCO$_2$CH$_3$, is a non-limiting example of a heteroatom-substituted amido group.

The term "alkylthio" includes straight-chain alkylthio, branched-chain alkylthio, cycloalkylthio, cyclic alkylthio, heteroatom-unsubstituted alkylthio, heteroatom-substituted alkylthio, heteroatom-unsubstituted $C_n$-alkylthio, and heteroatom-substituted $C_n$-alkylthio. The term "heteroatom-unsubstituted $C_n$-alkylthio" refers to a group, having the structure —SR, in which R is a heteroatom-unsubstituted $C_n$-alkyl, as that term is defined above. The group, —SCH$_3$, is an example of a heteroatom-unsubstituted alkylthio group. The term "heteroatom-substituted $C_n$-alkylthio" refers to a group, having the structure —SR, in which R is a heteroatom-substituted $C_n$-alkyl, as that term is defined above.

The term "alkenylthio" includes straight-chain alkenylthio, branched-chain alkenylthio, cycloalkenylthio, cyclic alkenylthio, heteroatom-unsubstituted alkenylthio, heteroatom-substituted alkenylthio, heteroatom-unsubstituted $C_n$-alkenylthio, and heteroatom-substituted $C_n$-alkenylthio. The term "heteroatom-unsubstituted $C_n$-alkenylthio" refers to a group, having the structure —SR, in which R is a heteroatom-unsubstituted $C_n$-alkenyl, as that term is defined above. The term "heteroatom-substituted $C_n$-alkenylthio" refers to a group, having the structure —SR, in which R is a heteroatom-substituted $C_n$-alkenyl, as that term is defined above.

The term "alkynylthio" includes straight-chain alkynylthio, branched-chain alkynylthio, cycloalkynylthio, cyclic alkynylthio, heteroatom-unsubstituted alkynylthio, heteroatom-substituted alkynylthio, heteroatom-unsubstituted $C_n$-alkynylthio, and heteroatom-substituted $C_n$-alkynylthio. The term "heteroatom-unsubstituted $C_n$-alkynylthio" refers to a group, having the structure —SR, in which R is a heteroatom-unsubstituted $C_n$-alkynyl, as that term is defined above. The term "heteroatom-substituted $C_n$-alkynylthio" refers to a group, having the structure —SR, in which R is a heteroatom-substituted $C_n$-alkynyl, as that term is defined above.

The term "arylthio" includes heteroatom-unsubstituted arylthio, heteroatom-substituted arylthio, heteroatom-unsubstituted $C_n$-arylthio, heteroatom-substituted $C_n$-arylthio, heteroarylthio, and heterocyclic arylthio groups. The term "heteroatom-unsubstituted $C_n$-arylthio" refers to a group, having the structure —SAr, in which Ar is a heteroatom-unsubstituted $C_n$-aryl, as that term is defined above. The group, —SC$_6$H$_5$, is an example of a heteroatom-unsubstituted arylthio group. The term "heteroatom-substituted $C_n$-arylthio" refers to a group, having the structure —SAr, in which Ar is a heteroatom-substituted $C_n$-aryl, as that term is defined above.

The term "aralkylthio" includes heteroatom-unsubstituted aralkylthio, heteroatom-substituted aralkylthio, heteroatom-unsubstituted $C_n$-aralkylthio, heteroatom-substituted $C_n$-aralkylthio, heteroaralkylthio, and heterocyclic aralkylthio groups. The term "heteroatom-unsubstituted $C_n$-aralkylthio" refers to a group, having the structure —SAr, in which Ar is a heteroatom-unsubstituted $C_n$-aralkyl, as that term is defined above. The group, —SCH$_2$C$_6$H$_5$, is an example of a heteroatom-unsubstituted aralkyl group. The term "heteroatom-substituted $C_n$-aralkylthio" refers to a group, having the structure —SAr, in which Ar is a heteroatom-substituted $C_n$-aralkyl, as that term is defined above.

The term "acylthio" includes straight-chain acylthio, branched-chain acylthio, cycloacylthio, cyclic acylthio, heteroatom-unsubstituted acylthio, heteroatom-substituted acylthio, heteroatom-unsubstituted $C_n$-acylthio, heteroatom-substituted $C_n$-acylthio, alkylcarbonyloxy, arylcarbonyloxy, alkoxycarbonyloxy, aryloxycarbonyloxy, and carboxylate groups. The term "heteroatom-unsubstituted $C_n$-acylthio" refers to a group, having the structure —SAc, in which Ac is a heteroatom-unsubstituted $C_n$-acyl, as that term is defined above. The group, —SCOCH$_3$, is an example of a heteroatom-unsubstituted acylthio group. The term "heteroatom-substituted $C_n$-acylthio" refers to a group, having the structure —SAc, in which Ac is a heteroatom-substituted $C_n$-acyl, as that term is defined above.

The term "alkylsilyl" includes straight-chain alkylsilyl, branched-chain alkylsilyl, cycloalkylsilyl, cyclic alkylsilyl, heteroatom-unsubstituted alkylsilyl, heteroatom-substituted alkylsilyl, heteroatom-unsubstituted $C_n$-alkylsilyl, and heteroatom-substituted $C_n$-alkylsilyl. The term "heteroatom-unsubstituted $C_n$-alkylsilyl" refers to a radical, having a single silicon atom as the point of attachment, further having one, two, or three saturated carbon atoms attached to the silicon atom, further having a linear or branched, cyclic or acyclic structure, containing a total of n carbon atoms, all of which are nonaromatic, 5 or more hydrogen atoms, a total of 1 silicon atom, and no additional heteroatoms. For example, a heteroatom-unsubstituted $C_1$-$C_{10}$-alkylsilyl has 1 to 10 carbon atoms. An alkylsilyl group includes dialkylamino groups. The groups, —Si(CH$_3$)$_3$ and —Si(CH$_3$)$_2$C(CH$_3$)$_3$, are non-limiting examples of heteroatom-unsubstituted alkylsilyl groups. The term "heteroatom-substituted $C_n$-alkylsilyl" refers to a radical, having a single silicon atom as the point of attachment, further having at least one, two, or three saturated carbon atoms attached to the silicon atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the silicon atom at the point of attachment, wherein each additional heteroatom is independently selected from the group consisting of N, O, F, Cl, Br, I, Si, P, and S. For example, a heteroatom-substituted $C_1$-$C_{10}$-alkylsilyl has 1 to 10 carbon atoms.

As used herein, a "chiral auxiliary" refers to a removable chiral group that is capable of influencing the stereoselectivity of a reaction. Persons of skill in the art are familiar with such compounds, and many are commercially available.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like. Suitable pharmaceutically acceptable salts may also be formed by reacting the agents of the invention with an organic base such as methylamine, ethylamine, ethanolamine, lysine, ornithine and the like.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, Selection and Use* (P. H. Stahl & C. G. Wermuth eds., Verlag Helvetica Chimica Acta, 2002), which is incorporated herein by reference.

As used herein, the term "patient" is intended to include living organisms in which certain conditions as described herein can occur. Examples include humans, monkeys, cows, sheep, goats, dogs, cats, mice, rats, and transgenic species thereof. In a preferred embodiment, the patient is a primate. In an even more preferred embodiment, the primate is a human. Other examples of subjects include experimental animals such as mice, rats, dogs, cats, goats, sheep, pigs, and cows. The experimental animal can be an animal model for a disorder, e.g., a transgenic mouse with an Alzheimer's-type neuropathology. A patient can be a human suffering from a neurodegenerative disease, such as Alzheimer's disease, or Parkinson's disease.

As used herein, the term "IC$_{50}$" refers to an inhibitory dose which is 50% of the maximum response obtained.

As used herein, the term "water soluble" means that the compound dissolves in water at least to the extent of 0.010 mole/liter or is classified as soluble according to literature precedence.

Other abbreviations used herein are as follows: DMSO, dimethyl sulfoxide; iNOS, inducible nitric oxide synthase; COX-2, cyclooxygenase-2; NGF, nerve growth factor; IBMX, isobutylmethylxanthine; FBS, fetal bovine serum; GPDH, glycerol 3-phosphate dehydrogenase; RXR, retinoid X receptor; TGF-β, transforming growth factor-β; IFN-γ, interferon-γ; LPS, bacterial endotoxic lipopolysaccharide; TNF-α, tumor necrosis factor-α; IL-1β, interleukin-1β; GAPDH, glyceraldehyde-3-phosphate dehydrogenase;

MTT, 3-[4,5-dimethylthiazol-2-yl]-2,5-diphenyltetrazolium bromide; TCA, trichloroacetic acid; HO-1, inducible heme oxygenase.

As used herein, "predominantly one enantiomer" means that the compound contains at least 85% of one enantiomer, or more preferably at least 90% of one enantiomer, or even more preferably at least 95% of one enantiomer, or most preferably at least 99% of one enantiomer. Similarly, the phrase "substantially free from other optical isomers" means that the composition contains at most 5% of another enantiomer or diastereomer, more preferably 2% of another enantiomer or diastereomer, and most preferably 1% of another enantiomer or diastereomer.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

III. Synthesis of TRAIL Death Receptor Agonists/Activators

The synthesis of the TRAIL Death Receptor Agonists/Activators (DRAs) can be achieved by a person of ordinary skill in the art using standard techniques of organic chemistry. See Smith & March, 2007, which is incorporated herein by reference.

DRAs or DRA-compounds include the compounds of Group A, shown here:

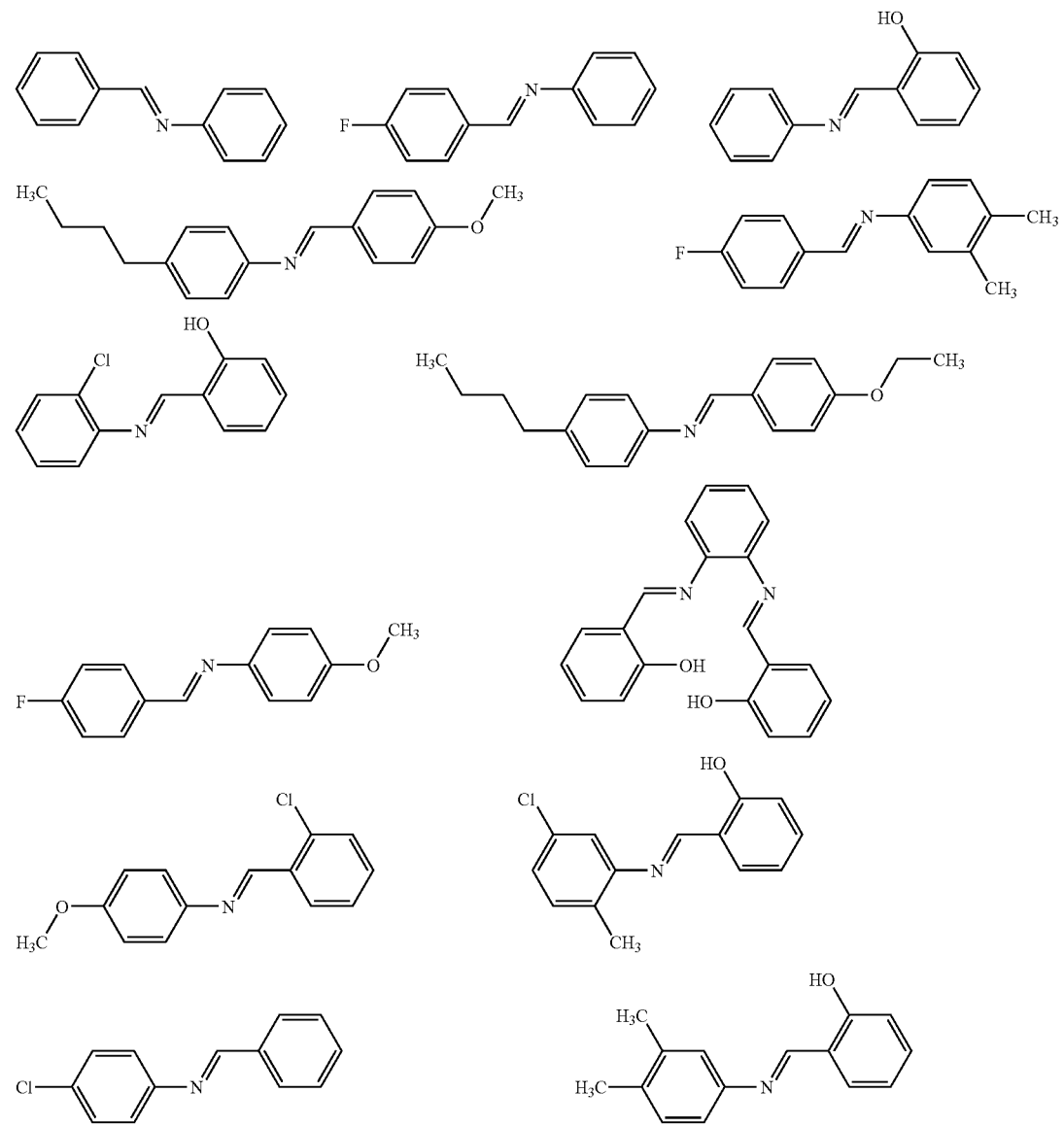

-continued
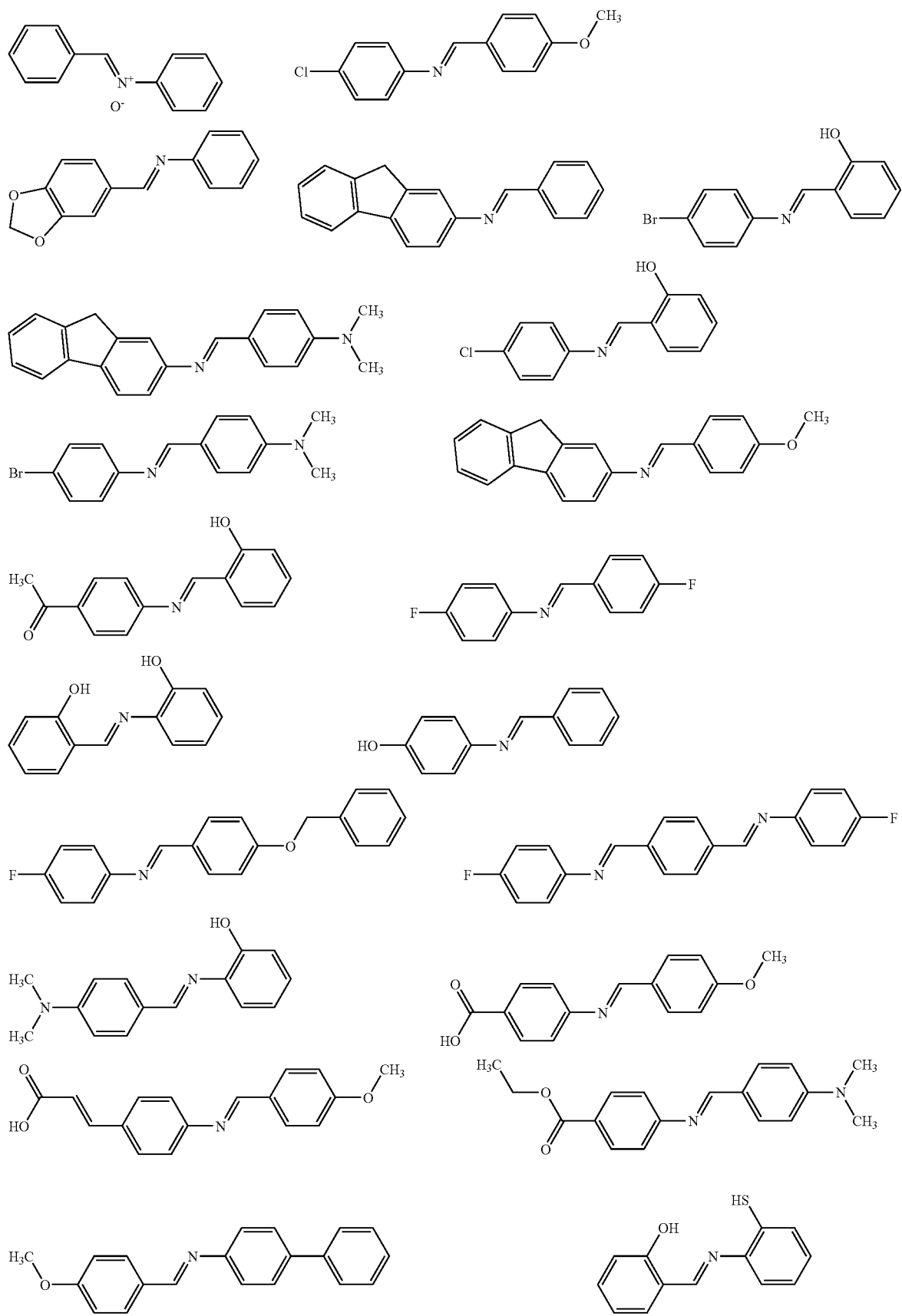

-continued
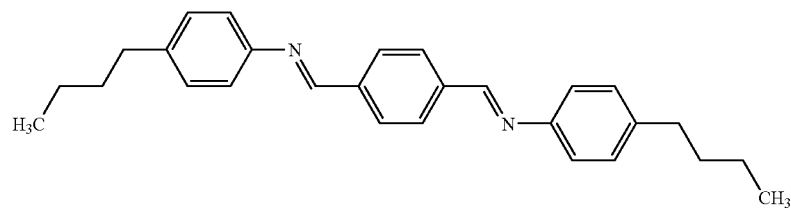
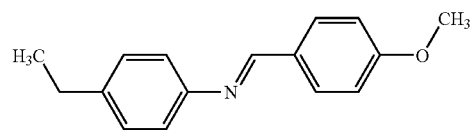
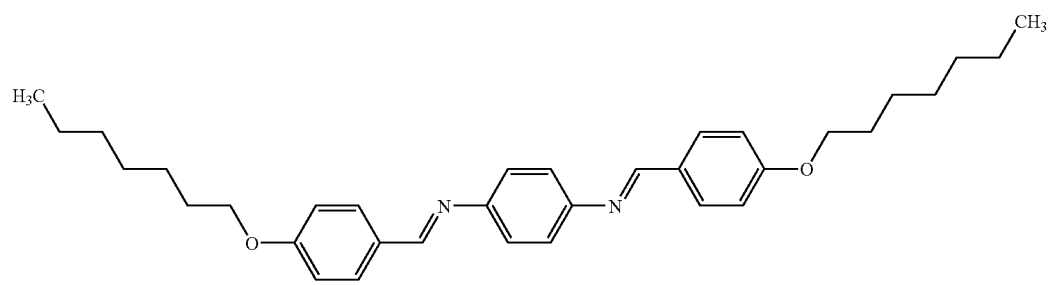
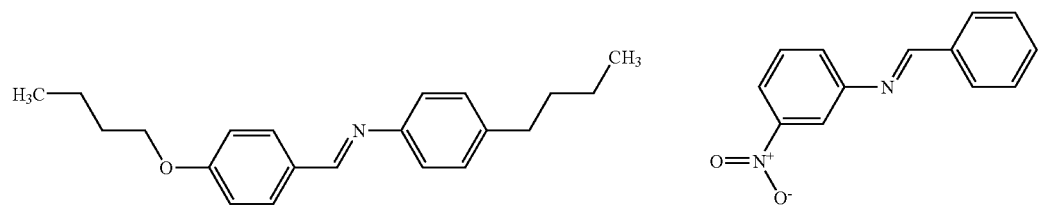
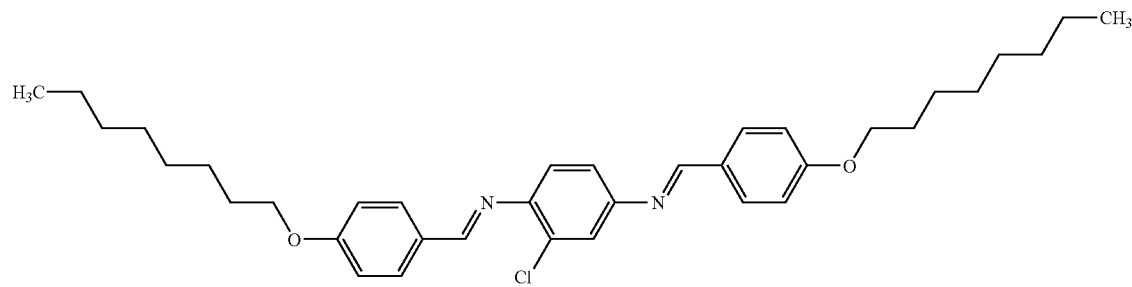
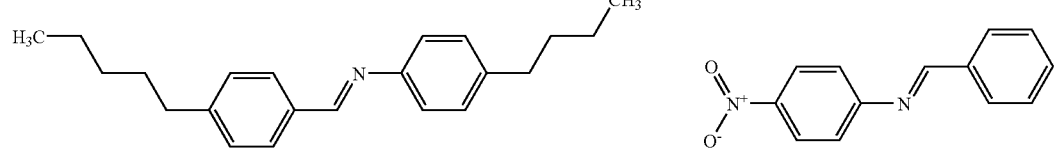
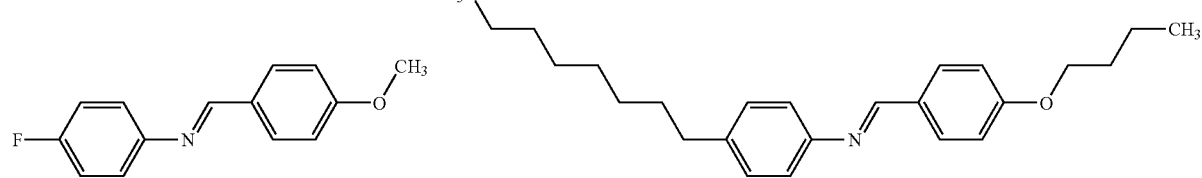

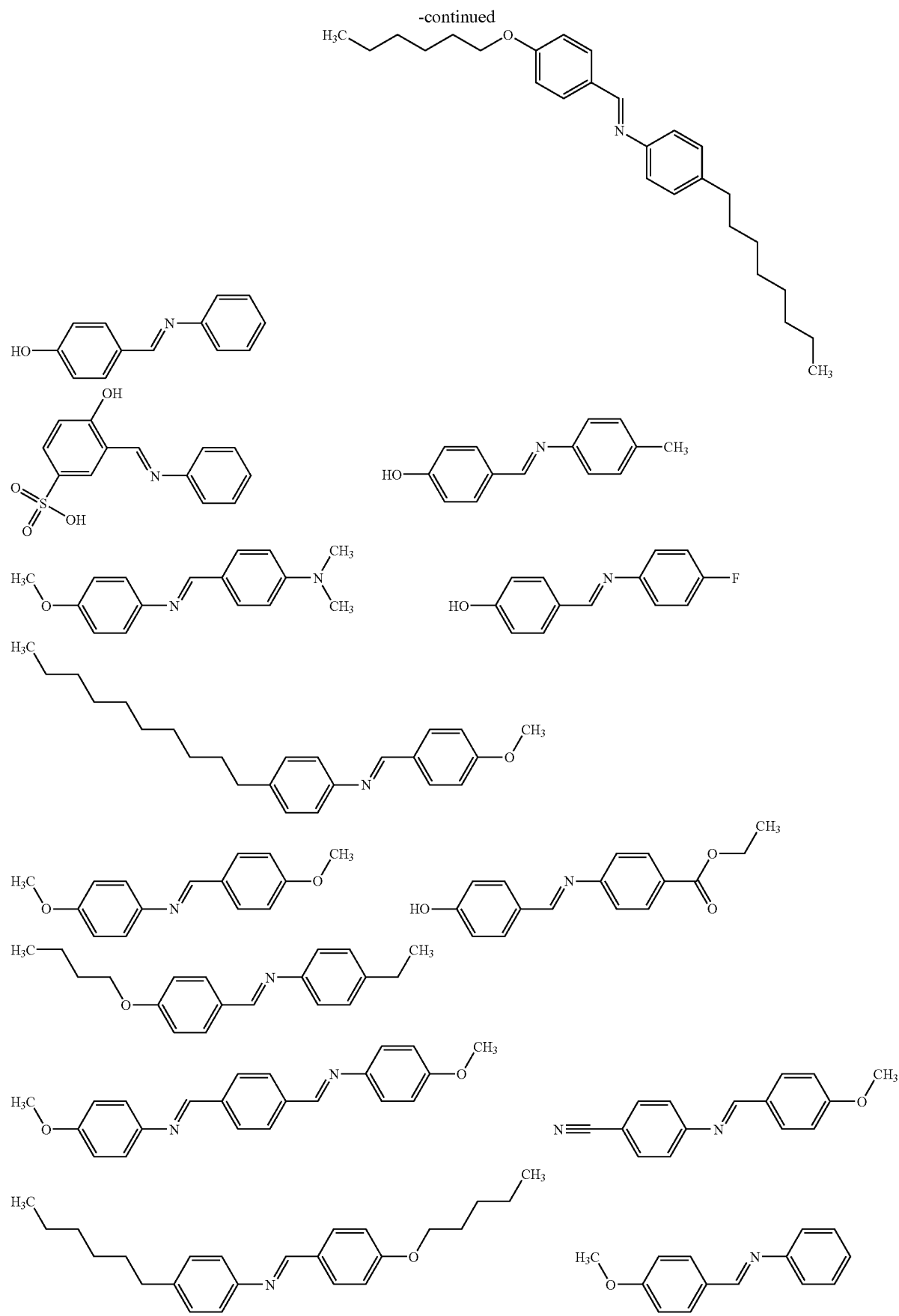

-continued
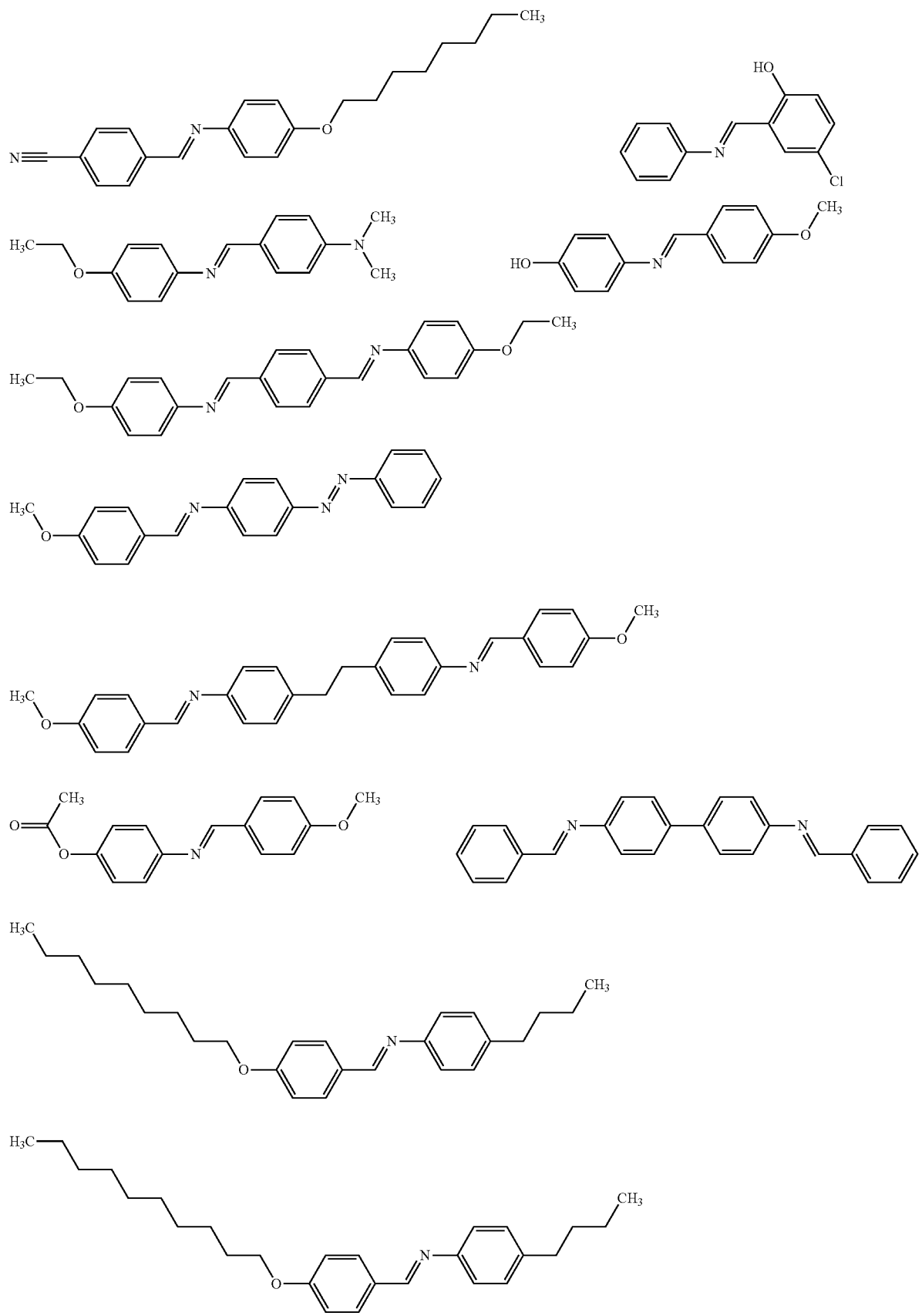

-continued
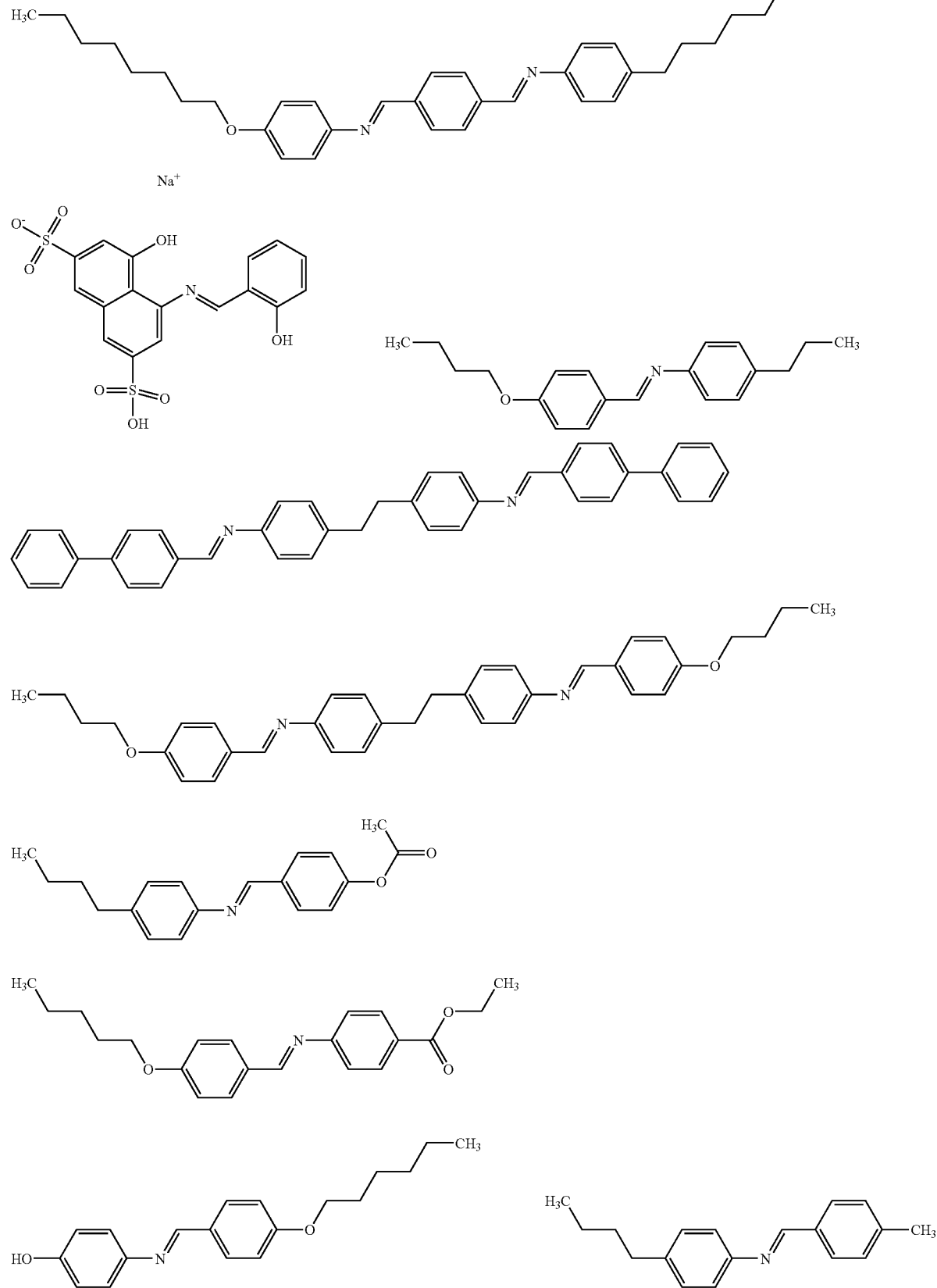

-continued
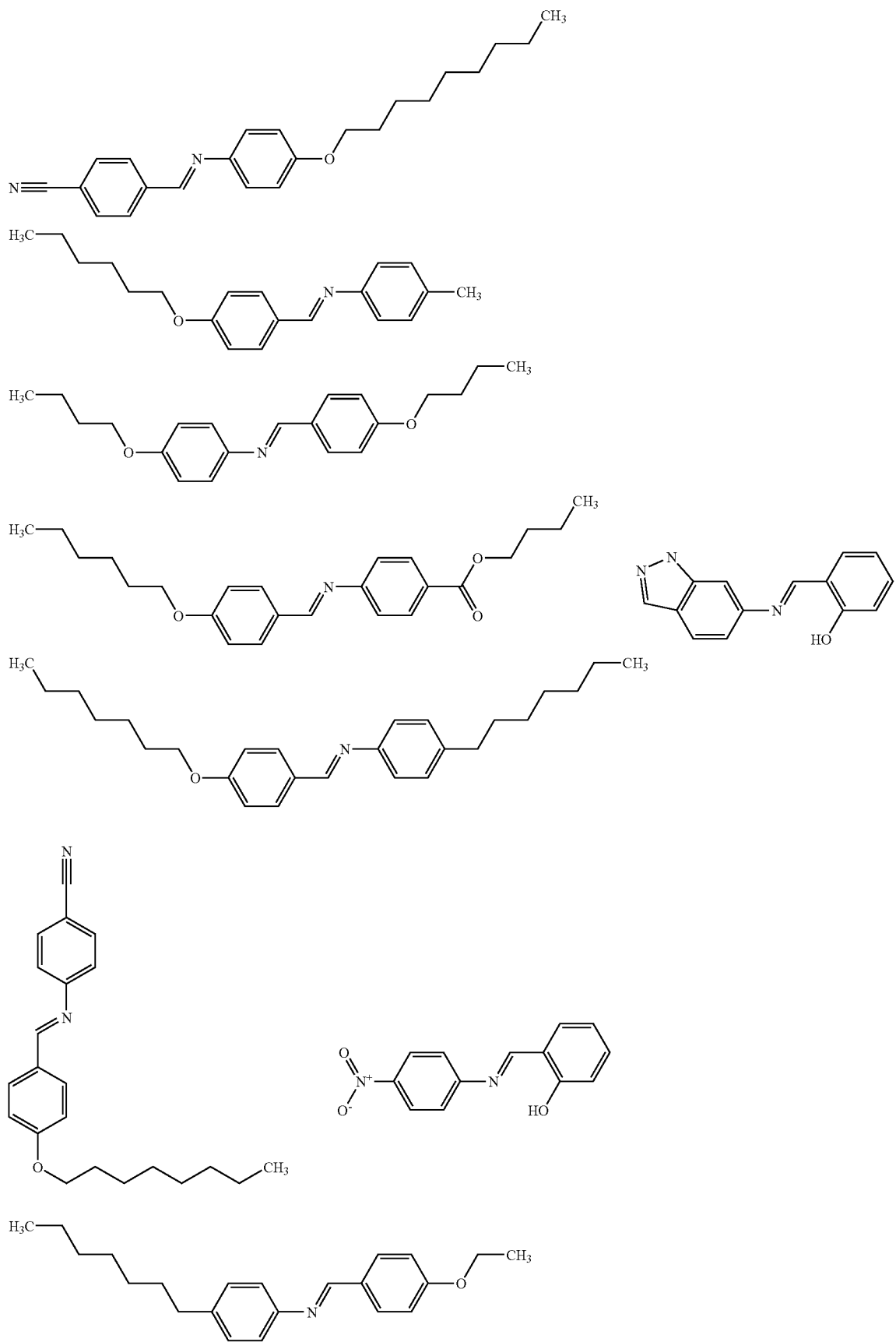

-continued
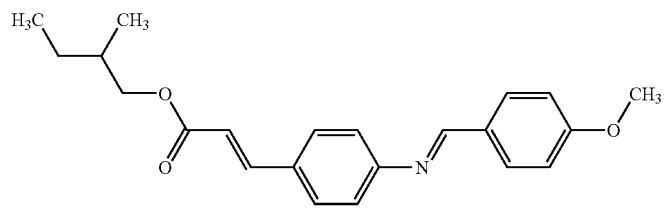
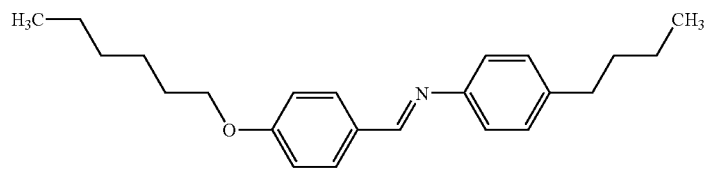
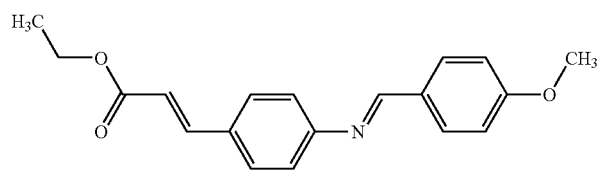
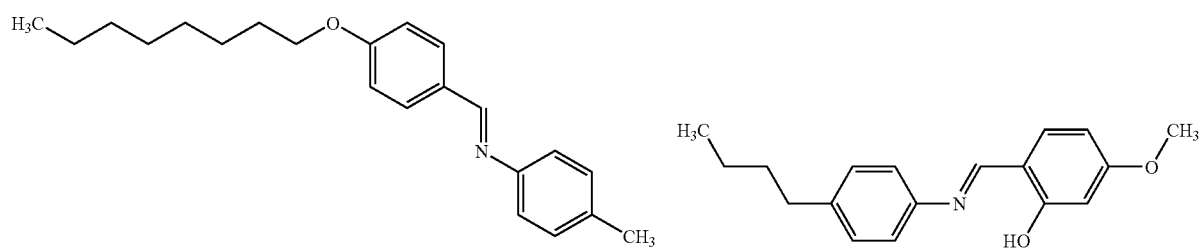
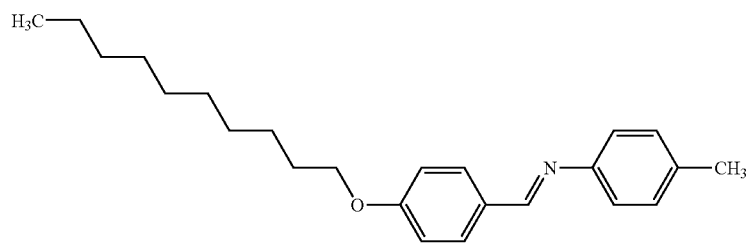
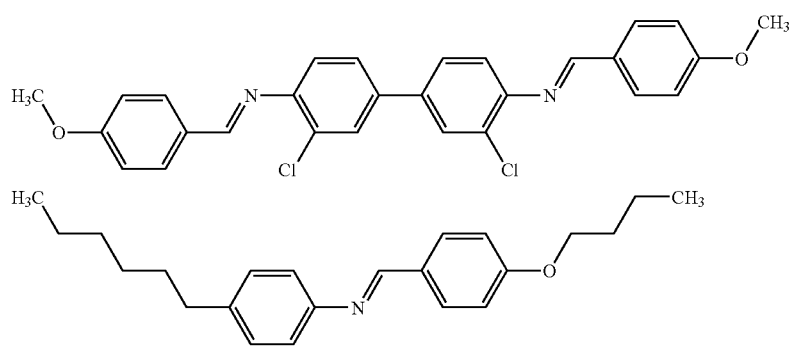

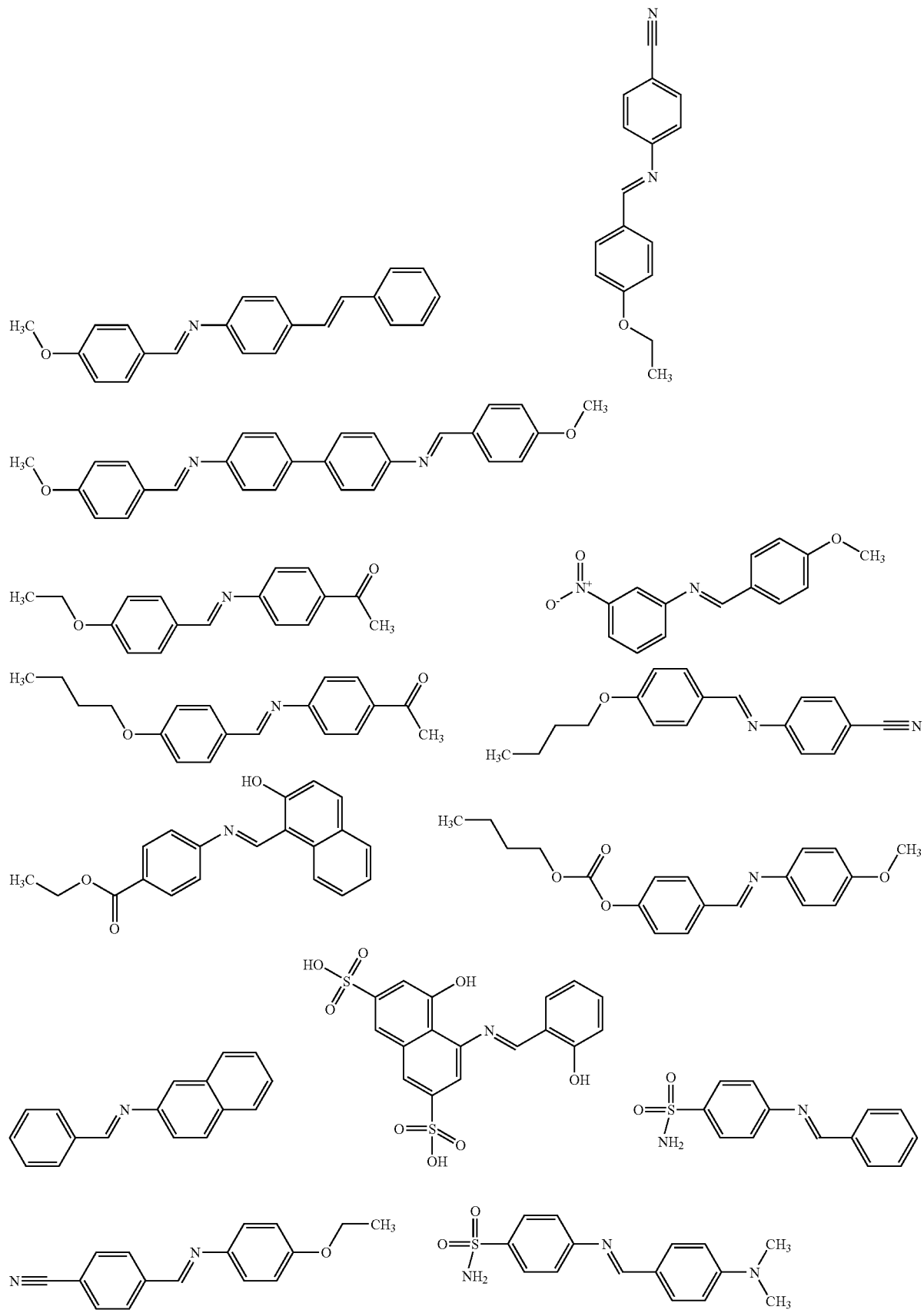

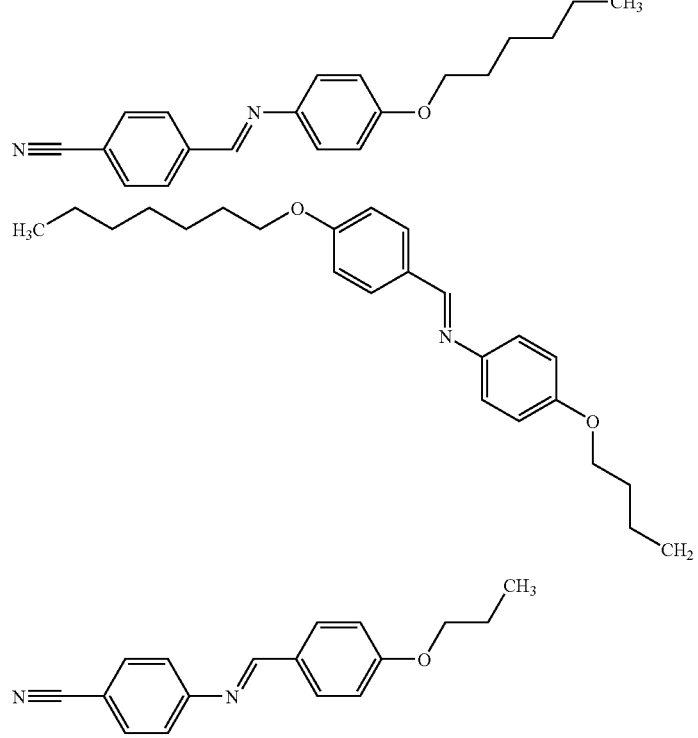
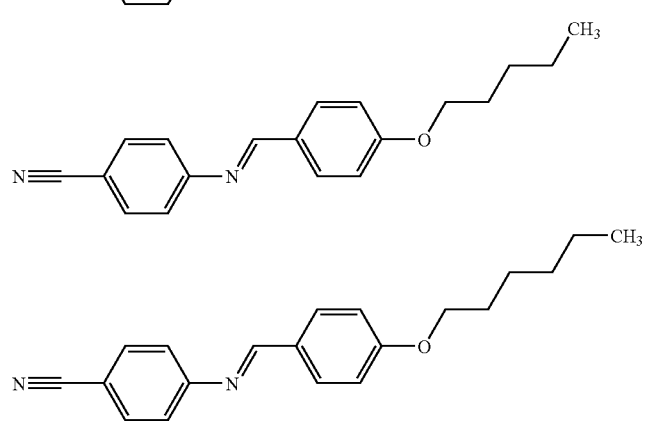
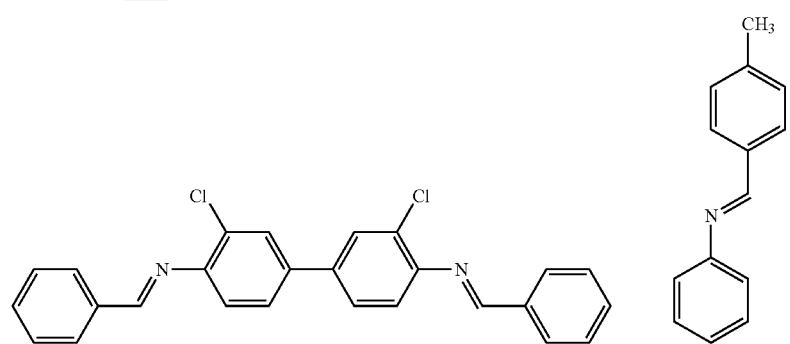
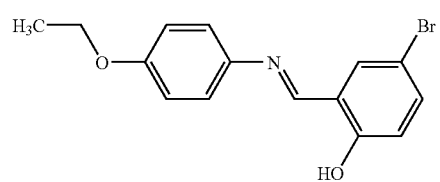

-continued
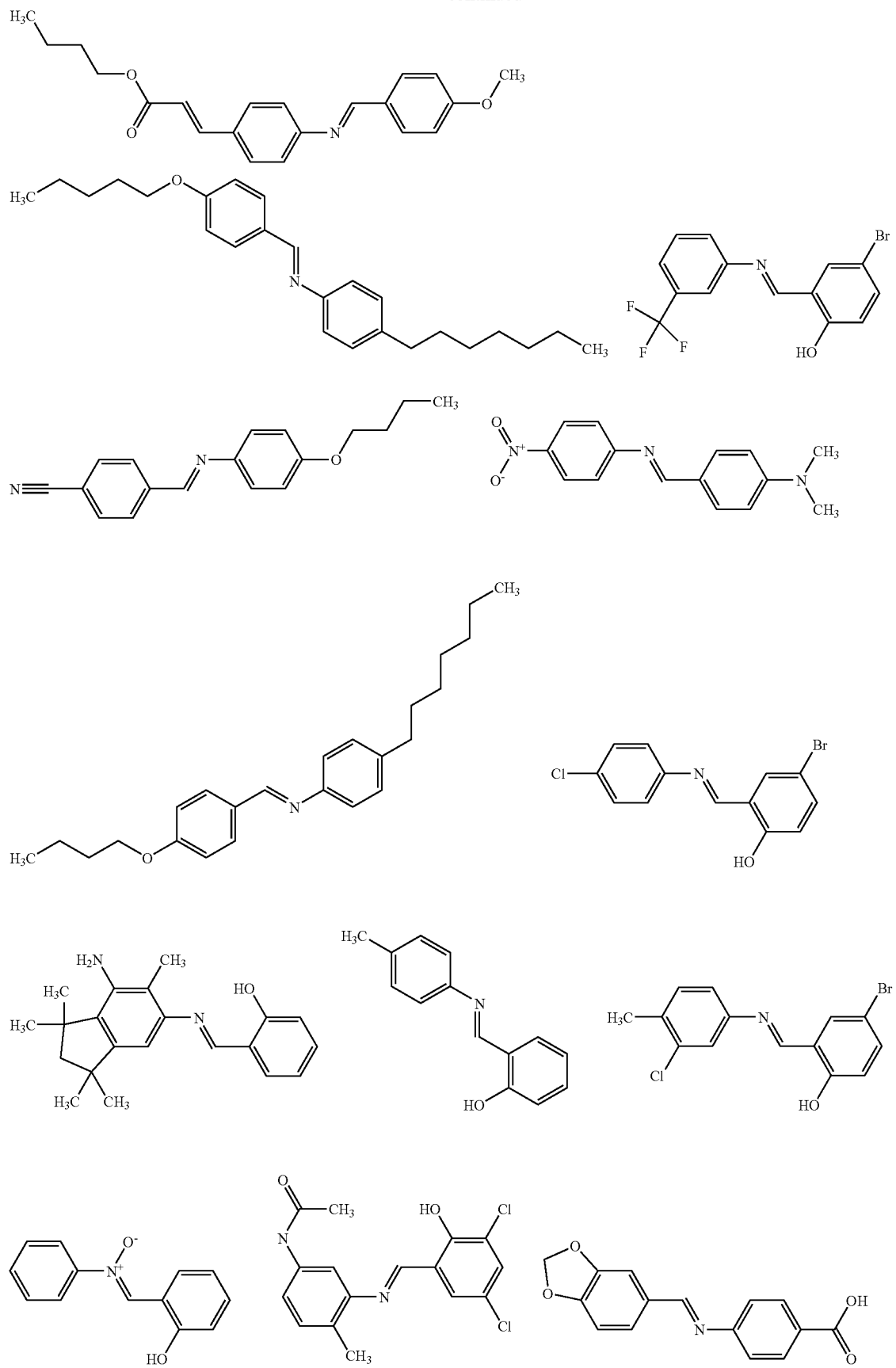

-continued
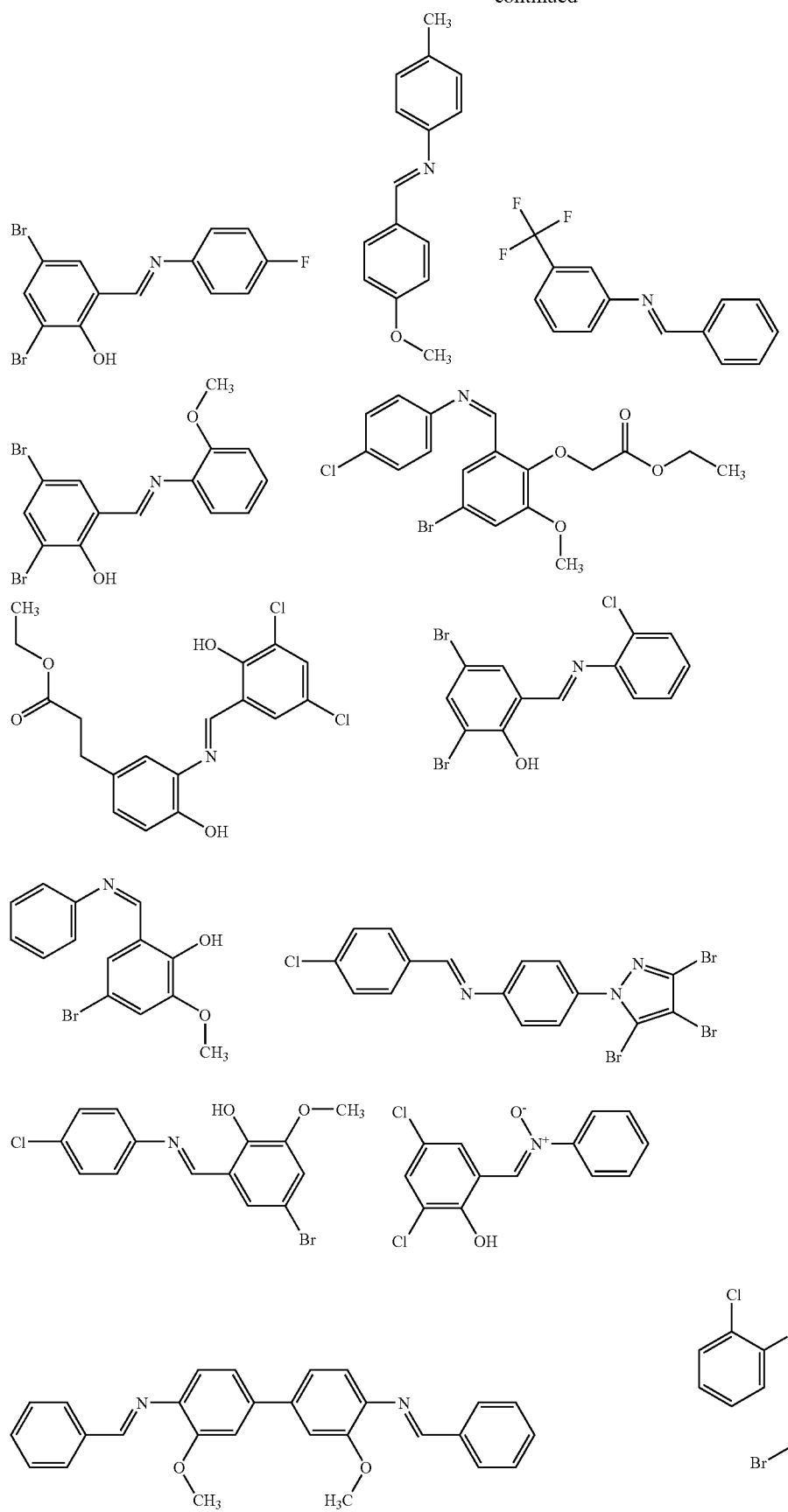

-continued
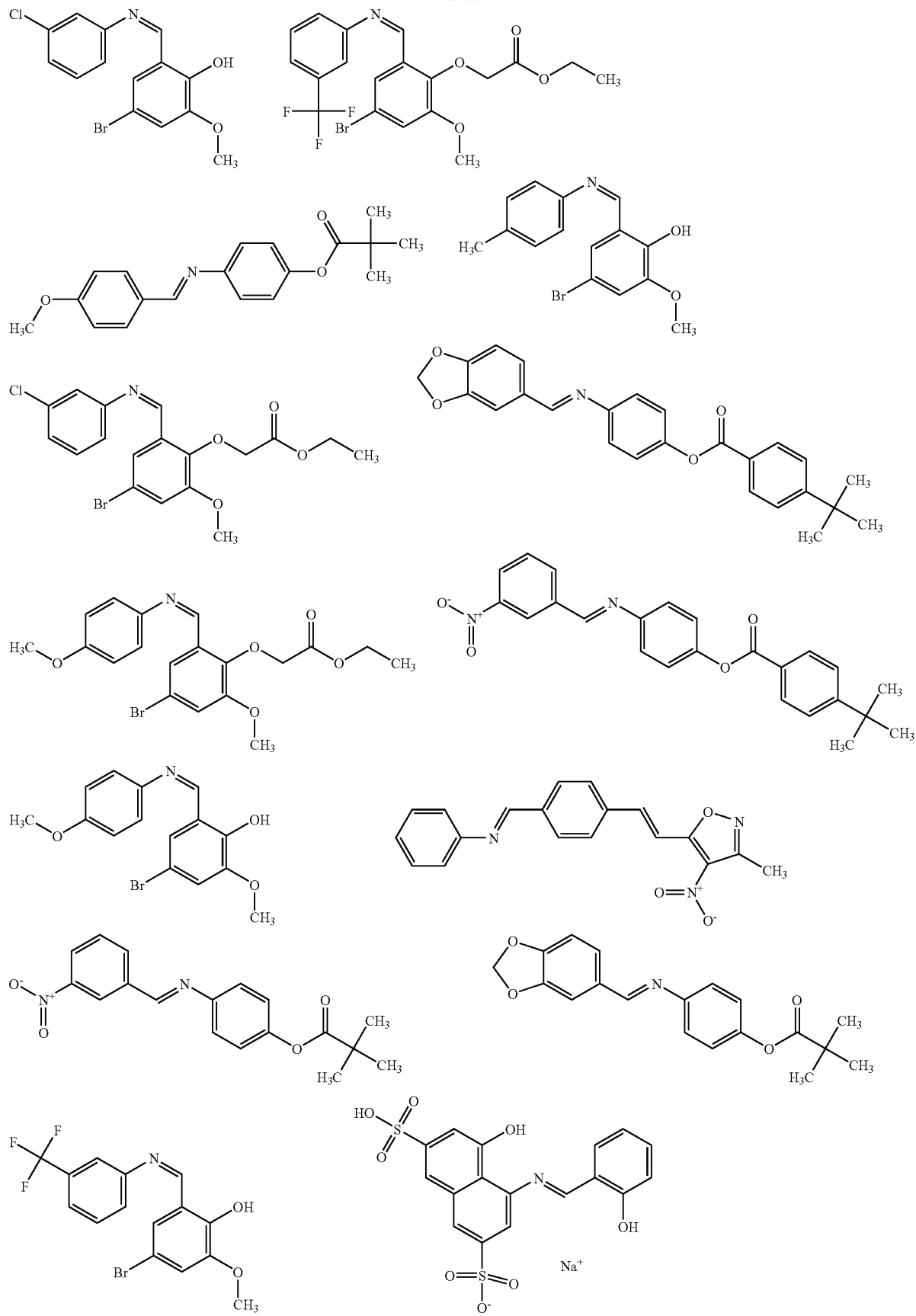

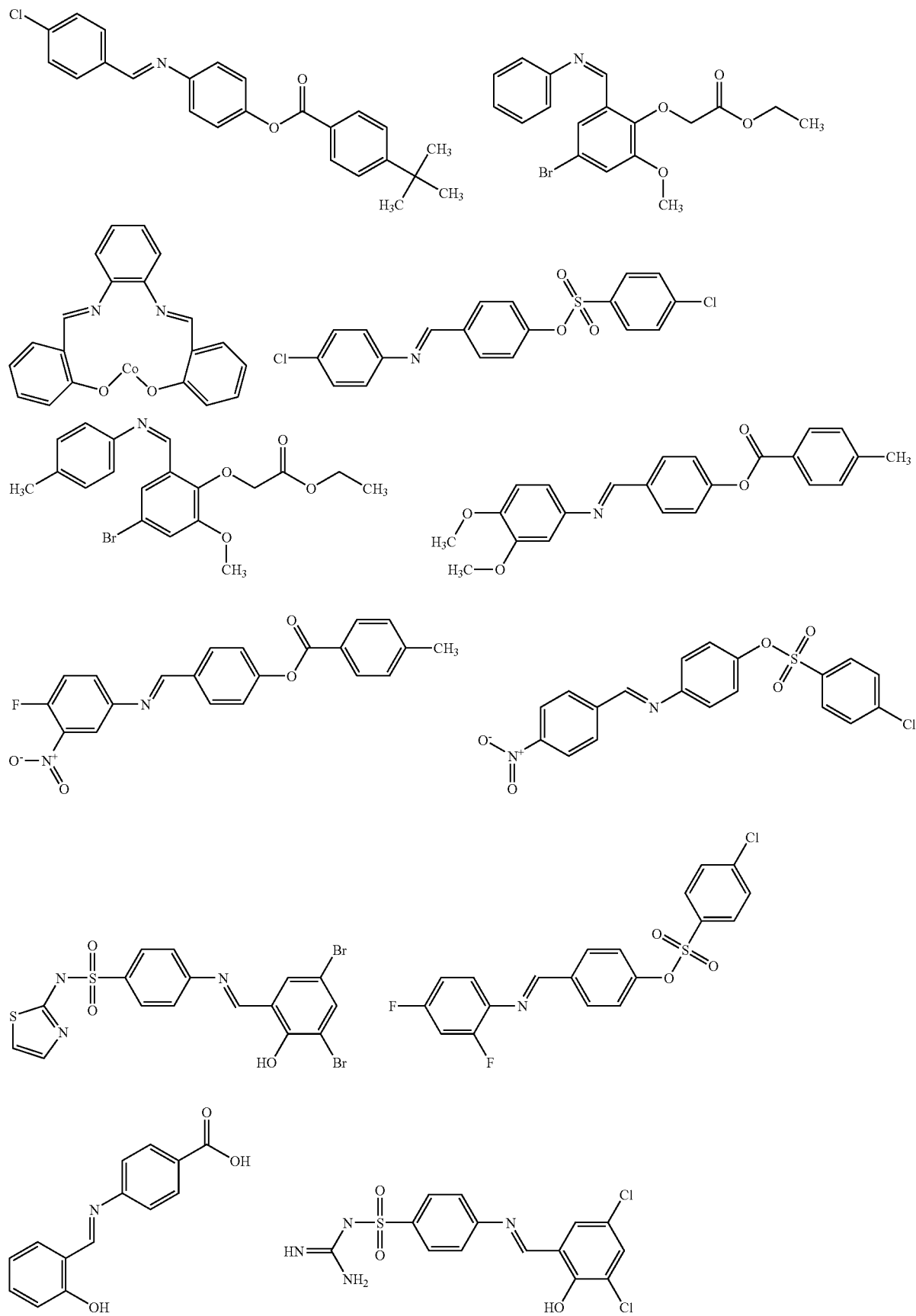

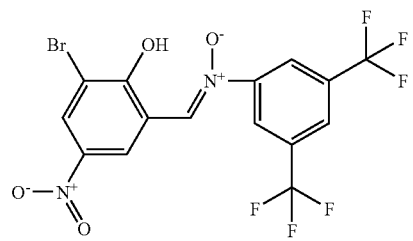
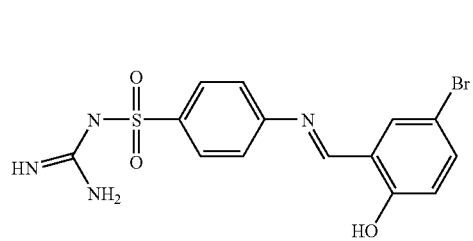
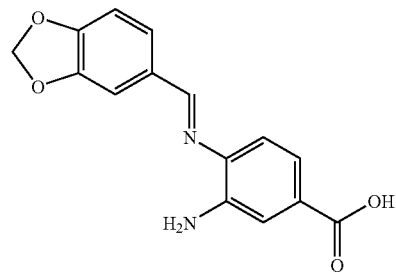
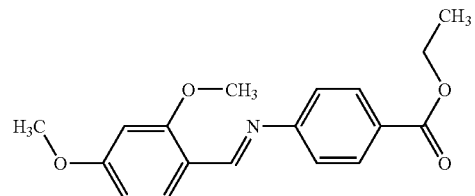
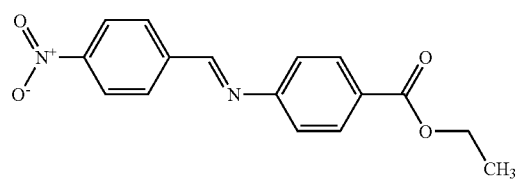
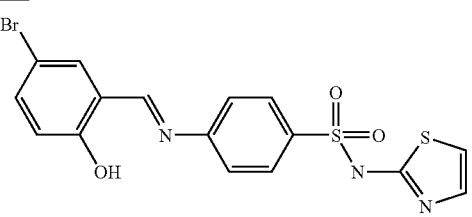
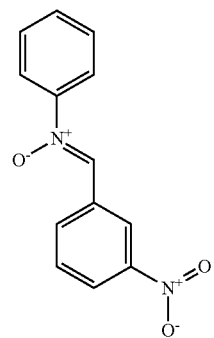
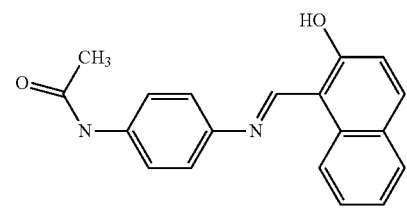
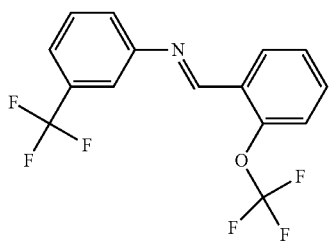
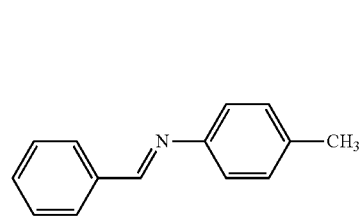
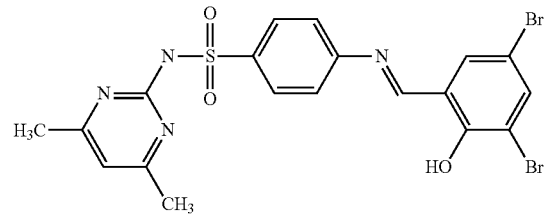
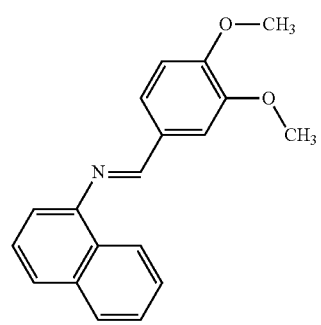
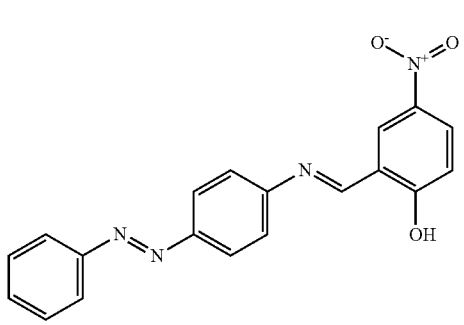

-continued
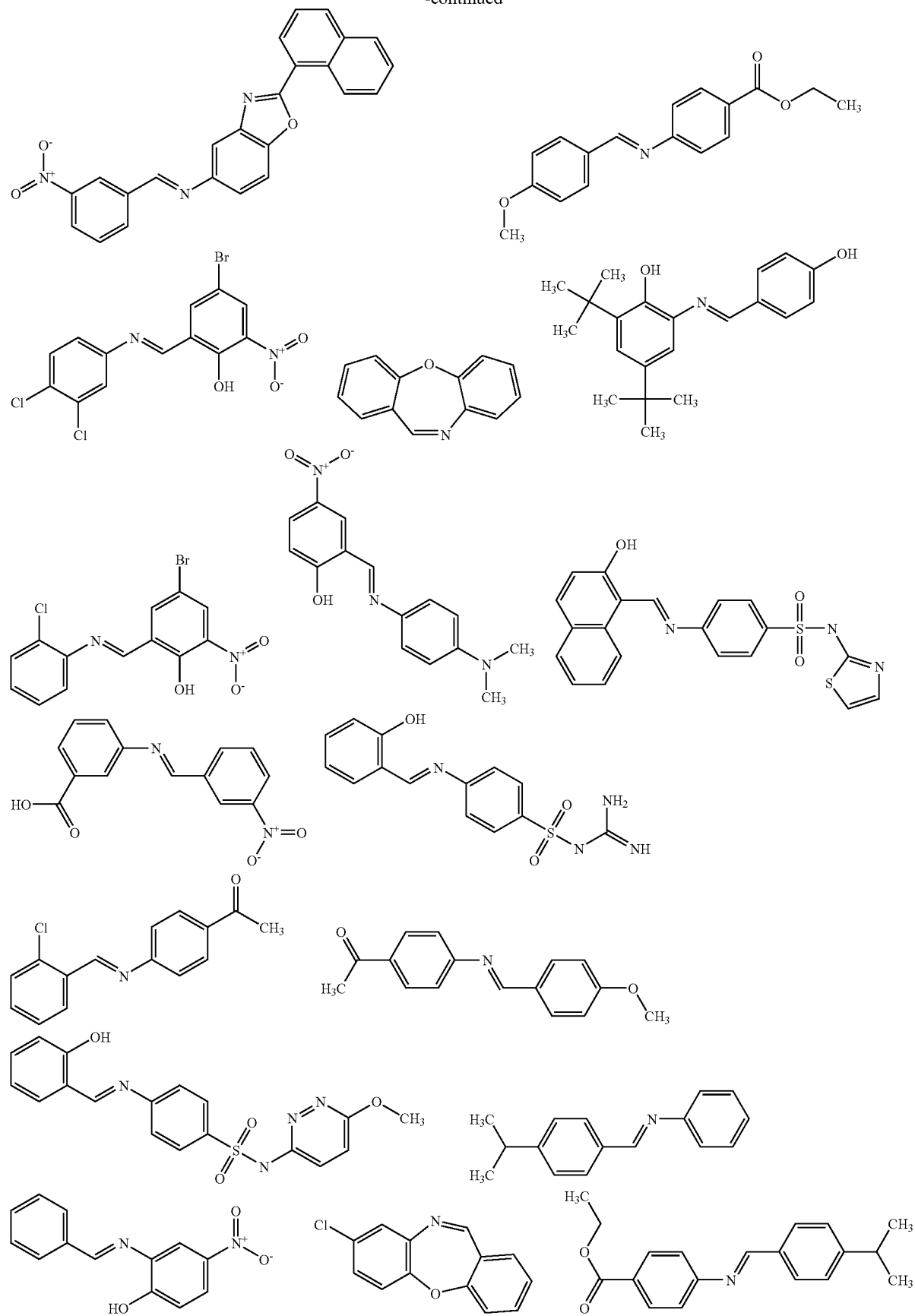

-continued
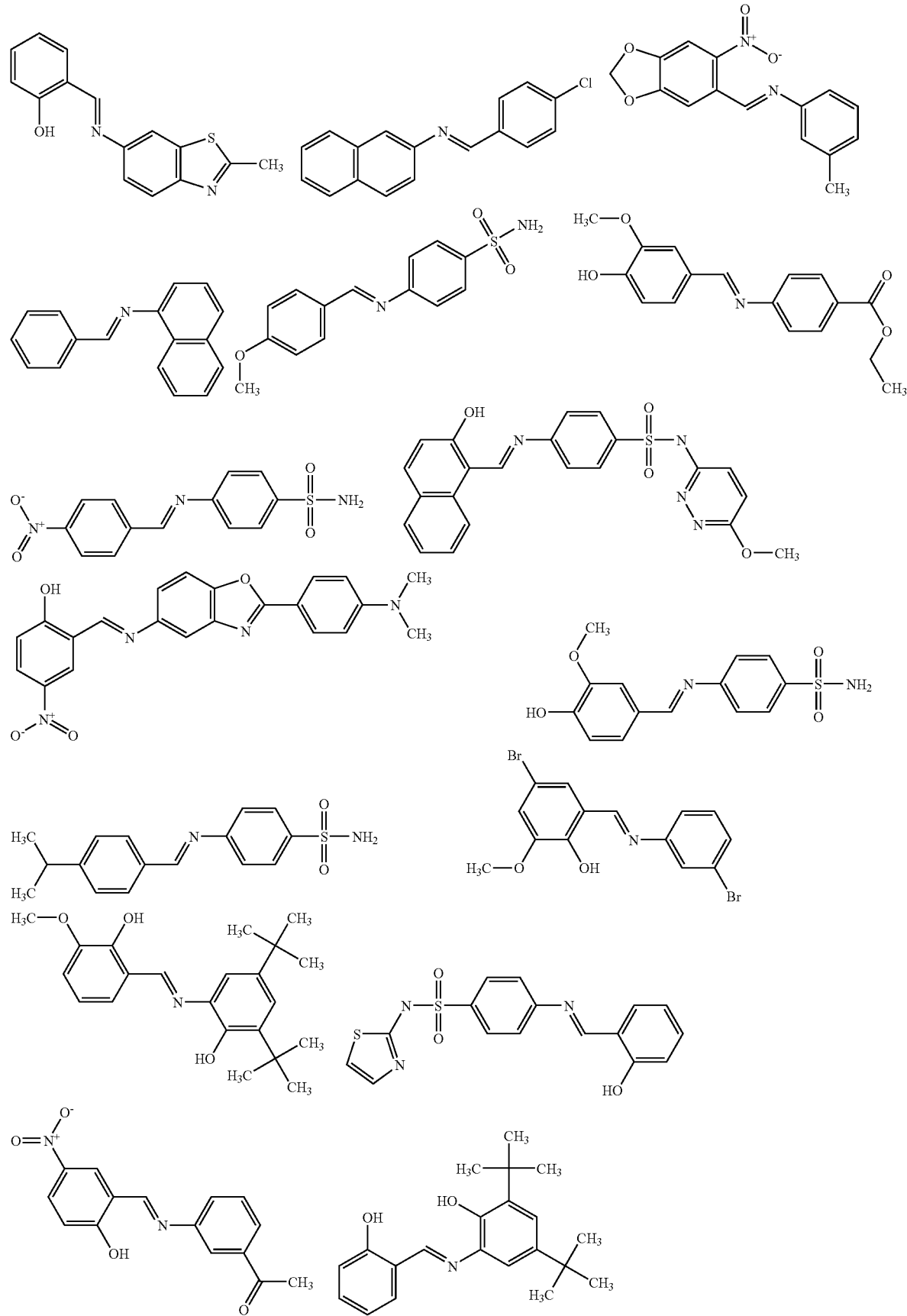

-continued
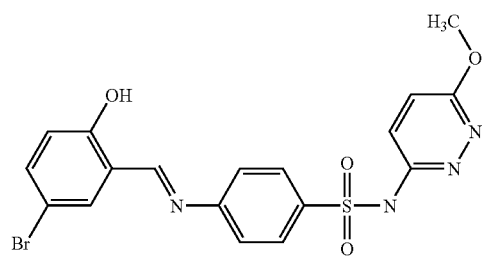
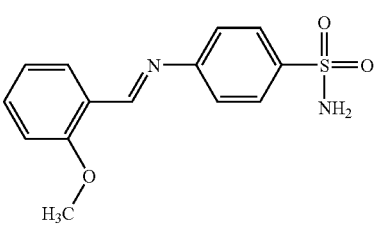
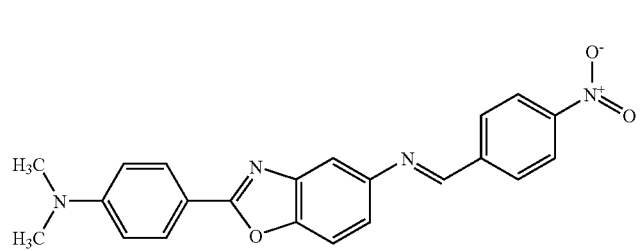
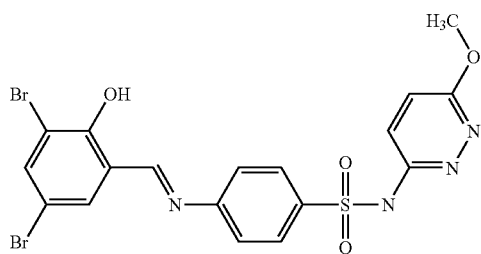
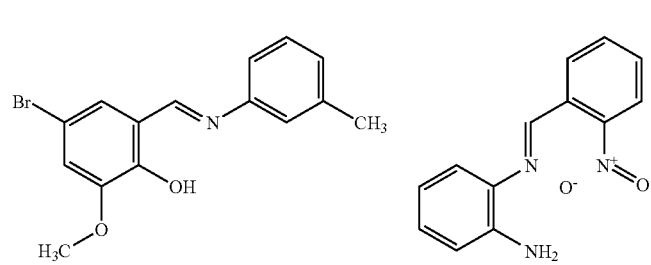
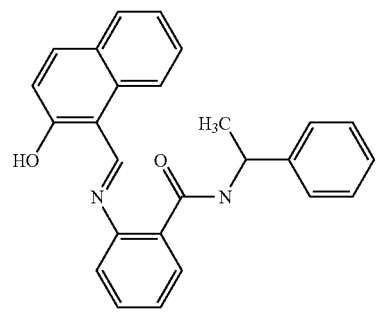
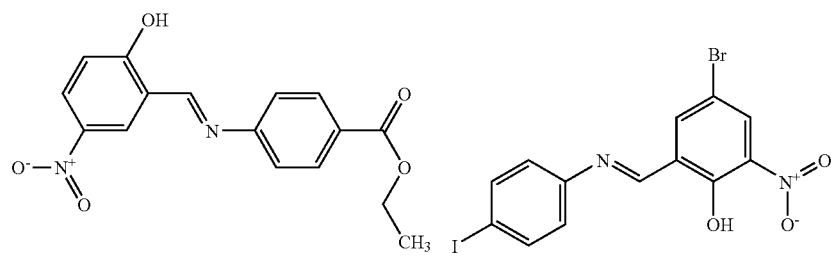
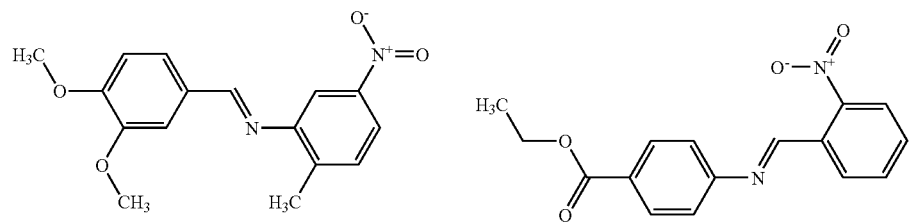
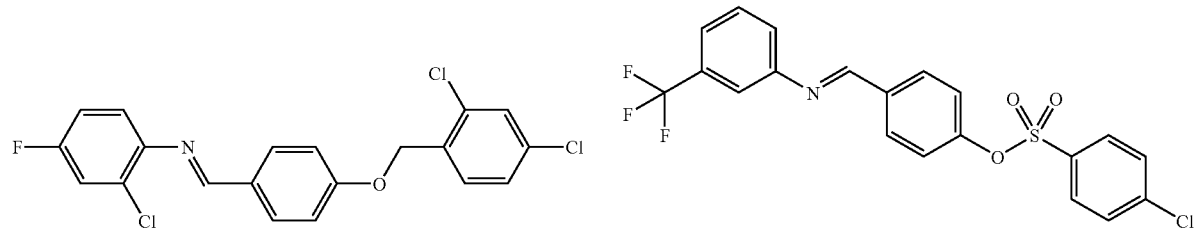

-continued
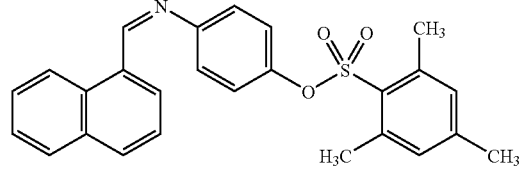
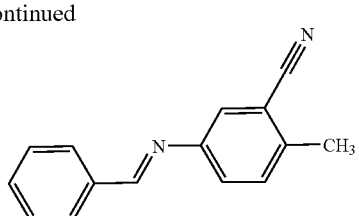
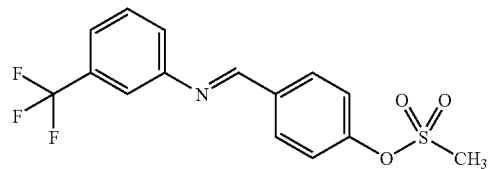
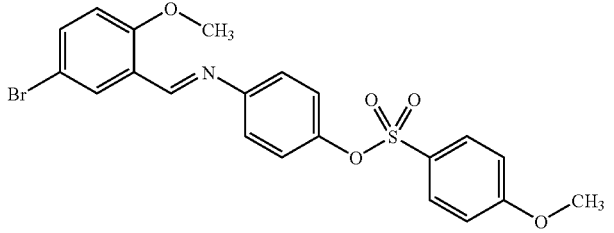
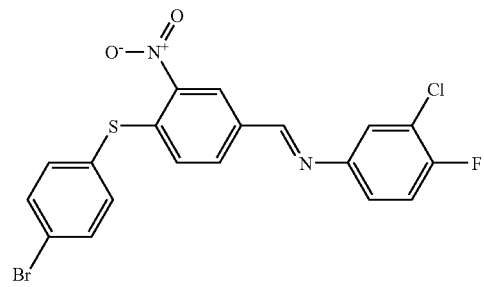
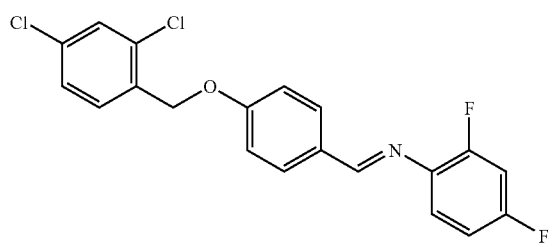
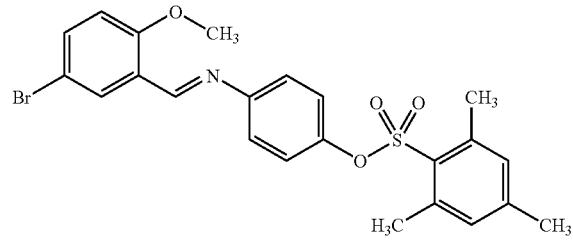
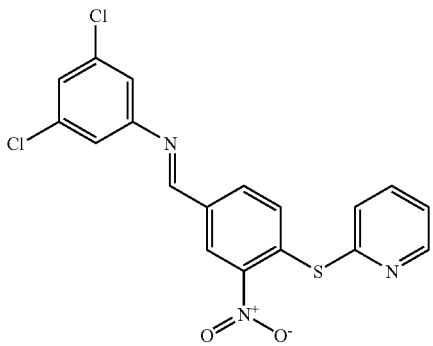
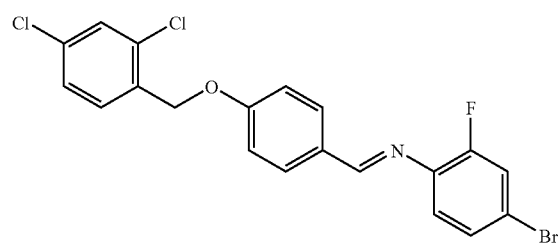
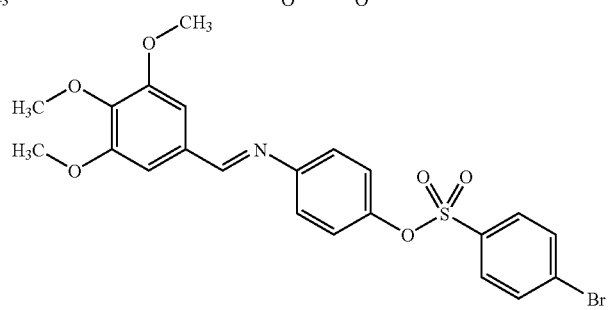
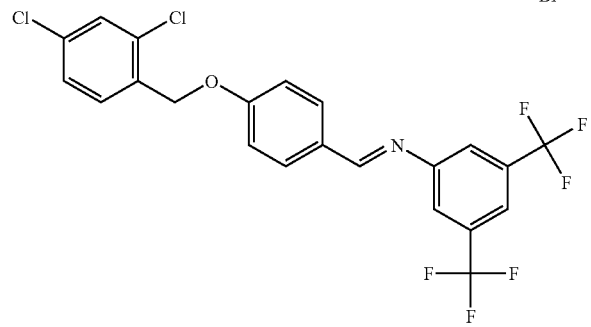

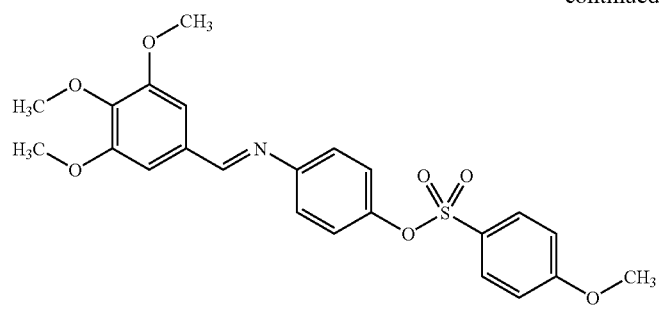
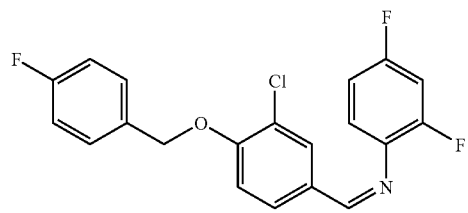
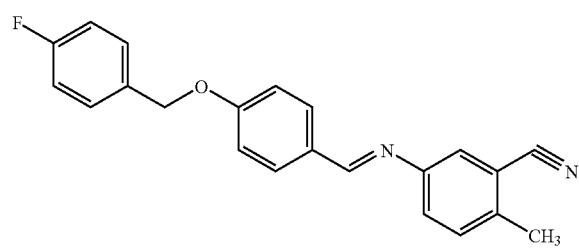
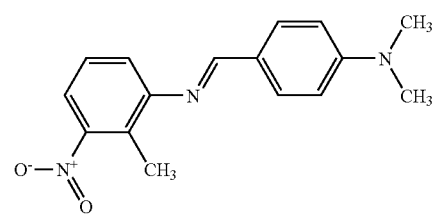
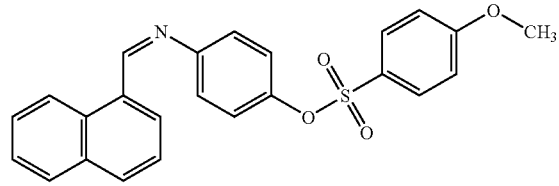
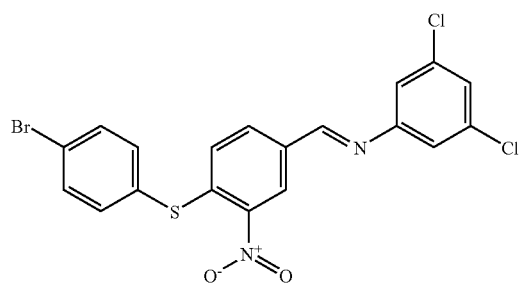
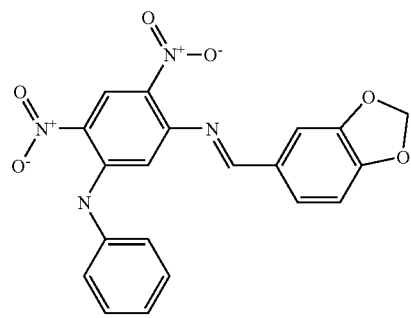
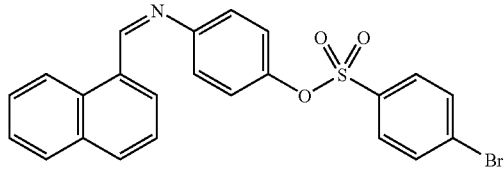
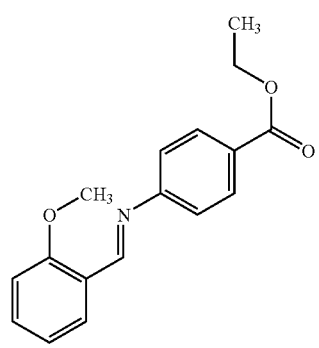
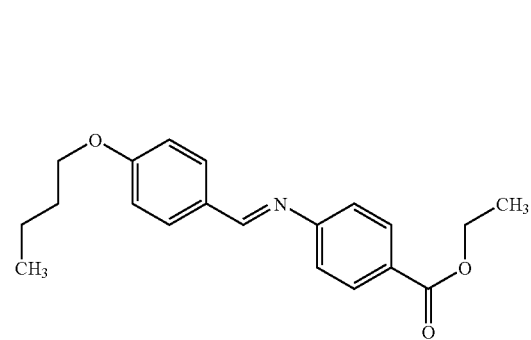

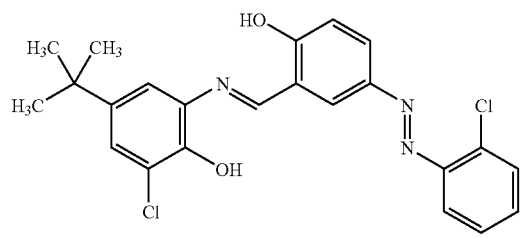
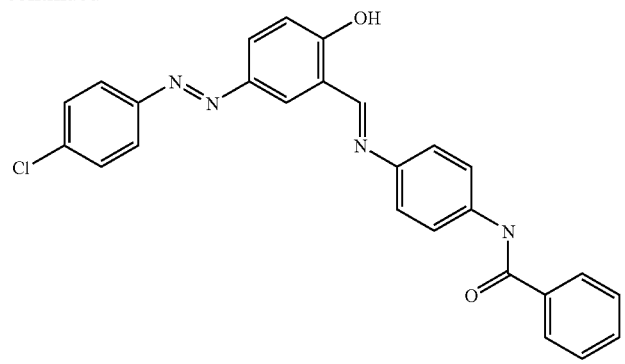
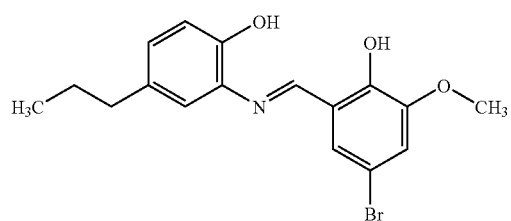
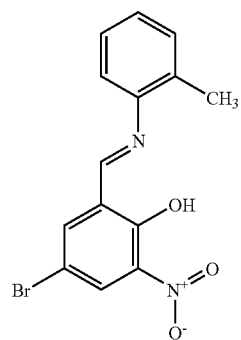
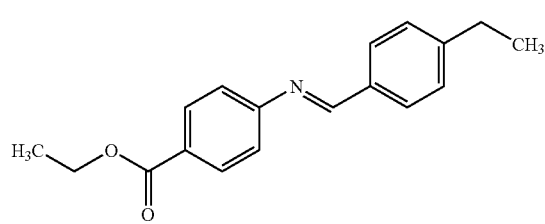
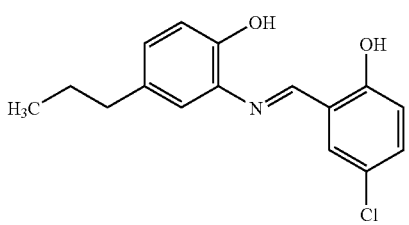
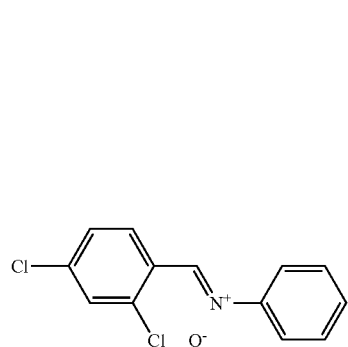
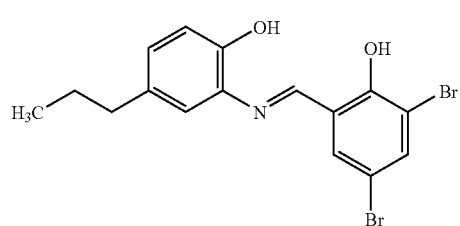
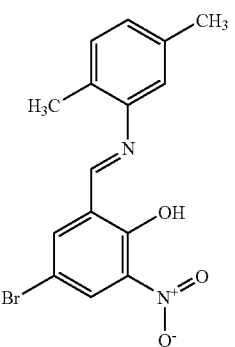
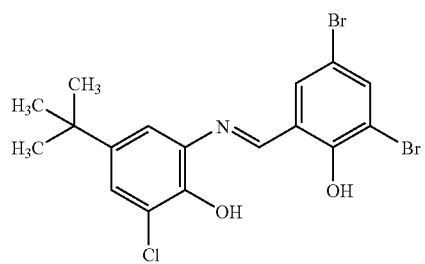
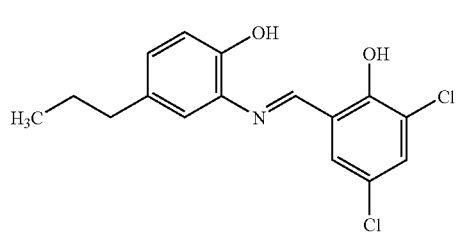

-continued
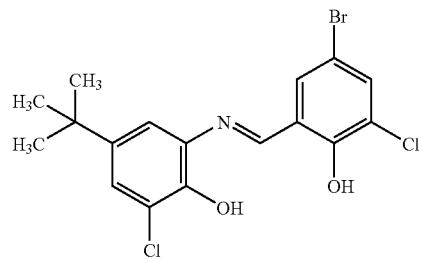
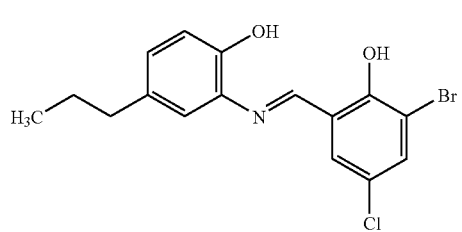
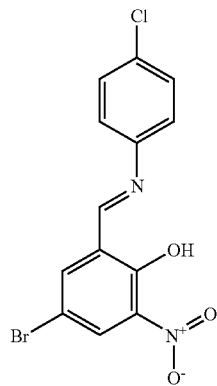
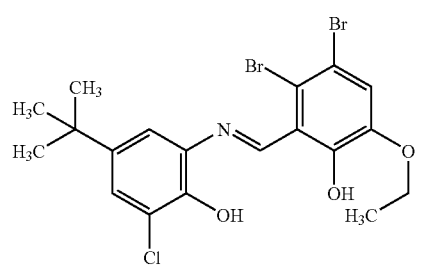
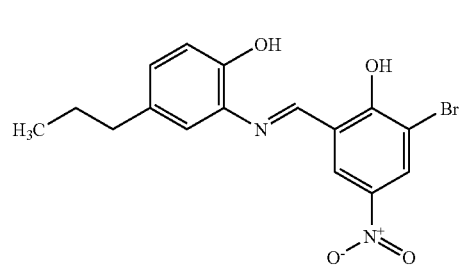
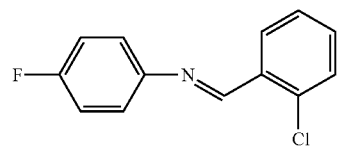
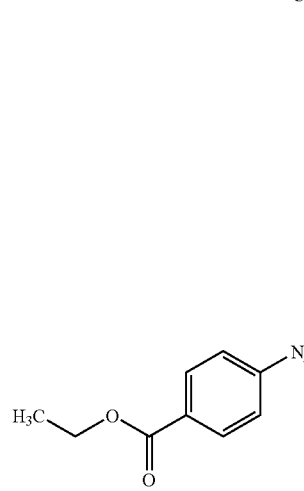
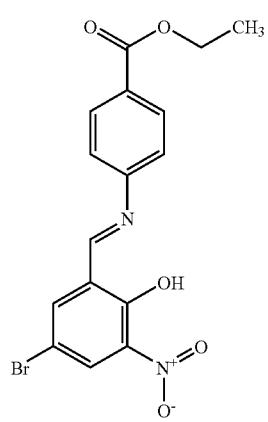
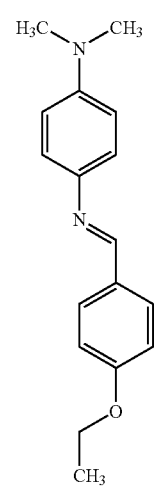
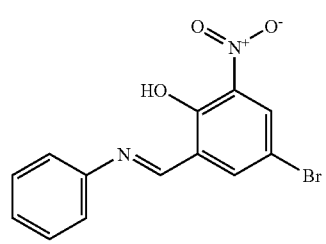
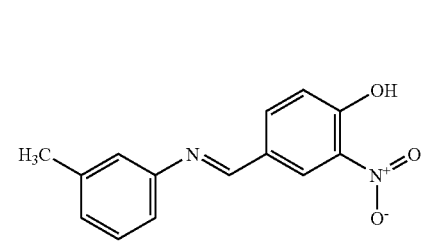
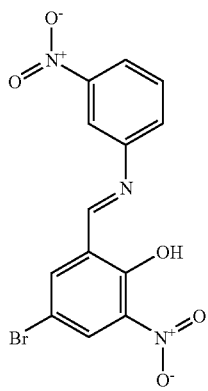

73 74
-continued
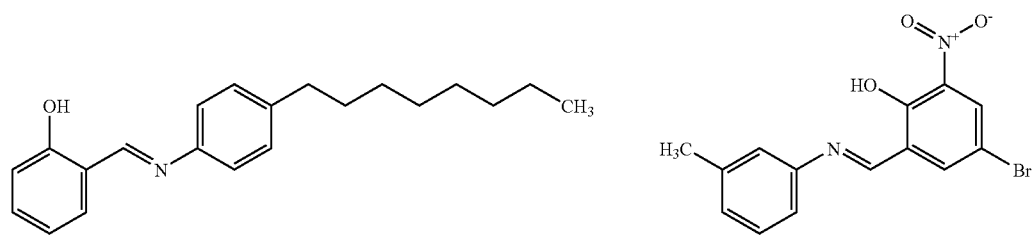
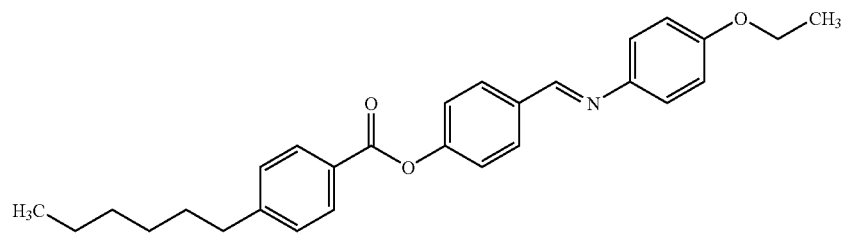
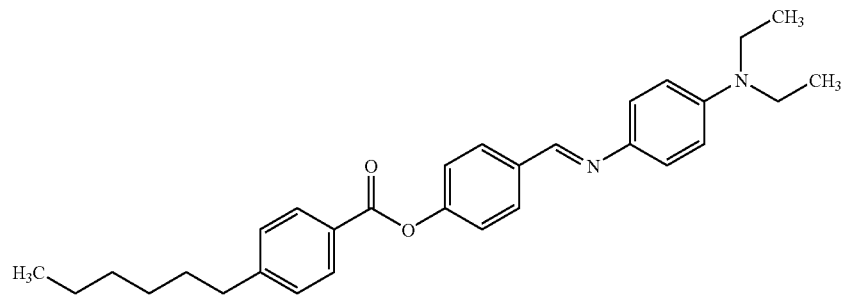
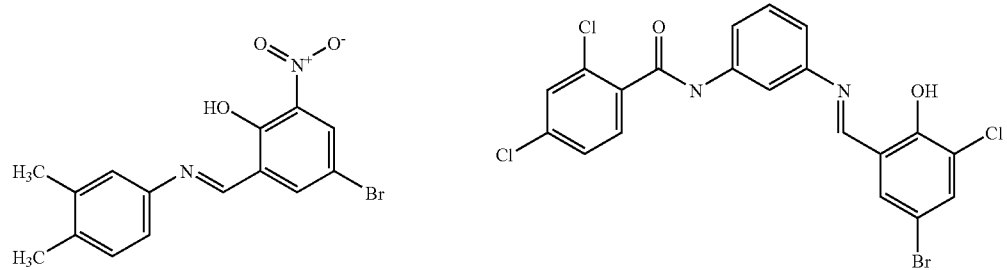
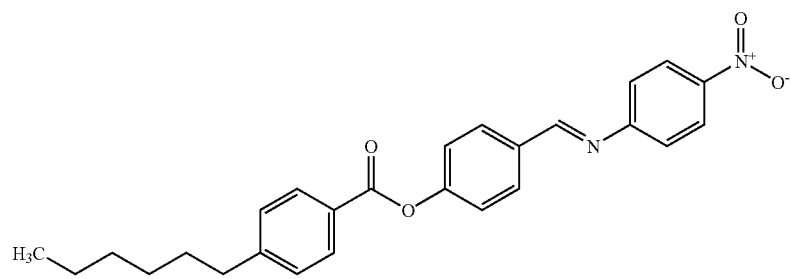
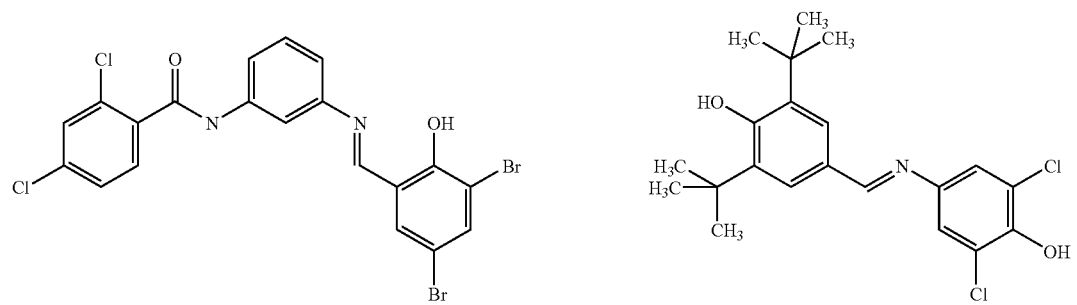

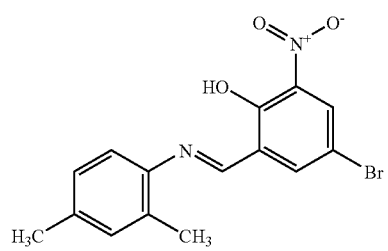
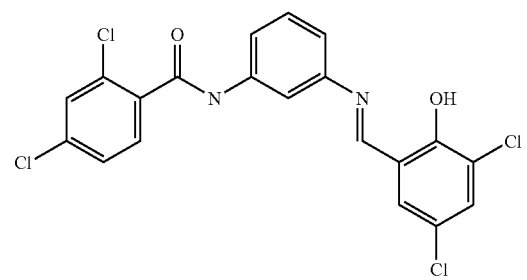
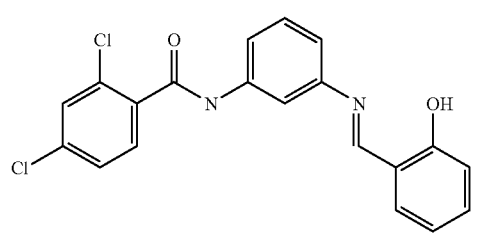
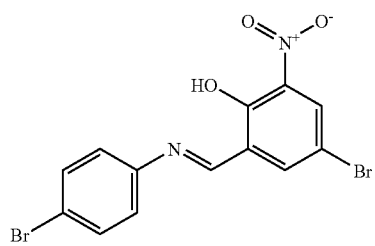
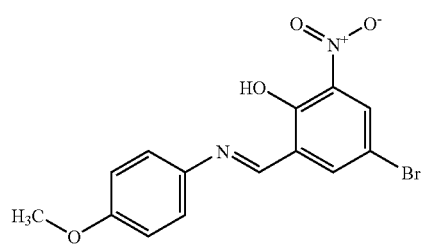
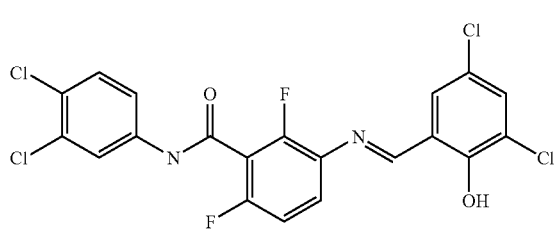
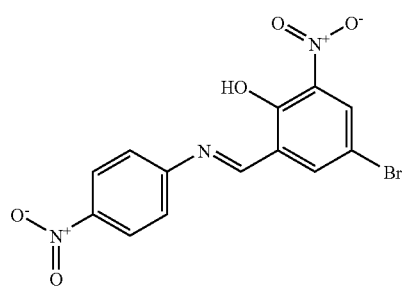
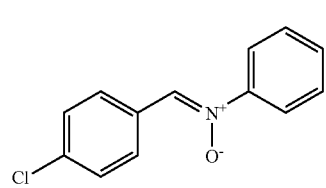
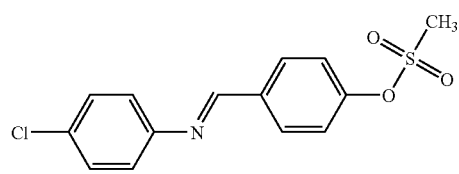
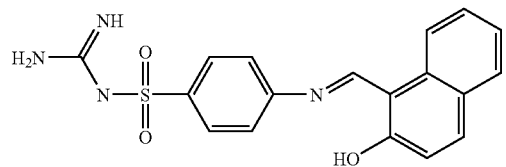
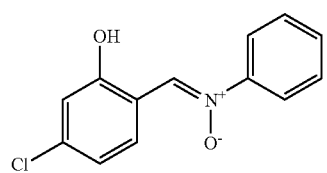
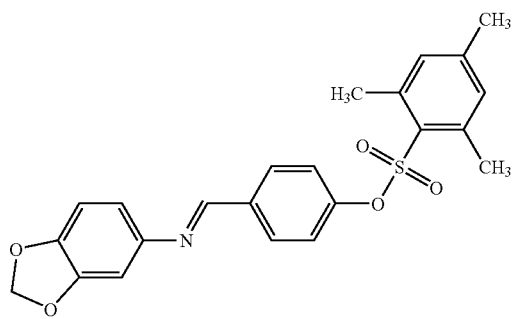

-continued
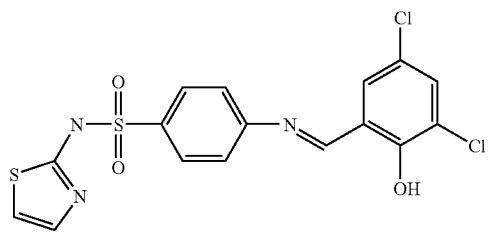
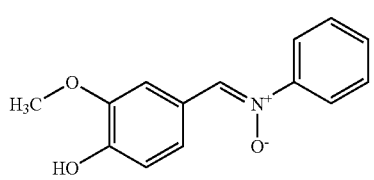
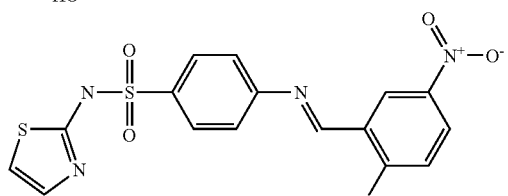
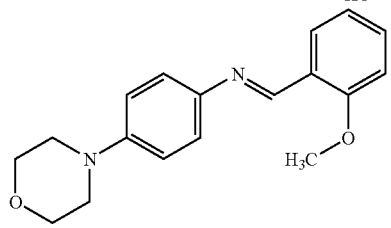
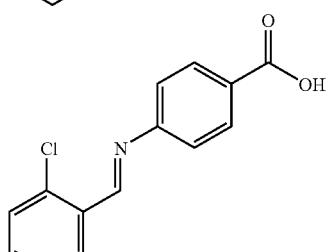
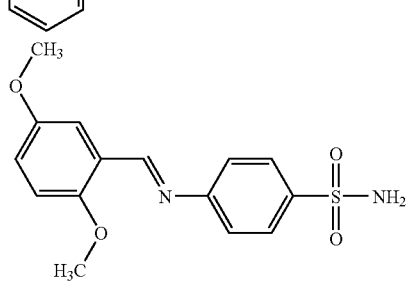

-continued
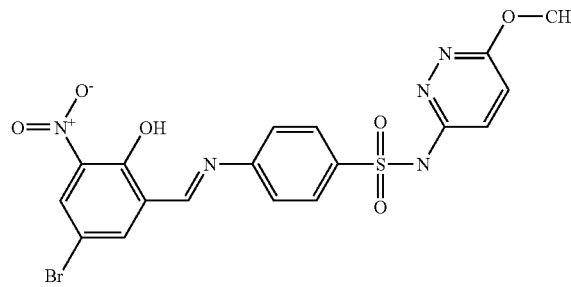
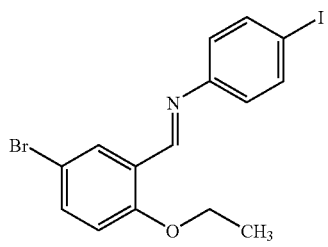
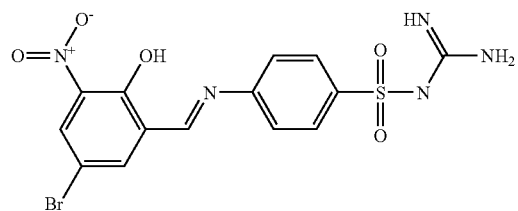
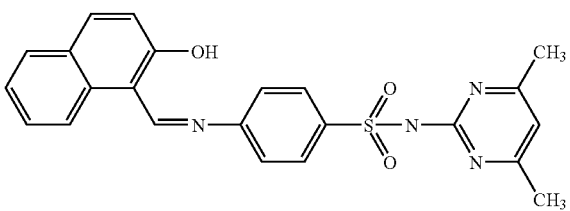
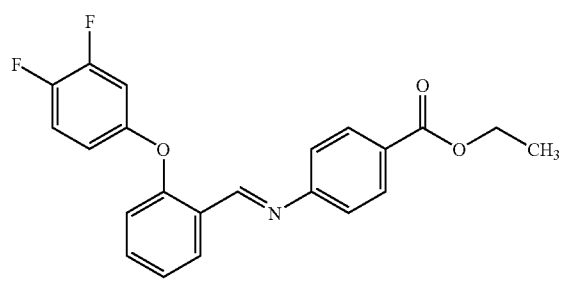
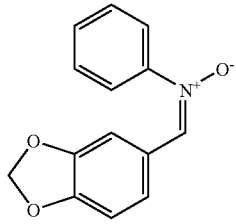
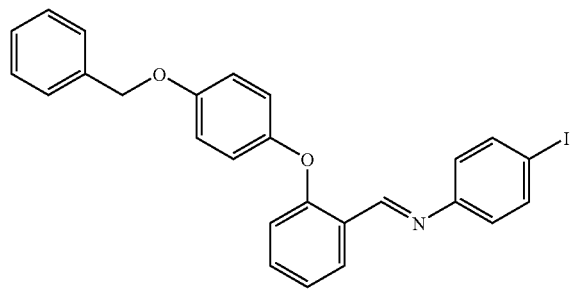
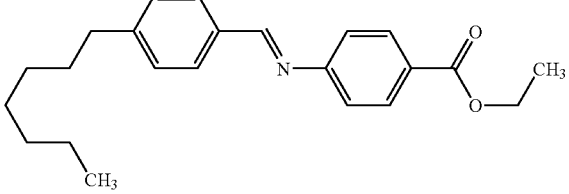
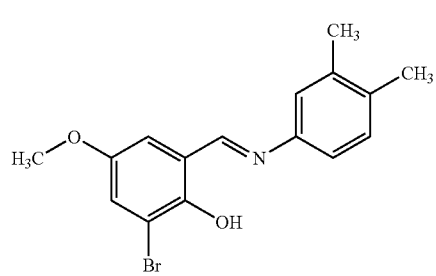
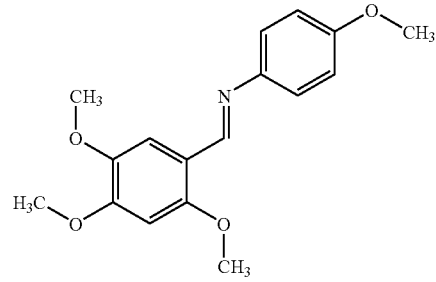
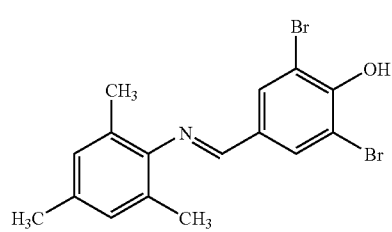
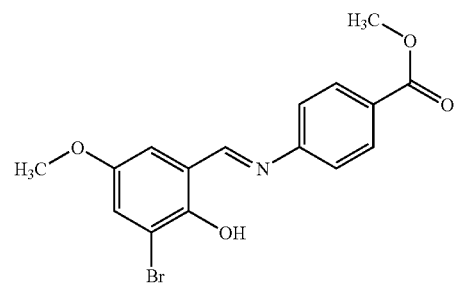

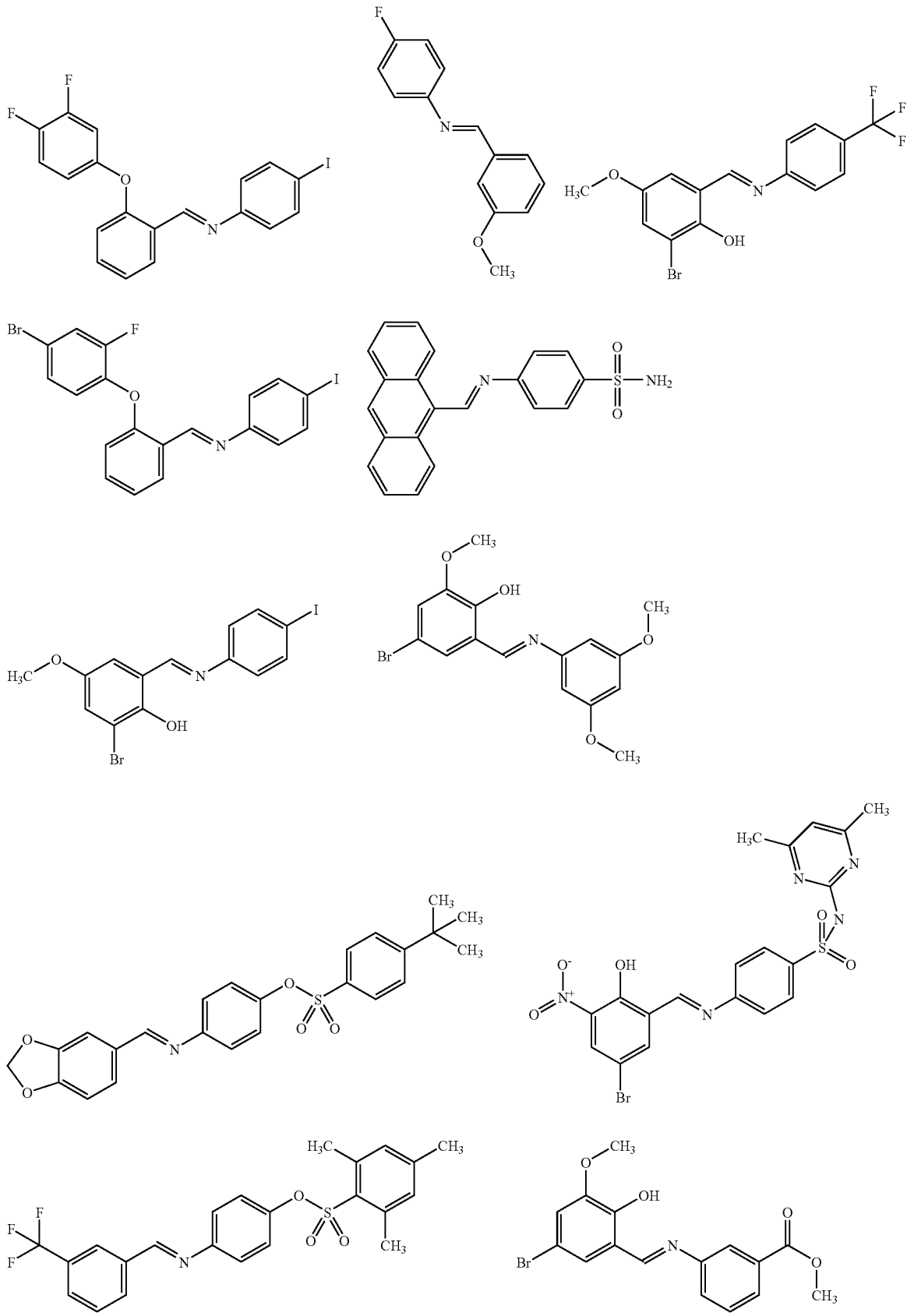

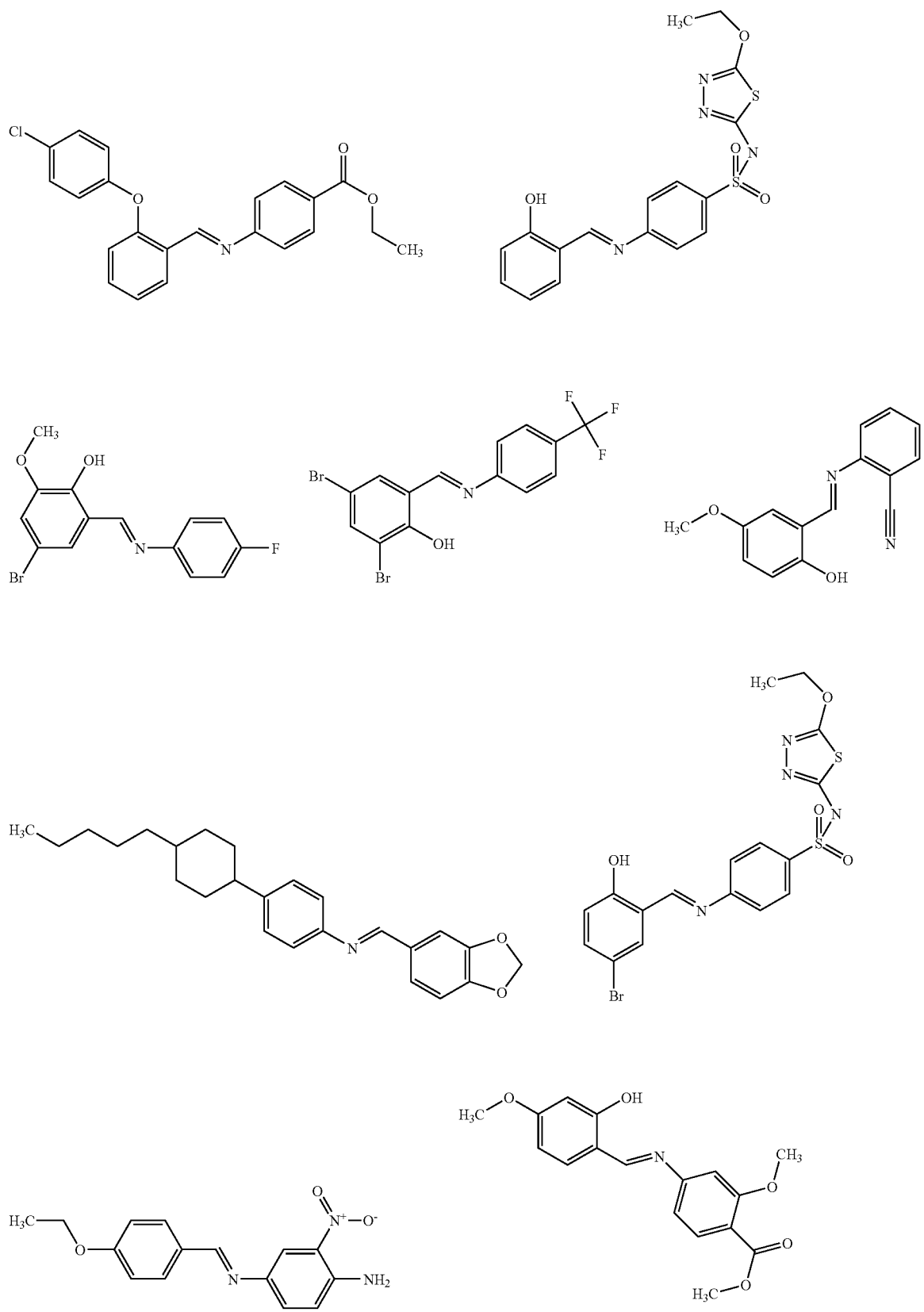

-continued
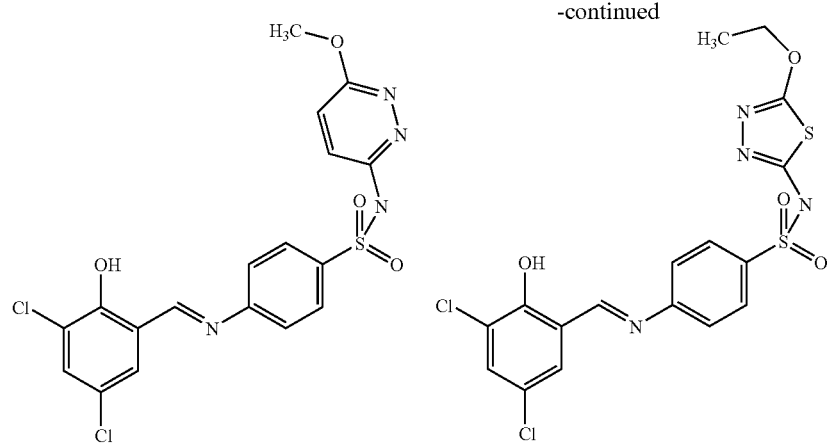
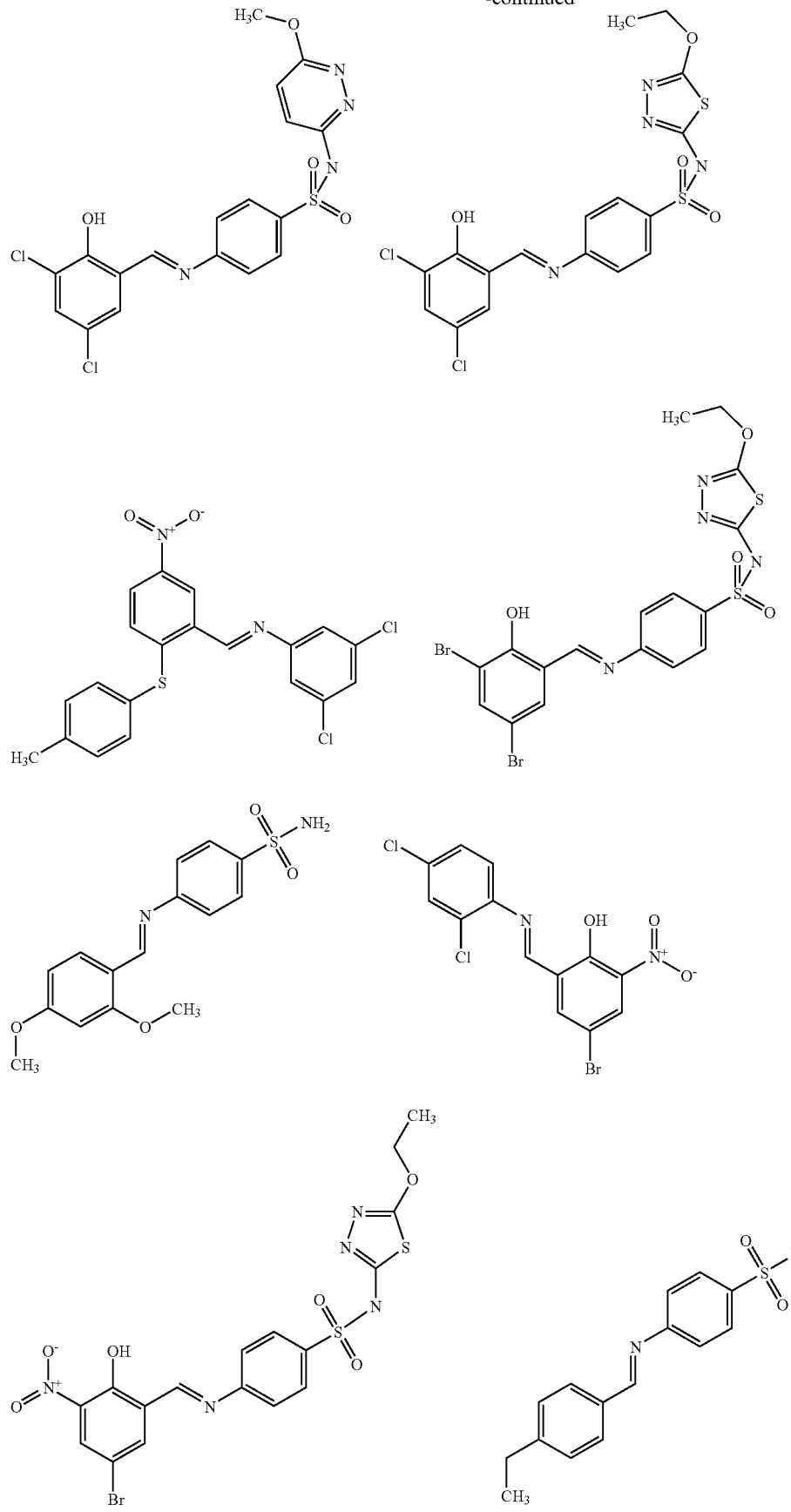

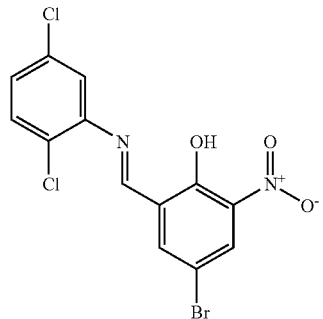
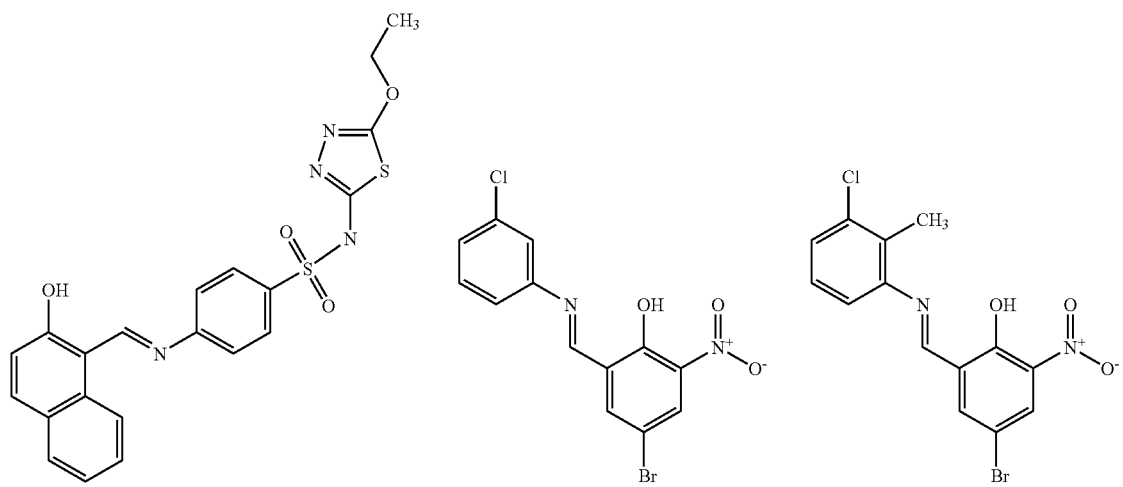
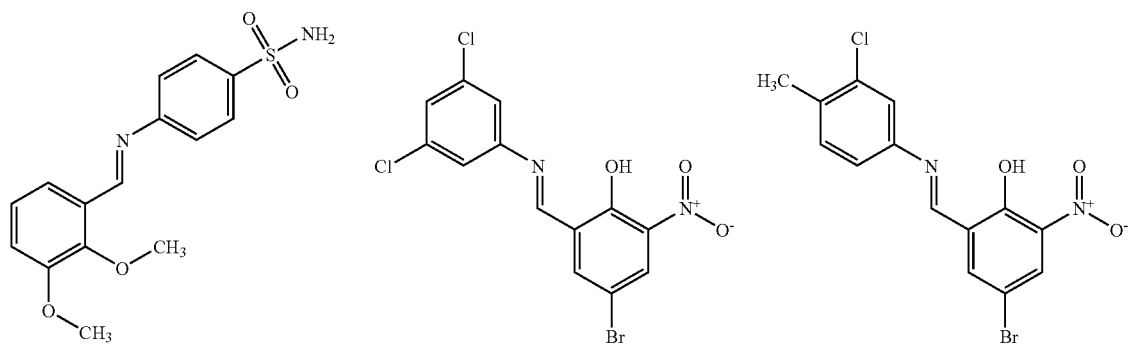
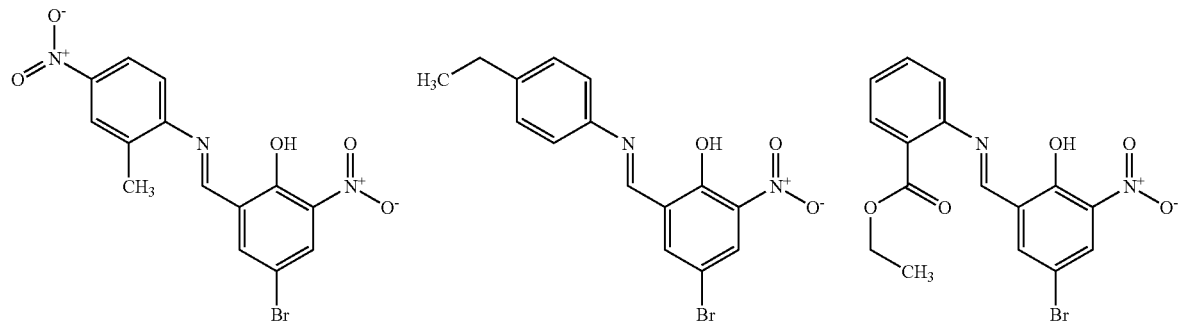

-continued
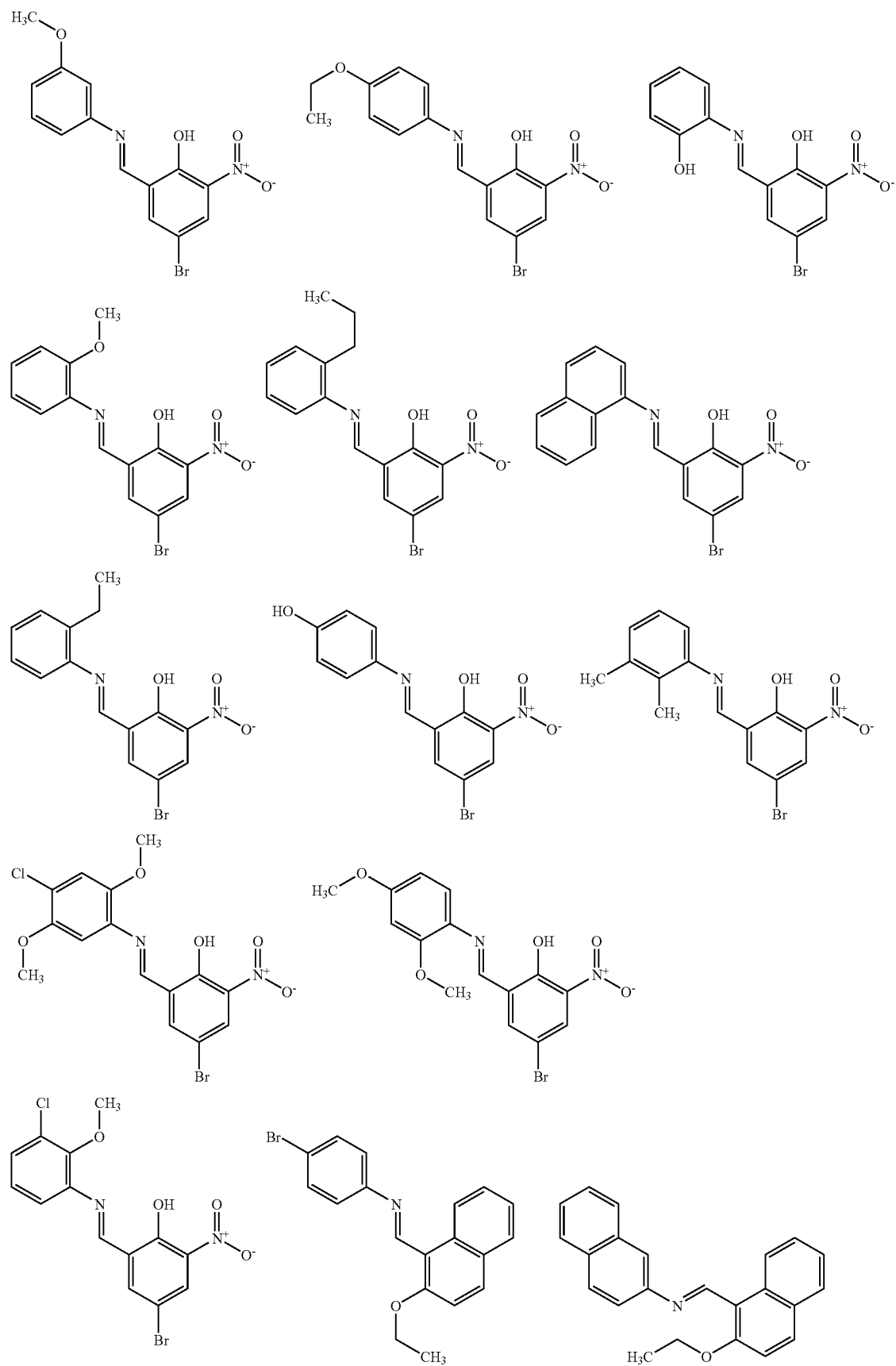

-continued
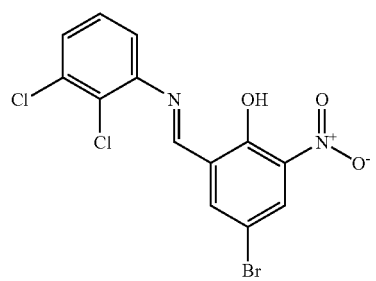
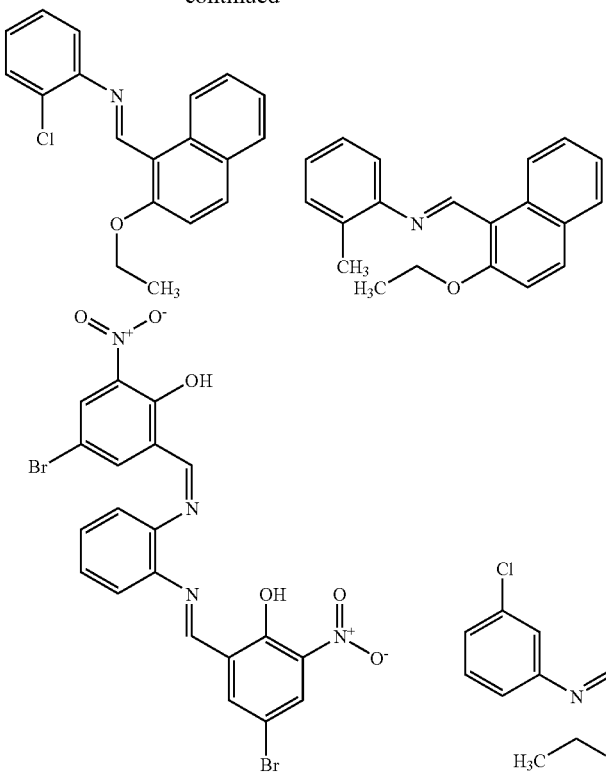
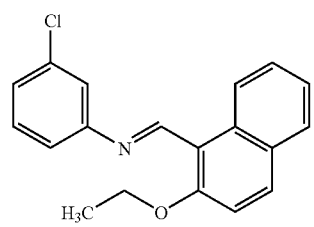
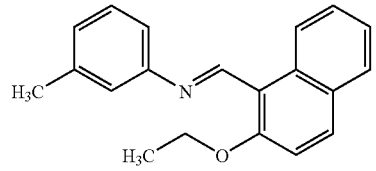
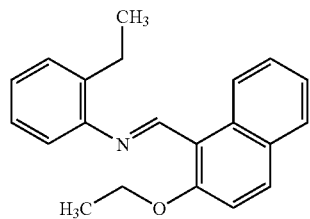
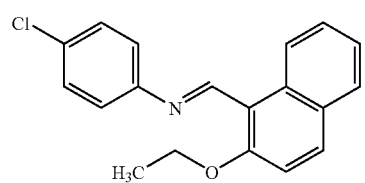
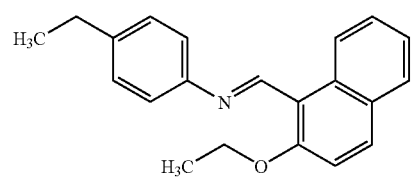
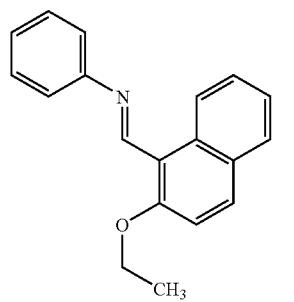
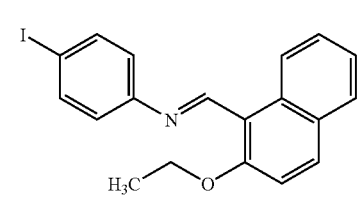
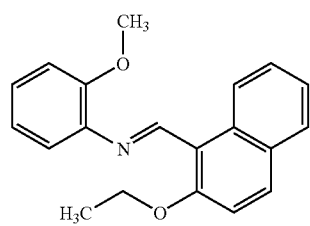
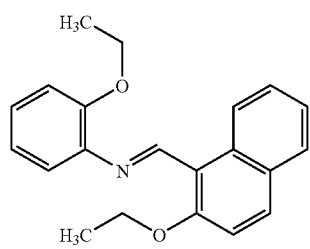
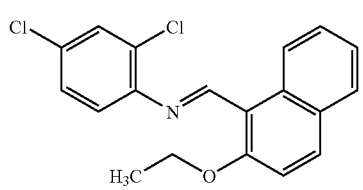
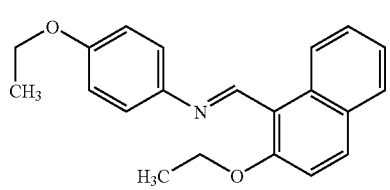

-continued
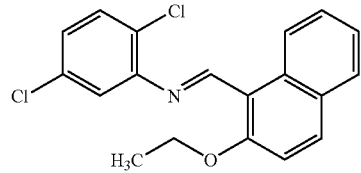
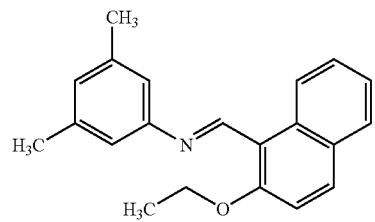
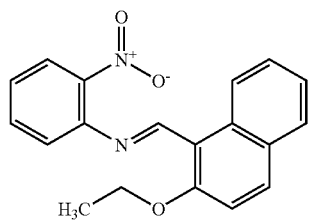
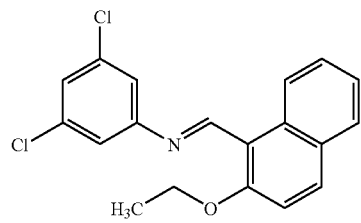
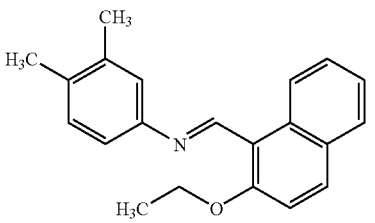
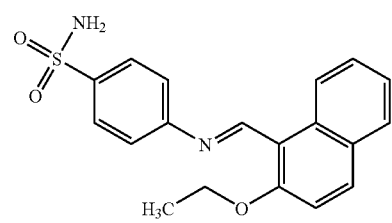
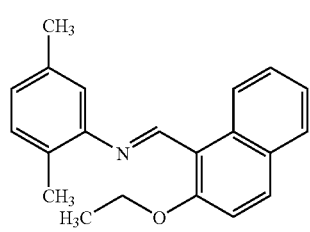
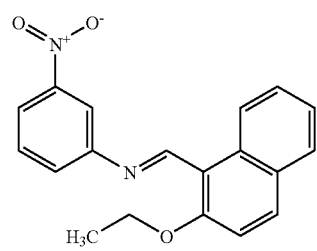
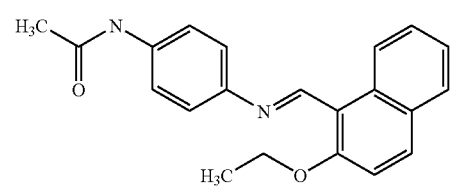
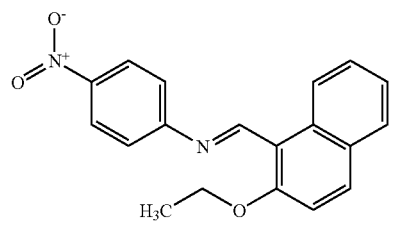
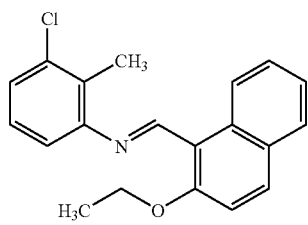
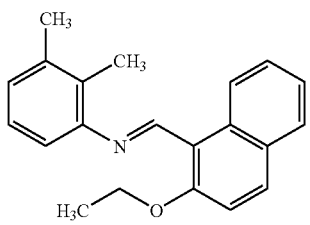
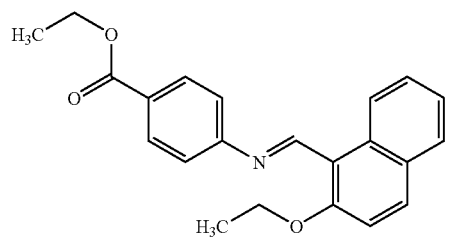
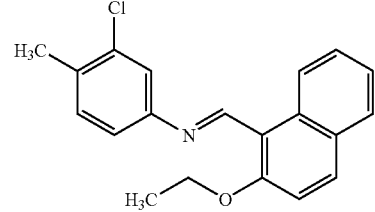
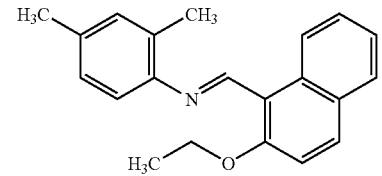
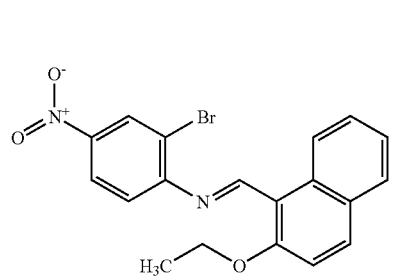
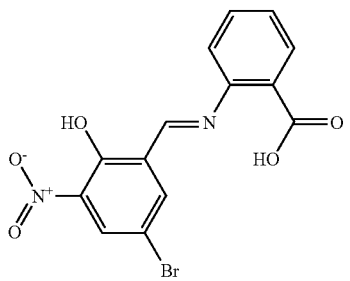
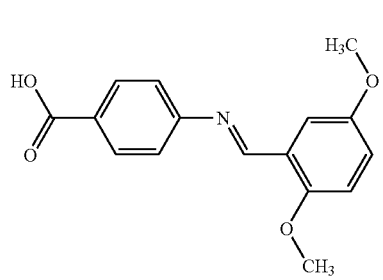

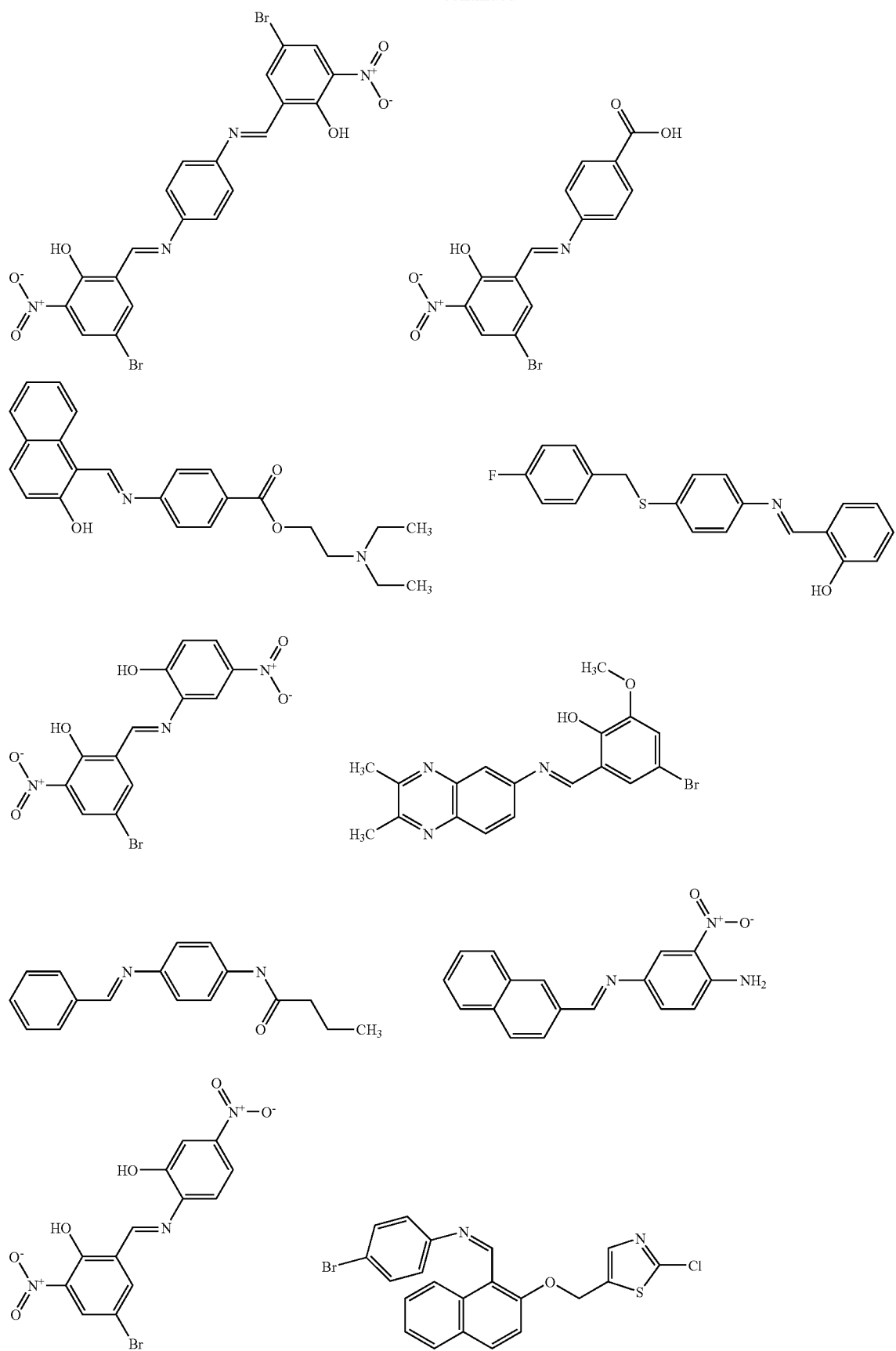

97 98
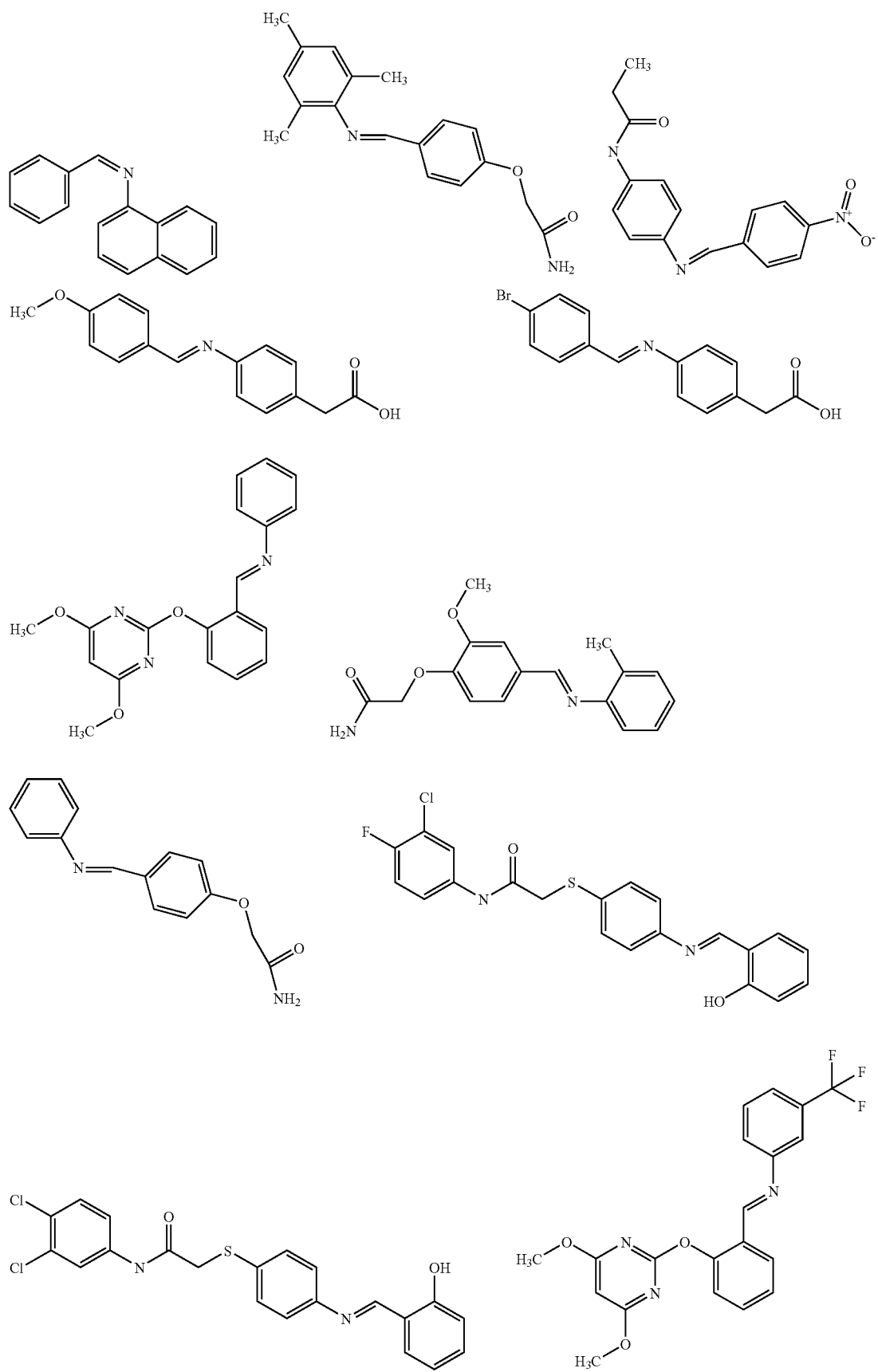
-continued

-continued
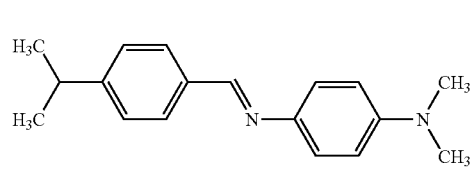
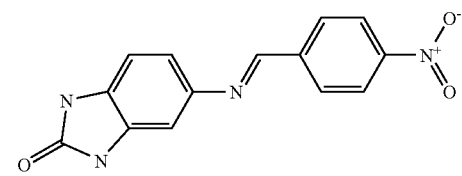
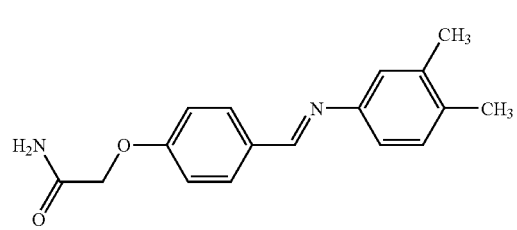
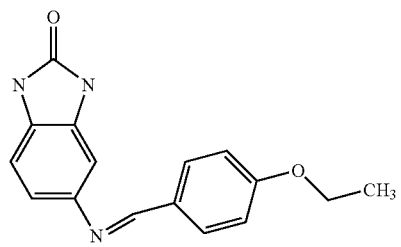
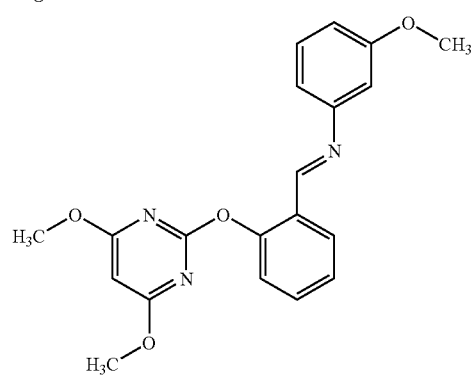
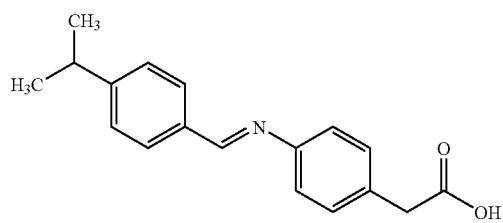
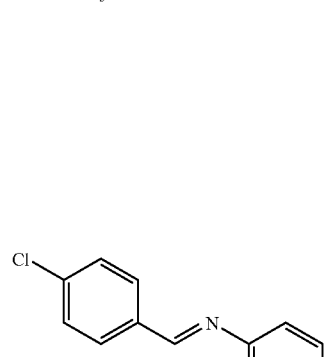
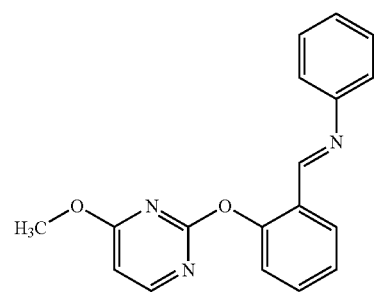
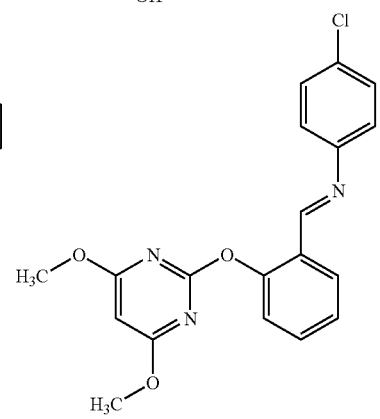
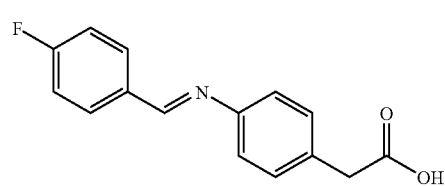
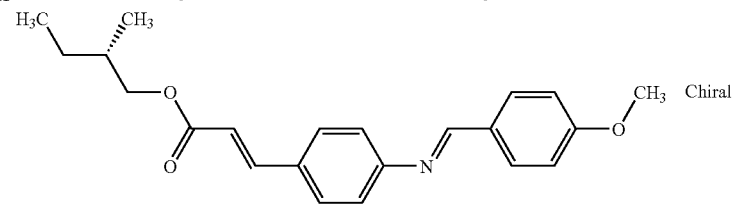
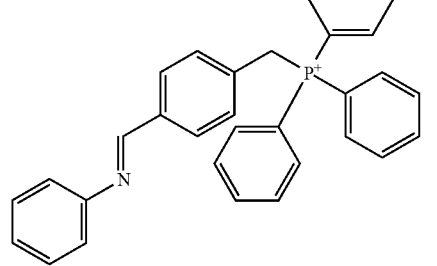
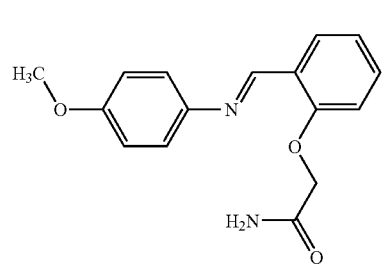

101                                                                                                          102
-continued
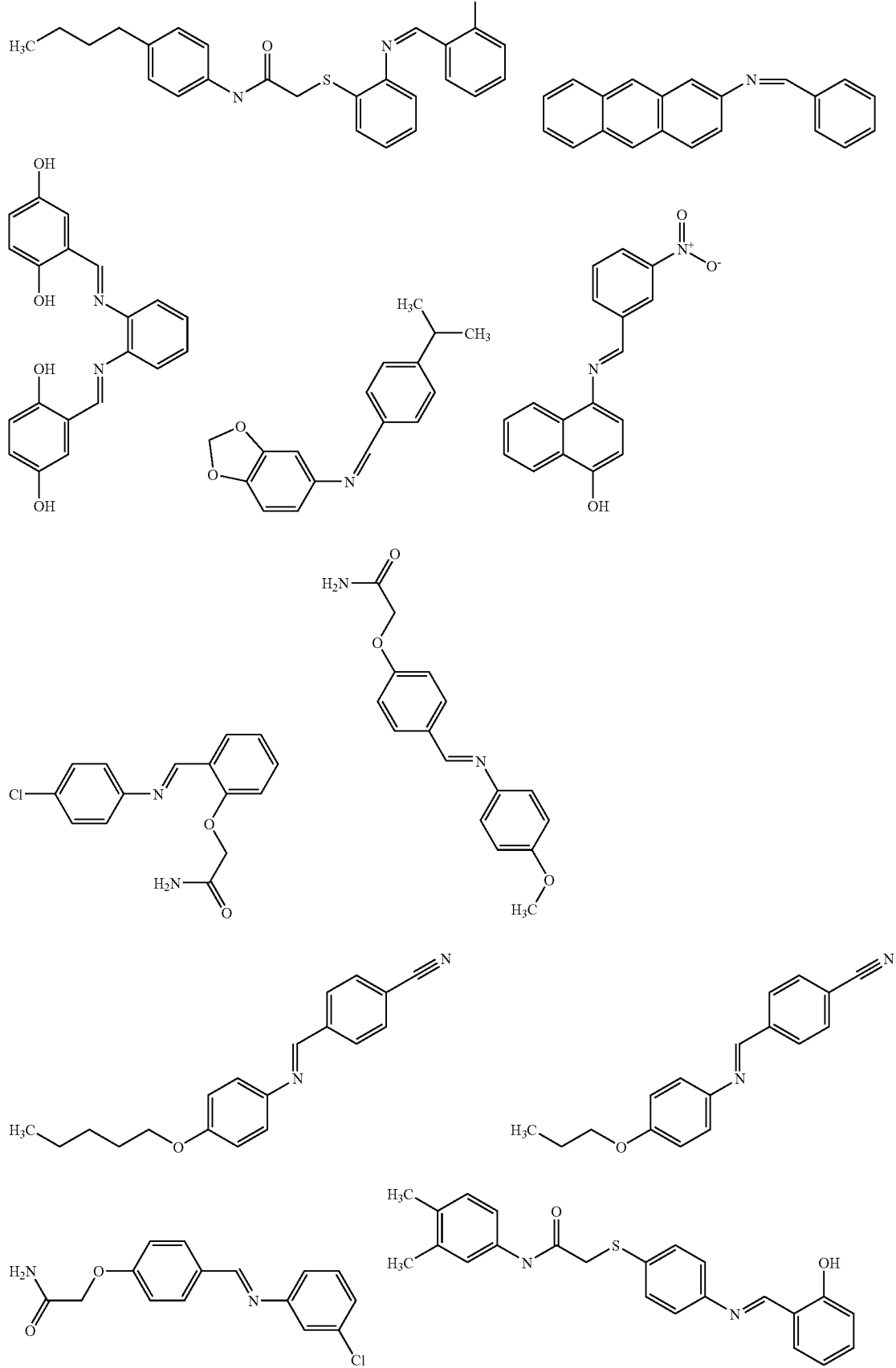

103
104
-continued
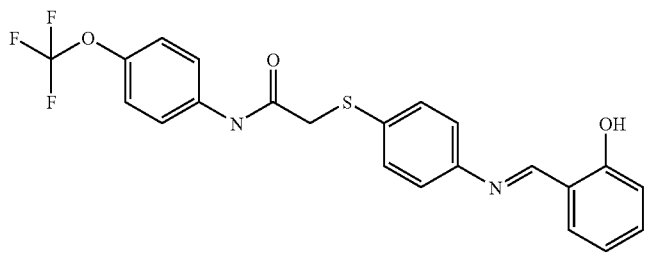
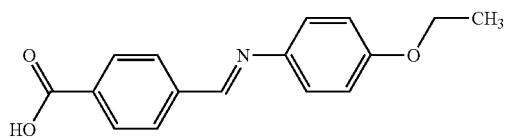
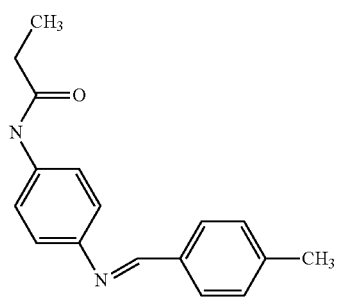 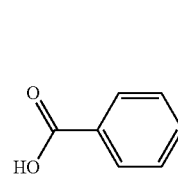
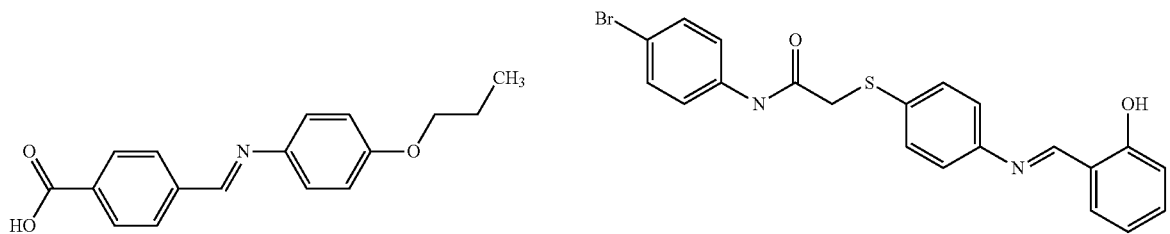
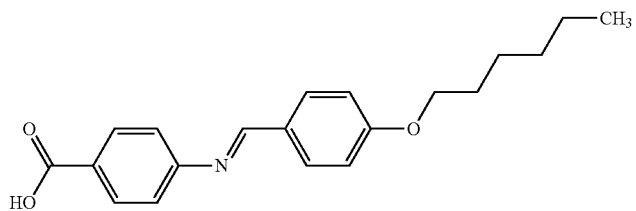
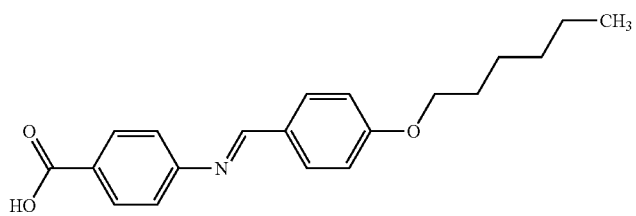
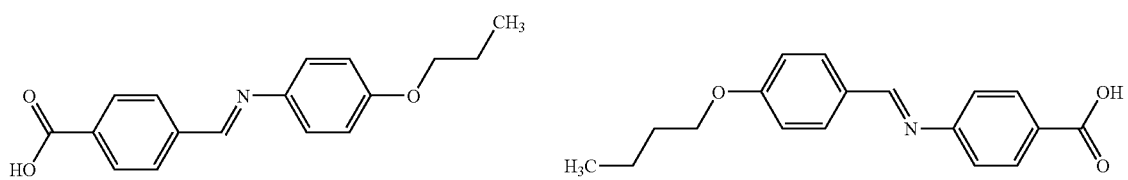

105 106
-continued
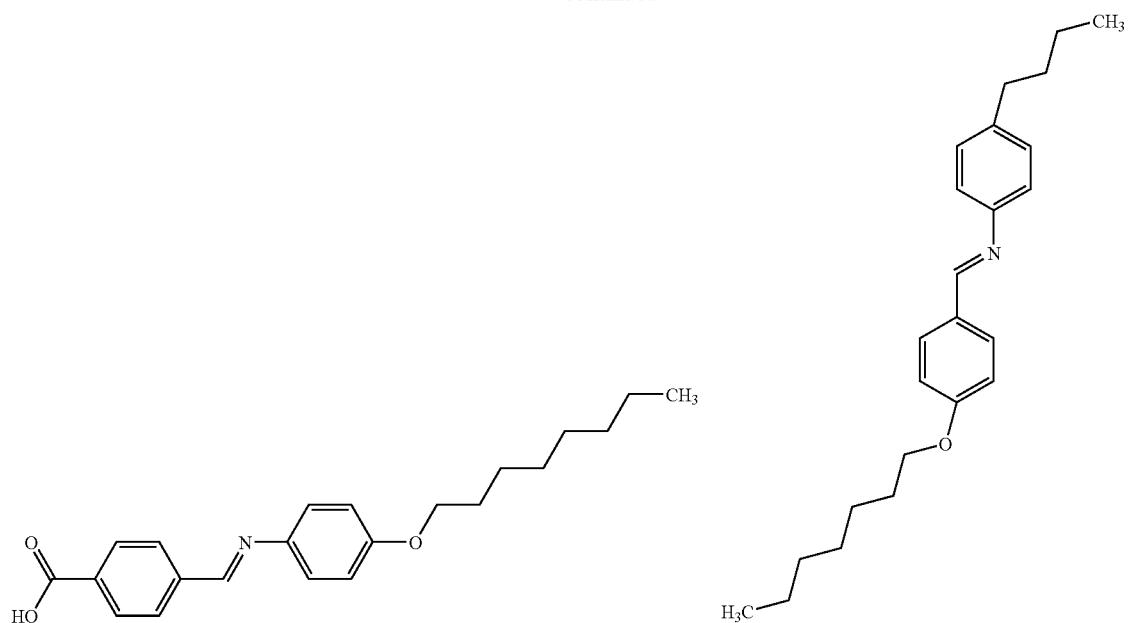
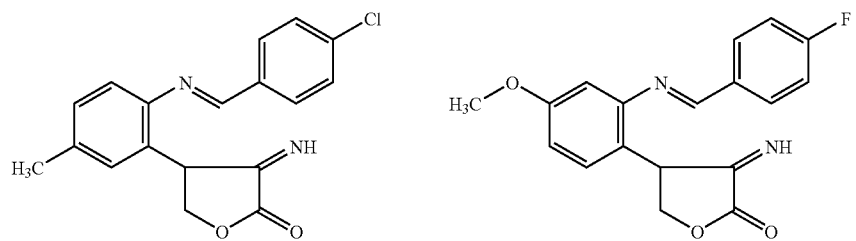
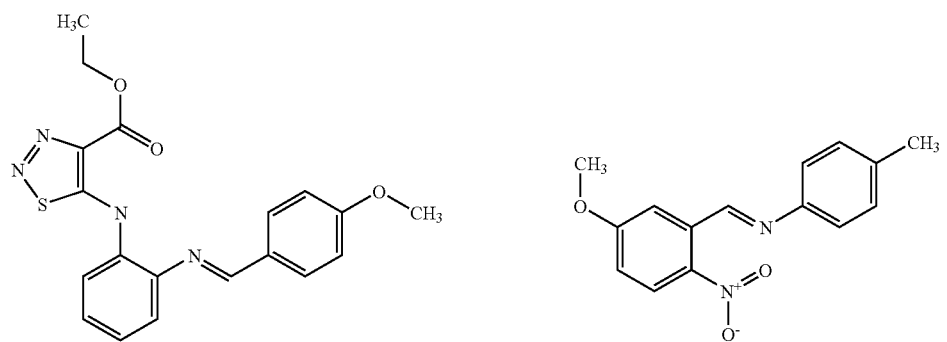
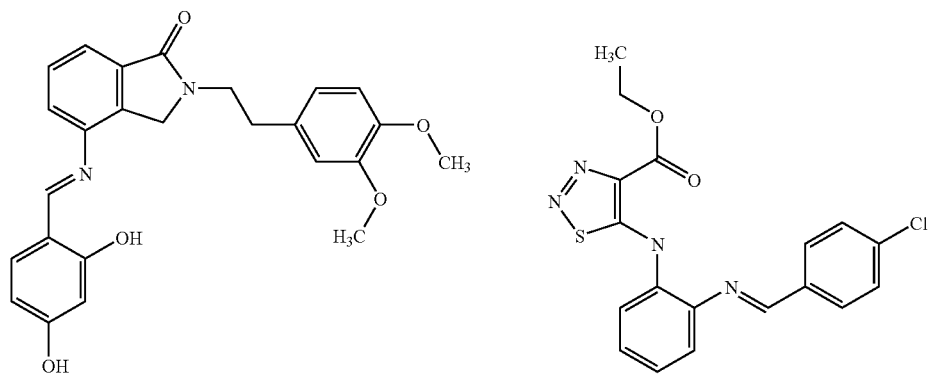

-continued
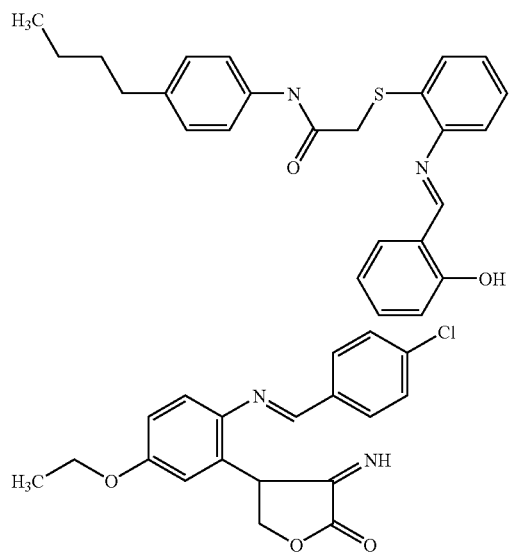
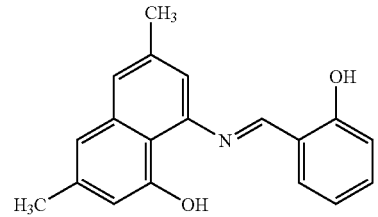
DRAs or DRA-compounds also include the compounds of Group B, shown here:
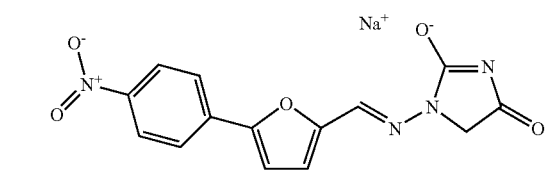
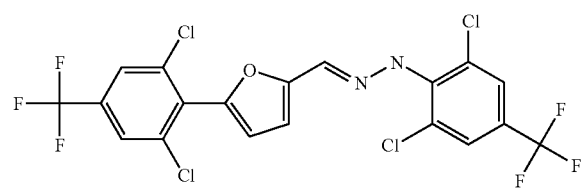
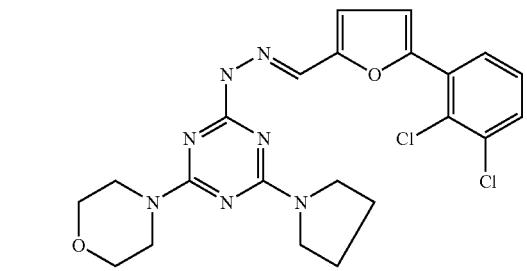
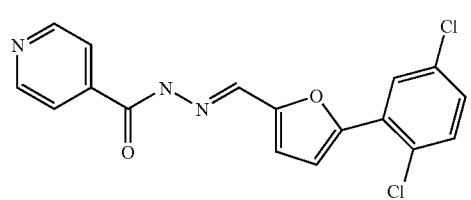
-continued
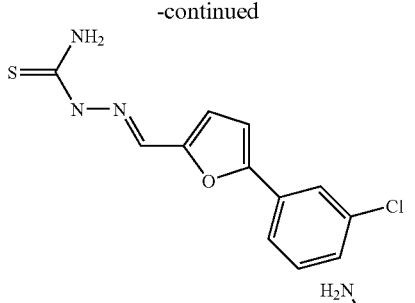
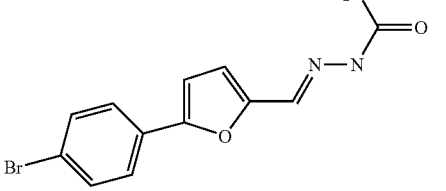
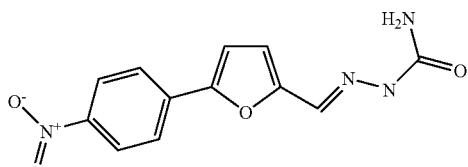
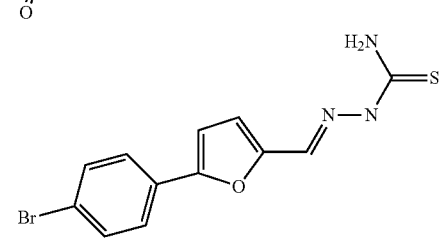
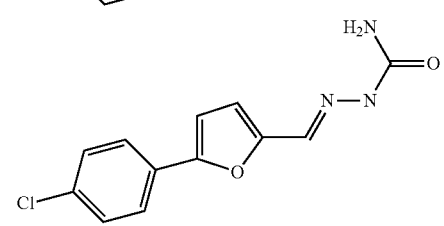

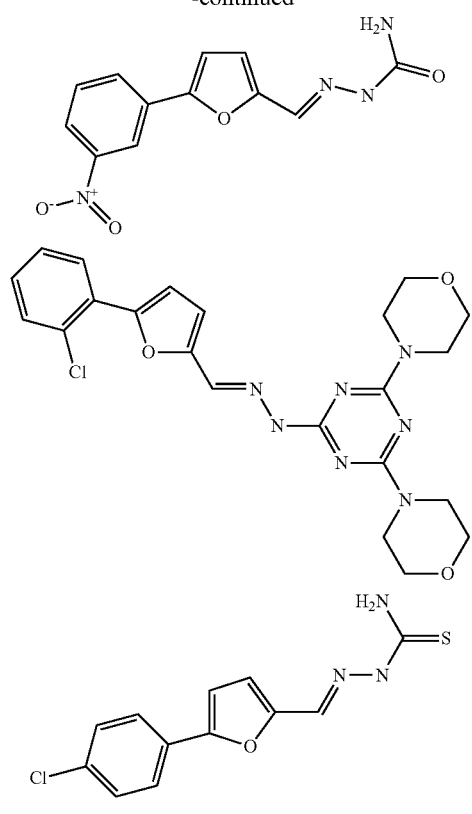
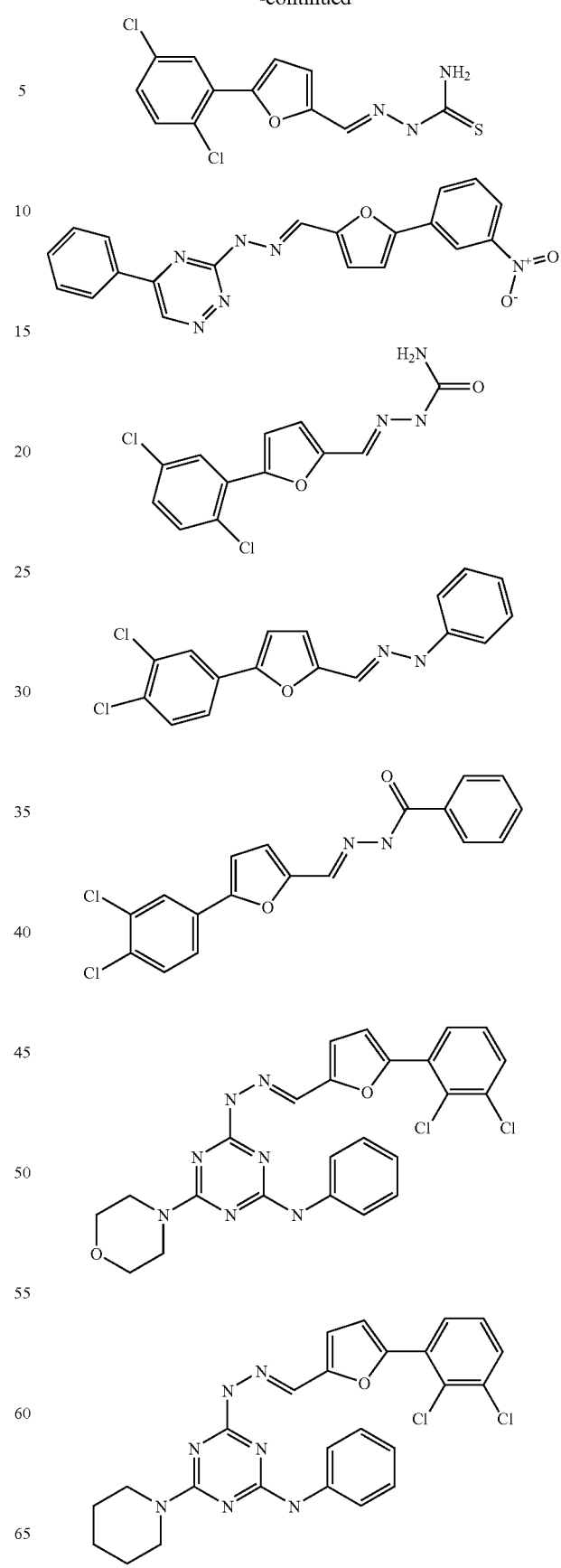

111
-continued
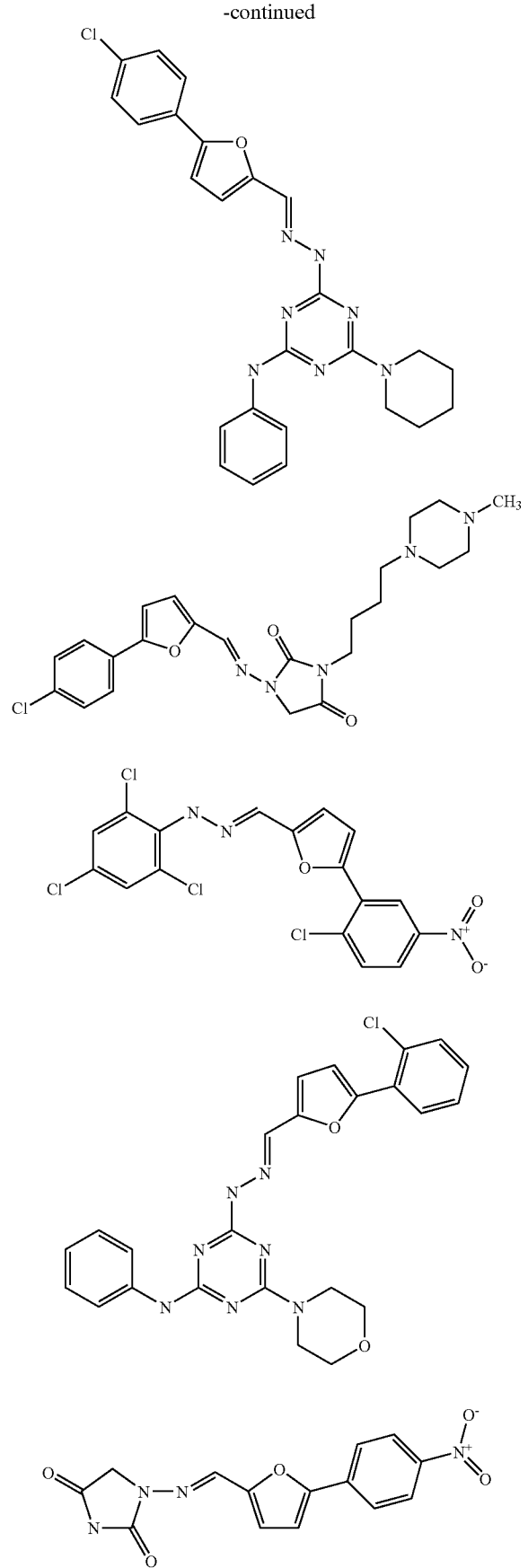
112
-continued
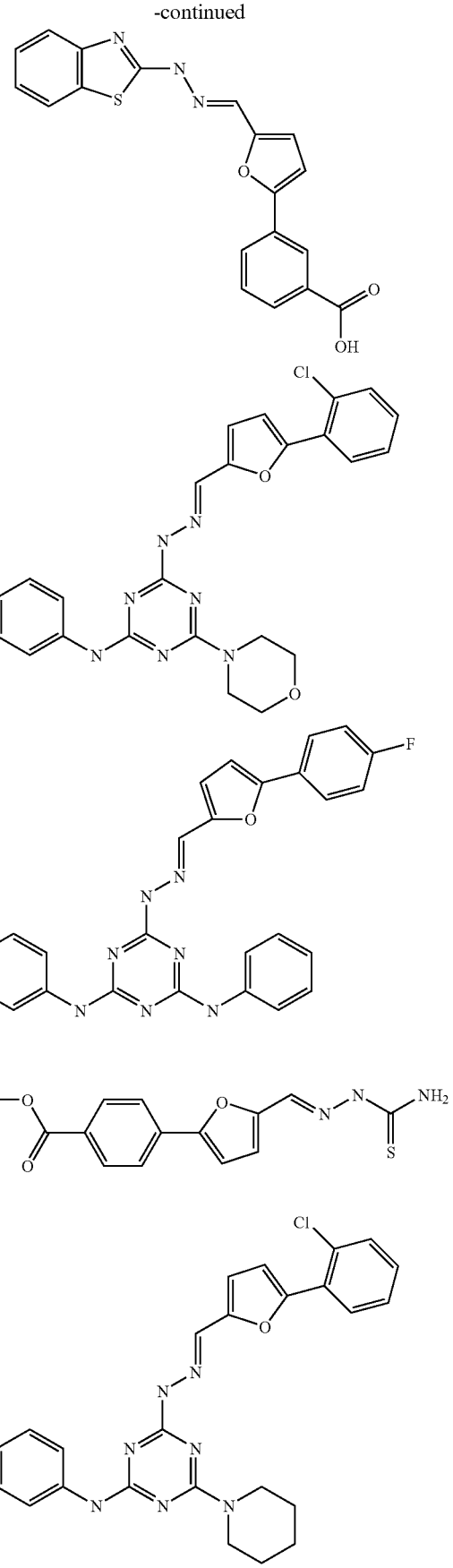

113
-continued
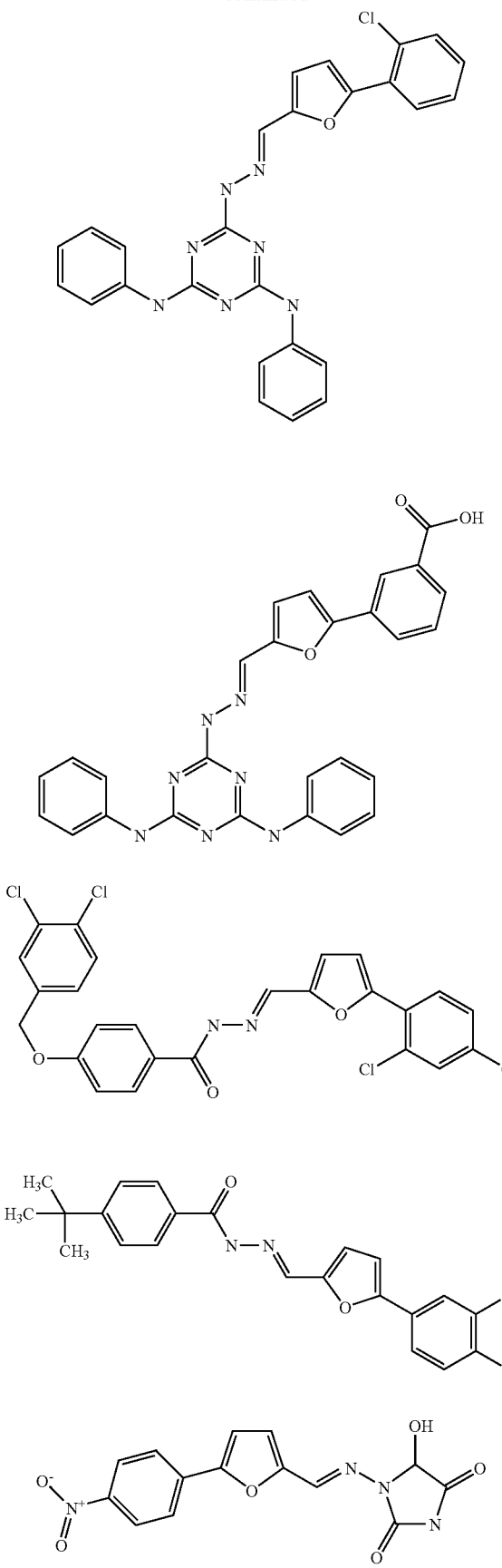
114
-continued
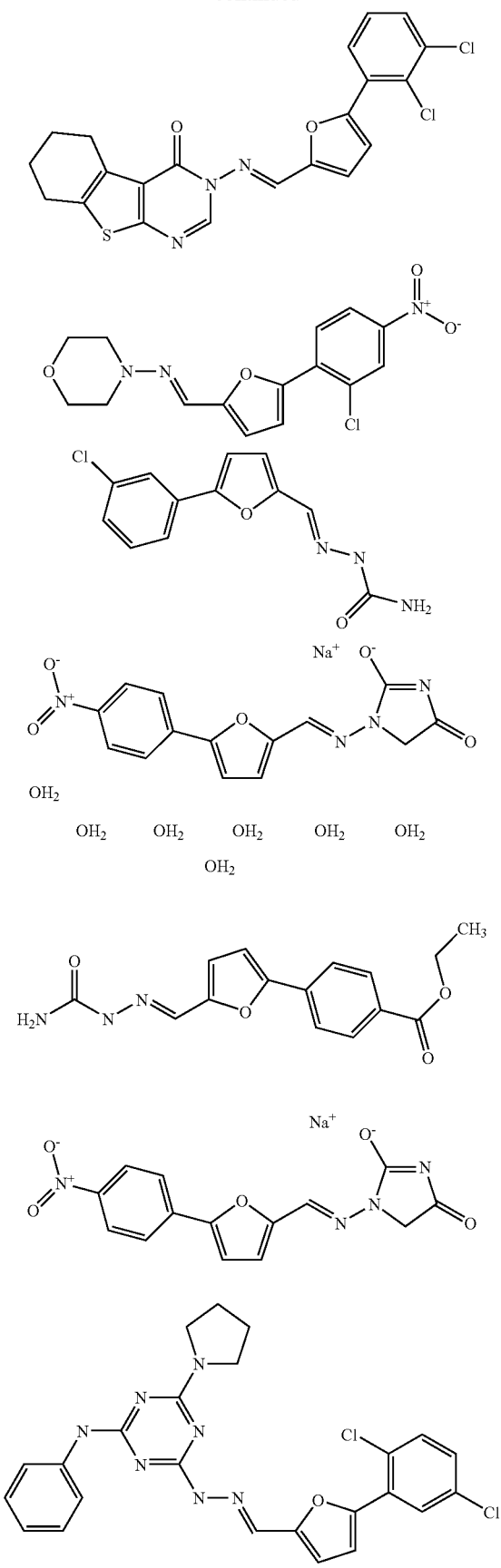

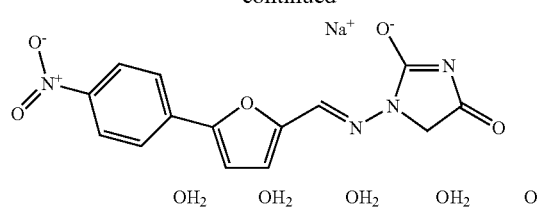
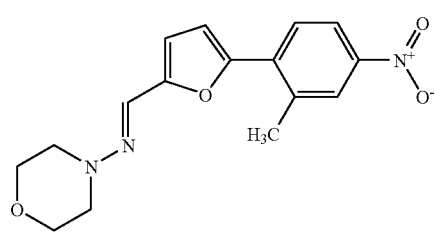
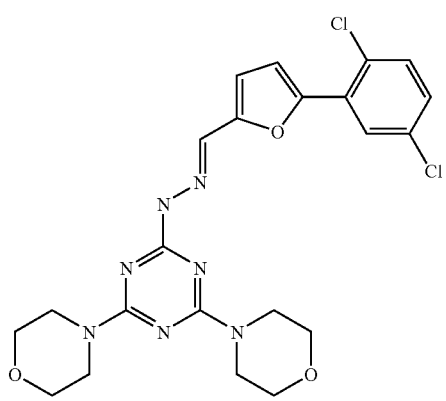
DRAs or DRA-compounds also include the compounds of Group C, shown here:
DRA71
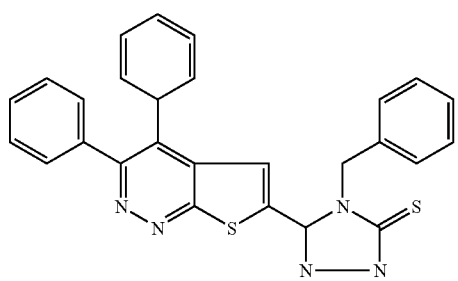
DRA72
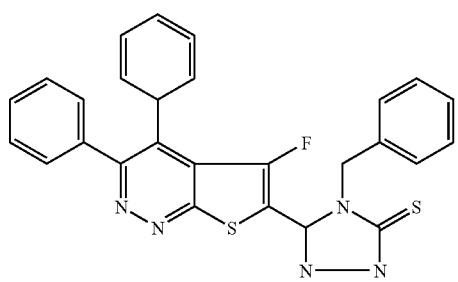
DRA73
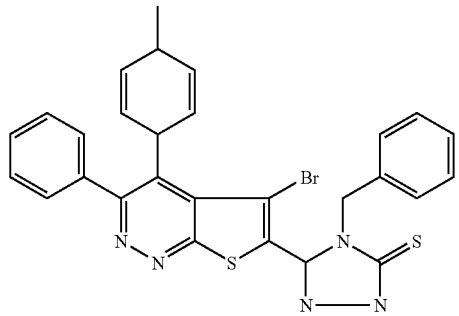
DRA74
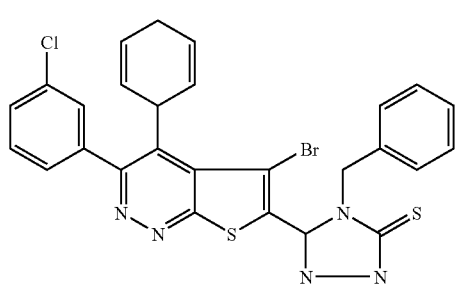
DRA75
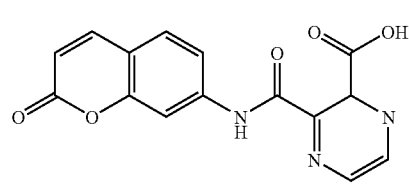
DRA76
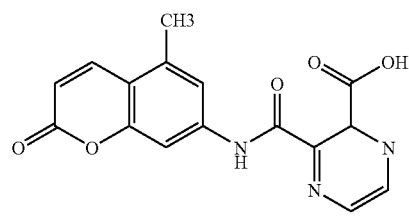
DRA77
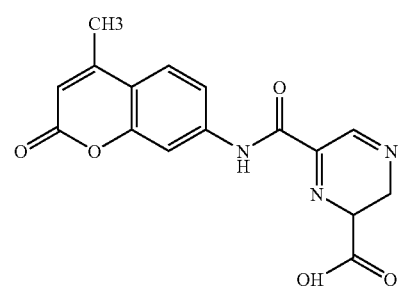
DRA78
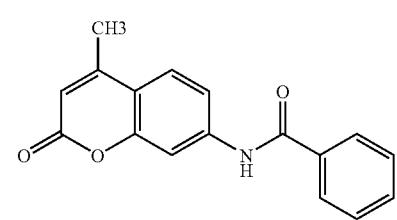

-continued

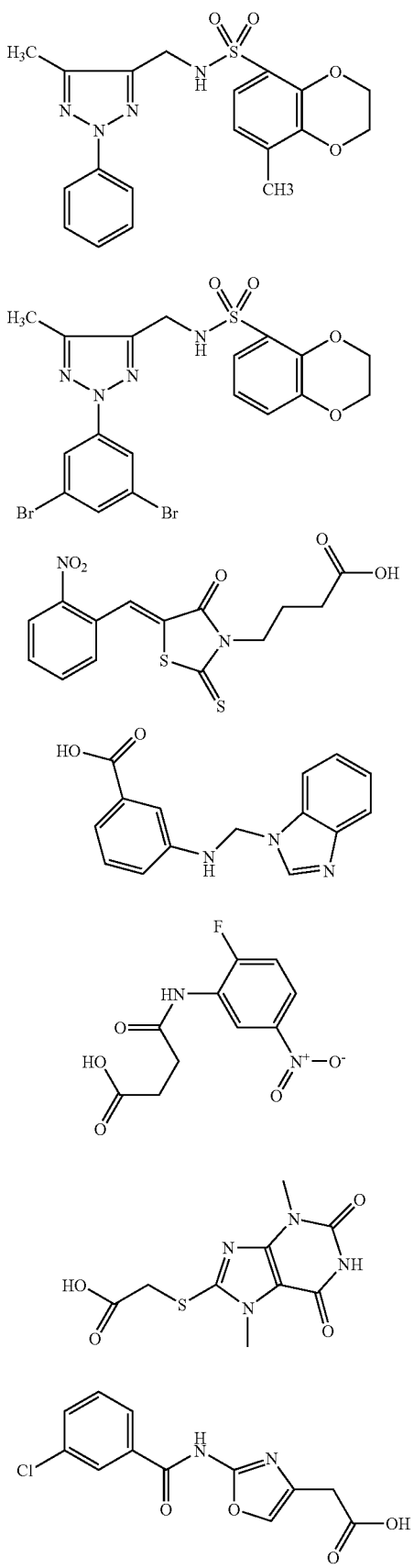

DRA79

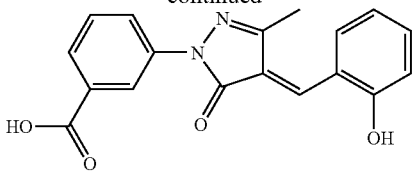

DRA80

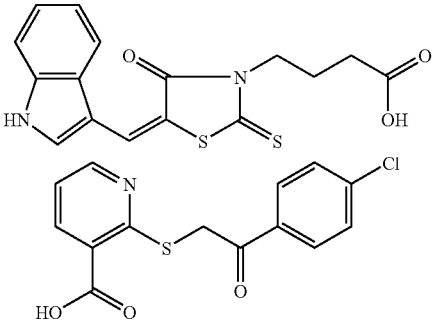

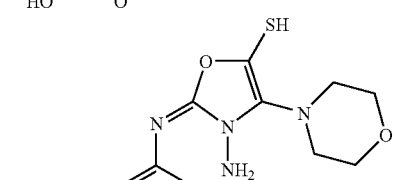

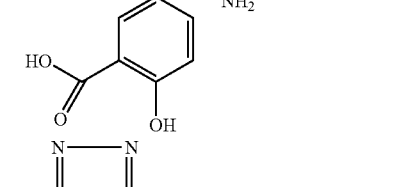

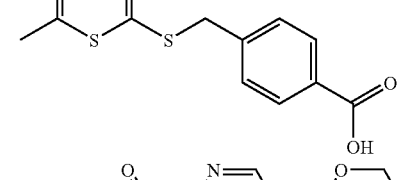

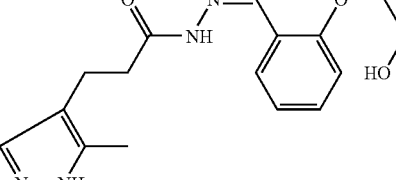

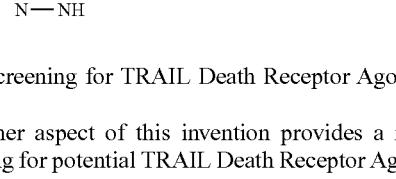

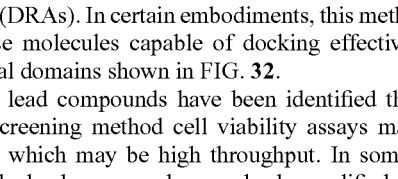

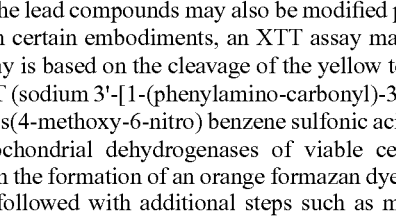

IV. Screening for TRAIL Death Receptor Agonists/Activators

Figure 32:
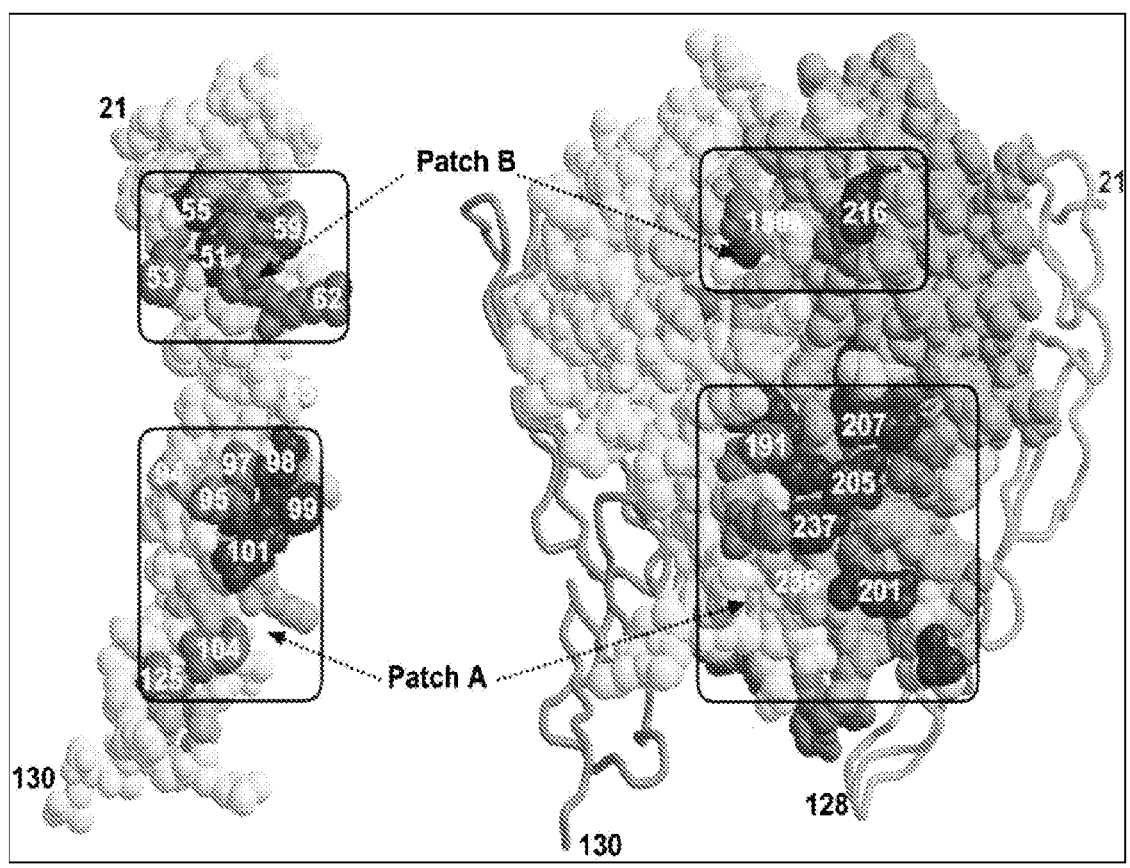
FIG. 32. View of the TRAIL-DR5 Interface. TRAIL and one receptor are rendered as space filling models. The interface divides into two patches, A and B (labeled). A probe size of 1.4 Å was used to calculate accessible surface area. See Hymowitz et al., 1999, which is incorporated herein by reference.
Figure 33:
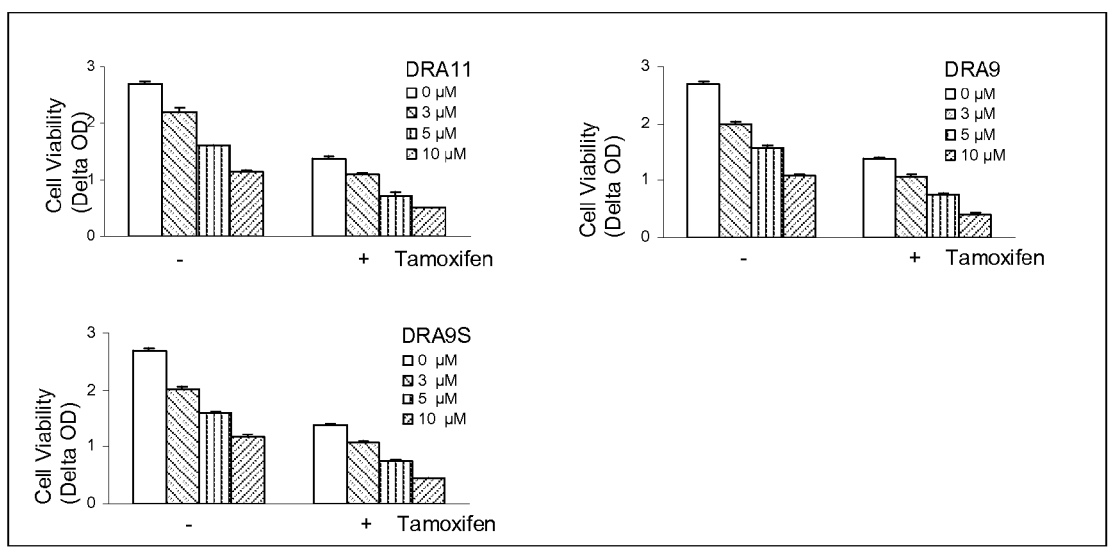
FIG. 33. Interactive effects of death receptor agonists and tamoxifen on cell viability of breast cancer MDA-MB-231 cell line. MDA-MB-231 cells were treated with various concentrations DRA11, DRA9, and DRA9S in the presence or absence of tamoxifen (10 μM) for 72 h. At the end of incubation, cell viability was measured by XTT assay. Data represent the mean±S.D.
Figure 34:
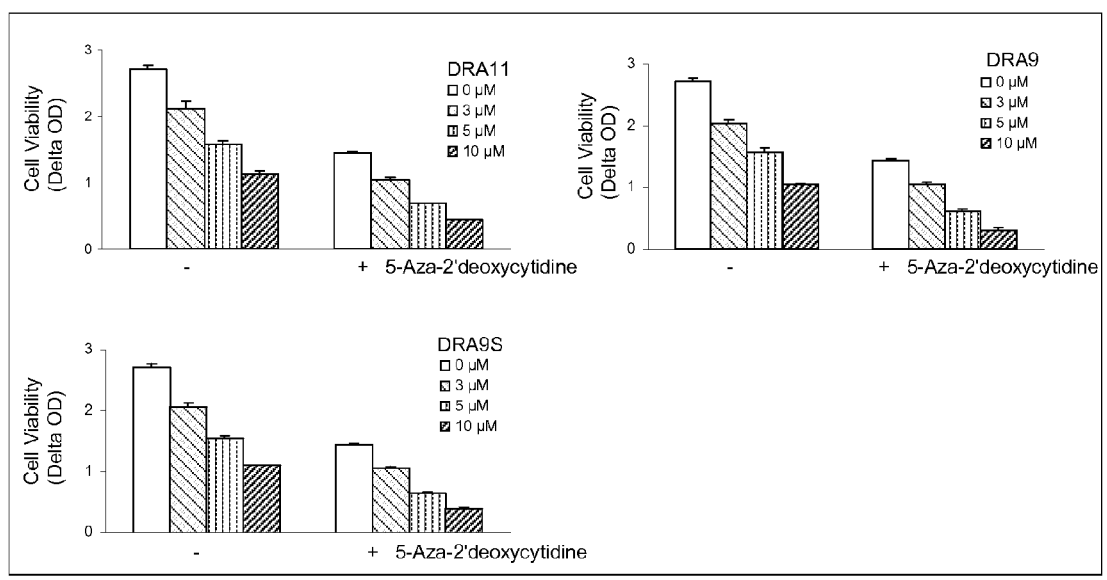
FIG. 34. Interactive effects of death receptor agonists and 5-Aza-2'deoxycytidineon cell viability of breast cancer MDA-MB-231 cell line. MDA-MB-231 cells were treated with various concentrations DRA11, DRA9, and DRA9S in the presence or absence of 5-Aza-2'deoxycytidine (5 μM) for 72 h. At the end of incubation, cell viability was measured by XTT assay. Data represent the mean±S.D.
Figure 35:
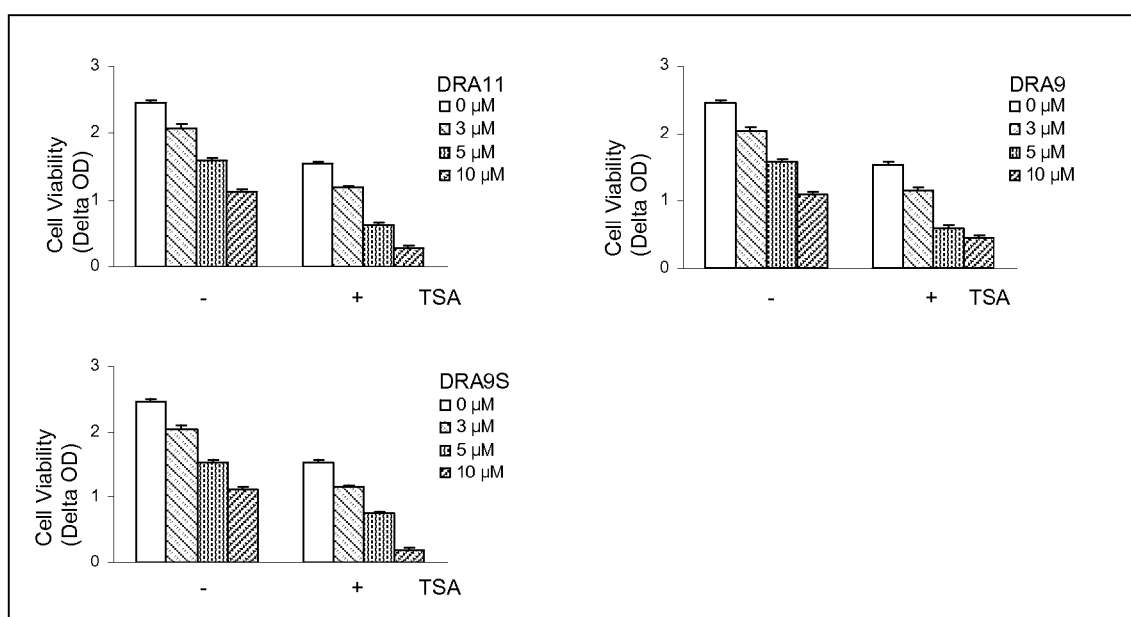
FIG. 35. Interactive effects of death receptor agonists and histone deacetylase inhibitor trichostatin A (TSA) on cell viability of breast cancer MDA-MB-231 cell line. MDA-MB-231 cells were treated with various concentrations DRA11, DRA9, and DRA9S in the presence or absence of TSA (100 nM) for 72 h. At the end of incubation, cell viability was measured by XTT assay. Data represent the mean±S.D.
Figure 36:
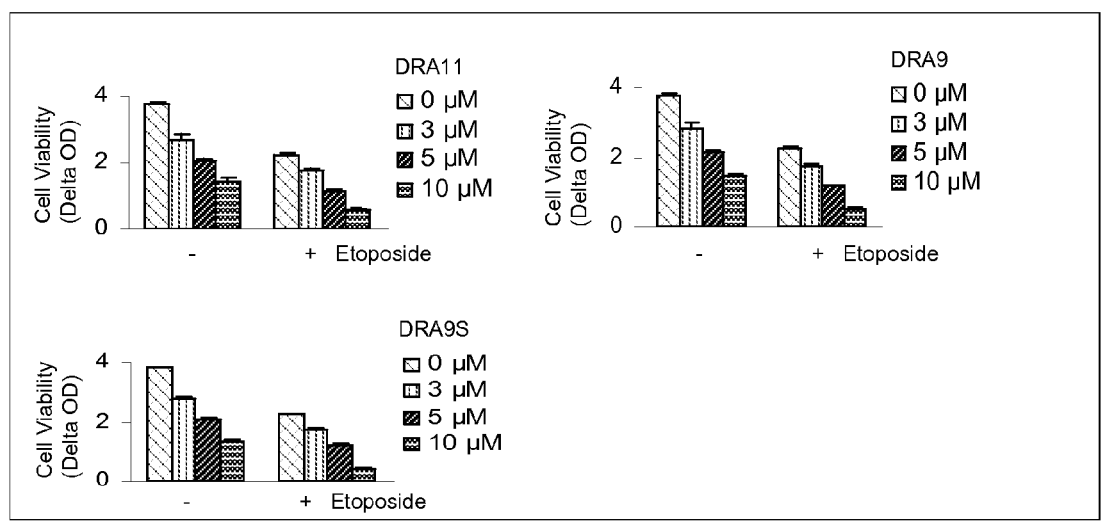
FIG. 36. Interactive effects of death receptor agonists and etoposide on cell viability of breast cancer MDA-MB-231 cell line. MDA-MB-231 cells were treated with various concentrations DRA11, DRA9, and DRA9S in the presence or absence of etoposide (50 μM) for 72 h. At the end of incubation, cell viability was measured by XTT assay. Data represent the mean±S.D.
Figure 37:
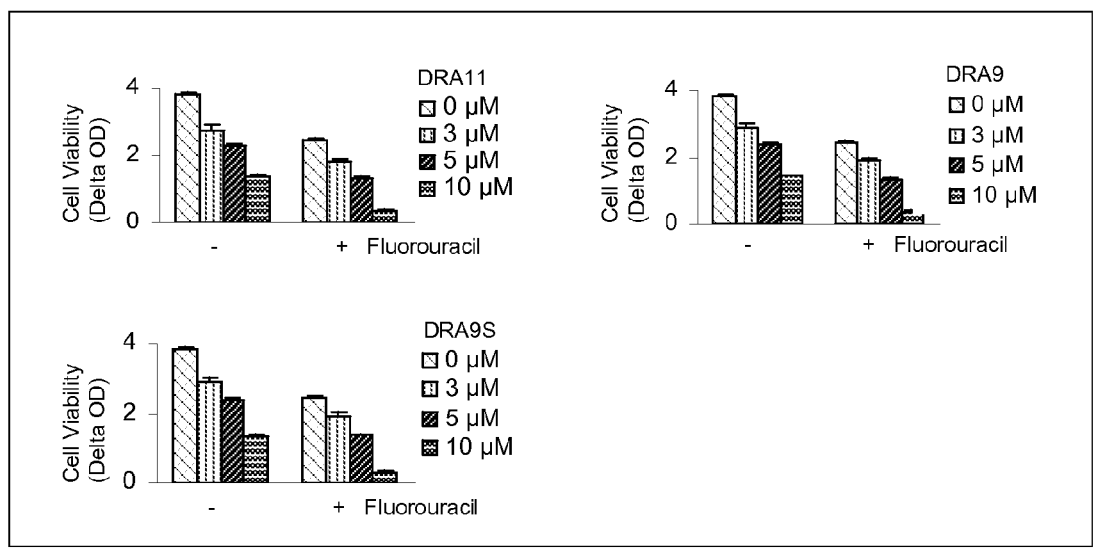
FIG. 37. Interactive effects of death receptor agonists and 5-fluorouracil (5-FU) on cell viability of breast cancer MDA-MB-231 cell line. MDA-MB-231 cells were treated with various concentrations DRA11, DRA9, and DRA9S in the presence or absence of 5-fluorouracil (5 μM) for 72 h. At the end of incubation, cell viability was measured by XTT assay. Data represent the mean±S.D.
Figure 38:
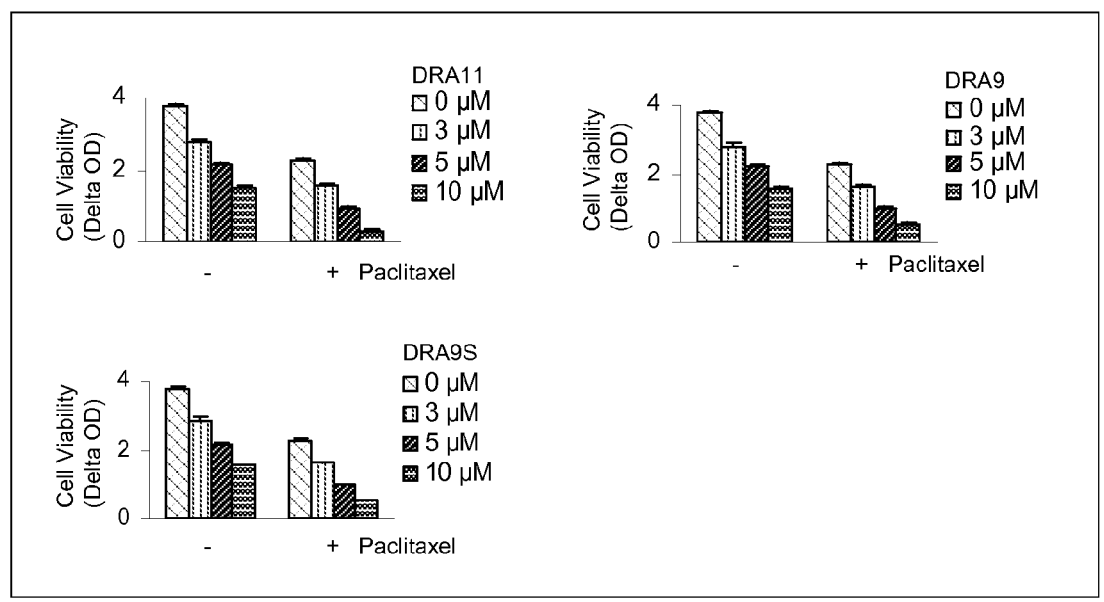
FIG. 38. Interactive effects of death receptor agonists and paclitaxel on cell viability of breast cancer MDA-MB-231 cell line. MDA-MB-231 cells were treated with various concentrations DRA11, DRA9, and DRA9S in the presence or absence of paclitaxel (10 nM) for 72 h. At the end of incubation, cell viability was measured by XTT assay. Data represent the mean±S.D.
Figure 39:
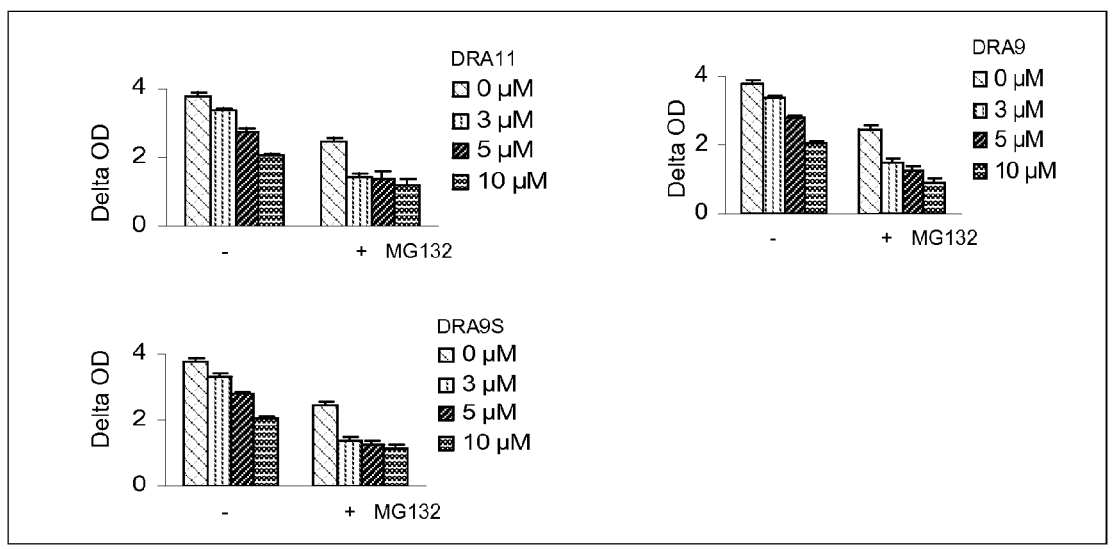
FIG. 39. NFκB inhibitor MG132 enhances the inhibitory effects of DRAs on cell viability of breast cancer MDA-MB-231 cell line. MDA-MB-231 cells were pretreated with NFκB inhibitor MG132 (2.5 μM) for 4 h followed by treatment with various concentrations of DRA11, DRA9, and DRA9S for 72 h. At the end of incubation, cell viability was measured by XTT assay. Data represent the mean±S.D.
Figure 40:
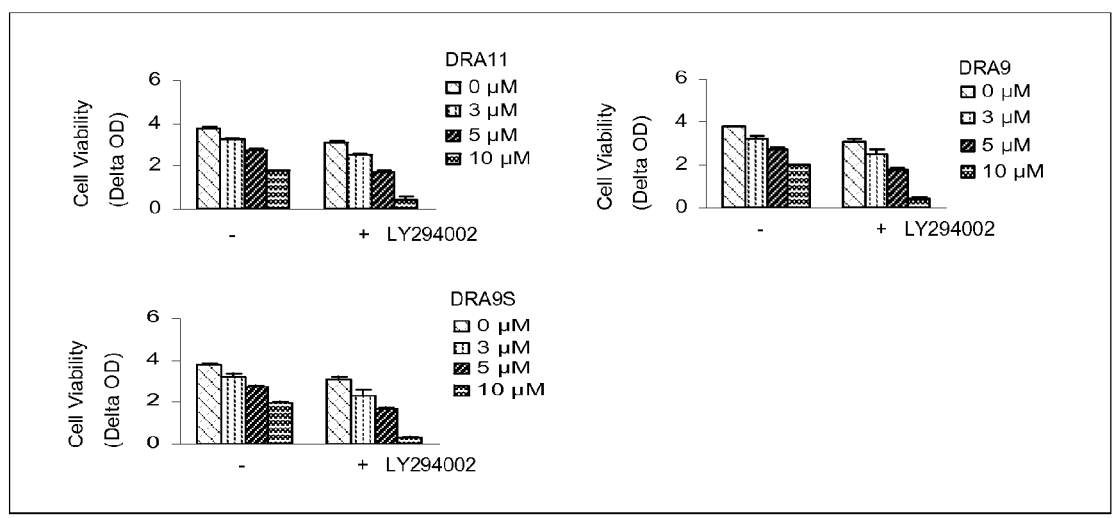
FIG. 40. PI-3 kinase inhibitor (LY294002) enhances the inhibitory effects of DRAs on cell viability of breast cancer MDA-MB-231 cell line. MDA-MB-231 cells were pretreated with LY294002 (2.5 μM) for 4 h followed by treatment with various concentrations of DRA11, DRA9, and DRA9S for 72 h. At the end of incubation, cell viability was measured by XTT assay. Data represent the mean±S.D.
Figure 41:
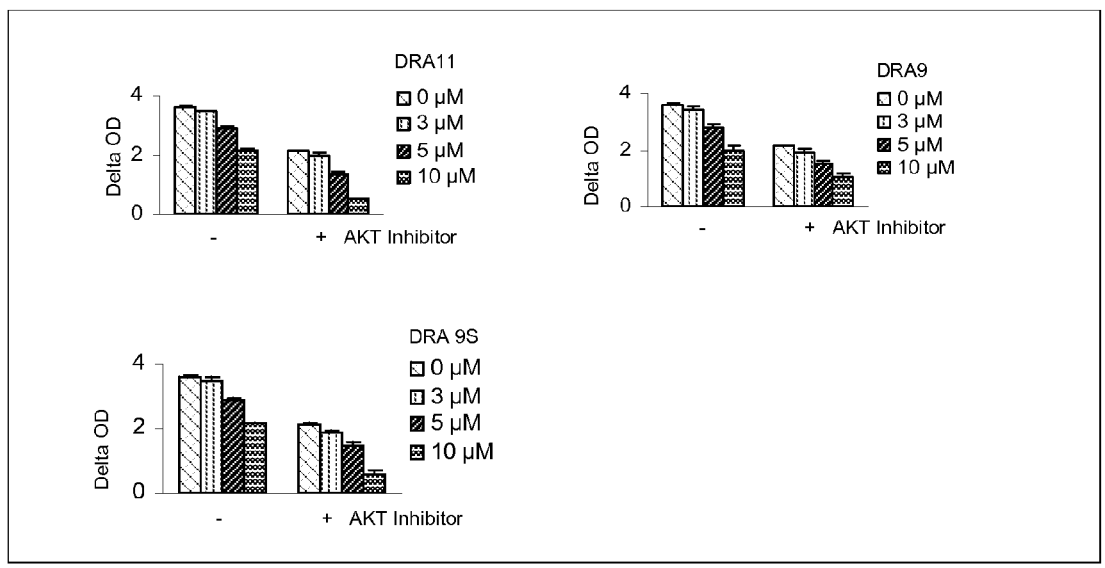
FIG. 41. Akt inhibitor enhances the inhibitory effects of DRAs on cell viability of breast cancer MDA-MB-231 cell line. MDA-MB-231 cells were pretreated with Akt inhibitor (0.5 μM) for 4 h followed by treatment with various concentrations of DRA11, DRA9, and DRA9S for 72 h. At the end of incubation, cell viability was measured by XTT assay. Data represent the mean±S.D.
Figure 42:
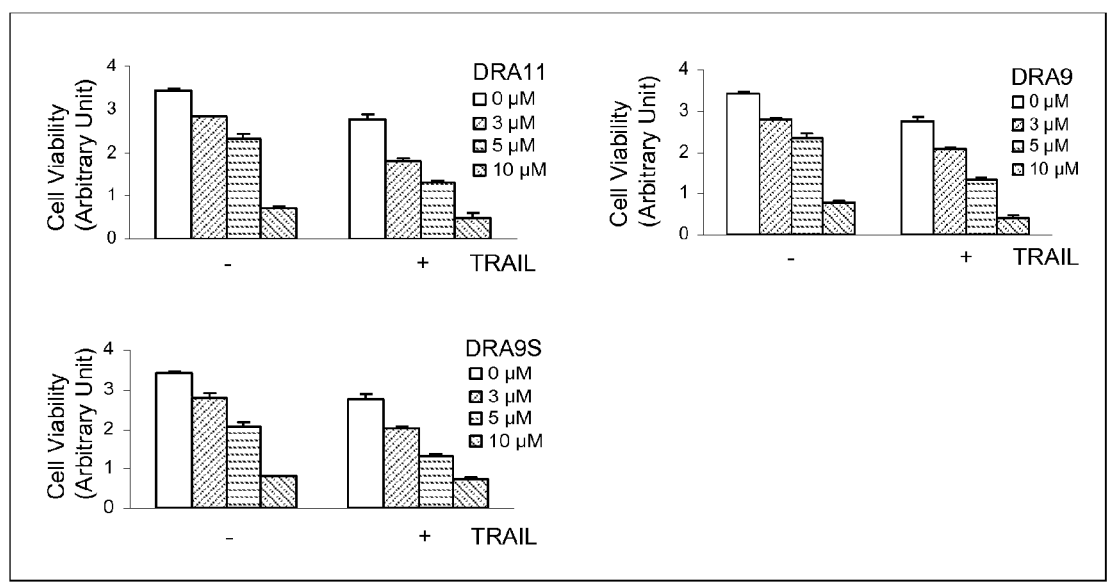
FIG. 42. Interactive effects of death receptor agonists and TRAIL on cell viability of mesothelioma M33K cell line. Mesothelioma M33K cells were treated with various concentrations DRA11, DRA9, and DRA9S in the presence or absence of TRAIL (50 ng/ml) for 72 h. At the end of incubation, cell viability was measured by XTT assay. Data represent the mean±S.D.
Figure 43:
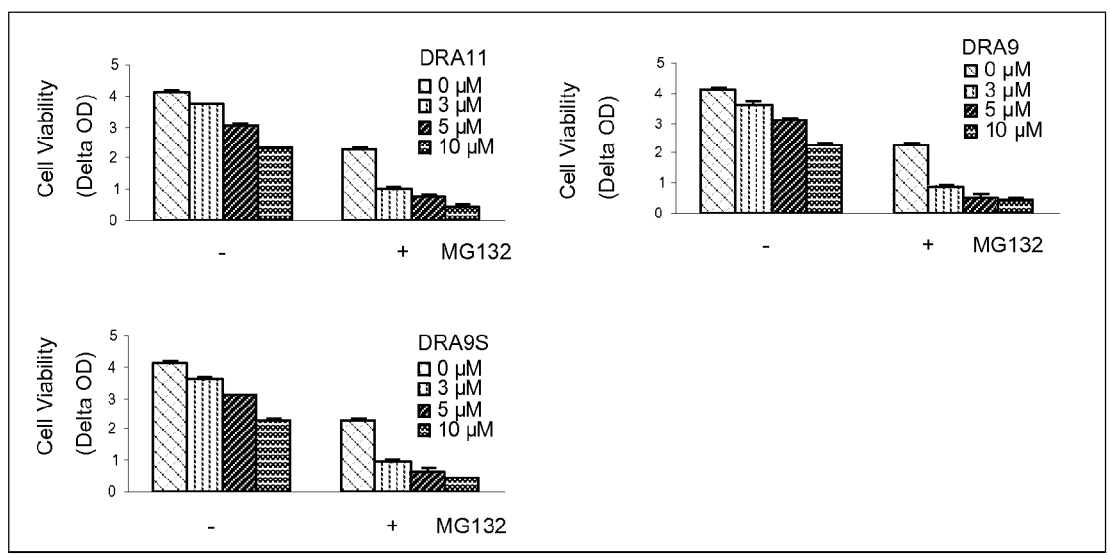
FIG. 43. NFκB inhibitor enhances the inhibitory effects of DRAs on cell viability of mesothelioma M9K cell line. Mesothelioma M9K cells were treated with NFκB inhibitor MG132 (2.5 μM) for 4 h followed by treatment with various concentrations of DRA11, DRA9, and DRA9S for 72 h. At the end of incubation, cell viability was measured by XTT assay. Data represent the mean±S.D.
Figure 44:
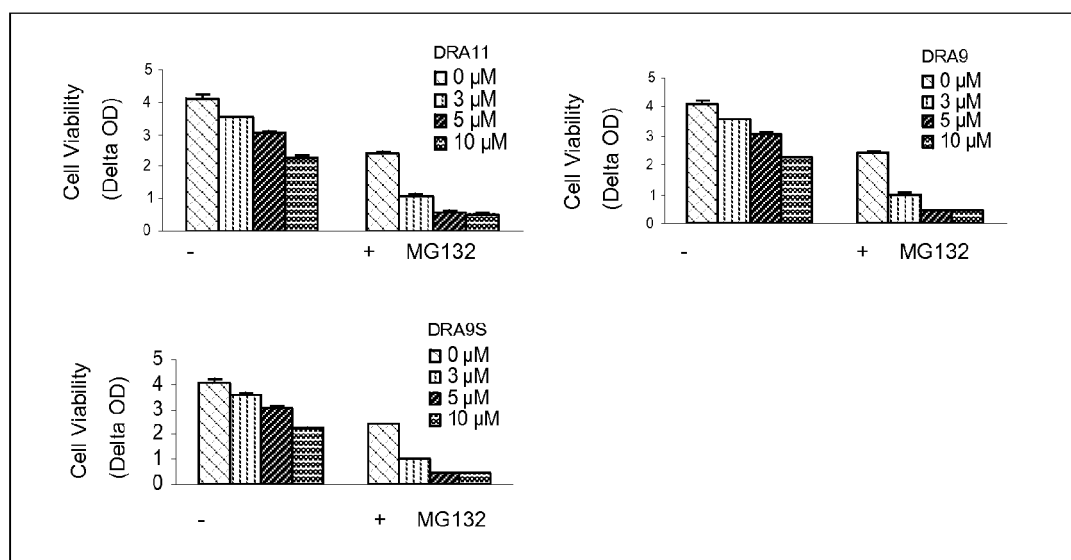
FIG. 44. NFκB inhibitor enhances the inhibitory effects of DRAs on cell viability of mesothelioma MS1 cell line. Mesothelioma MS1 cells were treated with NFκB inhibitor MG132 (2.5 μM) for 4 h followed by treatment with various concentrations of DRA11, DRA9, and DRA9S for 72 h. At the end of incubation, cell viability was measured by XTT assay. Data represent the mean±S.D.
Figure 45:
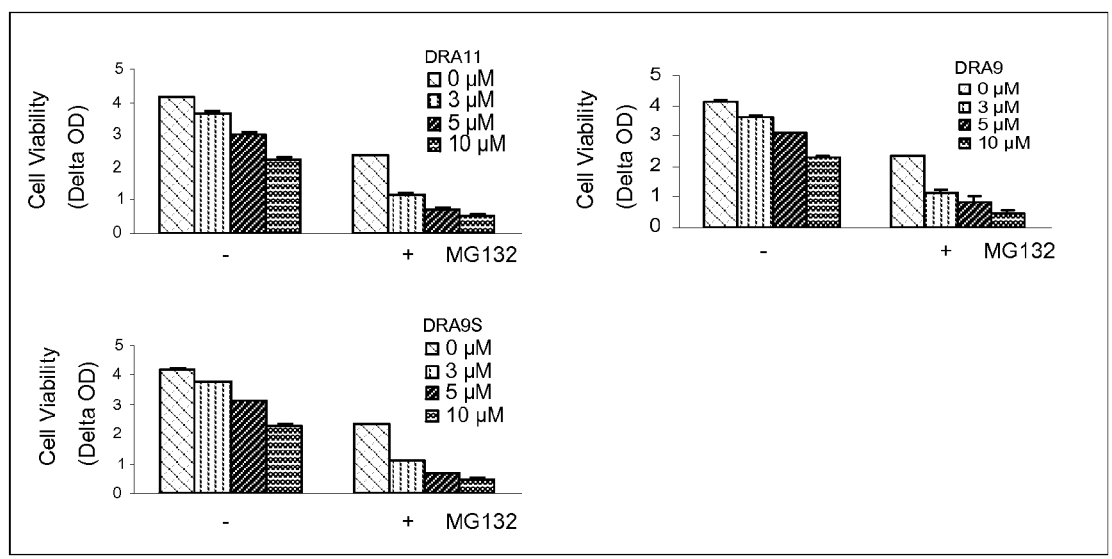
FIG. 45. NFκB inhibitor enhances the inhibitory effects of DRAs on cell viability of mesothelioma REN cell line. Mesothelioma REN cells were treated with NFκB inhibitor MG132 (2.5 μM) for 4 h followed by treatment with various concentrations of DRA11, DRA9, and DRA9S for 72 h. At the end of incubation, cell viability was measured by XTT assay. Data represent the mean±S.D.
Figure 46:
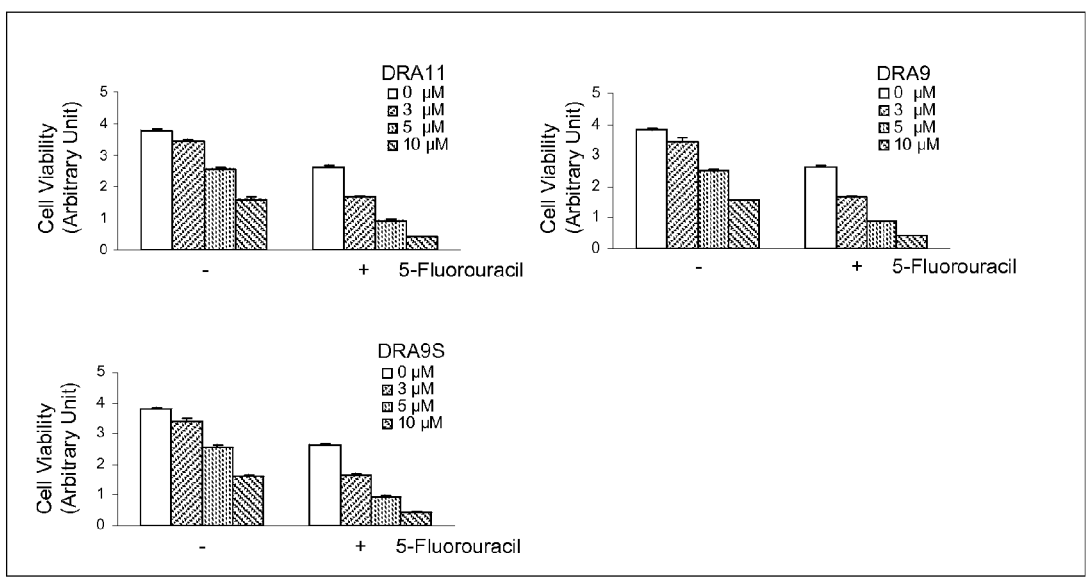
FIG. 46. Interactive effects of death receptor agonists and 5-fluorouracil on cell viability of mesothelioma MS1 cell line. Mesothelioma MS1 cells were treated with various concentrations DRA11, DRA9, and DRA9S in the presence or absence of 5-fluorouracil (5 μM) for 72 h. At the end of incubation, cell viability was measured by XTT assay. Data represent the mean±S.D.
Figure 47:
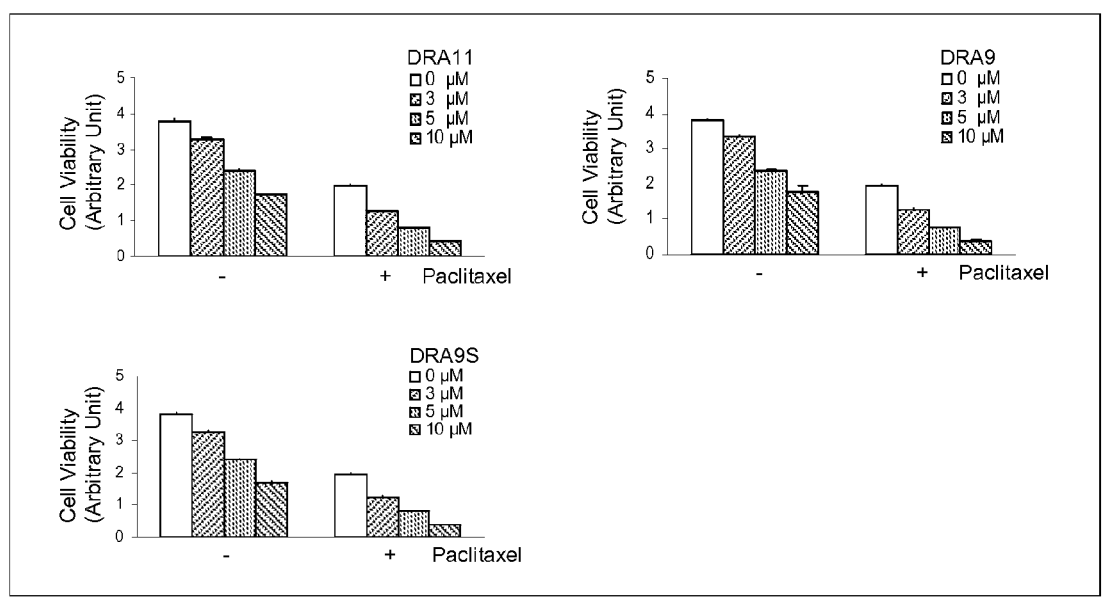
FIG. 47. Interactive effects of death receptor agonists and paclitaxel on cell viability of mesothelioma MS1 cell line. Mesothelioma MS1 cells were treated with various concentrations DRA11, DRA9, and DRA9S in the presence or absence of paclitaxel (10 μM) for 72 h. At the end of incubation, cell viability was measured by XTT assay. Data represent the mean±S.D.
Figure 48:
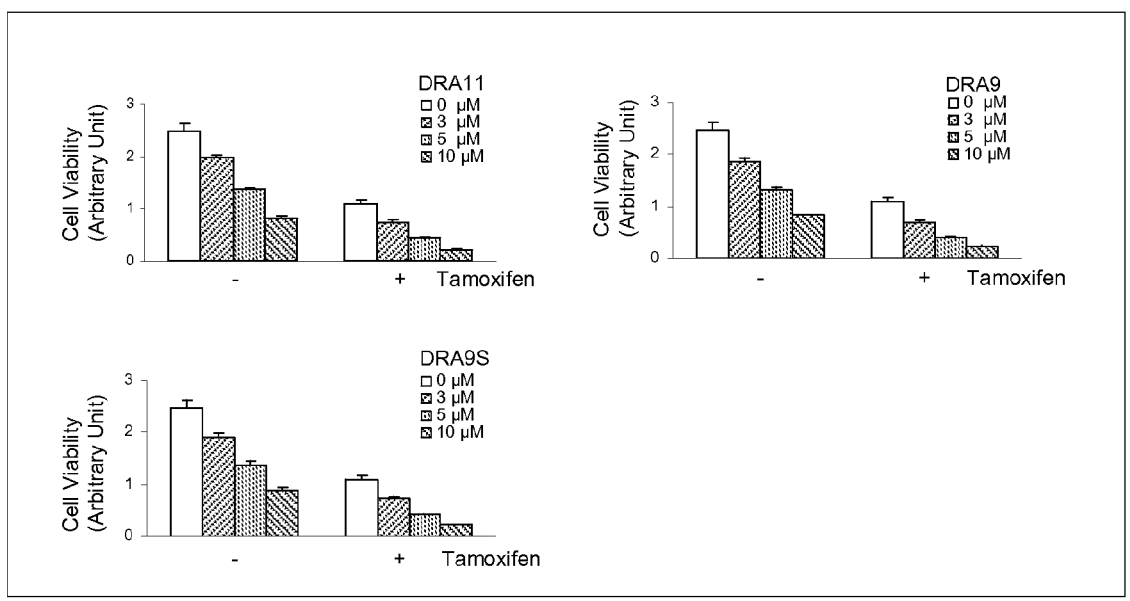
FIG. 48. Interactive effects of death receptor agonists and tamoxifen on cell viability of mesothelioma MS1 cell line. Mesothelioma MS1 cells were treated with various concentrations DRA11, DRA9, and DRA9S in the presence or absence of tamoxifen (10 μM) for 72 h. At the end of incubation, cell viability was measured by XTT assay. Data represent the mean±S.D.
Figure 49:
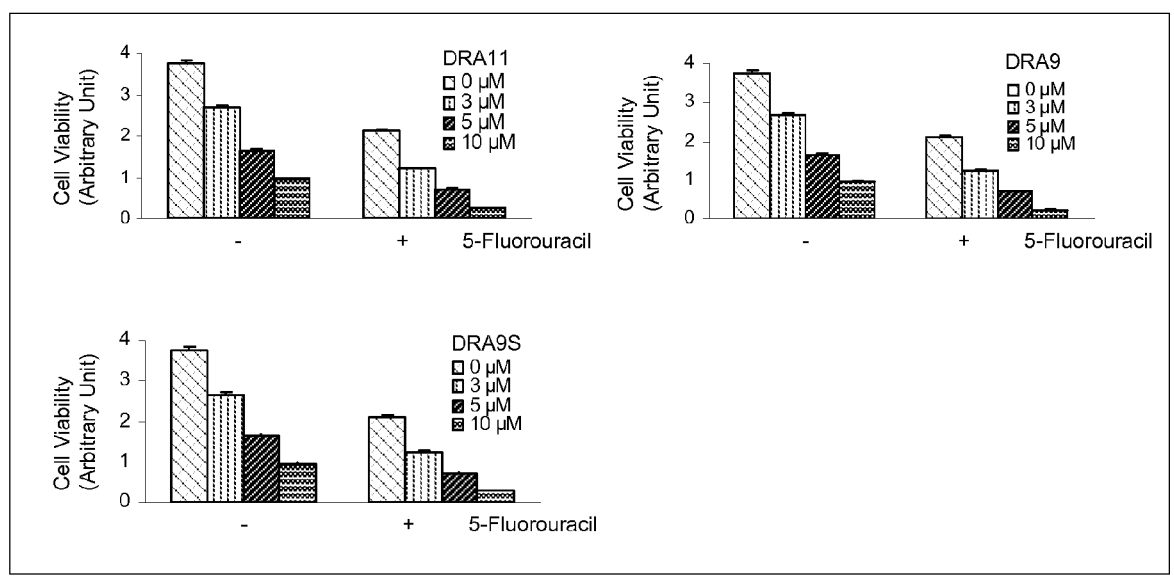
FIG. 49. Interactive effects of death receptor agonists and 5-fluorouracil on cell viability of mesothelioma M33K cell line. Mesothelioma M33K cells were treated with various concentrations DRA11, DRA9, and DRA9S in the presence or absence of 5-fluorouracil (5 μM) for 72 h. At the end of incubation, cell viability was measured by XTT assay. Data represent the mean±S.D.
Figure 50:
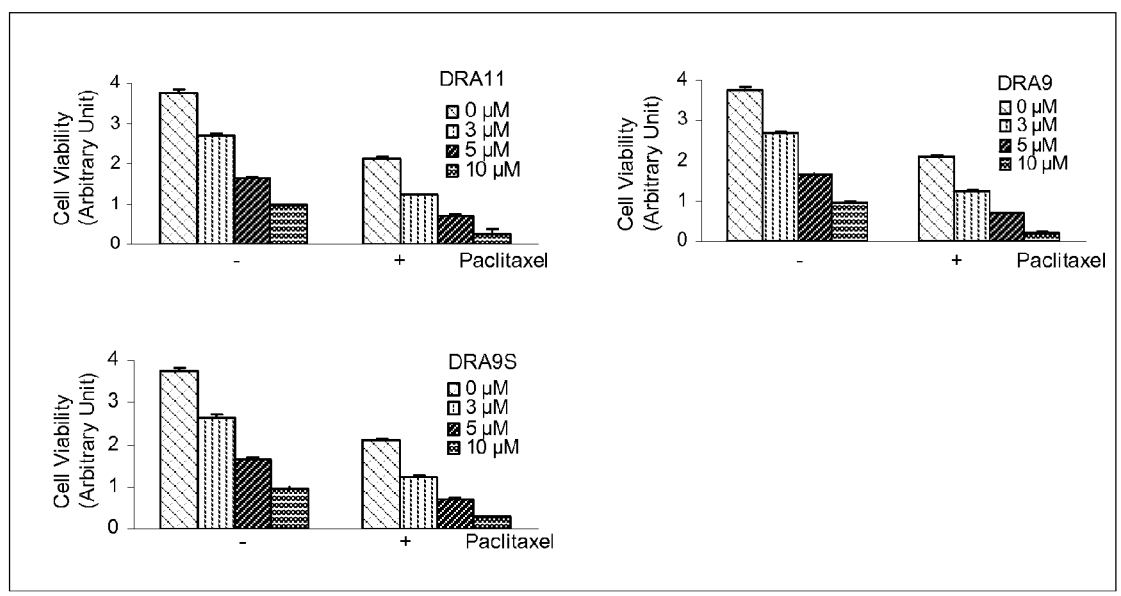
FIG. 50. Interactive effects of death receptor agonists and paclitaxel on cell viability of mesothelioma M33K cell line. Mesothelioma M33K cells were treated with various concentrations DRA11, DRA9, and DRA9S in the presence or absence of paclitaxel (10 μM) for 72 h. At the end of incubation, cell viability was measured by XTT assay. Data represent the mean±S.D.
Figure 51:
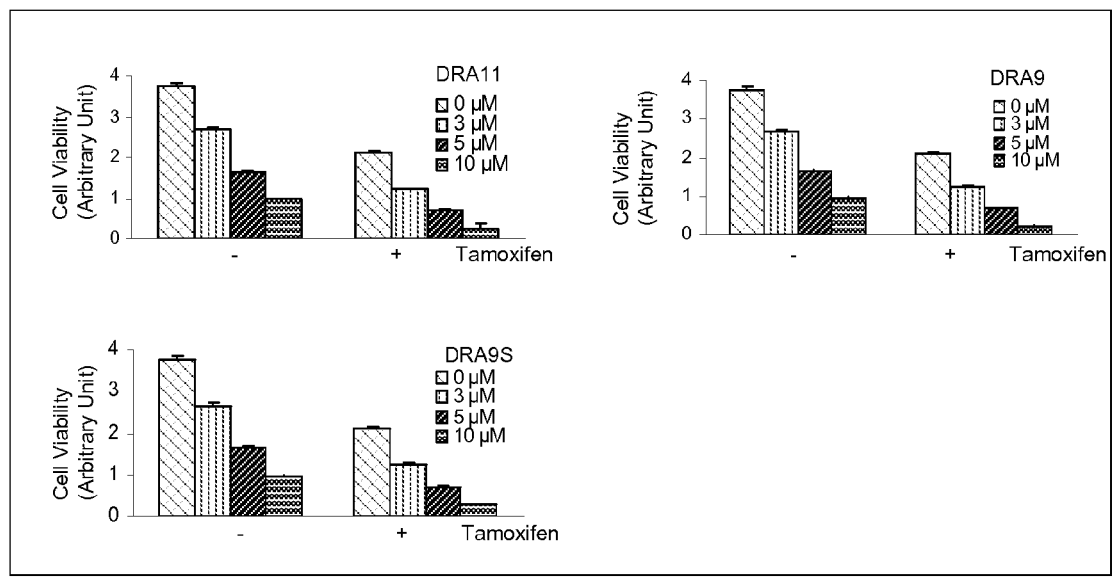
FIG. 51. Interactive effects of death receptor agonists and tamoxifen on cell viability of mesothelioma M33K cell line. Mesothelioma M33K cells were treated with various concentrations DRA11, DRA9, and DRA9S in the presence or absence of tamoxifen (10 μM) for 72 h. At the end of incubation, cell viability was measured by XTT assay. Data represent the mean±S.D.
Figure 52:
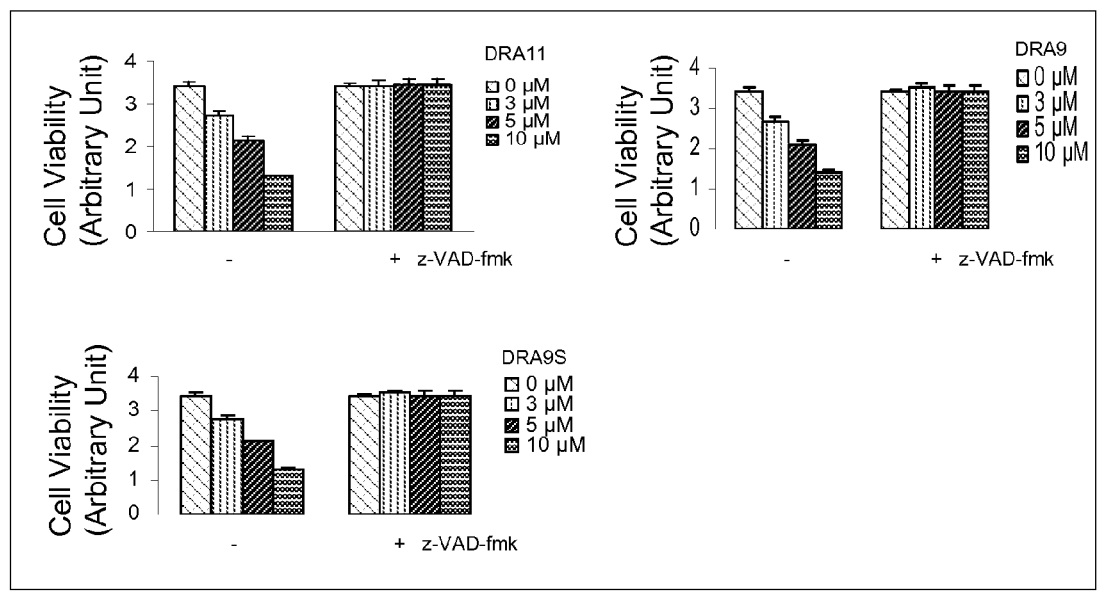
FIG. 52. Pan caspase inhibitor (z-VAD-fmk) blocks the inhibitory effects of DRA11, DRA9 and DRA9S on cell viability of mesothelioma M9K cell line. M9K cells were pretreated with either control peptide (10 μM) or pan caspase inhibitor (z-VAD-fmk, 25 µM) for 2 h, followed by treatment with various doses of DRA11, DRA9 and DRA9S for 72 h. At the end of incubation, cell viability was measured by XTT assay. Data represent the mean±S.D.
Figure 53:
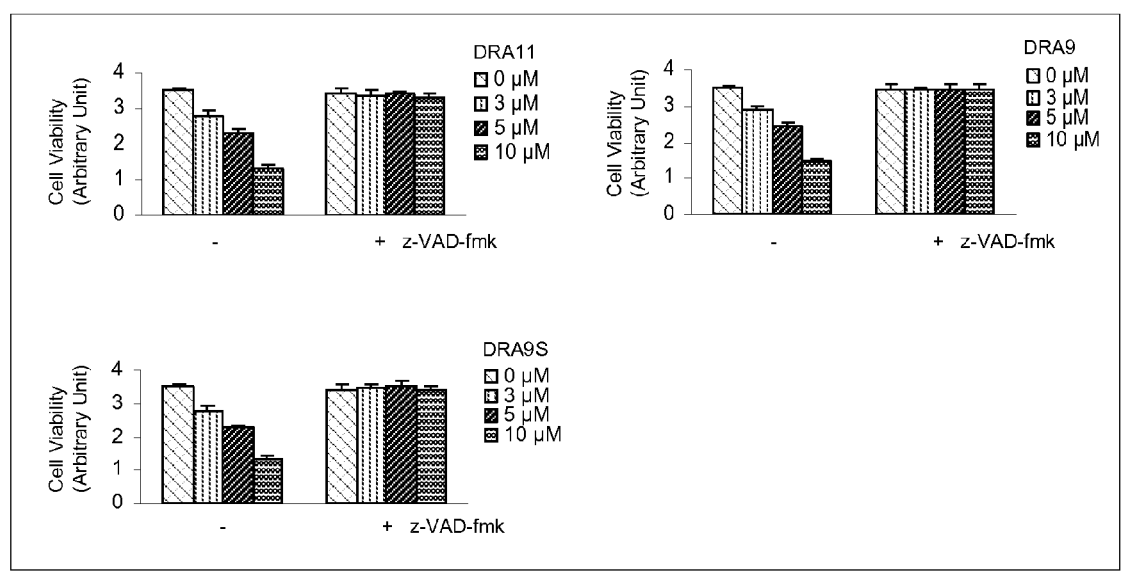
FIG. 53. Pan caspase inhibitor (z-VAD-fmk) blocks the inhibitory effects of DRA11, DRA9 and DRA33S on cell viability of mesothelioma M33K cell line. M33K cells were pretreated with either control peptide (10 µM) or pan caspase inhibitor (z-VAD-fmk, 25 µM) for 2 h, followed by treatment with various doses of DRA11, DRA9 and DRA9S for 72 h. At the end of incubation, cell viability was measured by XTT assay. Data represent the mean±S.D.
Figure 54:
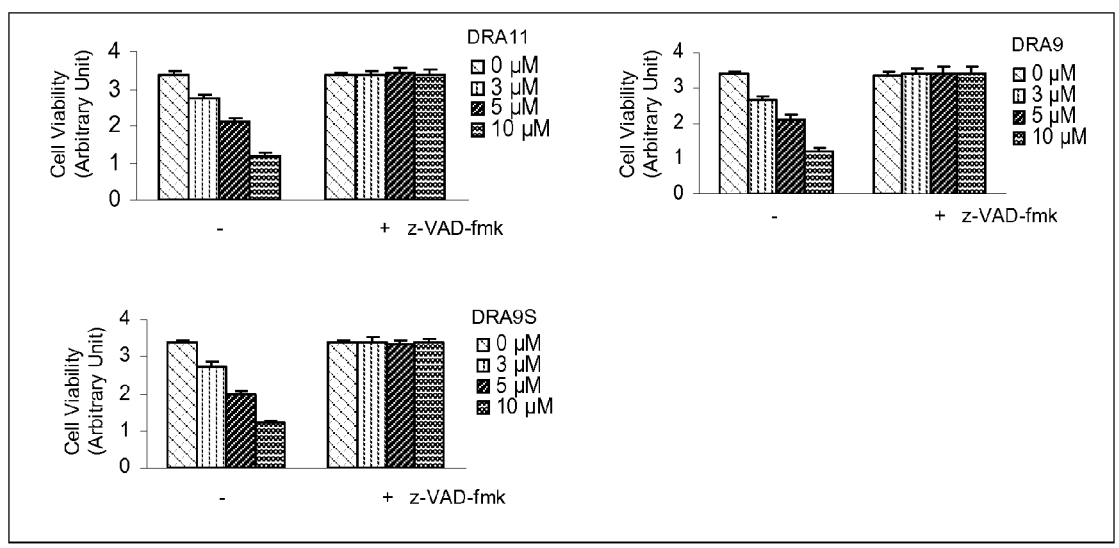
FIG. 54. Pan caspase inhibitor (z-VAD-fmk) blocks the inhibitory effects of DRA11, DRA9, and DRA33S on cell viability of mesothelioma MS1 cell line. MS1 cells were pretreated with either control peptide (10 µM) or pan caspase inhibitor (z-VAD-fmk, 25 µM) for 2 h, followed by treatment with various doses of DRA11, DRA9 and DRA9S for 72 h. At the end of incubation, cell viability was measured by XTT assay. Data represent the mean±S.D.
Figure 55:
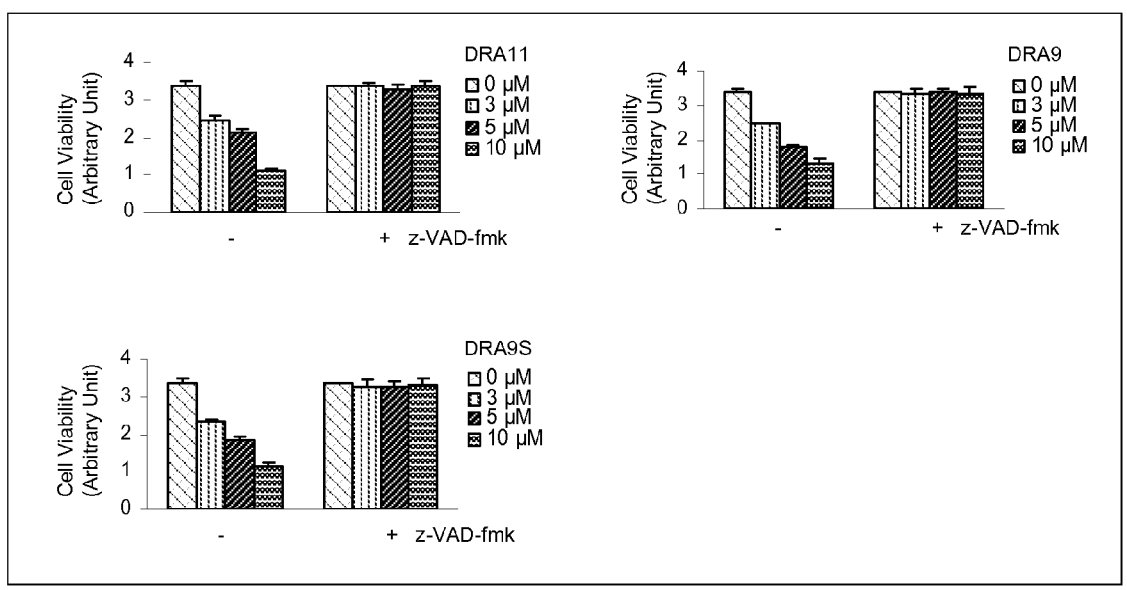
FIG. 55. Pan caspase inhibitor (z-VAD-fmk) blocks the inhibitory effects of DRA11, DRA9, and DRA33S on cell viability of mesothelioma REN cell line. REN cells were pretreated with either control peptide (10 µM) or pan caspase inhibitor (z-VAD-fmk, 25 µM) for 2 h, followed by treatment with various doses of DRA11, DRA9 and DRA9S for 72 h. At the end of incubation, cell viability was measured by XTT assay. Data represent the mean±S.D.
Figure 56:
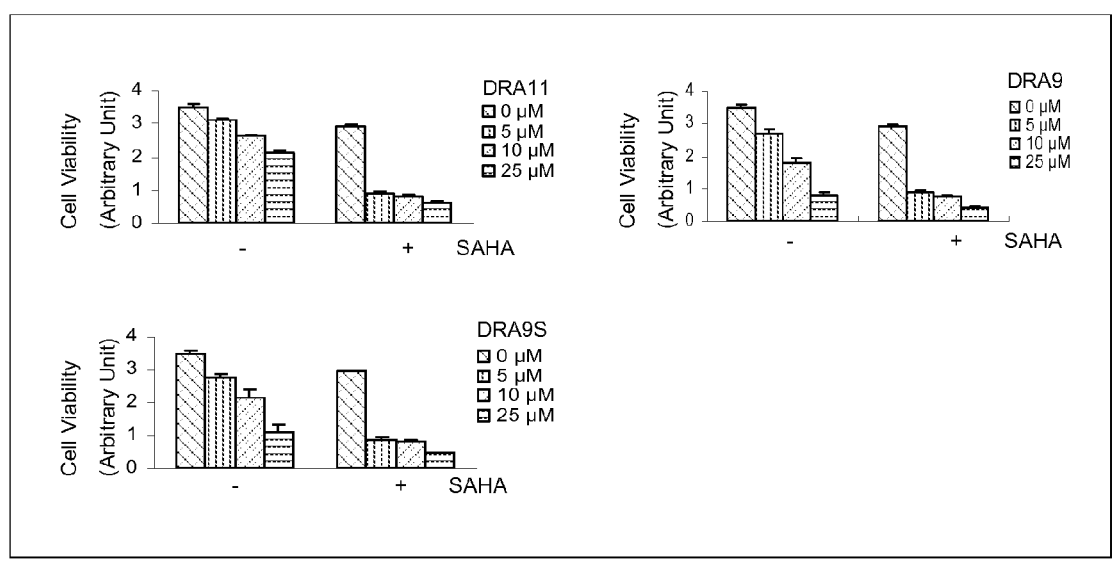
FIG. 56. Interactive effects of death receptor agonists and histone deacetylase inhibitor SAHA on cell viability of mesothelioma M33K cell line. Mesothelioma M33K cells were treated with various concentrations DRA11, DRA9, and DRA9S in the presence or absence of SAHA (5 µM) for 72 h. At the end of incubation, cell viability was measured by XTT assay. Data represent the mean±S.D.
Figure 57:
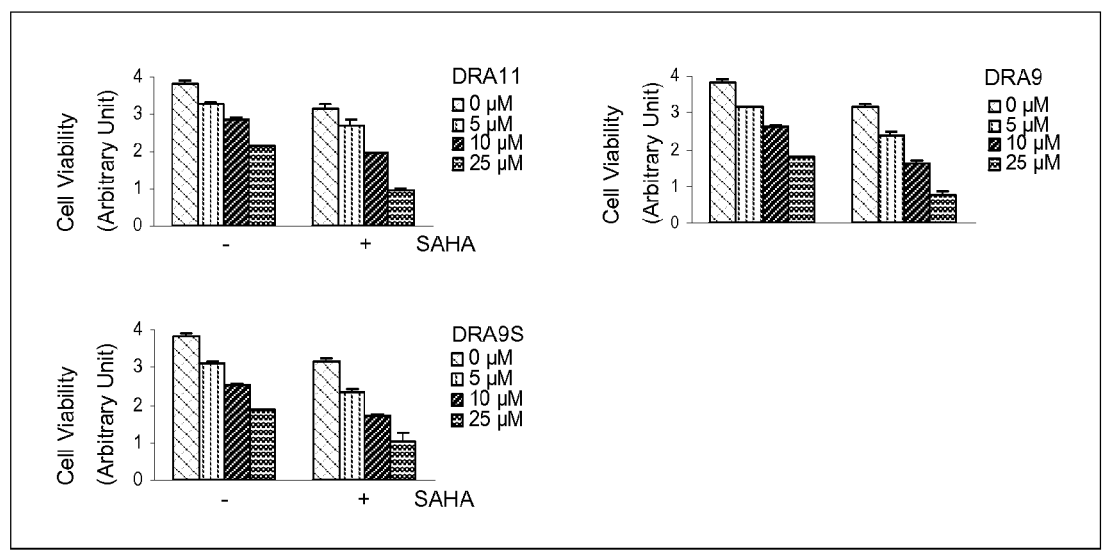
FIG. 57. Interactive effects of death receptor agonists and histone deacetylase inhibitor SAHA on cell viability of mesothelioma MS1 cell line. Mesothelioma MS1 cells were treated with various concentrations DRA11, DRA9, and DRA9S in the presence or absence of SAHA (5 µM) for 72 h. At the end of incubation, cell viability was measured by XTT assay. Data represent the mean±S.D.
Figure 58:
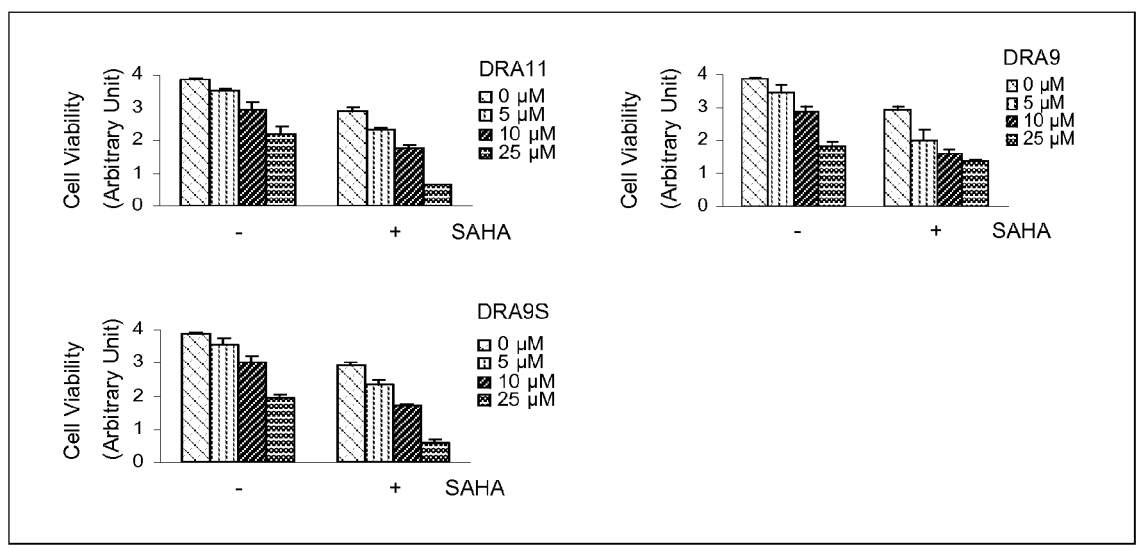
FIG. 58. Interactive effects of death receptor agonists and histone deacetylase inhibitor SAHA on cell viability of mesothelioma REN cell line. Mesothelioma REN cells were treated with various concentrations DRA11, DRA9, and DRA9S in the presence or absence of SAHA (5 µM) for 72 h. At the end of incubation, cell viability was measured by XTT assay. Data represent the mean±S.D.
Figure 59:
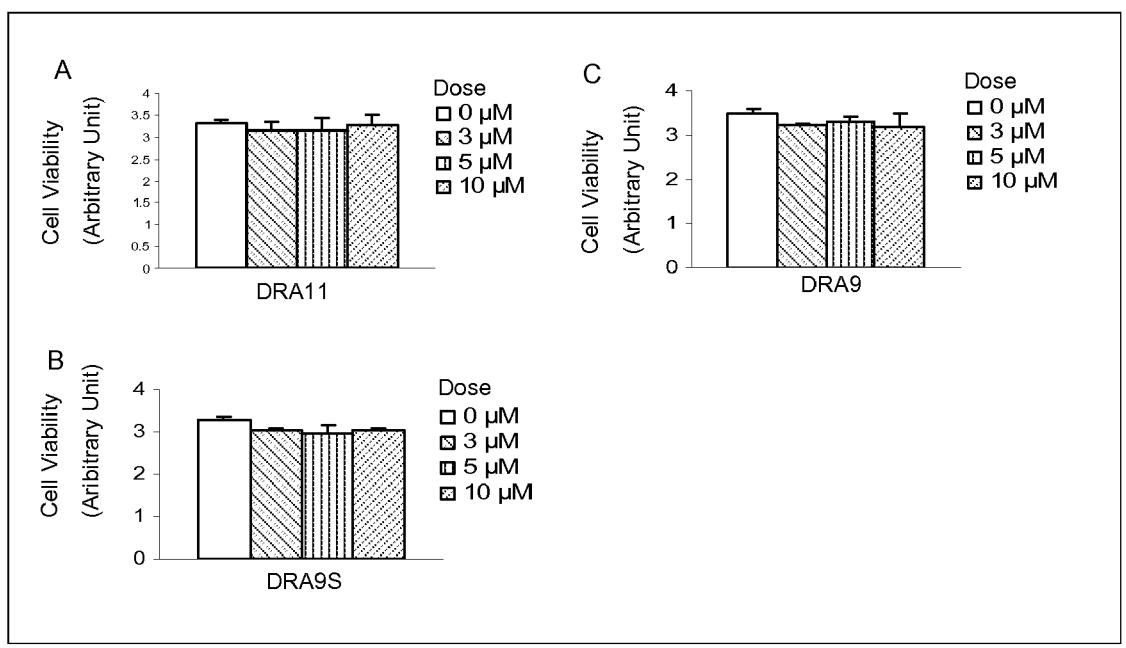
FIGS. 59 A, B & C. DRAs has no effect on cell viability of normal human hepatocytes. Normal human hepatocytes were incubated with various concentrations of DRA11 (0, 1, 3, 5 and 10 µM) (FIG. 59A), DRA9S (0, 1, 3, 5 and 10 µM) (FIG. 59B), and DRA9 (0, 1, 3, 5 and 10 µM) (FIG. 59C) for 72 h. At the end of incubation period, cell viability was measured by XTT assay.
Figure 60:
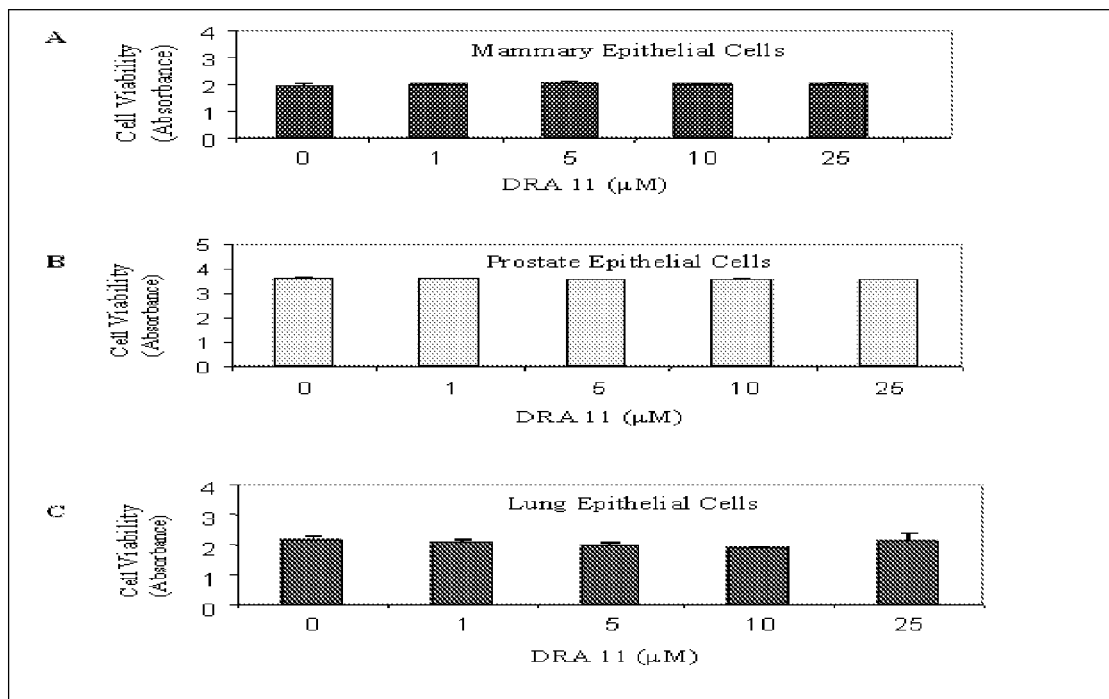
FIGS. 60 A, B & C. DRAs has no effect on cell viability of human normal mammary, prostate and lung epithelial cells. Human normal mammary (FIG. 60A), prostate (FIG. 60B) and lung (FIG. 60C) epithelial cells were treated with DRA11 (0-25 µM) for 72 h, and cell viability was measured by XTT assay.
Figure 61:
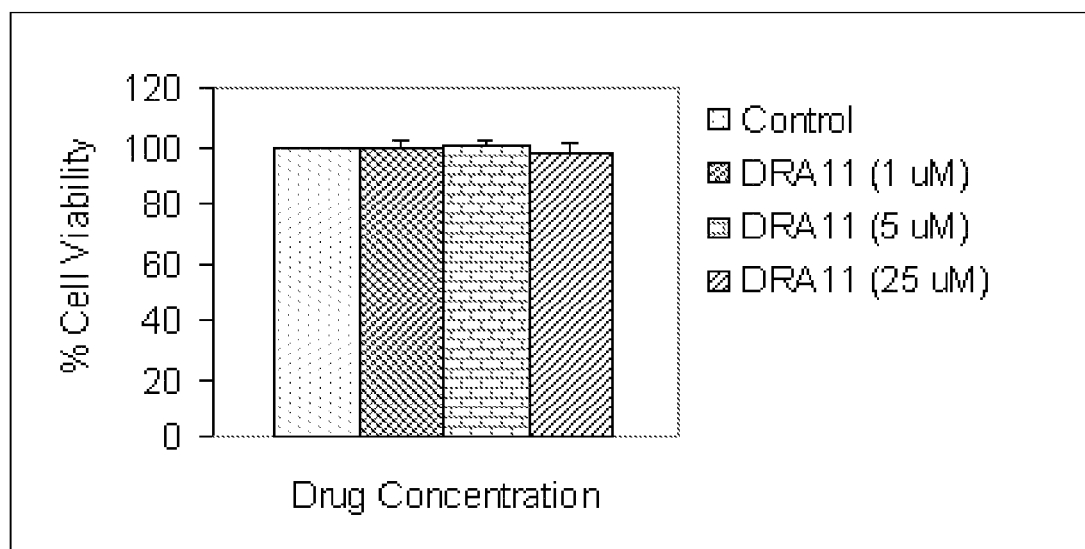
FIG. 61. DRA11 has no effect on cell viability in normal T lymphocytes. CD3+ normal T lymphocytes derived from peripheral blood of healthy humans were isolated and seeded in 96-well plates. Cells were treated with various concentrations of DRA11 (0, 1, 5 and 25 µM) for 48 h and call viability was measured by XTT assay.
Figure 62:
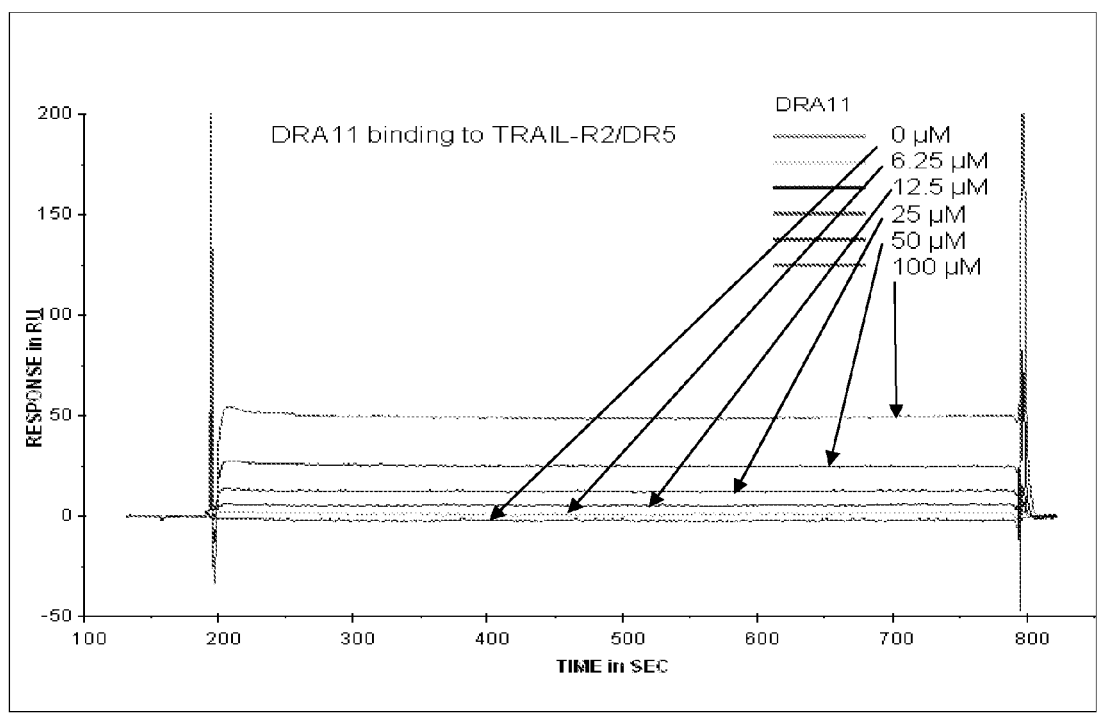
FIG. 62. DRA11 binds directly to TRAIL-R2/DR5 receptors. The binding of DRA11 to the purified DR5 protein was examined, using a Biacore 3000 system for real-time biomolecular interaction analysis using surface plasmon resonance (SPR) technology. This technique monitors the formation and dissociation of biomolecular complexes on a sensor surface as the interaction occurs. TRAIL-R2/DR5 protein was immobilized on a Biacore CM5 biosensor chip by amine coupling. DR5 at 200 µg/ml in 10 mM sodium acetate buffer, pH 4.0, is used for immobilization on the sensor chip. DR5 immobilization was aimed at a pre-concentration of 1000 resonance units. Various concentrations of DRA11 was then flowed over the immobilized DR5 surface in a degassed 25 mM HEPES buffer pH 7.9 containing 150 mM NaCl, 3 mM EDTA, and 0.005% P-20 surfactant at 25° C. at a flow rate of 5 µl/min for 10 min which gives sufficient time to reach a plateau and achieve a steady baseline. The steady state plateau RU response from sensograms for various concentrations of DRA11 was calculated using Biacore evaluation software. DR5 protein was purified and immobilized on a CM5 chip and various concentrations of DRA11 (0-100 µM) was allowed to pass over the chip. The binding was measured using Biacore equipment. DRA11 binds directly to the TRAIL-R2/DR5 protein in a dose-dependent manner.

Another aspect of this invention provides a method of screening for potential TRAIL Death Receptor Agonists/Activators (DRAs). In certain embodiments, this method selects for those molecules capable of docking effectively to the structural domains shown in FIG. 32.

Once lead compounds have been identified through the above screening method cell viability assays may be performed, which may be high throughput. In some embodiments, the lead compounds may also be modified prior to the assay. In certain embodiments, an XTT assay may be used; this assay is based on the cleavage of the yellow tetrazolium salt XTT (sodium 3'-[1-(phenylamino-carbonyl)-3,4-tetrazolium]-bis(4-methoxy-6-nitro) benzene sulfonic acid hydrate) by mitochondrial dehydrogenases of viable cells, which results in the formation of an orange formazan dye. This step can be followed with additional steps such as mechanistic studies and/or xenograft studies. This methodology is discussed in detail in Kandasamy, and Srivastava (2002), which is incorporated herein by reference.

V. Administration of TRAIL Death Receptor Agonists/Activators

The compounds of the present invention may be administered, e.g., orally or by injection (e.g. subcutaneous, intravenous, intraperitoneal, etc.) Depending on the route of administration, the active compound may be coated in a material to protect the compound from the action of acids and other natural conditions which may inactivate the compound. In the case of cancer therapy, the agents may be administered intratumorally, circumferential to a tumor mass, locally to the tumor vasculature or lypmphatic system, regionally or systemically. They may also be administered to a resected tumor bed, for example, by syringing or by a post-operative catheter with continuous perfusion/infusion.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

Compounds of the invention may also be formulated for local administration, e.g., for topical administration to the skin or mucosa, for topical administration to the eye, for delivery to the lungs by inhalation, or by incorporation into a biocompatible matrix for controlled release to a specified site over an extended period of time (e.g., as an active ingredient in a drug-eluting cardiac stent). In certain cases significant systemic concentrations may also be achieved by these routes of administration (e.g., via pulmonary or transmucosal delivery).

Active compounds are administered at a therapeutically effective dosage sufficient to treat a condition associated with a condition in a patient. A "therapeutically effective amount" preferably reduces the amount of symptoms of the condition in the infected patient by at least about 20%, more preferably by at least about 40%, even more preferably by at least about 60%, and still more preferably by at least about 80% relative to untreated subjects. For example, the efficacy of a compound can be evaluated in an animal model system that may be predictive of efficacy in treating the disease in humans, such as the model systems shown in the examples and drawings.

VI. DRAs, Uses and Mechanisms

The methods and compositions of the present invention have utility for prevention and treatment of diseases such as cancer. One aspect of the invention provides small molecule-based drugs that bind to death receptors TRAIL-R1/DR4 and/or TRAIL-R2/DR5 and induce apoptosis in cancer cells, while sparing normal cells. Induction of cells death may proceed by a mechanism comprising apoptosis and/or autophagy. In another aspect of this invention the TRAIL Death Receptor Agonists/Activators (DRAs) of the present invention, induce apoptosis through caspase-8 and caspase-3 activation. For example, DRAs may be used to kill malignant cells which express death receptors TRAIL-R1/DR4 and/or TRAIL-R2/DR5. For example, the DRAs of the present invention may used for the treatment of breast, prostate, colon, pancreatic, ovarian, lung, and brain cancers, leukemia, lymphoma, multiple myeloma, and mesothelioma. In a further aspect of this invention, DRAs form an active death-inducing signaling complex (DISC). For example, in certain embodiments, the DRAs of the present invention may be used to bind to TRAIL-R1/DR4 and/or TRAIL-R2/DR5, to form active TRAIL-DISC (death-associated signaling complex) and induce apoptosis through caspase-8 activation and PARP cleavage. In further embodiments, these compounds are effective in inhibiting the growth of established cancers, such as breast, prostate and pancreatic tumors.

In certain embodiments, the DRAs of the present invention are more effective at inducing apoptosis than TRAIL or TRAIL receptor agonistic antibodies. In further embodiments of this invention, and as demonstrated by the examples below, DRAs do not induce apoptosis in normal cells, such as normal human breast, prostate and lung epithelial cells. Cancer cells express high levels of death receptors DR4 and/DR5 and low levels of decoy receptors (DcR1 and DcR2) compared to normal human epithelial cells. Therefore, in another aspect of the invention, DRAs may be used to induce caspase-dependent apoptosis in a variety of cancer cells, while sparing human normal mammary and prostate epithelial cells. The efficacy of specific compounds of this invention has been demonstrated in xenograft models of nude mice (see examples, below).

The practice of the present invention will employ, unless otherwise indicated, conventional techniques of cell biology, cell culture, molecular biology, microbiology, recombinant DNA, medicine, pharmacology and immunology, which are within the skill of the art. Such techniques are explained fully in the literature. See, for example, Sambrook et al., 1989; Ausubel et al., 1994; Glover, 1985; Gait, 1984; U.S. Pat. No. 4,683,195; Hames and Higgins, 1985; Mayer and Walker, 1988; Weir and Blackwell, 1986.

A. Binding of DRAs to TRAIL/APO-2L Receptors

Recent studies have identified four distinct cell surface TRAIL receptors: (a) TRAIL-R1 (DR4) (Pan et al., 1997a,b); (b) TRAIL-R2 (DR5/TRICK2/KILLER) (Pan et al., 1997b; Schneider et al., 1997; Screaton et al., 1997; Sheridan et al., 1997; Walczak et al., 1997; Wu et al., 1997); (c) TRAIL-R3 (DcR1/TRID/LIT) (Degli-Esposti et al., 1997b; Schneider et al., 1997); and (d) TRAIL-R4 (DcR2/TRUNDD) (Degli-Esposti et al., 1997a; Marsters et al., 1997; Pan et al., 1998) (see FIG. 1). All these receptors have high sequence homology in their extracellular domains. A fifth receptor is the soluble osteoprotegerin, which may act as a decoy receptor and does not induce apoptosis (Emery et al., 1998). While TRAIL binds to all the receptors, the function of their intracellular domains is not uniform. The intracellular domains of TRAIL-R1/DR4 and TRAIL-R2/DR5 have been found to be essential for induction of apoptosis following receptor ligation (Pan et al., 1997b; Suliman et al., 2001; Walczak et al., 1997). In one aspect of the invention, the DRAs of the present invention bind to the intracellular domains of TRAIL-R1/DR4 and TRAIL-R2/DR5 receptors.

TRAIL-R3/DcR1 and TRAIL-R4/DcR2/TRUNDD lack a functional cytoplasmic domain (Degli-Esposti et al., 1997a,b; Marsters et al., 1997; Pan et al., 1998; Schneider et al., 1997); TRAIL-R3 and TRAIL-R4 may serve as 'decoys' that compete with TRAIL-R1/TRAIL-R2 for binding to the TRAIL. Overexpression of either DcR1 or 121 DcR2 protein confers protection against TRAIL-induced apoptosis (Pan et al., 1997a; Sheridan et al., 1997). In certain embodiments, it is contemplated that the DRAs of the present invention will bind preferentially to the intracellular domains of TRAIL-R1/DR4 and TRAIL-R2/DR5 receptors. In further embodiments, it is contemplated that the DRAs of the present invention do not bind to TRAIL-R3 and TRAIL-R4 at all. In other embodiments, the DRAs of the present invention may only exhibit limited binding to TRAIL-R3 and TRAIL-R4.

B. Recruitment of FADD

TRAIL-R1/DR4 and TRAIL-R2/DR5 contain an intracellular globular protein interaction domain called death domain (DD). Studies have shown that association of death receptors with their cognate ligands results in receptor trimerization, and recruitment of adaptor protein called Fas-associated death domain (FADD) (Ashkenazi and Dixit, 1998). FADD consists of two protein interaction domains: a death domain and a death effector domain (DED) (Ashkenazi and Dixit, 1998; Schulze-Osthoff et al., 1998; Suliman et al., 2001). FADD binds to the receptor through interactions between DDs and to pro-caspase-8 or pro-caspase-10 through DED interactions to form a complex at the receptor called the death-inducing signaling complex (DISC). Recruitment of caspase-8 or caspase-10 through FADD leads to its autocleavage and activation. Active caspase-8 or caspase-10, in turn, activates effector caspases such as caspase-3 causing the cell to undergo apoptosis by digesting several protein substrates (Ashkenazi and Dixit, 1998; Schulze-Osthoff et al., 1998; Suliman et al., 2001). This ultimately results in an irreversible commitment of cells to undergo apoptosis (Ashkenazi and Dixit, 1998; Kischkel et al., 2001; Schulze-Osthoff et al., 1998; Suliman et al., 2001). This invention contemplates that association of death receptors with the DRAs of the present invention will result in receptor trimerization, and recruitment of adaptor protein called Fas-associated death domain (FADD) (Ashkenazi and Dixit, 1998). In one aspect of the invention, the DRAs of the present invention recruit FADD to DISC, thereby activating caspase-8 or caspase-10 to induce apoptosis.

C. Caspase Cascade in DRA-Induced Apoptosis

Caspases are a group of cysteine proteases requiring specifically the presence of aspartate at the cleavage site. The caspase gene family has at least 14 mammalian members (Alnemri et al., 1996). These are initially expressed as single-chain zymogens, which upon apoptotic signaling are activated by proteolytic processing, either by autoactivation, transactivation, or by cleavage by other caspases (Green, 1998; Wolf and Green, 1999). Once activated, they proteolytically cleave a multitude of cellular proteins, leading to apoptosis. Therefore, the caspase activation is a key regulatory point in the commitment of the cell to apoptosis. In certain embodiments, the present invention provides for methods leading to caspase activation.

Figure 2:
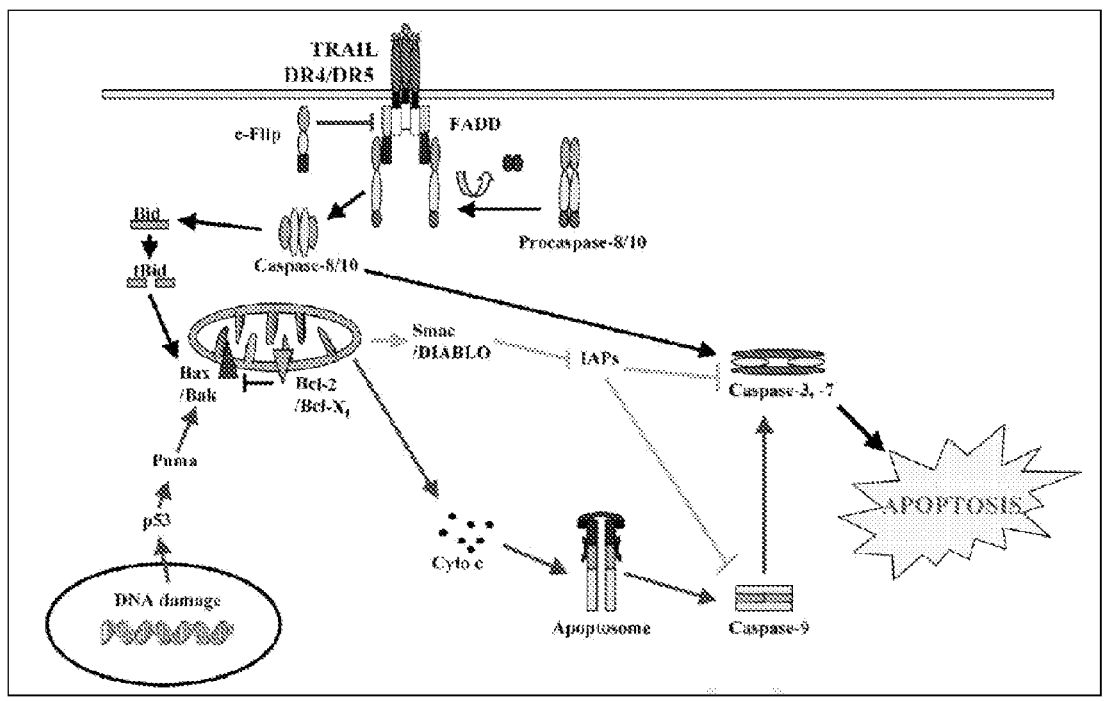
FIG. 2. Intracellular mechanism of TRAIL-induced apoptosis. Apoptosis pathways activated by TRAIL and mitochondria are depicted. Ligation of death receptors by TRAIL leads to formation of DISC which in turn initiates two pathways: (a) activation of caspase-8 or caspase-10 causes activation of effector caspases such as caspase-3, and (b) activation of Bid to truncated Bid by caspase-8 or caspase-10 results in an engagement and disruption of mitochondria. Cytochrome c along with Apaf-1 and dATP forms apoptosomes which activate caspase-9. Active forms of caspase-8 and caspase-9 initiate a cascade of effector caspases such as caspase-3 and caspase-7. Activated caspases cleaved several substrates leading to apoptosis. Bcl-2 and BCl-XL antagonize the effects of Bax and Bak at the level of mitochondria. IAPs inhibit caspase-3, caspase-7 and caspase-9 activity. Smac/DIABLO induces apoptosis by inhibiting IAPs functions. In response to DNA damage, p53 induces PUMA which may trigger activation of Bax and/or Bak at the mitochondria.

Two main pathways that activate caspases, the primary drivers of apoptosis, have been identified (FIG. 2). TRAIL-mediated signaling involves both of these pathways (Krammer, 1998, 1999; Suliman et al., 2001). After initial activation of caspase-8 or caspase-10 by TRAIL-DISC, divergence of signal occurs in two directions: (1) direct activation of caspase-3 without the involvement of mitochondria; and (2) formation of apoptosomes (mitochondrial proteins, dATP and Apaf-1) which lead to activation of caspase-9 (Gross et al., 1999; Li et al., 1998; Luo et al., 1998; Suliman et al., 2001). These two pathways appear to converge on caspase-3. In a mechanism not entirely understood, cytochrome c and dATP/ATP act as cofactors and stimulate Apaf-1 self-oligomerization. Once activated, caspase-9 can activate effector caspases-3 and -7 that finally dismantle the cell (Green, 1997; Srinivasula et al., 1998; Zou et al., 1997). The decline in mitochondrial membrane potential ($\Delta\psi_m$) can be blocked by caspase-8 inhibitor, but not by caspase-9 inhibitor (Kandasamy et al., 2003; Keogh et al., 2000; Suliman et al., 2001). Thus, caspase-8 links the apoptotic signal from the activated TRAIL-DR to mitochondria leading to dissipation of $\Delta\psi m$ and directly to downstream apoptosis-executing caspases. Cleavage of caspase-3 occurs following activation of either pathway (FIG. 2). In certain embodiments, the methods of the present invention may be used to activate caspase-8, caspase-10, or both.

D. Mitochondria and DRA Signaling

Apoptosis can be induced by both cell-intrinsic (mitochondria-dependent) and cell-extrinsic (death receptor) pathways (Green, 1998; Kandasamy et al., 2003; Singh et al., 2003; Fulda and Debatin, 2003). Membrane depolarization and subsequent loss of cytochrome c and other cofactors from the mitochondrial intermembrane space appear to be the early event in the mitochondrial dependent pathway (Green, 1998; Kroemer et al., 1998). Permeabilization of the outer mitochondrial membrane is controlled by members of the Bcl-2 family (Desagher and Martinou, 2000). The anti-apoptotic members such as Bcl-2 or Bcl-XL inhibit the release of mitochondrial apoptogenic factors (AIF, Smac/DIABLO, Omi/HtrA2, endonuclease G, and cytochrome c) whereas the proapoptotic members (e.g. Bax and Bak) trigger the release (Du et al., 2000; Hegde et al., 2002; Kandasamy et al., 2003; Susin et al., 1999; Suzuki et al., 2001; Verhagen et al., 2000). It is not clear how Bcl-2 family members modulate permeabilization of the outer mitochondrial membrane and also preserve mitochondrial function. Overexpression of Bcl-2 or Bcl-XL does not block (Keogh et al., 2000; Kim et al., 2001) TRAIL-induced apoptosis in lymphoid cells, suggesting cancer cells that have already acquired resistance to chemotherapeutic drugs by Bcl-2 or Bcl-XL can be killed by TRAIL.

There are important mechanistic similarities between the DRAs of the present invention and TRAIL. Therefore, it is contemplated that in certain embodiments, overexpression of Bcl-2 or Bcl-XL will not block DRA-induced apoptosis in lymphoid cells, thereby allowing cancer cells that have already acquired resistance to chemotherapeutic drugs by Bcl-2 or Bcl-XL to be killed by the DRAs of the present invention. Thus, the DRAs of the present invention may be promising candidates for the treatment of patients carrying drug-resistant tumors.

Bid seems to promote death by activating Bax and Bak, and it might also inactivate pro-survival relatives (Wang et al., 1996). Bid might act by inducing Bax and Bak to oligomerize and form pores in the mitochondrial membrane, but the oligomers do not contain Bid (Wei et al., 2000), which seems to form homotrimers in the membrane (Grinberg et al., 2002). Bid activation indicates the requirement for caspase amplification in the TRAIL-DR pathway by a mechanism reported to take place through translocation of activated Bid to mitochondria, oligomerization of Bax and Bak, facilitating cytochrome c release and activation of caspase-9 and then caspase-3 and/or caspase-7 leading to apoptosis (Kandasamy et al., 2003; Li et al., 1998; Luo et al., 1998; Suliman et al., 2001). Translocation of Bid to mitochondria results in activation of Bax and Bak, providing a mechanism for cross-talk between the DRs and the intrinsic pathway (Li et al., 1998; Luo et al., 1998). Synergistic activation of caspase-3 by TRAIL appears to be one of the mechanisms of enhanced apoptosis both in vitro and in vivo. Given the mechanistic similarities between DRAs and TRAIL, in some embodiments, the inventors contemplate that DRAs will synergistic activate caspase-3, leading to enhanced apoptosis.

E. TRAIL and Immune Response

The apoptosis-inducing members of the tumor necrosis factor (TNF) family, the so-called death ligands, include, for example, TNF, FasL, and TNF-related apoptosis-inducing ligand (TRAIL). These ligands and their receptors are known to play pivotal roles in the regulation of the immune system, especially via induction of apoptosis in activated lymphocytes (Droin et al., 2003). For example, they have been implicated in the process of activation-induced cell death (AICD) in T lymphocytes, in which repeated antigen stimulation of T cells induces apoptosis through the induction of death ligand expression and sensitization to death receptor-induced apoptosis. The process of death ligand-mediated AICD is one possible mechanism for peripheral deletion, the process whereby expanding clones of activated T cells subsequently decrease in number (Droin et al., 2003). Given the mechanistic similarities between DRAs and TRAIL, in another aspect of the invention, it is contemplated that the DRAs of the present invention will evoke an immune response according to a similar manner as TRAIL.

VII. Combination Therapy

In addition to being used as a monotherapy, the TRAIL Death Receptor Agonists/Activators (DRAs) of the present invention will also find use in combination therapies. Such combination therapies may include the use of anti-inflammatory agents generally, or inhibitors of COX-2 and/or iNOS. Alternatively, the combination may be include a second anti-cancer therapy, as discussed in detail below.

An "anti-cancer" agent is capable of negatively affecting cancer in a patient, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the DRAs and the other agent(s) at the same time. This may be achieved by contacting the cell with a single composition or pharmacological formulation that includes both agents, or by contacting the cell with two distinct compositions or formulations, at the same time, wherein one composition includes the DRAs and the other includes the second agent(s).

Alternatively, the therapy involving DRAs may precede or follow the other agent treatment by intervals ranging from minutes to weeks. In embodiments where the other agent and expression construct are applied separately to the cell, one would generally ensure that a significant period of time did not expire between the time of each delivery, such that the agent and the DRA would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, DRA therapy is "A" and the secondary agent, such as radio- or chemotherapy, is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the TRAIL Death Receptor Agonists/Activators of the present invention to a patient will follow general protocols for the administration of chemotherapeutics, taking into account the toxicity, if any, of the drug. It is expected that the treatment cycles would be repeated as necessary. It also is contemplated that various standard therapies, as well as surgical intervention, may be applied in combination with the described hyperproliferative cell therapies.

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present invention, it is contemplated that DRA therapy could be used similarly in conjunction with chemotherapeutic, radiotherapeutic, or immunotherapeutic intervention, in addition to other pro-apoptotic or cell cycle regulating agents, as discussed below.

A. Sensitization of Cancer Cells

Some breast, prostate, ovarian and lung carcinoma, multiple myeloma and leukemia cells are resistant to apoptosis induced by TRAIL. This resistance may be caused by deregulated expression of antiapoptotic molecules. These data suggest that the use of TRAIL alone may not be viable option to treat these cancers. While the DRAs of the present invention lack many of the structural features of TRAIL, it is contemplated that TRAIL-resistant or DRA-resistant cancer cells can be sensitized to enhance apoptosis induced by the methods of the current invention.

i. Combination of DRAs and Histone Deacetylase Inhibitors

Histone proteins organize DNA into nucleosomes, which are regular repeating structures of chromatin (Marks et al., 2001b). The acetylation status of histones alters chromatin structure, which, in turn, is involved in gene expression (Gregory et al., 2001; Marks et al., 2001b). Two classes of enzymes can affect the acetylation of histones, histone acetyltransferases (HATs) and histone deacetylases (HDACs) (Deckert and Struhl, 2001; Gray and 585 Teh, 2001; Gregory et al., 2001; Khochbin et al., 2001). Altered HAT or HDAC activity has been identified in several cancers (Cress and Seto, 2000; Mahlknecht and Hoelzer, 2000; Timmermann et al., 2001). The acetylation of nucleosomal histones is regulated by the opposing activities of HDACs and HATs (Marks et al., 2000, 2001a,b). It has been postulated that hypoacetylated histones maintain the repressed state of a gene by condensing the associated chromatin and restricting access of transcription factors to DNA, whereas acetylation of histones is generally associated with activation of gene expression (Struhl, 1998). Enhanced acetylation of the H4 histone has been associated with increased binding of transcription factors (Van Lint et al., 1996), DNA fragmentation (Lee et al., 1996), and increased production of proteins such as caspase-3 (Medina et al., 1997), which trigger the apoptotic cascade. Histone deacetylase inhibitors have emerged recently as promising chemotherapeutic agents (Butler et al., 2000; Coffey et al., 2000, 2001; Marks et al., 2001a,b; Henderson and Brancolini, 2003). Inhibition of HDACs may contribute to the induction of differentiation and/or apoptosis in transformed cells—but not in normal cells—by activating transcription of target genes (Marks et al., 2001a,b; Timmermann et al., 2001). Evidence provided by DNA microarrays using malignant cell lines cultured with a HDAC inhibitor shows that there are a small (1-2%) number of genes of which the products are altered (Van Lint et al., 1996). Several HDAC inhibitors, administered intravenously or intraperitoneally, inhibit tumor growth in animal models of breast, prostate, lung and stomach cancers, neuroblastoma and leukemia, with little or no toxicity (Butler et al., 2000, 2001; Cohen et al., 2002; Kim et al., 1999). Recent studies have shown that malignant mesothelioma, leukemia and myeloma cells can be sensitized with HDAC inhibitors to undergo apoptosis by TRAIL (Neuzil et al., 2004; Rosato et al., 2003; Zhang et al., 2003). The sensitization of TRAIL resistant cells appears to be due to downregulation of the anti-apoptotic protein Bcl-XL, upregulation of proapoptotic genes Bax, Bak, TRAIL-R1/DR4 and/or TRAIL-R2/DR5, and activation of caspases.

Given the mechanistic similarities between TRAIL and the DRAs of the present invention, in some embodiments, the invention contemplates that HDAC inhibitors may be used to sensitize TRAIL-resistant cancer cells to undergo apoptosis by one of more of the DRAs of the present invention.

ii. Retinoids

Retinoids play an important role in regulating the growth and differentiation of normal, premalignant and malignant cell types, mainly through interaction with two types of nuclear receptors: retinoic acid receptors (RARα, β and γ) and retinoid X receptors (RXRα, β and γ). The therapeutic and preventive activities of retinoids in cancer are due to their ability to modulate the growth, differentiation, and survival or apoptosis of cancer cells (Ortiz et al., 2002). Vitamin A deficiency in experimental animals has been associated with a higher incidence of cancer and with increased susceptibility to chemical carcinogens. This is in agreement with the epidemiological studies indicating that individuals with a lower dietary vitamin A intake are at a higher risk to develop cancer. At the molecular level, aberrant expression and function of nuclear retinoid receptors have been found in various types of cancer including premalignant lesions. Thus, aberrations in retinoid signaling are early events in carcinogenesis. Retinoids at pharmacological doses exhibit a variety of effects associated with cancer prevention. They suppress transformation of cells in vitro, inhibit carcinogenesis in various organs in animal models, reduce premalignant human epithelial lesions and prevent second primary tumors following curative therapy for epithelial malignancies such as head and neck, lung, liver, and breast cancer.

The majority of ovarian cancer cells are resistant to apoptosis induced by TRAIL. Subtoxic concentrations of the semisynthetic retinoid N-(4-hydroxyphenyl)retinamide (4HPR) enhanced TRAIL-mediated apoptosis in ovarian cancer cell lines but not in immortalized non-tumorigenic ovarian epithelial cells (Cuello et al., 2004). The enhancement of TRAIL-mediated apoptosis by 4HPR was not due to changes in the levels of proteins known to modulate TRAIL sensitivity. The combination of 4HPR and TRAIL enhanced cleavage of multiple caspases in the death receptor pathway, including the two initiator caspases, caspases-8 and -9. The 4HPR and TRAIL combination leads to mitochondrial permeability transition, significant increase in cytochrome c release, and increased caspase-9 activation. Caspase-9 may further activate caspase-8, generating an amplification loop. Stable overexpression of Bcl-XL abrogates the interaction between 4HPR and TRAIL at the mitochondrial level by blocking cytochrome c release. As a consequence, a decrease in activation of caspases-9 and -8, and TRAIL-mediated apoptosis occurs. In addition, TRAIL synergizes with a synthetic retinoid (CD437) in inducing apoptosis of human lung and prostate cancer cells by up-regulating death receptors and activating caspase-3 (Sun et al., 2000a,b).

Given the mechanistic similarities between the DRAs of the present invention and TRAIL, the invention contemplates, that in certain embodiments, the ability of the one of more of the DRAs to induce apoptosis in TRAIL-resistant cancer cell lines, such as ovarian cancer, will be enhanced by subtoxic concentrations of the semisynthetic retinoid N-(4-hydroxyphenyl)retinamide (4HPR). Similarly, in other embodiments, the inventors contemplate that the DRAs of the present invention will synergize with a synthetic retinoid (CD437) in inducing apoptosis of human lung and prostate cancer cells by up-regulating death receptors and activating caspase-3.

iii. Combination Therapy with Conventional Chemotherapeutic Drugs

It has been shown that although TRAIL is capable of inducing apoptosis in tumor cells of diverse origin, a majority of tumor cells are resistant to the apoptotic effects of TRAIL (Igney and Krammer, 2002; Shankar et al., 2004a,b; Singh et al., 2003; Wajant et al., 2002), suggesting that TRAIL alone may be ineffective for the treatment of these cancers. Furthermore, several studies have shown that chemotherapeutic drugs (e.g. cisplatin, carboplatin, etoposide, camptothecin, paclitaxel, vincristine, and vinblastine, doxorubicin, gemcitabine and 5-fluorouracil) can sensitize TRAIL-resistant breast, prostate, colon, bladder, and pancreatic cancer cells to TRAIL (Ashkenazi et al., 1999; Chinnaiyan et al., 2000; Gibson et al., 2000; Gliniak and Le, 1999; Hotta et al., 2003; Keane et al., 1999; Singh et al., 2003) in vitro and in vivo, indicating that combination therapy may be a possibility. Furthermore, it was shown that chemotherapeutic drugs not only induce death receptors in vitro, but also in tumor xenografts in nude mice (Singh et al., 2003), suggesting that these conventional chemotherapeutic drugs might enhance the cytotoxicity of TRAIL in humans. Several breast and prostate cancer cells are resistant to apoptosis by TRAIL, and chemotherapeutic drugs sensitize TRAIL-resistant cells to undergo apoptosis by up-regulating DR4 and/or DR5 and activating caspase. The chemotherapeutic drugs synergize with TRAIL in reducing tumor growth, inducing tumor-cell apoptosis and enhancing survival of tumor-bearing mice (Singh et al., 2003). Furthermore, it as been shown that chemotherapeutic drugs such as cisplatin, carboplatin, etoposide, camptothecin, doxorubicin, gemcitabine, 5-fluorouracil, paclitaxel, vincristine, and vinblastine can be used with TRAIL to kill TRAIL-sensitive and -resistant breast cancer cells.

The present invention contemplates that, in certain embodiments, the compounds of this invention, will function, through a mechanism described above. For example, it is contemplated that chemotherapeutic drugs such as cisplatin, carboplatin, etoposide, camptothecin, paclitaxel, vincristine, and vinblastine, doxorubicin, gemcitabine and 5-fluorouracil, can be used to sensitize TRAIL-resistant breast, prostate, colon, bladder, and pancreatic cancer cells to a DRA of the present invention in vitro and/or in vivo, indicating that combination therapy may be a possibility. It is contemplated that in some embodiments, this approach might also be useful in killing drug-resistant cells, expressing high levels of death receptors DR4 and/or DR5, by the one or more of the DRAs of the present invention. For example, for breast and prostate cancer cells that are resistant to apoptosis by DRA, the invention contemplates that chemotherapeutic drugs will synergize with a DRA in reducing tumor growth, inducing tumor-cell apoptosis and enhancing survival of tumor-bearing individual. Thus, in certain aspects, the invention provides that chemotherapeutic drugs, such as cisplatin, carboplatin, etoposide, camptothecin, doxorubicin, gemcitabine, 5-fluorouracil, paclitaxel, vincristine, and vinblastine, can be used with one or more of the DRAs of the present invention to kill TRAIL-sensitive, TRAIL-resistant, DRA-sensitive, or DRA-resistant cancer cells, such as human breast cancer cells. Combination chemotherapies also include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

iv. Irradiation

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

In order to overcome the resistance of cancer cells to irradiation and problems of its toxicity, strategies either to increase normal tissue tolerance or to reduce the radiation dose required may prove beneficial. Therefore, therapies which induce apoptosis in irradiation-resistant tumor cells may prove to be beneficial in killing cancer cells. Studies have shown that ionizing radiation enhances the therapeutic potential of TRAIL in TRAIL-sensitive cells, and sensitizes TRAIL-resistant cells (Shankar et al., 2004a,b). Ionizing radiation induces death receptor DR5, and subsequent treatment with TRAIL causes apoptosis in an additive or synergistic manner in TRAIL-sensitive cells, and sensitizes TRAIL-resistant prostate cancer cells (Chinnaiyan et al., 2000; Gibson et al., 2000; Kim and Gupta, 2000; Marini and Belka, 2003; Marini et al., 2003; Shankar et al., 2004a,b; Wu et al., 1997). The sequential treatment of mice with irradiation followed by TRAIL resulted in enhanced caspase-3 activity and apoptosis in tumor cells, which is accompanied by a regression of tumor growth and an enhancement of survival of xenografted mice (Shankar et al., 2004a,b). The interactions of irradiation and TRAIL involve multiple genes such as DR5, caspases-8, -3, and -7, Bax, Bak and Bcl-2 (Shankar et al., 2004a,b). Induced expression Bax and Bak, and down-regulation of Bcl-2 were also observed and these proteins are likely to have played significant roles in tumor cell apoptosis.

The observation that irradiation can induce death receptors, and that low doses of irradiation can cooperate synergistically with TRAIL in enhancing apoptosis may have implications for clinical therapy. Radiation induces caspases-8, -3, and -7 activation, leading to proteolytic cleavage of cellular proteins such as poly(ADP-ribose) polymerase (Gong et al., 1999). TRAIL-induced apoptosis required caspase-8, whereas it was not essential for irradiation-induced apoptosis. Activation of death receptors by TRAIL also induced cleavage and activation of caspase-8 and -3, similar to our previous findings in breast, prostate and lung cancer (Chen et al., 2001; Kandasamy et al., 2003; Singh et al., 2003; Suliman et al., 2001), indicating that irradiation may mediate its apoptotic effects not only through increased levels of the DR5 receptors, but also through caspase cascade by directly engaging mitochondria.

Given the mechanistic similarities between the DRAs of this present invention and TRAIL, the invention contemplates that, in some embodiments, ionizing radiation will enhance the therapeutic potential of one or more of the DRAs of the present invention in TRAIL-sensitive or DRA-sensitive cells, and/or sensitize TRAIL-resistant or DRA-resistant cells (Shankar et al., 2004a,b). In further embodiments, it is contemplated that ionizing radiation will induce death receptor DR5, and subsequent treatment with a DRA of the present invention will cause apoptosis in an additive or synergistic manner in TRAIL-sensitive or DRA-sensitive cells, or will sensitize TRAIL-resistant or DRA-resistant cancer cells, such as prostate cancer cells.

v. Chemopreventative Drugs

Carcinogenesis is a multistep process occurring over decades which is characterized by disruption of the normal regulatory pathways controlling cellular proliferation, programmed cell death and differentiation. Administration of agents to reverse, inhibit or slow this process of malignant transformation is known as chemoprevention. Chemoprevention represents a promising approach to reducing the morbidity and mortality of cancer. A variety of agents are currently being studied in phase 2 clinical trials, some of which may warrant subsequent evaluation in phase 3 trials with definitive cancer end points.

Epidemiological and laboratory studies have provided convincing evidence that diet, genetic factors, and lifestyle are major causes of cancer. Although surgery, radiotherapy, and hormone therapy are the most widely accepted curative options for a selected group of patients suffering from cancer, the side effects of these treatments are many. The low incidence of cancer in Asian population has been attributed to the dietary consumption of large amounts of plant-based foods rich in phytochemicals (Park and Pezzuto, 2002). Because of these observations, nutritional supplements such as soybean, garlic, grapes, turmeric, green tea, and so on, have been used to augment the anticancer therapies. In recent years, many dietary agents have been described that show a wide range of chemopreventive effects in cell culture and selected animal model systems of breast and prostate carcinogenesis.

Curcumin, the active component of turmeric, and resveratrol (3,5,4'-trihydroxystilbene), found in grapes, are two such dietary constituents that have received a great deal of attention recently as chemoprotective agents. Phytochemicals inhibit proliferation and induce apoptosis in human and mouse leukemia cell lines. Curcumin augments TRAIL-mediated apoptosis in androgen-sensitive prostate cancer cells (Deeb et al., 2003). The induction of apoptosis by combined curcumin and TRAIL treatment involves the activation of initiator/effector caspases (caspases-8, -9, and -3), cleavage of proapoptotic Bid, and the release of cytochrome c from mitochondria.

Given the mechanistic similarities between the DRAs of this present invention and TRAIL, the invention contemplates that, in some embodiments, the induction of apoptosis by combined curcumin and DRA treatment will involve the activation of initiator/effector caspases (caspases-8, -9, and -3), cleavage of proapoptotic Bid, and the release of cytochrome c from mitochondria. Thus, combination of one or more of the DRAs of the present invention with curcumin, a pharmacologically safe compound, may provide a more effective adjuvant treatment for variety of cancers, including prostate cancer.

Epidemiological studies, preclinical investigations and clinical intervention trials support the role of selenium (an essential micronutrient and a constituent of antioxidant enzymes) as potent cancer chemopreventive agent for prostate and other cancers (Sinha and El-Bayoumy, 2004; Whanger, 2004). Induction of apoptosis and inhibition of cell proliferation are considered important cellular events that can account for the cancer preventive effects of selenium. Differential inhibition of PKCδ, NF-κB and cIAP-2 by selenium may represent important intracellular signaling processes through which selenium induces apoptosis and subsequently exerts its anticarcinogenic effect (Gopee et al., 2004). Selenium prevents clonal expansion of nascent tumors by causing cell-cycle arrest, promoting apoptosis, and modulating p53-dependent DNA repair mechanisms (Klein, 2004). Selenium induces apoptosis by upregulating TRAIL-R2/DR5, activating caspase-8 and cleaving Bid in human prostate cancer cells (He et al., 2002), thereby suggesting the existence of a potential cross-talk between the death receptor and the mitochondrial pathways. Thus, DR5 is specifically regulated by selenium and its activation may play an important role in selenium-mediated chemoprevention. Furthermore, selenium may sensitize cancer cells to TRAIL treatment by upregulating DR5 receptors. Given the mechanistic similarities between the DRAs of this present invention and TRAIL, the invention contemplates that, in some embodiments, selenium may sensitize cancer cells to DRA treatment by upregulating DR5 receptors.

In recent years, naturally occurring antioxidant compounds present in diet and beverages such as resveratrol have gained considerable attention because of their beneficial effects on health as cancer chemopreventive or cardioprotective agents (Cal et al., 2003; Gusman et al., 2001; Ratan et al., 2002). Resveratrol (trans-3,5,4'-trihydroxystilbene) is a naturally occurring polyphenol with cancer chemopreventive and antitumor properties in preclinical models of carcinogenesis, including those of breast, prostate and colorectal cancer (Cal et al., 2003; Fulda and Debatin, 2004; Gusman et al., 2001). It is present in dietary items such as grapes and red wine (Cal et al., 2003). Resveratrol is a potent sensitizer of tumor cells for TRAIL-induced apoptosis through p53-independent induction of p21 and p21-mediated cell cycle arrest associated with survivin depletion.

The potential of resveratrol for anticancer therapy may largely reside in its ability to sensitize tumor cells to apoptosis. Resveratrol sensitizes cancer cells to TRAIL, CD95 and several anticancer drugs (Fulda and Debatin, 2004). Resveratrol sensitizes a variety of human cancer cell lines to TRAIL-induced apoptosis independent of wild-type p53 status through cell cycle arrest-mediated survivin depletion (Fulda and Debatin, 2004).

Given the mechanistic similarities between the DRAs of this present invention and TRAIL, the invention contemplates that, in some embodiments, resveratrol will sensitizes cancer cells to one or more of the DRAs of the present invention. In some embodiments, it is contemplated that resveratrol will significantly potentiate the cytotoxic activity of a DRA even at relatively low DRA concentrations. For example, resveratrol may be used in DRA-based therapies to reduce the doses of DRA required for inhibition of tumor growth. Also, resveratrol may be particularly useful to sensitize resistant tumor cells to DRA-induced apoptosis, without affecting primary nonmalignant human cells, e.g. fibroblasts. It may serve as a novel therapeutic to target survivin expression in cancers through p21-mediated cell cycle arrest.

B. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with DRA therapy. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

C. Gene Therapy

In yet another embodiment, the secondary treatment is a secondary gene therapy in which a therapeutic polynucleotide is administered before, after, or at the same time a trail death receptor agonist/activator (DRA). Therapeutic genes may include an antisense version of an inducer of cellular proliferation (sometimes called an oncogene), an inhibitor of cellular proliferation (sometimes called a tumor suppressor), or an inducer of programmed cell death (sometimes called a pro-apoptotic gene).

D. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines.

It is further contemplated that, the DRAs of the present invention may be used together with compounds that upregulate the expression of cell surface receptors involved in apoptotic signaling (e.g., DR4 and DR5) and may therefore have additive or synergistic effects in combination with ligands for these receptors. The upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increasing intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

F. Anti-Inflammatory Agents

It is contemplated that anti-inflammatory agents will be used in conjunction with the TRAIL Death Receptor Agonists/Activators of the current invention. COX inhibitors may be used, including arylcarboxylic acids (salicylic acid, acetylsalicylic acid, diflunisal, choline magnesium trisalicylate, salicylate, benorylate, flufenamic acid, mefenamic acid, meclofenamic acid and triflumic acid), arylalkanoic acids (diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin and sulindac) and enolic acids (phenylbutazone, oxyphenbutazone, azapropazone, feprazone, piroxicam, and isoxicam. (U.S. Pat. No. 6,025,395)

Histamine H2 receptor blocking agents may also be used in conjunction with the TRAIL Death Receptor Agonists/Activators of the current invention, including cimetidine, ranitidine, famotidine and nizatidine.

VIII. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Computer Aided Drug Design (CADD). The 3D structure of DR5 (Hymowitz et al., 1999) was used for the CADD studies to screen a virtual library of commercially available small molecular weight compounds to identify ligands which bind to DR5. In silico screening targeted the DR5 monomer in the region of the protein that interacts directly with TRAIL based on the crystallographic structure. From the in silico screen, compounds were obtained for biological assay. These compounds were further modified and tested in cell culture and in vivo mice experiments for antitumor activity. In addition to CADD, we have also screen chemical library of small molecular weight organic compounds through high throughput assay to identify TRAIL-death receptor agonists.

Cells and Culture Conditions. Cancer cells were obtained from the American Type Culture Collection (Manassas, Va.). Cells were maintained in RPMI-1640 medium supplemented with 10% fetal bovine serum and 1% penicillin/streptomycin. Human normal breast and prostate epithelial cells were purchased from Cambrex Bio Science (Walkersville, Md.).

Western Blot Analysis. Cells were lysed in a buffer containing 10 mM Tris-HCl (pH 7.6), 150 mM NaCl, 0.5 mM EDTA, 1 mM EGTA, 1% SDS, 1 mM sodium orthovanadate, and a mixture of protease inhibitors (1 mM phenylmethylsulfonyl fluoride, 1 μg/ml pepstatin A, 2 μg/ml aprotinin). Lysates were sonicated for 10 s, centrifuged for 20 min at 10,000×g and stored at −70° C. Equal amounts of lysate proteins were run on 10% SDS-PAGE and electrophoretically transferred to nitrocellulose. Nitrocellulose blots were blocked with 6% nonfat dry milk in TBS buffer (20 mM Tris-HCl (pH 7.4), and 500 mM NaCl), and incubated with primary antibody in TBS containing 1% bovine serum albumin overnight at 4° C. Immunoblots were washed three times (15, 5 and 5 min each) with TBST (TBS and 0.01% Tween 20). Immunoreactivity was detected by sequential incubation with horseradish peroxidase-conjugated secondary antibody and ECL reagents.

XTT Assay. Cells ($1 \times 10^4$ cells per well) were seeded in 96-well plates (flat bottom), and treated with death receptor agonists/activators/small molecules in the presence or absence of TNF-related apoptosis inducing ligand (TRAIL). Plates were incubated for various time points at 37° C. and 5% $CO_2$. Before the end of the experiment, 50 μl XTT (sodium 3'[1-(phenylaminocarbonyl)-3,4-tetrazolium]-bis(4-methoxy-6-nitro) benzene sulfonic acid hydrate) labeling mixture (final concentration, 125 μM sodium XTT and 25 μM PMS) per well was added and plates were incubated for a further 4 h at 37° C. and 5% $CO_2$. The spectrophotometric absorbance of the sample was measured using a microtitre plate (ELISA) reader. The wavelength to measure absorbance of the formazan product was 450 nm, and the reference wavelength was 650 nm.

Receptor Binding Assay. Breast cancer MDA-MB-231 cells were harvested and resuspended using ice-cold PBS in test tubes ($1 \times 10^4$ cells/tube). Cells were incubated with His-tagged TRAIL (25 nM) in the presence or absence of small molecules (1 to 100 μM) for 1 h at 4° C. Cells were washed twice with ice-cold PBS and stained with anti-His-FITC antibody for 1 h at 4° C. Cells were then washed twice with ice-cold PBS, and transferred to 1 ml cuvettes. Fluorescent intensity was measured by scanning fluorometer.

Soft Agar Assay. Cells ($2 \times 10^4$ cells/well) were seeded in 12-well culture dishes in RPMI/0.35% bacto-agar over a bottom layer of RPMI/0.6% bacto-agar. Cells were then fed with growth media (100-200 μl/well) once a week until colonies grew to a suitable size for observation (3-4 weeks). Number of colonies were counted after they were stained with 3-(4,5-dimethylthiazol-2-yl)-2,5-diphenyltetrazolium bromide (1 mg/ml, 100 μl/well) overnight for better visualization.

Example 1

Effects of DRA9S on the Binding of TRAIL to Death Receptors

Figure 3:
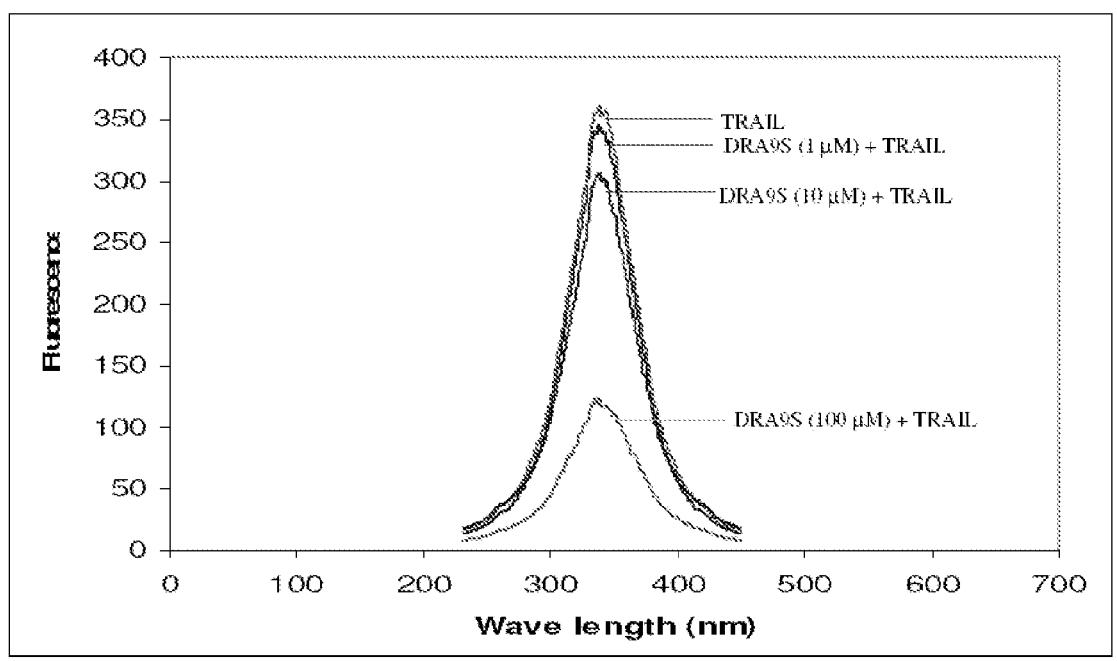
FIG. 3. Effects of death receptor agonist 9S (DRA9S) on the binding of TRAIL to death receptors. MDA-MB-231 cells were incubated with His-tagged TRAIL in the presence or absence of various concentrations of DRA9S (1, 10 and 100 µM) for 1 h at 4° C. Cells were then treated with anti-his antibody conjugated with FITC for 45 minutes. Fluorescence was measured by a scanning fluorometer.

MDA-MB-231 cells were incubated with His-tagged TRAIL in the presence or absence of various concentrations of DRA9S (1, 10 and 100 μM) for 1 h at 4° C. Cells were then treated with anti-his antibody conjugated with FITC for 45 minutes. Fluorescence was measured by a scanning fluorometer. See, for example, FIG. 3.

Example 2

Figure 4:
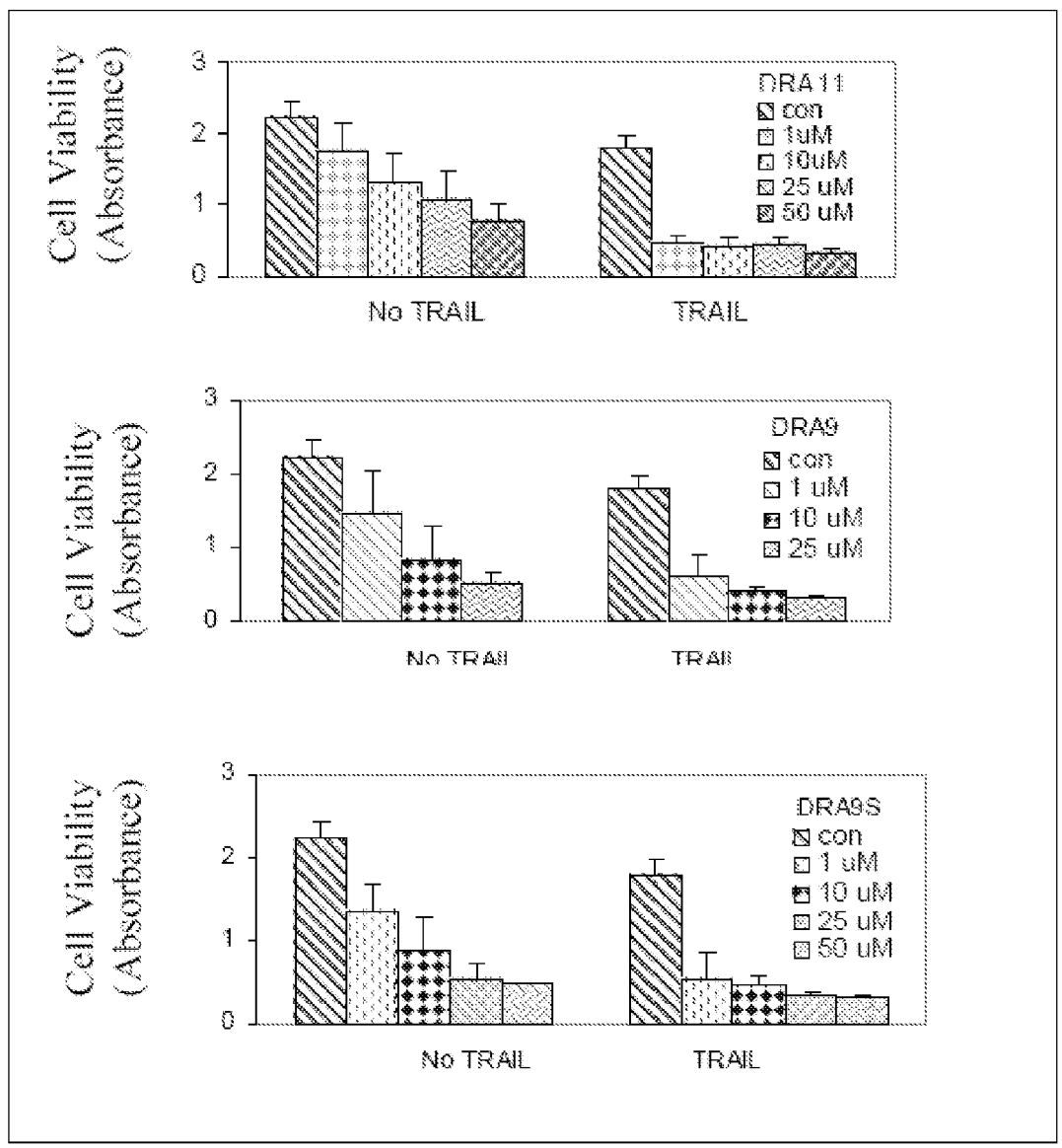
FIG. 4. Interactive effects of death receptor agonists and TRAIL on cell viability in human pancreatic cancer. Pancreatic cancer AsPC-1 cells were treated with various concentrations DRA11, DRA9, and DRA9S in the presence or absence of TRAIL (50 ng/ml) for 72 h. At the end of incubation, cell viability was measured by XTT assay. Data represent the mean±S.D. Control refers to a group treated with DMSO (0.01%).

Interactive Effects of Death Receptor Agonists and TRAIL on Cell Viability in Human Pancreatic Cancer Pancreatic cancer AsPC-1 cells were treated with various concentrations DRA11, DRA9, and DRA9S in the presence or absence of TRAIL (50 ng/ml) for 72 h. At the end of incubation, cell viability was measured by XTT assay. See, for example, FIG. 4. Data represent the mean±S.D. Control refers to a group treated with DMSO (0.01%).

Example 3

Figure 5:
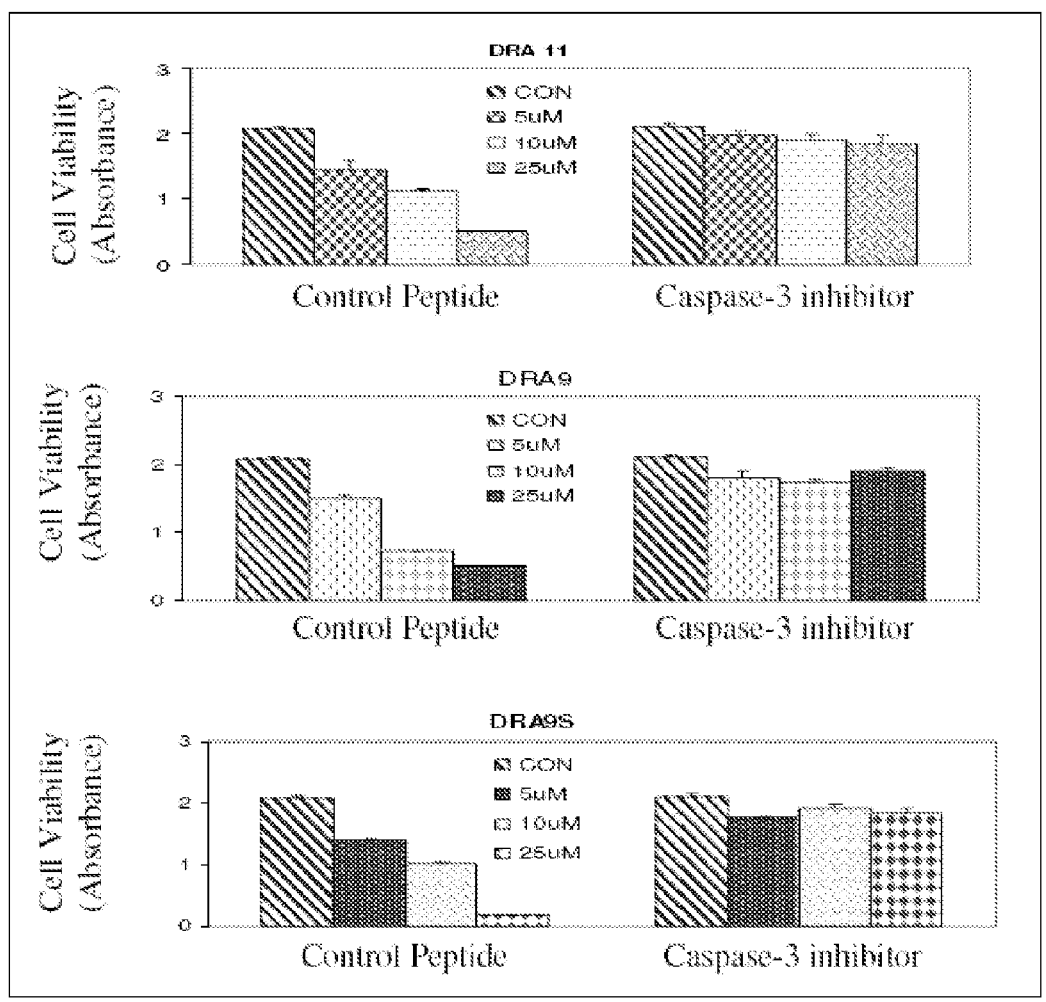
FIG. 5. Caspase-3 inhibitor (z-DEVD-fmk) blocks the effects of DRA11, DRA9, and DRA9S on cell viability in pancreatic cancer. AsPC-1 cells were pretreated with either control peptide (25 µM) or caspase-3 inhibitor (Z-DEVD-fmk, 25 µM) for 2 h, followed by treatment with various doses of DRA11, DRA9 and DRA9S for 72 h. At the end of incubation, cell viability was measured by XTT assay. Data represent the mean±S.D. Control refers to a group treated with DMSO (0.01%).

Caspase-3 Inhibitor (z-DEVD-fmk) Blocks the Effects of DRA11, DRA9, and DRA9S on Cell Viability in Pancreatic Cancer AsPC-1 cells were pretreated with either control peptide (25 μM) or caspase-3 inhibitor (Z-DEVD-fink, 25 μM) for 2 h, followed by treatment with various doses of DRA11, DRA9 and DRA9S for 72 h. At the end of incubation, cell viability was measured by XTT assay. See, for example, FIG. 5. Data represent the mean±S.D. Control refers to a group treated with DMSO (0.01%).

Example 4

Figure 6:
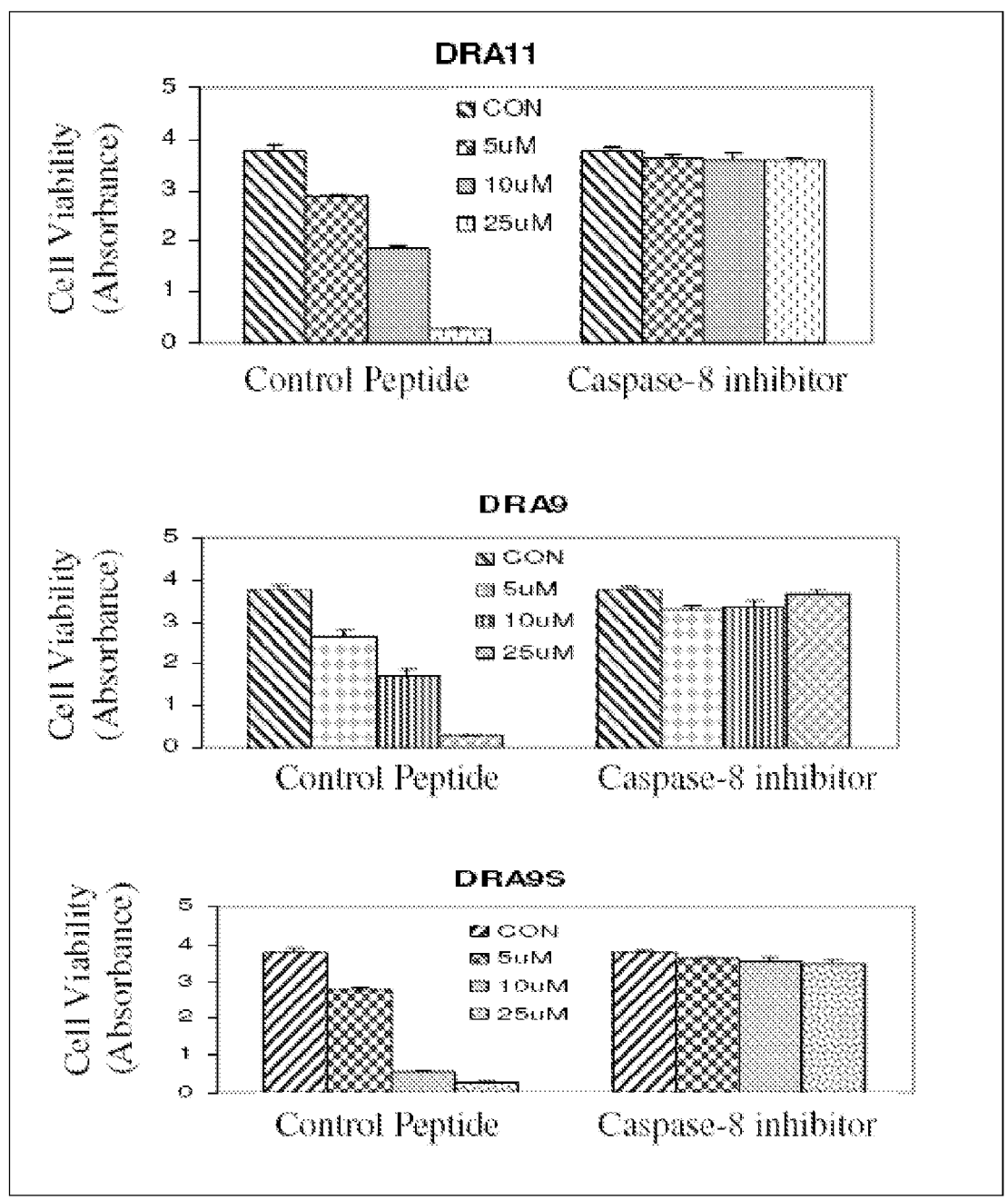
FIG. 6. Caspase-8 inhibitor (Ac-IETD-CHO, N-acetyl-Ile-Glu-Thr-Asp-CHO) blocks the effects of DRA11, DRA9, and DRA9S on cell viability in pancreatic cancer. AsPC-1 cells were pretreated with either control peptide (25 µM) or caspase-8 inhibitor (25 µM) for 2 h, followed by treatment with various doses of DRA11, DRA9 and DRA9S for 72 h. At the end of incubation, cell viability was measured by XTT assay. Data represent the mean±S.D. Control refers to a group treated with DMSO (0.01%).

Caspase-8 Inhibitor Blocks the Effects of DRA11, DRA9, and DRA9S on Cell Viability in Pancreatic Cancer Caspase-8 inhibitor (Ac-IETD-CHO, N-acetyl-Ile-Glu-Thr-Asp-CHO) blocks the effects of DRA11, DRA9, and DRA9S on cell viability in pancreatic cancer. AsPC-1 cells were pretreated with either control peptide (25 μM) or caspase-8 inhibitor (25 μM) for 2 h, followed by treatment with various doses of DRA11, DRA9 and DRA9S for 72 h. At the end of incubation, cell viability was measured by XTT assay. See, for example, FIG. 6. Data represent the mean±S.D. Control refers to a group treated with DMSO (0.01%).

Example 5

Figure 7:
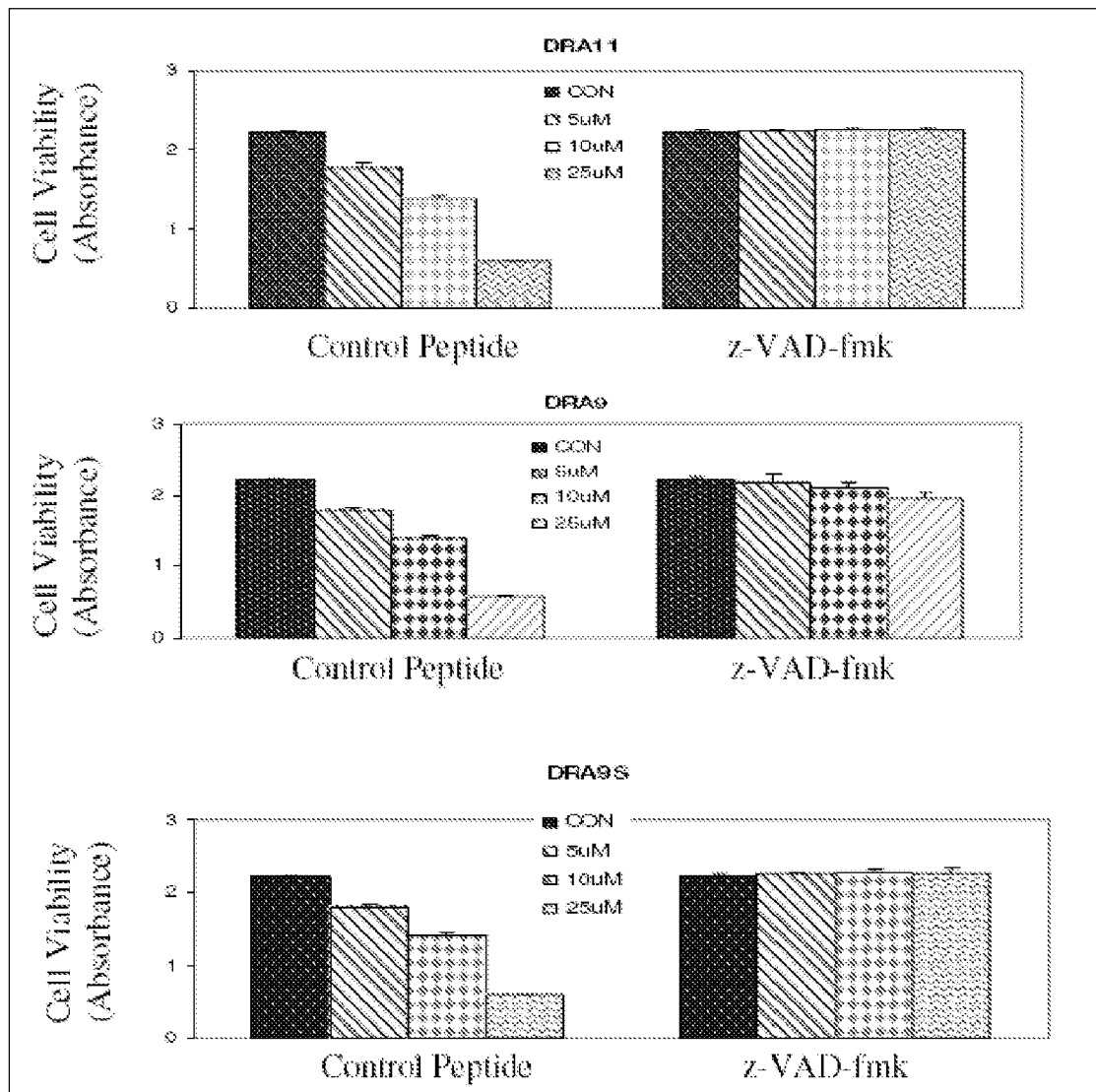
FIG. 7. Pan caspase inhibitor (z-VAD-fmk) blocks effects of DRAs on cell viability in pancreatic cancer. AsPC-1 cells were pretreated with either control peptide (25 µM) or caspase-8 inhibitor (25 µM) for 2 h, followed by treatment with various doses of DRA11, DRA9 and DRA9S for 72 h. At the end of incubation, cell viability was measured by XTT assay. Data represent the mean±S.D. Control refers to a group treated with DMSO (0.01%).

Pan Caspase Inhibitor (z-VAD-fmk) Blocks Effects of DRAs on Cell Viability in Pancreatic Cancer AsPC-1 cells were pretreated with either control peptide (25 µM) or caspase-8 inhibitor (25 µM) for 2 h, followed by treatment with various doses of DRA11, DRA9 and DRA9S for 72 h. At the end of incubation, cell viability was measured by XTT assay. See, for example, FIG. 7. Data represent the mean±S.D. Control refers to a group treated with DMSO (0.01%).

Example 6

Figure 8:
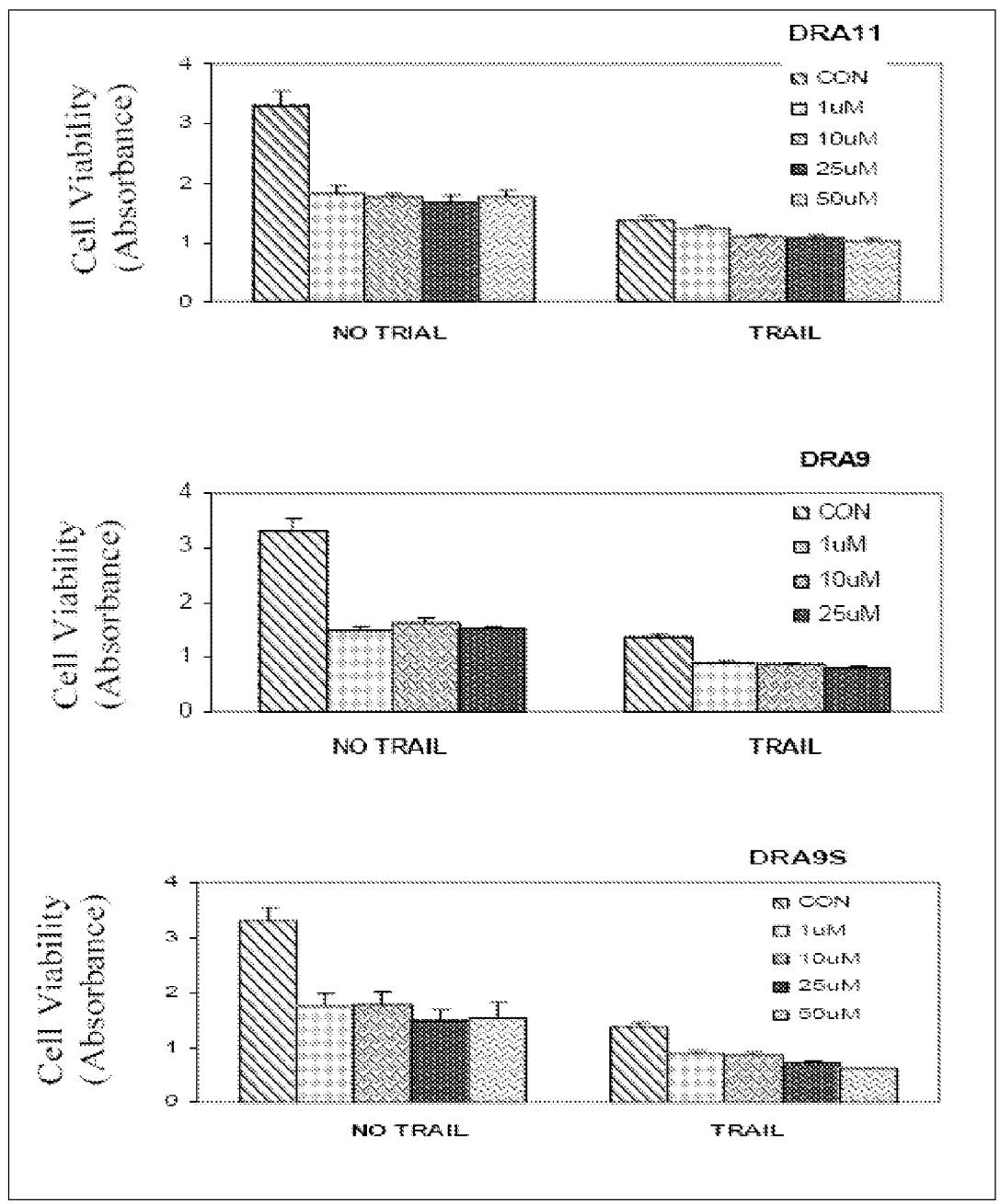
FIG. 8. Interactive effects of death receptor agonists and TRAIL on cell viability in human pancreatic cancer. Pancreatic cancer MIA PaCa2 cells were treated with various concentrations DRA11, DRA9, and DRA9S in the presence or absence of TRAIL (50 ng/ml) for 72 h. At the end of incubation, cell viability was measured by XTT assay. Data represent the mean±S.D. Control refers to a group treated with DMSO (0.01%) alone.

Interactive Effects of Death Receptor Agonists and TRAIL on Cell Viability in Human Pancreatic Cancer Pancreatic cancer MIA PaCa2 cells were treated with various concentrations DRA11, DRA9, and DRA9S in the presence or absence of TRAIL (50 ng/ml) for 72 h. At the end of incubation, cell viability was measured by XTT assay. See, for example, FIG. 8. Data represent the mean±S.D. Control refers to a group treated with DMSO (0.01%) alone.

Example 7

Figure 9:
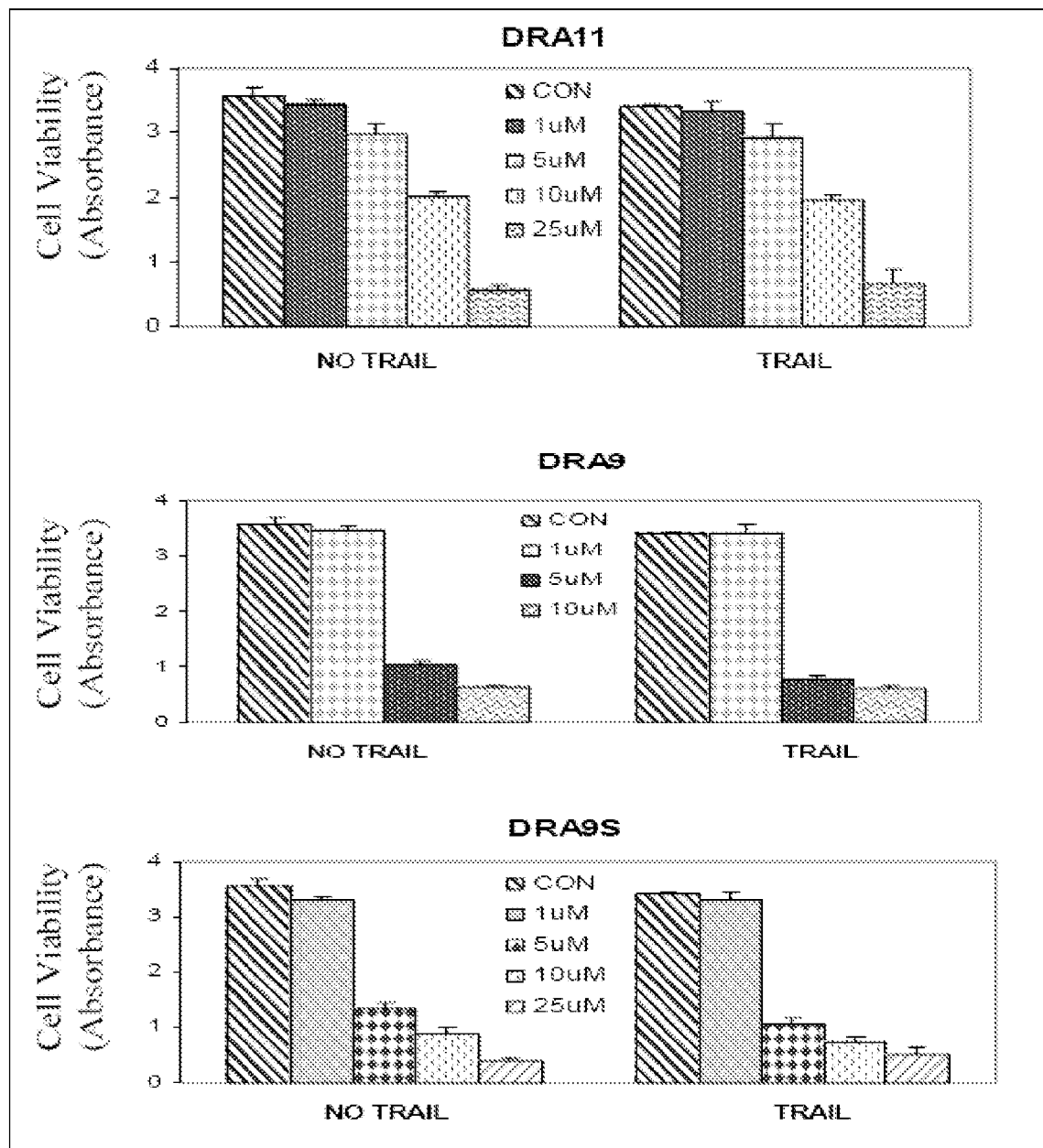
FIG. 9. Interactive effects of death receptor agonists and TRAIL on cell viability in human prostate cancer. Androgen-dependent prostate cancer LNCaP cells were treated with various concentrations DRA11, DRA9, and DRA9S in the presence or absence of TRAIL (50 ng/ml) for 72 h. At the end of incubation, cell viability was measured by XTT assay. Data represent the mean±S.D. Control refers to a group treated with DMSO (0.01%) alone.

Interactive Effects of Death Receptor Agonists and TRAIL on Cell Viability in Human Prostate Cancer Androgen-dependent prostate cancer LNCaP cells were treated with various concentrations DRA11, DRA9, and DRA9S in the presence or absence of TRAIL (50 ng/ml) for 72 h. At the end of incubation, cell viability was measured by XTT assay. See, for example, FIG. 9. Data represent the mean±S.D. Control refers to a group treated with DMSO (0.01%) alone.

Example 8

Figure 10:
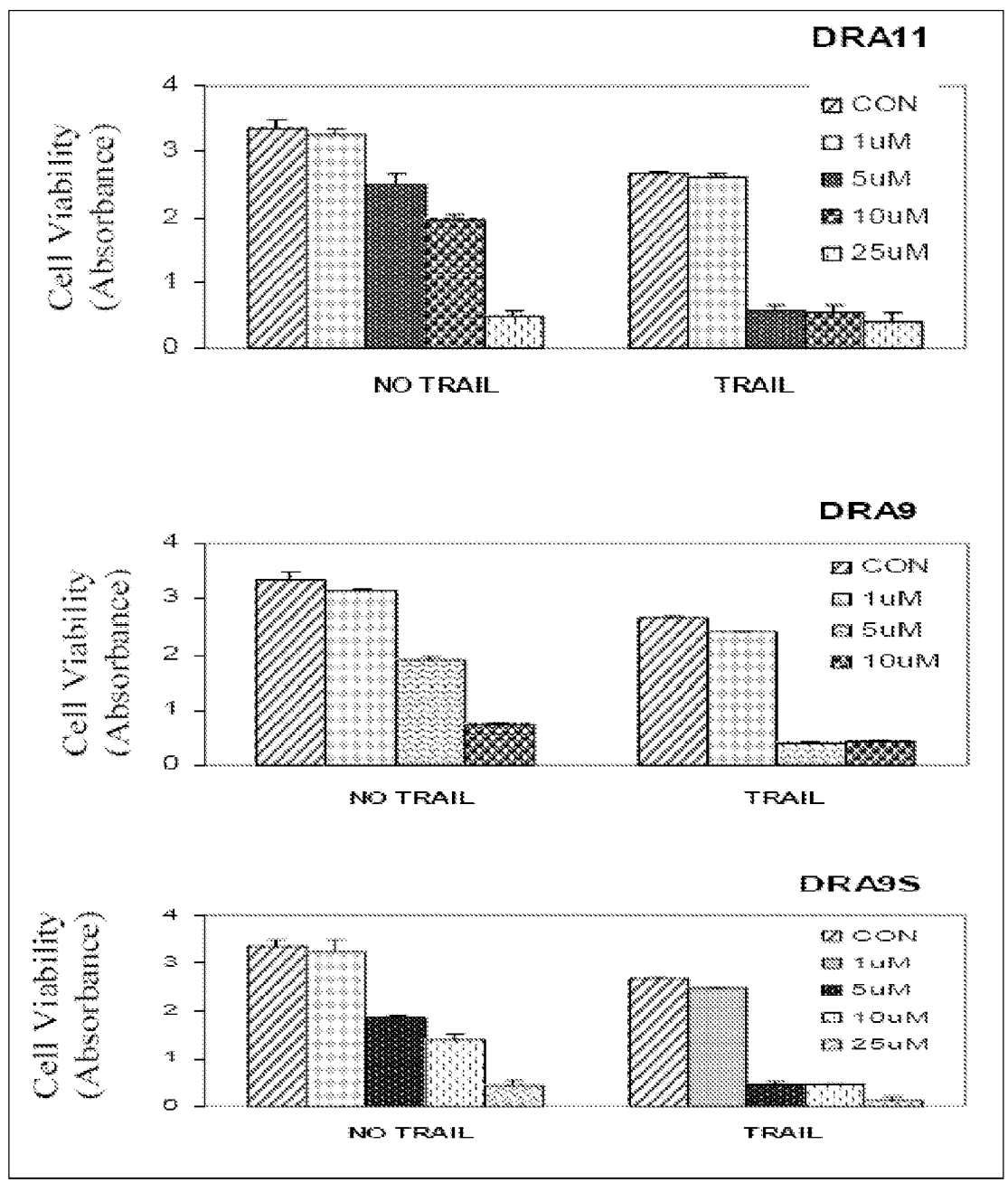
FIG. 10. Interactive effects of death receptor agonists and TRAIL on cell viability in human prostate cancer. Androgen-independent prostate cancer PC-3 cells were treated with various concentrations DRA11, DRA9, and DRA9S in the presence or absence of TRAIL (50 ng/ml) for 72 h. At the end of incubation, cell viability was measured by XTT assay. Data represent the mean±S.D. Control refers to a group treated with DMSO (0.01%) alone.

Interactive Effects of Death Receptor Agonists and TRAIL on Cell Viability in Human Prostate Cancer Androgen-independent prostate cancer PC-3 cells were treated with various concentrations DRA11, DRA9, and DRA9S in the presence or absence of TRAIL (50 ng/ml) for 72 h. At the end of incubation, cell viability was measured by XTT assay. See, for example, FIG. 10. Data represent the mean ±S.D. Control refers to a group treated with DMSO (0.01%) alone.

Example 9

Figure 11:
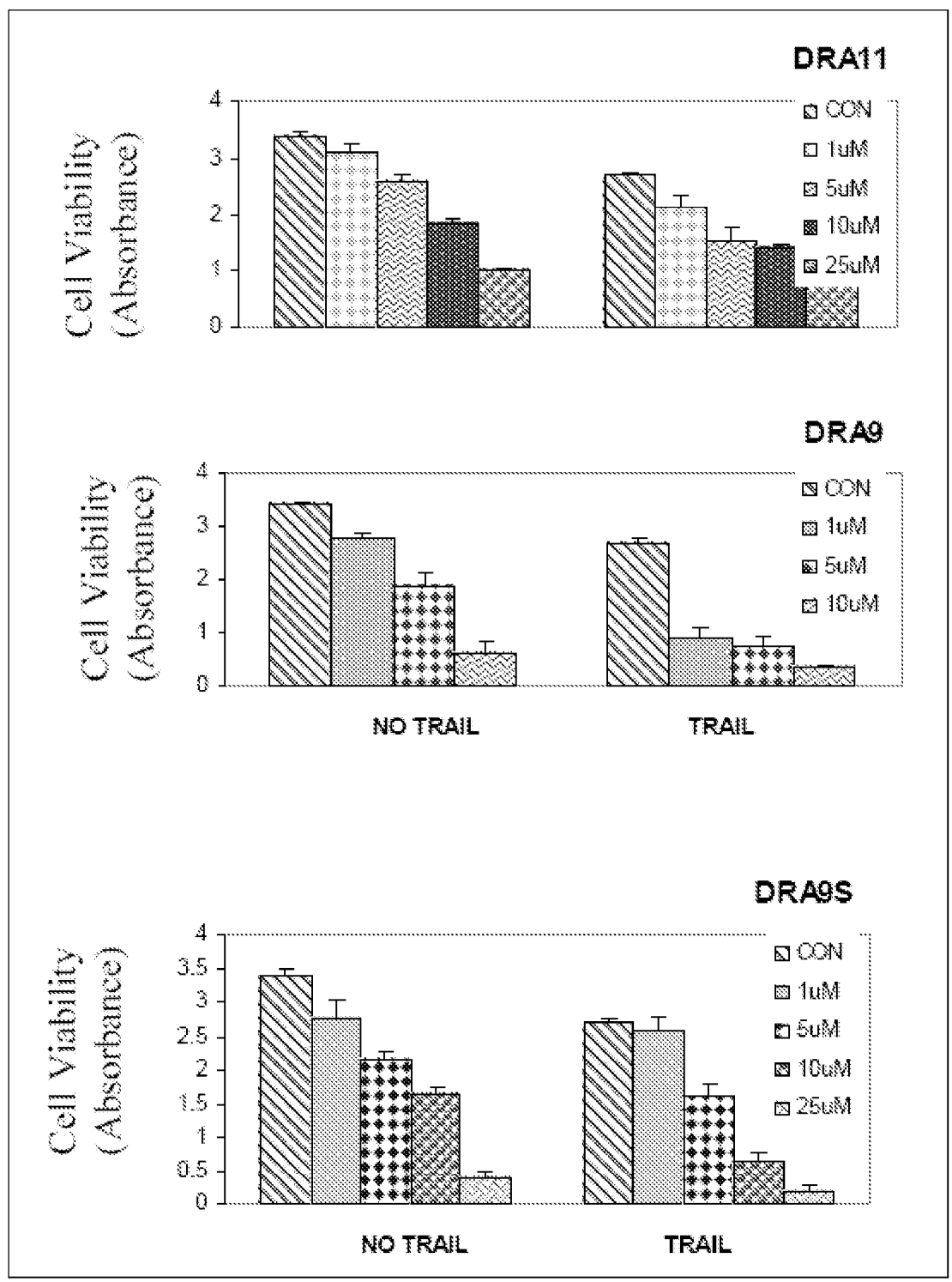
FIG. 11. Interactive effects of death receptor agonists and TRAIL on cell viability in human breast cancer. Estrogen-independent breast cancer MDA-MB-231 cells were treated with various concentrations DRA11, DRA9, and DRA9S in the presence or absence of TRAIL (50 ng/ml) for 72 h. At the end of incubation, cell viability was measured by XTT assay. Data represent the mean±S.D. Control refers to a group treated with DMSO (0.01%) alone.

Interactive Effects of Death Receptor Agonists and TRAIL on Cell Viability in Human Breast Cancer Estrogen-independent breast cancer MDA-MB-231 cells were treated with various concentrations DRA11, DRA9, and DRA9S in the presence or absence of TRAIL (50 ng/ml) for 72 h. At the end of incubation, cell viability was measured by XTT assay. See, for example, FIG. 11. Data represent the mean ±S.D. Control refers to a group treated with DMSO (0.01%) alone.

Example 10

Figure 12:
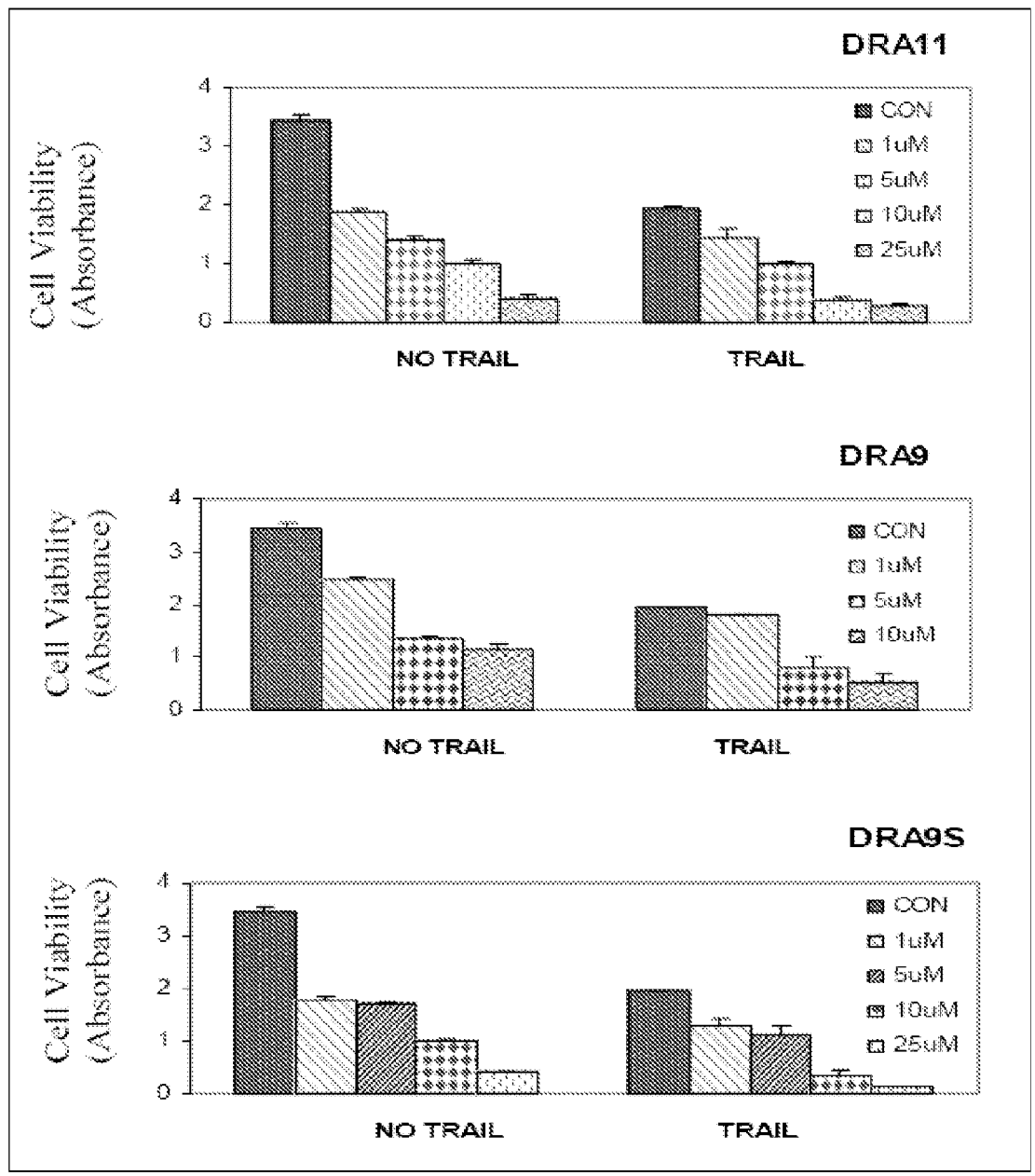
FIG. 12. Interactive effects of death receptor agonists and TRAIL on cell viability in human breast cancer. Estrogen-dependent breast cancer MCF-7 cells were treated with various concentrations DRA11, DRA9, and DRA9S in the presence or absence of TRAIL (50 ng/ml) for 72 h. At the end of incubation, cell viability was measured by XTT assay. Data represent the mean±S.D. Control refers to a group treated with DMSO (0.01%) alone.

Interactive Effects of Death Receptor Agonists and TRAIL on Cell Viability in Human Breast Cancer Estrogen-dependent breast cancer MCF-7 cells were treated with various concentrations DRA11, DRA9, and DRA9S in the presence or absence of TRAIL (50 ng/ml) for 72 h. At the end of incubation, cell viability was measured by XTT assay. See, for example, FIG. 12. Data represent the mean ±S.D. Control refers to a group treated with DMSO (0.01%) alone.

Example 11

Figure 13:
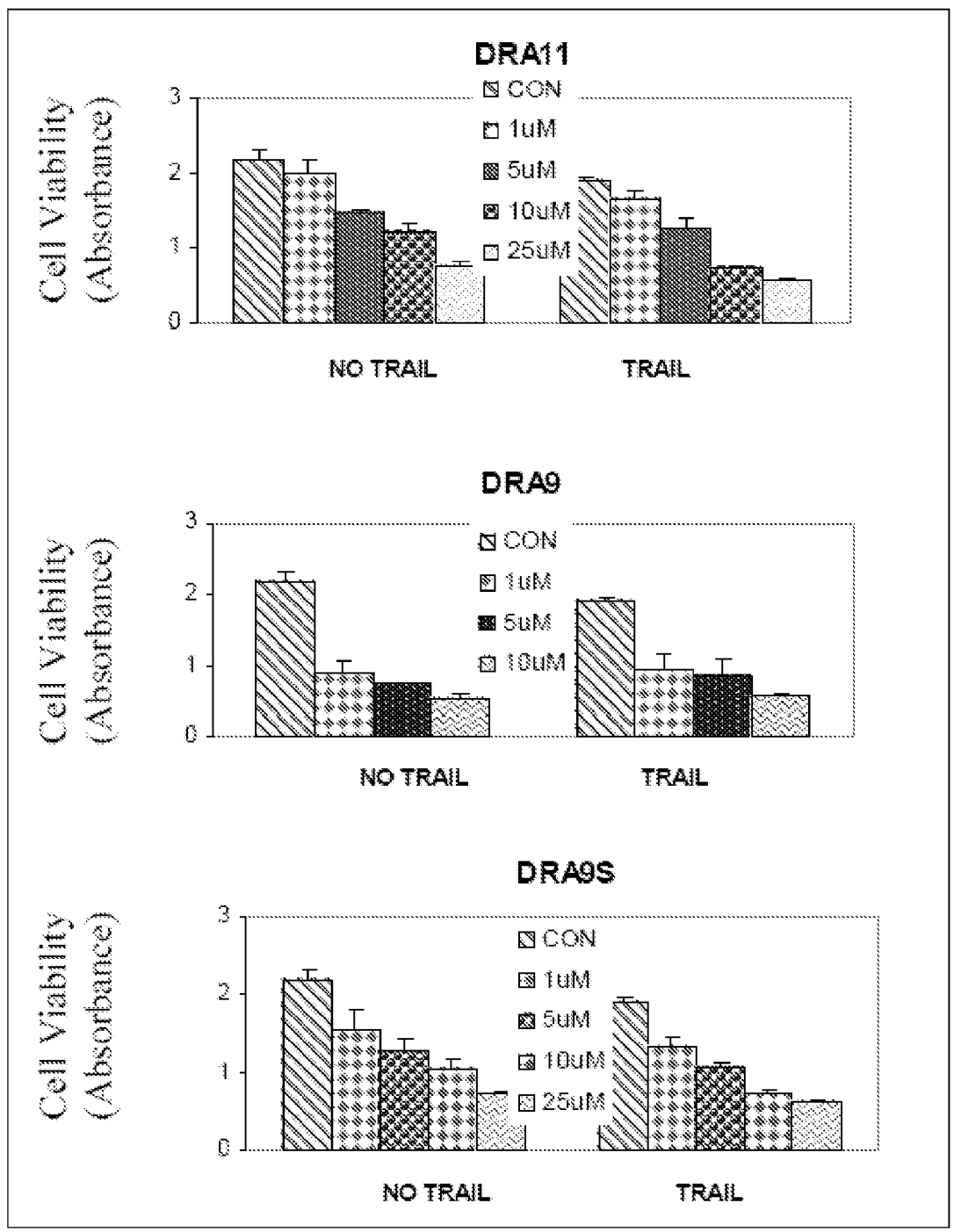
FIG. 13. Interactive effects of death receptor agonists and TRAIL on cell viability in human leukemia. HL60 cells were treated with various concentrations DRA11, DRA9, and DRA9S in the presence or absence of TRAIL (25 ng/ml) for 72 h. At the end of incubation, cell viability was measured by XTT assay. Data represent the mean±S.D. Control refers to a group treated with DMSO (0.01%) alone.

Interactive Effects of Death Receptor Agonists and TRAIL on Cell Viability in Human Leukemia HL60 cells were treated with various concentrations DRA11, DRA9, and DRA9S in the presence or absence of TRAIL (25 ng/ml) for 72 h. At the end of incubation, cell viability was measured by XTT assay. See, for example, FIG. 13. Data represent the mean ±S.D. Control refers to a group treated with DMSO (0.01%) alone.

Example 12

Figure 14:
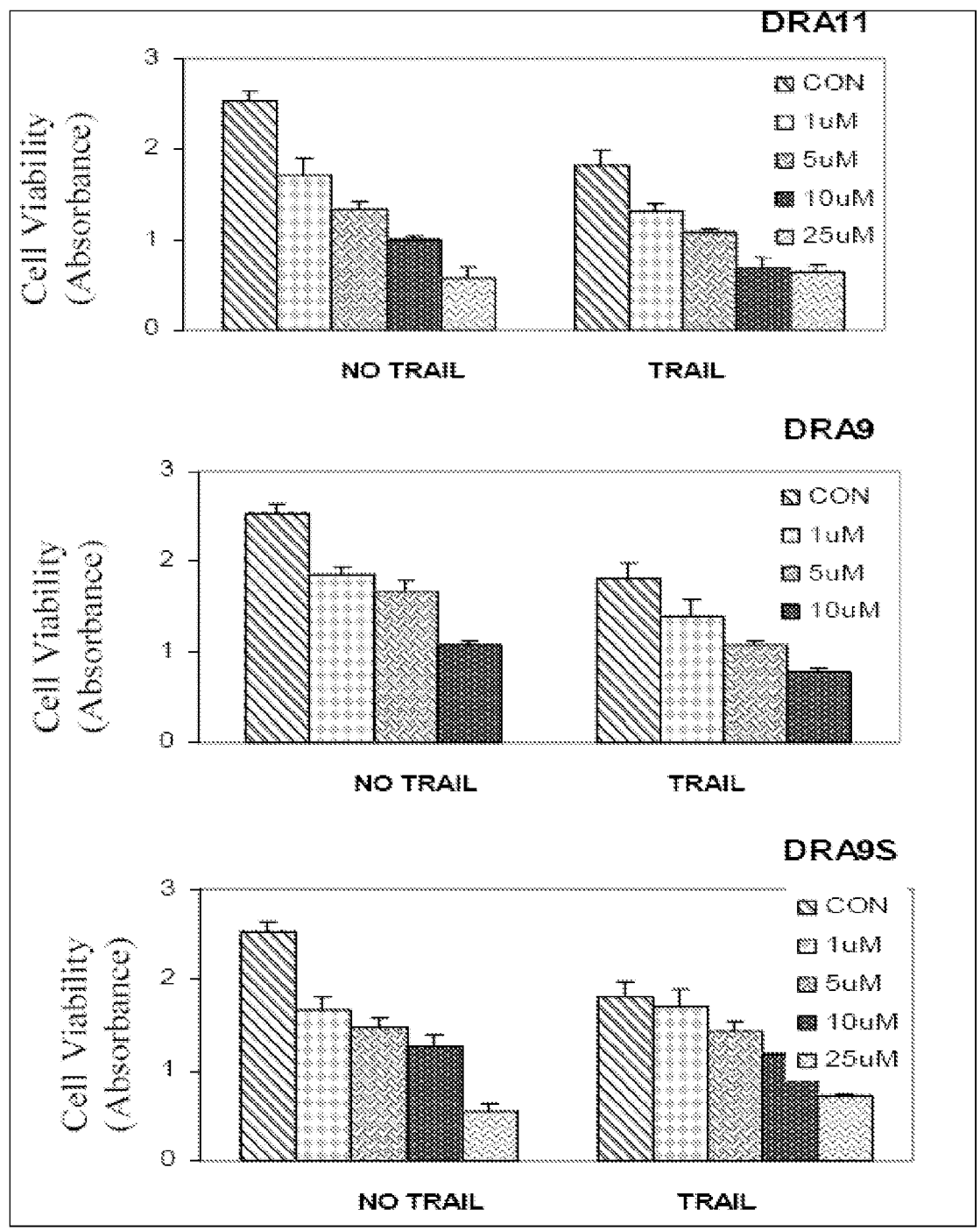
FIG. 14. Interactive effects of death receptor agonists and TRAIL on cell viability in human leukemia. K562 cells were treated with various concentrations DRA11, DRA9, and DRA9S in the presence or absence of TRAIL (25 ng/ml) for 72 h. At the end of incubation, cell viability was measured by XTT assay. Data represent the mean±S.D. Control refers to a group treated with DMSO (0.01%) alone.

Interactive Effects of Death Receptor Agonists and TRAIL on Cell Viability in Human Leukemia K562 cells were treated with various concentrations DRA11, DRA9, and DRA9S in the presence or absence of TRAIL (25 ng/ml) for 72 h. At the end of incubation, cell viability was measured by XTT assay. See, for example, FIG. 14. Data represent the mean ±S.D. Control refers to a group treated with DMSO (0.01%) alone.

Example 13

Figure 15:
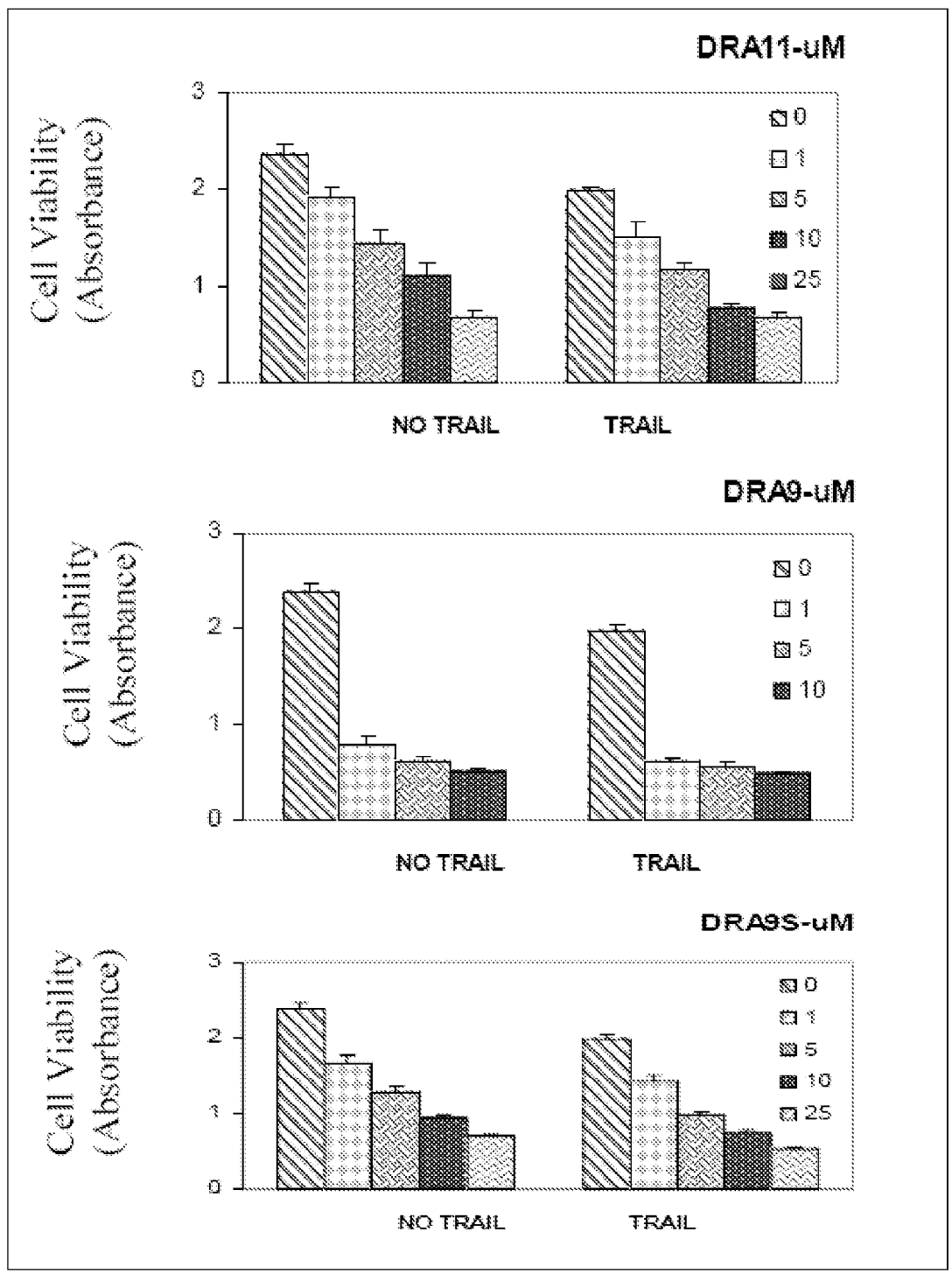
FIG. 15. Interactive effects of death receptor agonists and TRAIL on cell viability in human histiocytic lymphoma. U937 cells were treated with various concentrations DRA11, DRA9, and DRA9S in the presence or absence of TRAIL (25 ng/ml) for 72 h. At the end of incubation, cell viability was measured by XTT assay. Data represent the mean±S.D. Control refers to a group treated with DMSO (0.01%) alone.

Interactive Effects of Death Receptor Agonists and TRAIL on Cell Viability in Human Histiocytic Lymphoma U937 cells were treated with various concentrations DRA11, DRA9, and DRA9S in the presence or absence of TRAIL (25 ng/ml) for 72 h. At the end of incubation, cell viability was measured by XTT assay. See, for example, FIG. 15. Data represent the mean ±S.D. Control refers to a group treated with DMSO (0.01%) alone.

Example 14

Figure 16:
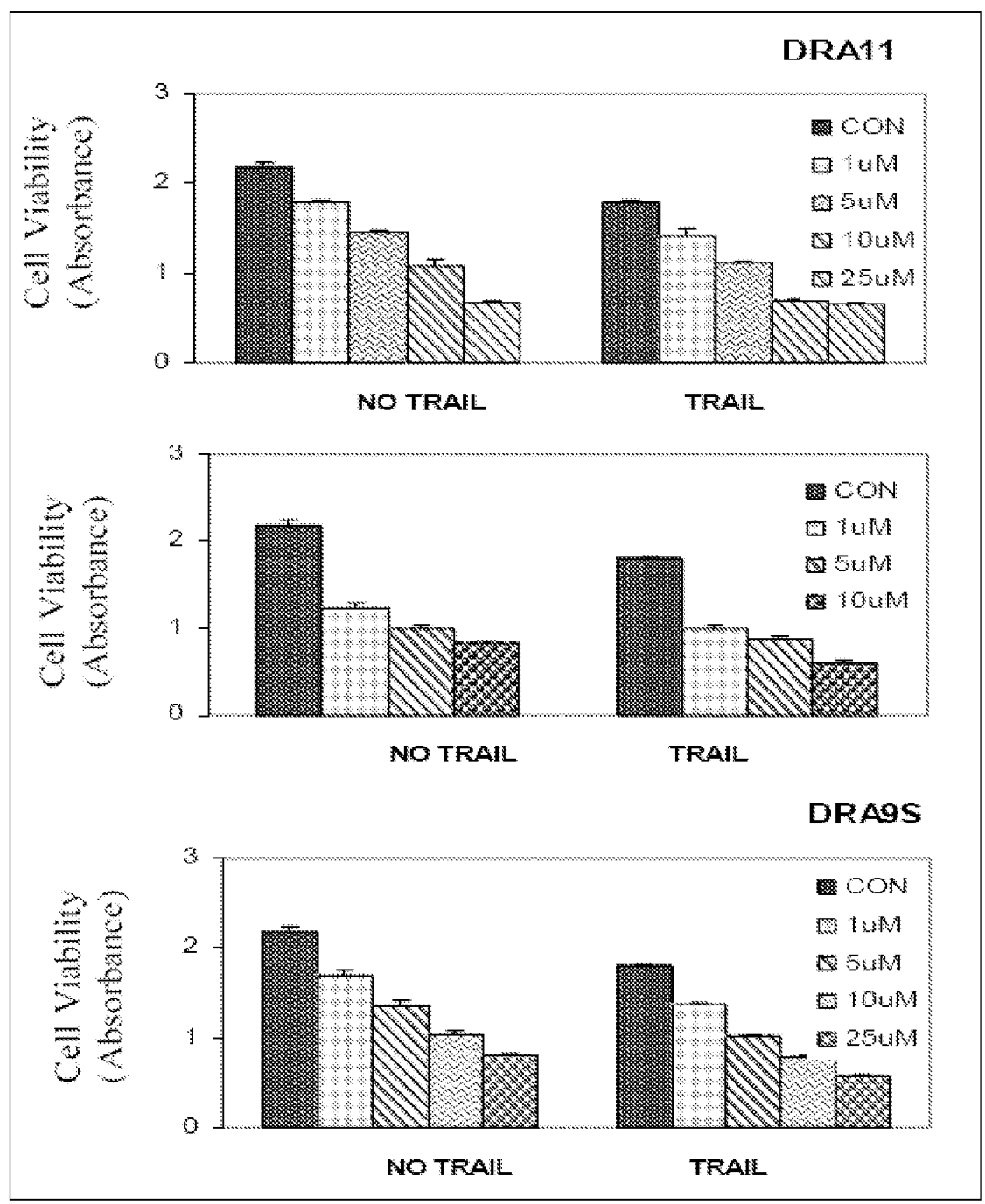
FIG. 16. Interactive effects of death receptor agonists and TRAIL on cell viability in human leukemia. Jurkat cells were treated with various concentrations DRA11, DRA9, and DRA9S in the presence or absence of TRAIL (25 ng/ml) for 72 h. At the end of incubation, cell viability was measured by XTT assay. Data represent the mean±S.D. Control refers to a group treated with DMSO (0.01%) alone.

Interactive Effects of Death Receptor Agonists and TRAIL on Cell Viability in Human Leukemia Jurkat cells were treated with various concentrations DRA11, DRA9, and DRA9S in the presence or absence of TRAIL (25 ng/ml) for 72 h. At the end of incubation, cell viability was measured by XTT assay. See, for example, FIG. 16. Data represent the mean ±S.D. Control refers to a group treated with DMSO (0.01%) alone.

Example 15

Figure 17:
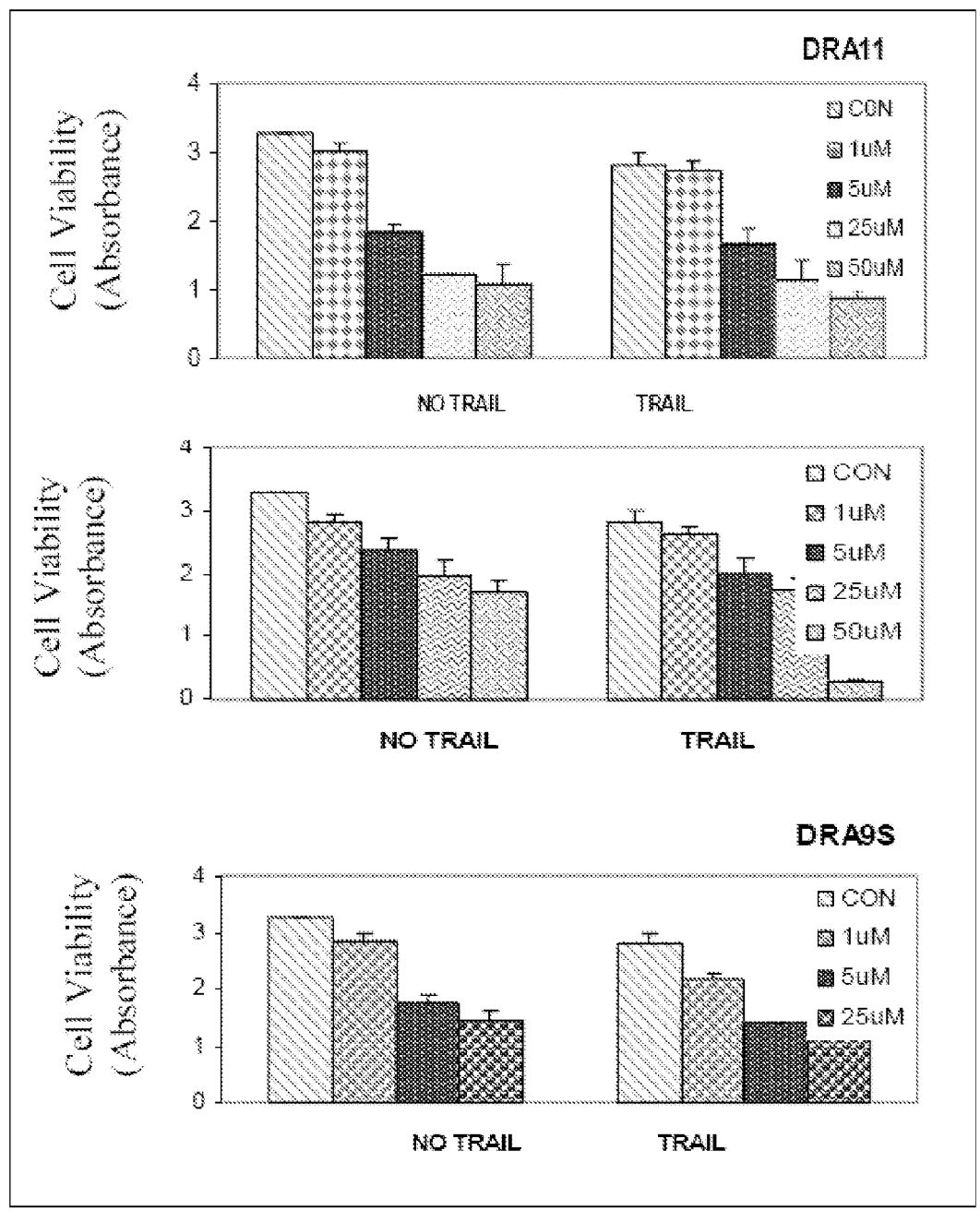
FIG. 17. Interactive effects of death receptor agonists and TRAIL on cell viability in human lung cancer. NCI-H460 lung cancer cells were treated with various concentrations DRA11, DRA9 (middle graph), and DRA9S in the presence or absence of TRAIL (50 ng/ml) for 72 h. At the end of incubation, cell viability was measured by XTT assay. Data represent the mean±S.D. Control refers to a group treated with DMSO (0.01%) alone.

Interactive Effects of Death Receptor Agonists and TRAIL on Cell Viability in Human Lung Cancer NCI-H460 lung cancer cells were treated with various concentrations DRA11, DRA9, and DRA9S in the presence or absence of TRAIL (50 ng/ml) for 72 h. At the end of incubation, cell viability was measured by XTT assay. See, for example, FIG. 17. Data represent the mean ±S.D. Control refers to a group treated with DMSO (0.01%) alone.

Example 16

Figure 18:
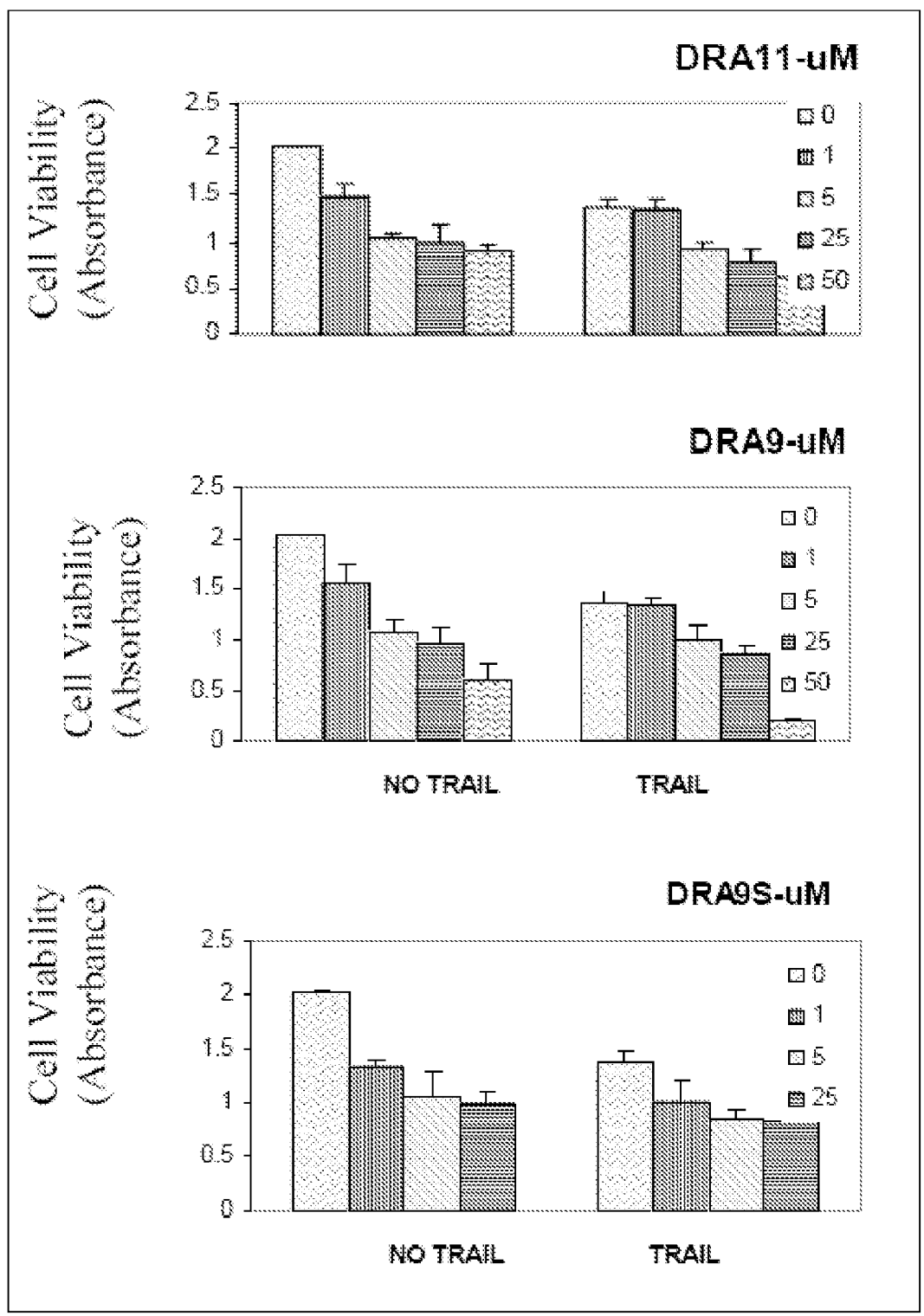
FIG. 18. Interactive effects of death receptor agonists and TRAIL on cell viability in human lung cancer. Non-small cell lung cancer (NSCLC) A549 cells were treated with various concentrations DRA11, DRA9, and DRA9S in the presence or absence of TRAIL (50 ng/ml) for 72 h. At the end of incubation, cell viability was measured by XTT assay. Data represent the mean±S.D. Control refers to a group treated with DMSO (0.01%) alone.

Interactive Effects of Death Receptor Agonists and TRAIL on Cell Viability in Human Lung Cancer Non-small cell lung cancer (NSCLC) A549 cells were treated with various concentrations DRA11, DRA9, and DRA9S in the presence or absence of TRAIL (50 ng/ml) for 72 h. At the end of incubation, cell viability was measured by XTT assay. See, for example, FIG. 18. Data represent the mean ±S.D. Control refers to a group treated with DMSO (0.01%) alone.

Example 17

Figure 19:
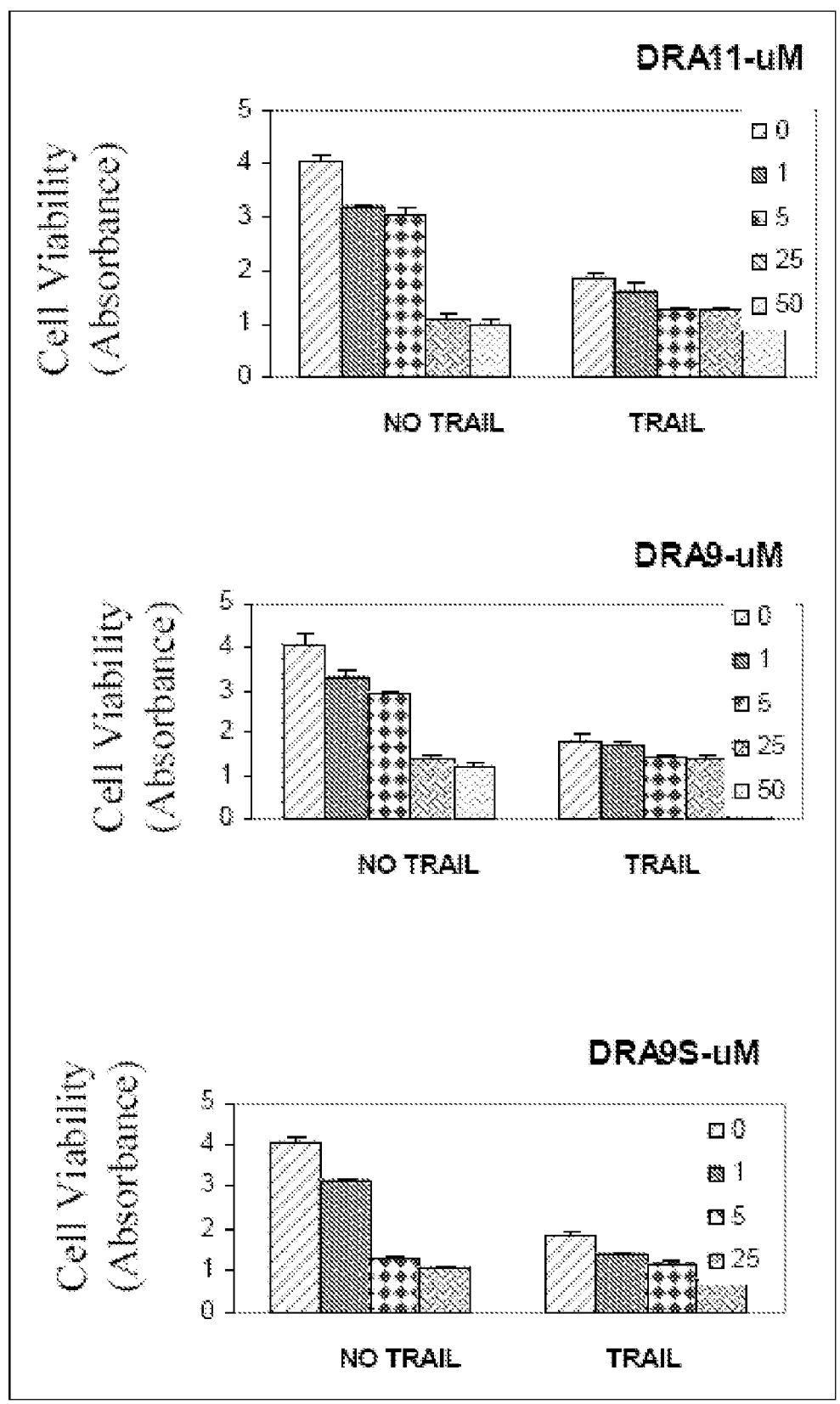
FIG. 19. Interactive effects of death receptor agonists and TRAIL on cell viability in human lung cancer. Squamous cell carcinoma NCI-H157 cells were treated with various concentrations DRA11, DRA9, and DRA9S in the presence or absence of TRAIL (50 ng/ml) for 72 h. At the end of incubation, cell viability was measured by XTT assay. Data represent the mean±S.D. Control refers to a group treated with DMSO (0.01%) alone.

Interactive Effects of Death Receptor Agonists and TRAIL on Cell Viability in Human Lung Cancer Squamous cell carcinoma NCI-H157 cells were treated with various concentrations DRA11, DRA9, and DRA9S in the presence or absence of TRAIL (50 ng/ml) for 72 h. At the end of incubation, cell viability was measured by XTT assay. See, for example, FIG. 19. Data represent the mean ±S.D. Control refers to a group treated with DMSO (0.01%) alone.

Example 18

Figure 20:
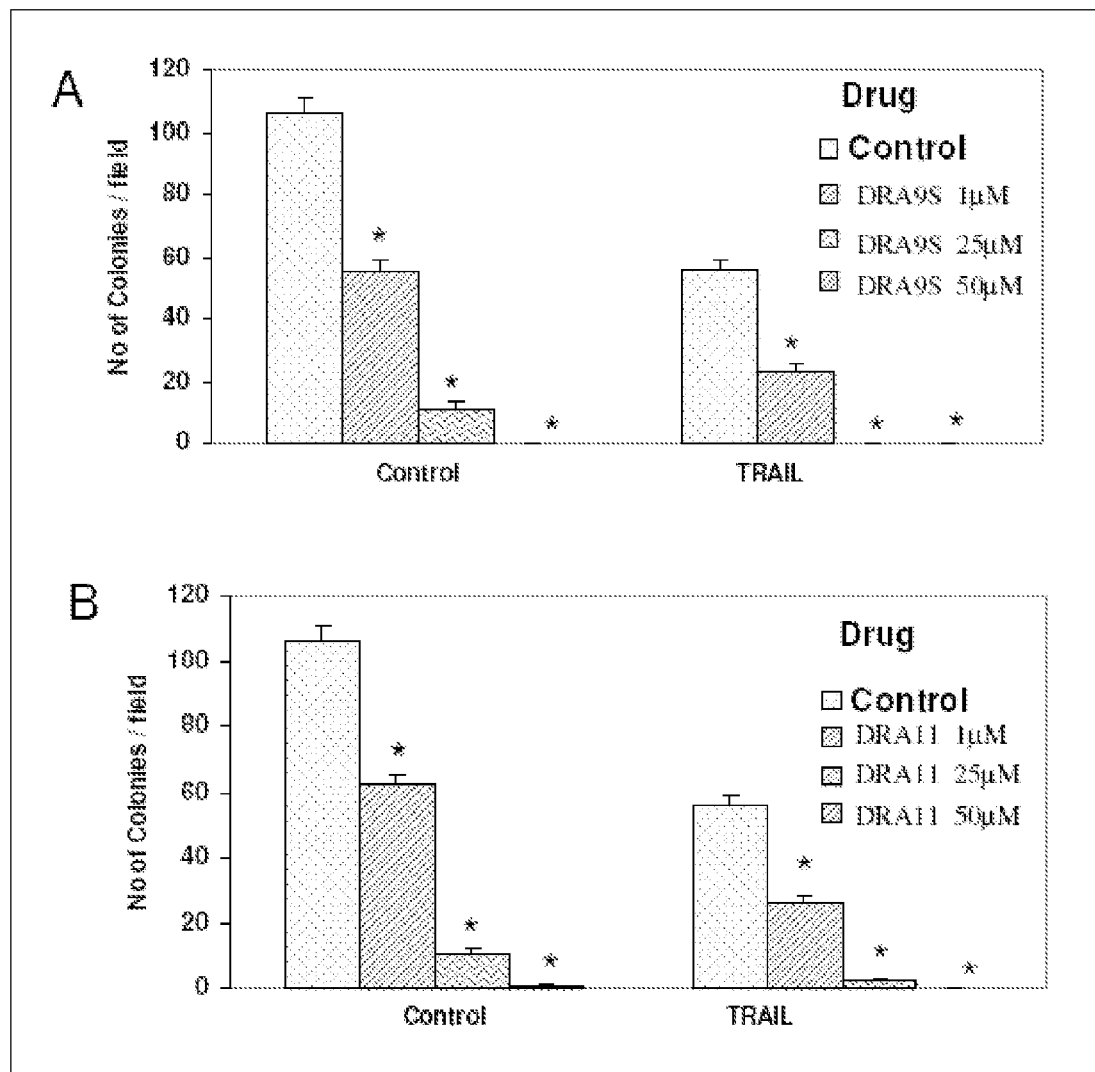
FIGS. 20A & B. Interactive effects of death receptor agonists and TRAIL on colony formation by lung cancer cells. Lung cancer A549 cells were seeded in 12-well plates in soft agar and treated with DRA9S (FIG. A), and DRA11 (FIG. B) in the presence or absence of TRAIL (25 nM). At the end of three weeks, number of colonies per field were counted by a microscope. Data represent the mean±S.D. *=significantly different from respective controls, P<0.05. Control refers to group treated with DMSO (0.01%).

Interactive Effects of Death Receptor Agonists and TRAIL on Colony Formation by Lung Cancer Cells Lung cancer A549 cells were seeded in 12-well plates in soft agar and treated with DRA9S, and DRA11 in the presence or absence of TRAIL (25 nM). At the end of three weeks, number of colonies per field were counted by a microscope. See, for example, FIG. 20. Data represent the mean ±S.D. *=significantly different from respective controls, $P<0.05$. Control refers to group treated with DMSO (0.01%).

Example 19

DRAs have No Effect on Cell Viability in Human Normal Mammary Epithelial Cells (HMECs)

Figure 21:
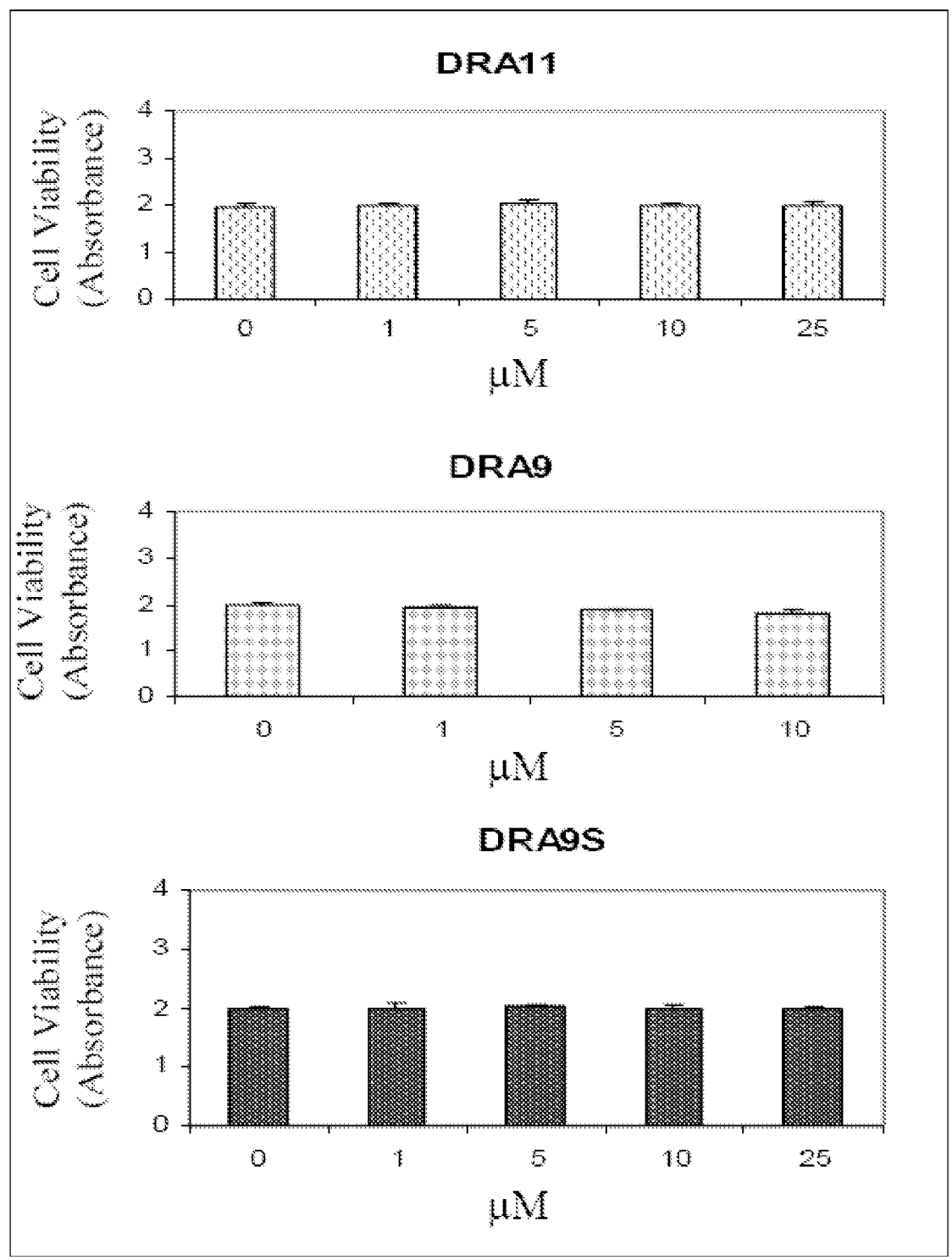
FIG. 21. DRAs have no effect on cell viability in human normal mammary epithelial cells (HMECs), HMECs were treated with DRA11, DRA9 and DRA9S for 72 h. At the end of incubation period, cell viability was measured by XTT assay. Data represent the mean±S.D. Control refers to group treated with DMSO (0.01%).

HMECs were treated with DRA11, DRA9 and DRA9S for 72 h. At the end of incubation period, cell viability was measured by XTT assay. See, for example, FIG. 21. Data represent the mean ±S.D. Control refers to group treated with DMSO (0.01%).

Example 20

DRAs have No Effect on Cell Viability in Human Normal Prostate Epithelial Cells (PrECs)

Figure 22:
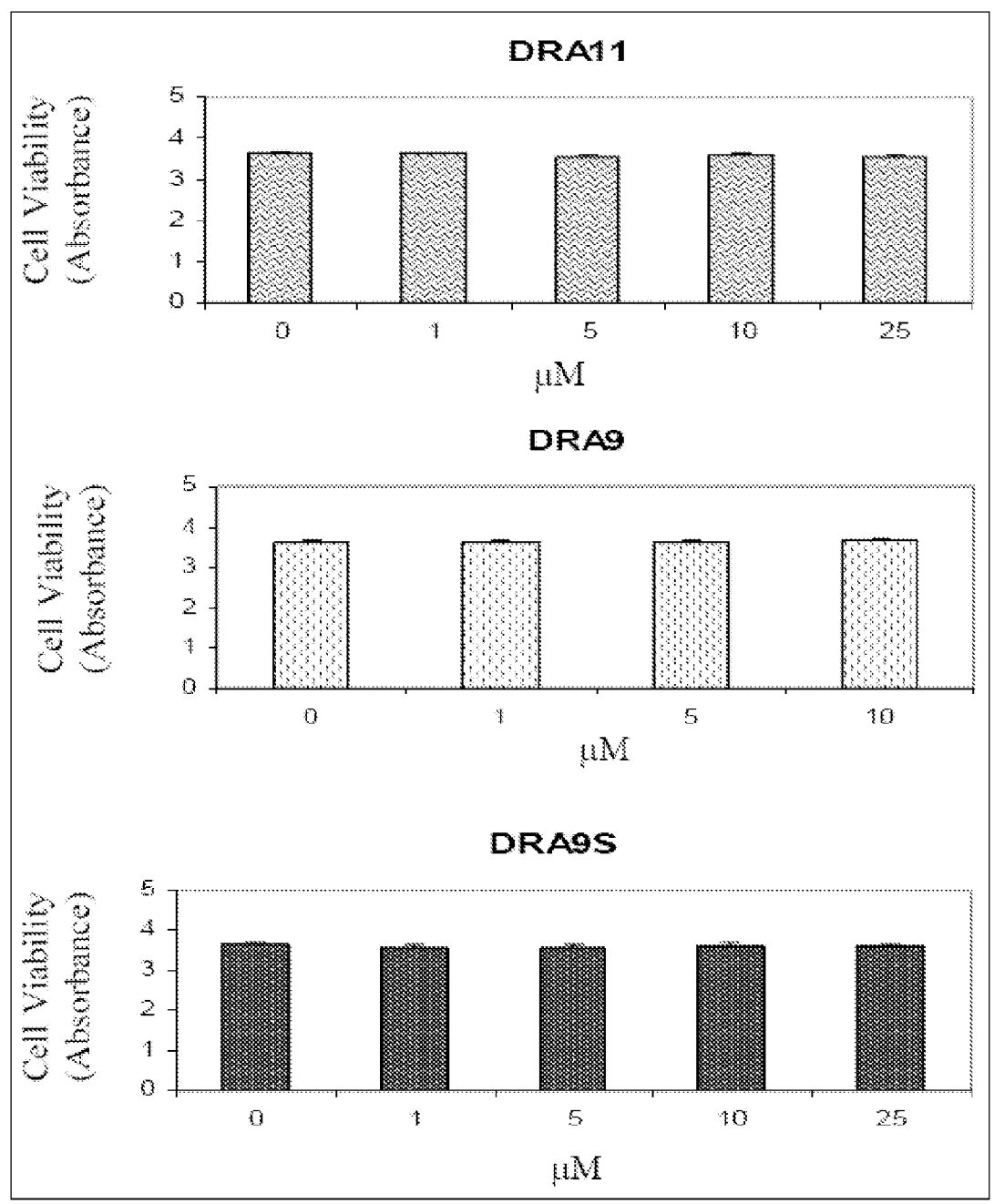
FIG. 22. DRAs have no effect on cell viability in human normal prostate epithelial cells (PrECs). PrECs were treated with DRA11, DRA9 and DRA9S for 72 h. At the end of incubation period, cell viability was measured by XTT assay. Data represent the mean±S.D. Control refers to group treated with DMSO (0.01%).

PrECs were treated with DRA11, DRA9 and DRA9S for 72 h. At the end of incubation period, cell viability was measured by XTT assay. See, for example, FIG. 22. Data represent the mean ±S.D. Control refers to group treated with DMSO (0.01%).

Example 21

DRAs have No Effect on Cell Viability in Human Bronchial Epithelial Cells (Beas2B)

Figure 23:
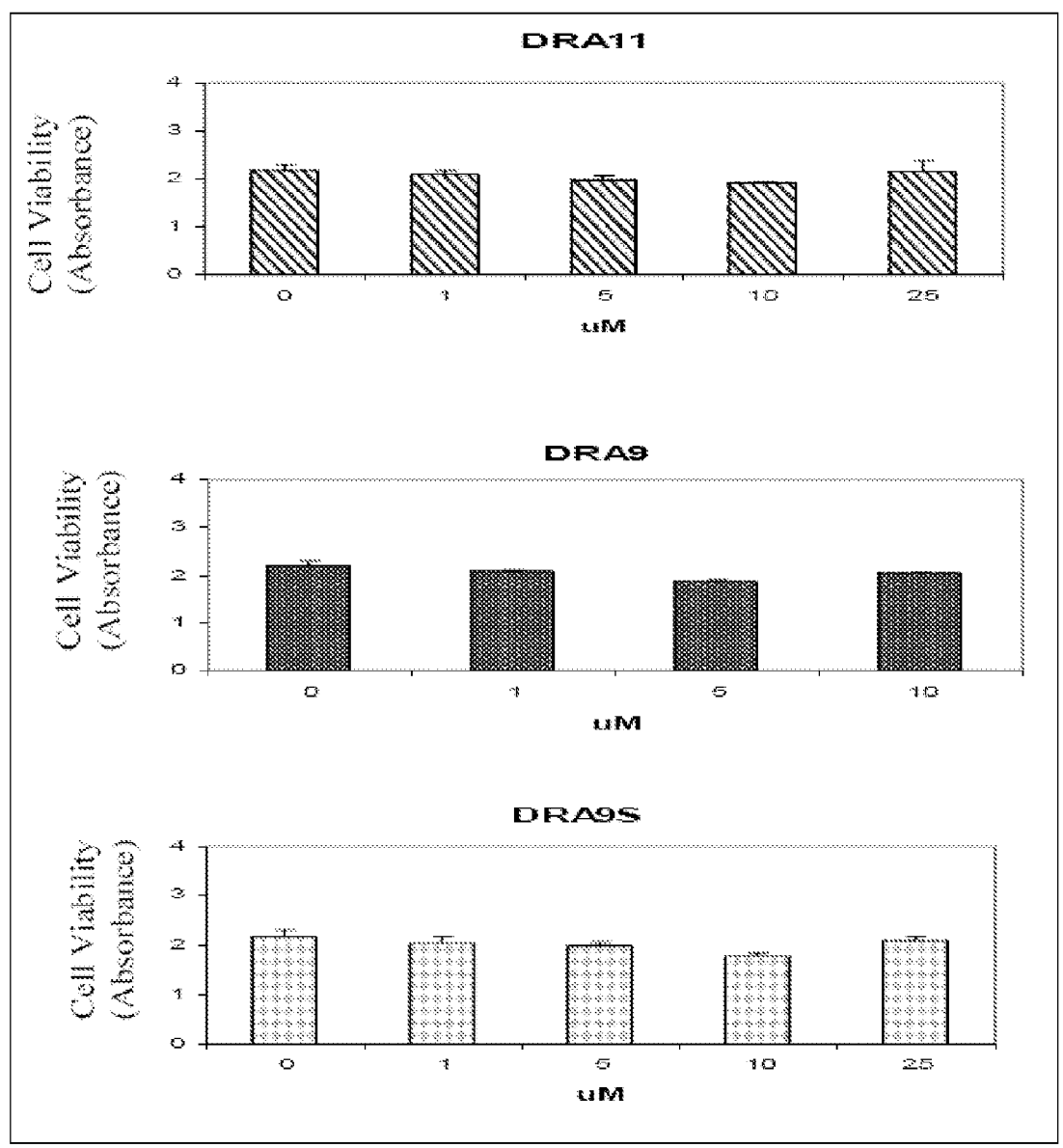
FIG. 23. DRAs have no effect on cell viability in human bronchial epithelial cells (Beas2B). Beas2B cells were treated with DRA11, DRA9 and DRA9S for 72 h. At the end of incubation period, cell viability was measured by XTT assay. Data represent the mean±S.D. Control refers to group treated with DMSO (0.01%).

Beas2B cells were treated with DRA11, DRA9 and DRA9S for 72 h. At the end of incubation period, cell viability was measured by XTT assay. See, for example, FIG. 23. Data represent the mean ±S.D. Control refers to group treated with DMSO (0.01%).

Example 22

Effects of DRA11 and TRAIL on Death-Inducing Signaling Complex (DISC) Formation

Figure 24:
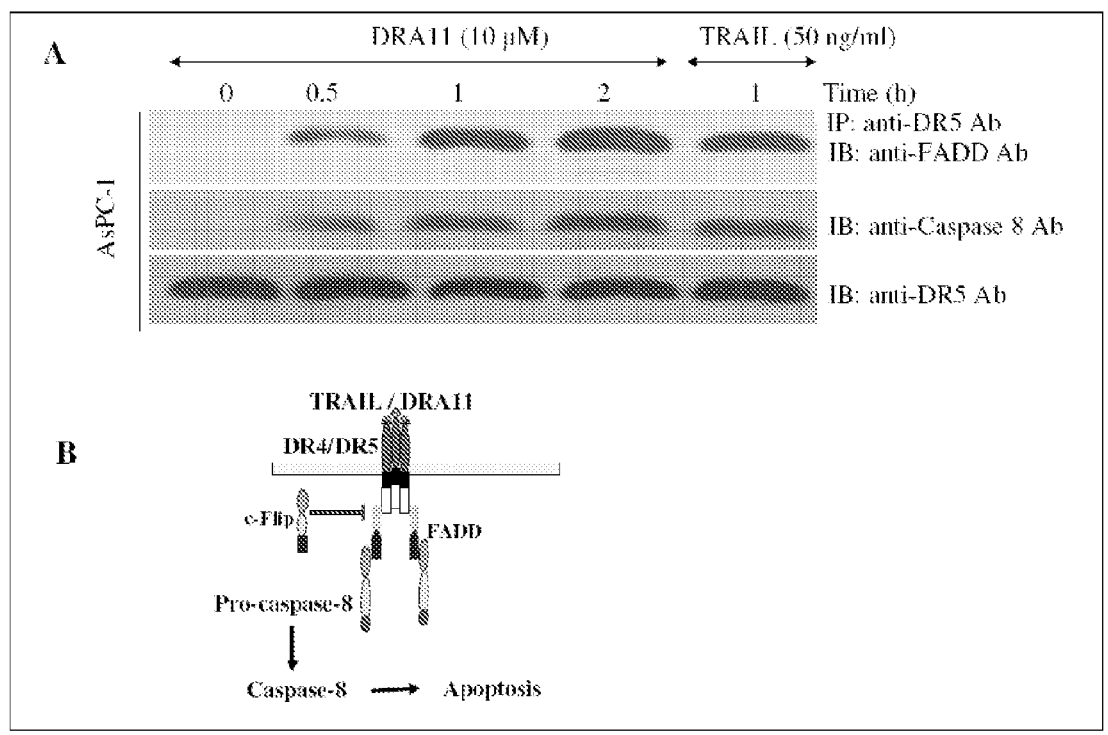
FIGS. 24A & B. Effects of DRA11 and TRAIL on death-inducing signaling complex (DISC) formation.
FIG. 24B: Model of DISC formation. Death receptor agonist DRA11 forms active DISC by recruiting FADD and thereby activating caspase-8.

Pancreatic cancer AsPC-1 cells were treated with either DRA11 (10 µM) for 0, 0.5, 1 and 2 h or TRAIL (50 ng/ml) for 1 h. Cell lysates were prepared, immunoprecipitated with anti-DR5 antibody, and immunoblotted with anti-FADD antibody, and anti-caspase-8 antibody. See, for example, FIG. 24A. The same blot was reprobed with anti-DR5 antibody as a loading control.

Example 23

Figure 25:
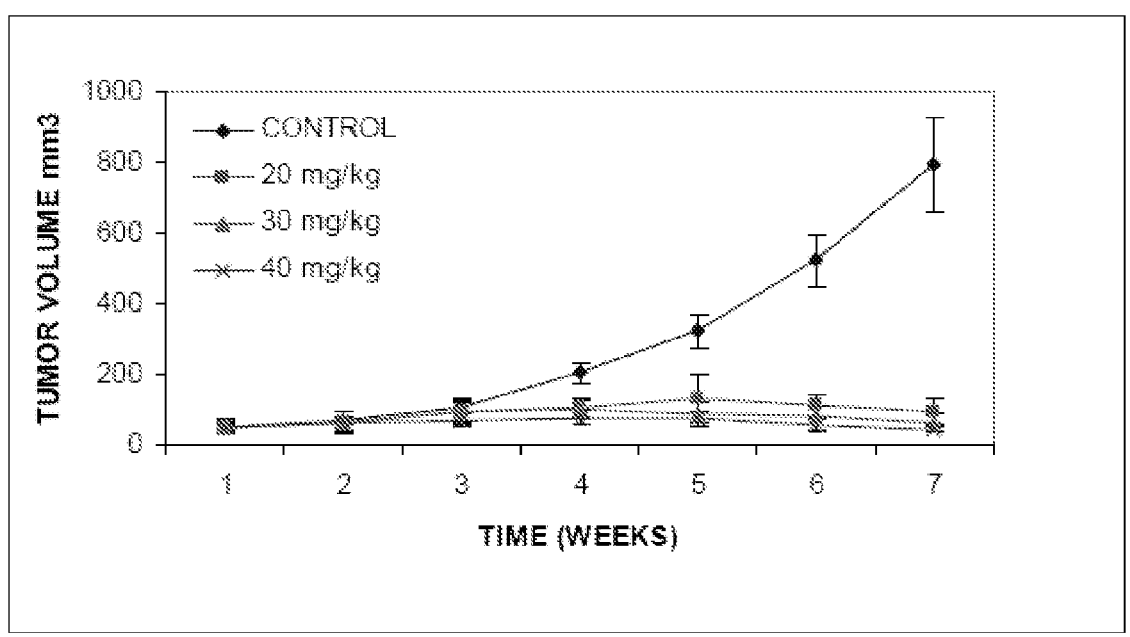
FIG. 25. DRA11 inhibits growth of breast cancer MDA-MB-231 cells xenografted in Balb c nude mice. MDA-MB-231 cells ($2\times10^6$ cells, in a final volume of 0.1 ml) were injected into the mammary fatpad of female Balb c nude mice. After tumor formation (about 100 mm$^3$), nude mice were treated (iv) with vehicle control (0.1 ml normal saline), DRA11 (20 mg/kg, 0.1 ml volume), DRA11 (30 mg/kg, 0.1 ml volume), and DRA11 (40 mg/kg, 0.1 ml volume) everyday 5 days per week throughout the duration of the experiment. Tumor volume was calculated using the equation: (volume=length×width×depth×0.5236 mm$^3$).

DRA11 Inhibits Growth of Breast Cancer MDA-MB-231 Cells Xenografted in Balb c Nude Mice MDA-MB-231 cells ($2 \times 10^6$ cells, in a final volume of 0.1 ml) were injected into the mammary fatpad of female Balb c nude mice. After tumor formation (about 100 mm$^3$), nude mice were treated (iv) with vehicle control (0.1 ml normal saline), DRA11 (20 mg/kg, 0.1 ml volume), DRA11 (30 mg/kg, 0.1 ml volume), and DRA11 (40 mg/kg, 0.1 ml volume) everyday 5 days per week throughout the duration of the experiment. See, for example, FIG. 25. Tumor volume was calculated using the equation: (volume=length×width×depth×0.5236 mm$^3$).

Example 24

Figure 26:
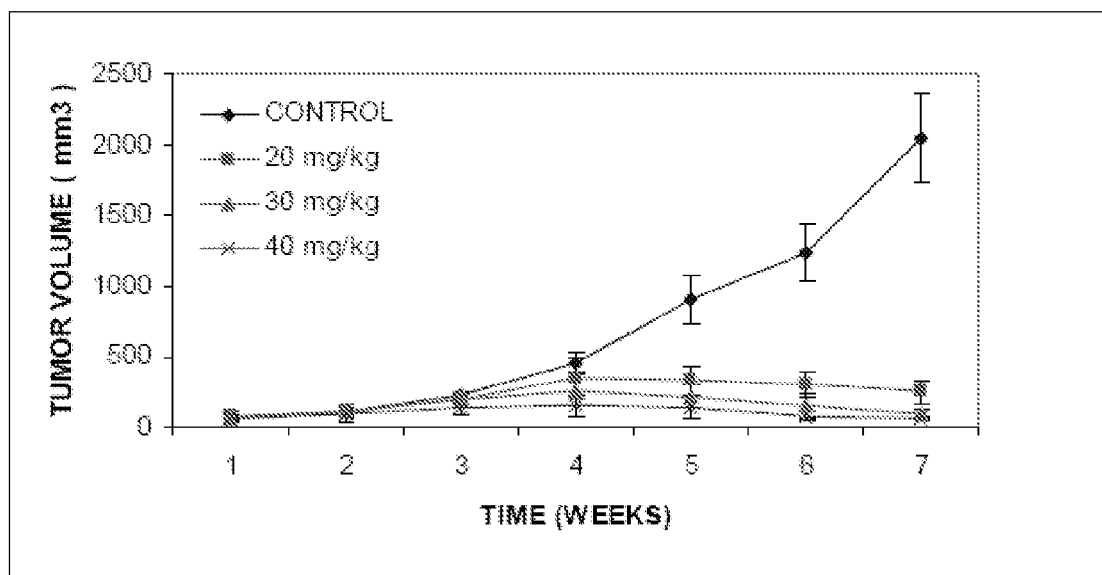
FIG. 26. DRA11 inhibits growth of prostate cancer PC-3 cells xenografted in Balb c nude mice. PC-3 cells ($2\times10^6$ cells, in a final volume of 0.1 ml) were injected subcutaneously in the right flank of Balb c nude mice. After tumor formation (about 100 mm$^3$), nude mice were treated (iv) with vehicle control (0.1 ml normal saline), DRA11 (20 mg/kg, 0.1 ml volume), DRA11 (30 mg/kg, 0.1 ml volume), and DRA11 (40 mg/kg, 0.1 ml volume) everyday 5 days per week throughout the duration of the experiment. Tumor volume was calculated using the equation: (volume=length×width×depth×0.5236 mm$^3$). Data represent mean±S.E.

DRA11 Inhibits Growth of Prostate Cancer PC-3 Cells Xenografted in Balb c Nude Mice PC-3 cells ($2 \times 10^6$ cells, in a final volume of 0.1 ml) were injected subcutaneously in the right flank of Balb c nude mice. After tumor formation (about 100 mm$^3$), nude mice were treated (iv) with vehicle control (0.1 ml normal saline), DRA11 (20 mg/kg, 0.1 ml volume), DRA11 (30 mg/kg, 0.1 ml volume), and DRA11 (40 mg/kg, 0.1 ml volume) everyday 5 days per week throughout the duration of the experiment. Tumor volume was calculated using the equation: (volume=length×width×depth×0.5236 mm$^3$). See, for example, FIG. 26. Data represent mean ±S.E.

Example 25

Figure 27:
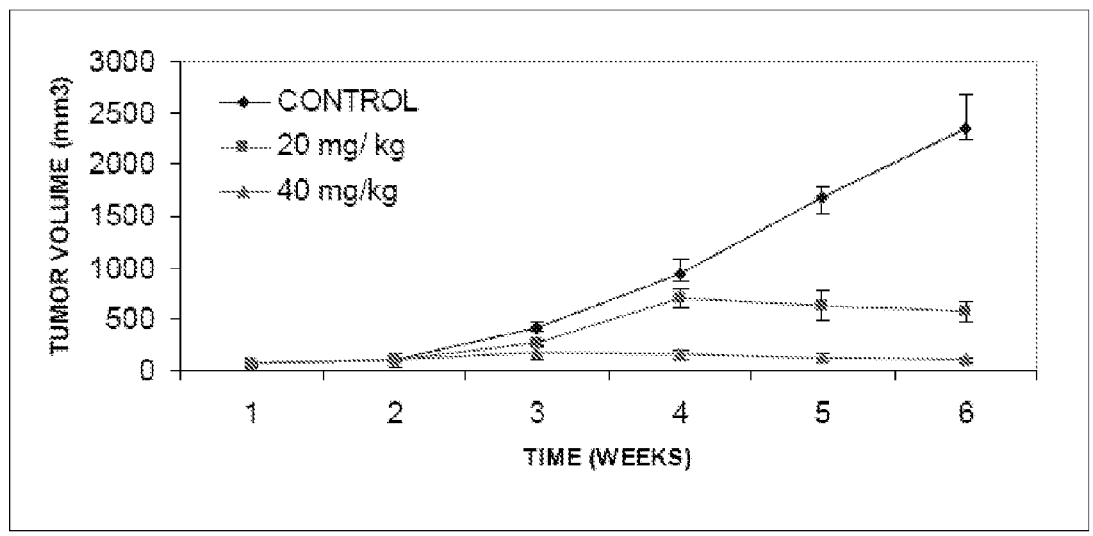
FIG. 27. DRA11 inhibits growth of pancreatic cancer AsPC-1 cells xenografted in Balb c nude mice. AsPC-1 cells ($2\times10^6$ cells as a 50% suspension in Matrigel, Becton Dickinson, Bedford, Mass., in a final volume of 0.1 ml) were injected subcutaneously in the right flank of Balb c nude mice. After tumor formation (about 100 mm$^3$), nude mice (10 per group) were treated (iv) with vehicle control (0.1 ml normal saline), DRA11 (20 mg/kg, 0.1 ml volume), and DRA11 (40 mg/kg, 0.1 ml volume) everyday 5 days per week throughout the duration of the experiment. Tumor volume was calculated using the equation: (volume=length×width×depth×0.5236 mm$^3$). Data represent mean±S.E. *=significantly different from respective controls, P<0.05.

DRA11 Inhibits Growth of Pancreatic Cancer AsPC-1 Cells Xenografted in Balb c Nude Mice AsPC-1 cells ($2 \times 10^6$ cells as a 50% suspension in Matrigel, Becton Dickinson, Bedford, Mass., in a final volume of 0.1 ml) were injected subcutaneously in the right flank of Balb c nude mice. After tumor formation (about 100 mm$^3$), nude mice (10 per group) were treated (iv) with vehicle control (0.1 ml normal saline), DRA11 (20 mg/kg, 0.1 ml volume), and DRA11 (40 mg/kg, 0.1 ml volume) everyday 5 days per week throughout the duration of the experiment. Tumor volume was calculated using the equation: (volume=length×width× depth×0.5236 mm$^3$). See, for example, FIG. 27. Data represent mean ±S.E. *=significantly different from respective controls, P<0.05.

Example 26

Figure 28:
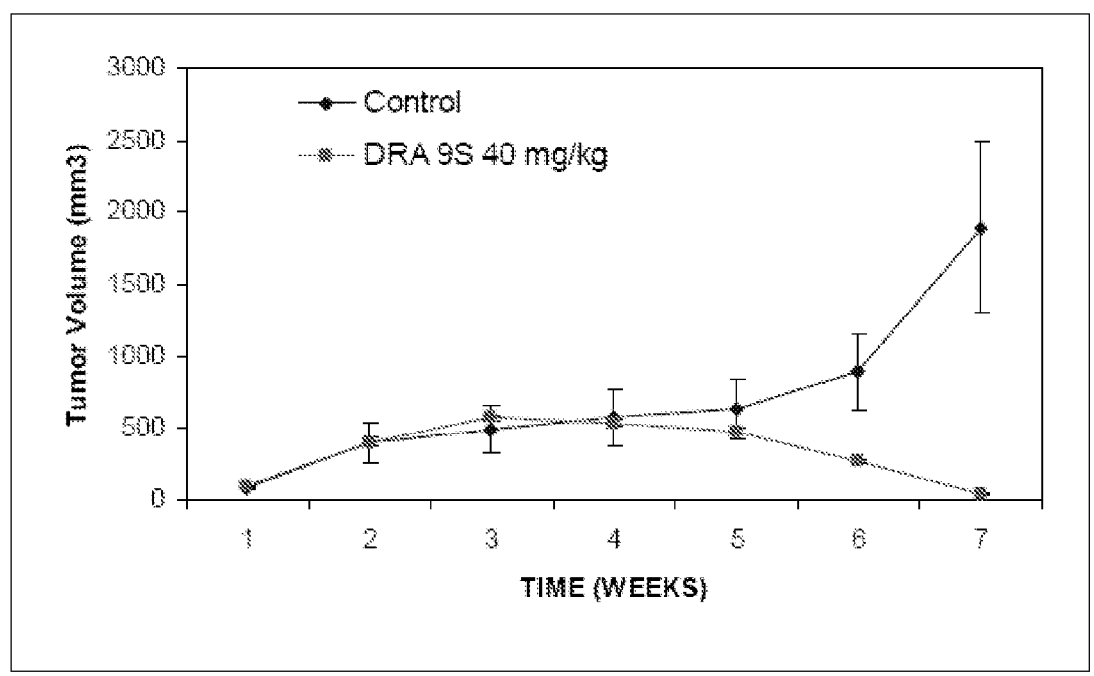
FIG. 28. DRA9S inhibits growth of prostate cancer LNCaP cells xenografted in Balb c nude mice. LNCaP cells ($2\times10^6$ cells as a 50% suspension in Matrigel, Becton Dickinson, Bedford, Mass., in a final volume of 0.1 ml) were injected subcutaneously in the right flank of Balb c nude mice. After tumor formation (about 100 mm$^3$), nude mice were treated (iv) with vehicle control (0.1 ml normal saline), and DRA9S (40 mg/kg, 0.1 ml volume) everyday 5 days per week throughout the duration of the experiment. Tumor volume was calculated using the equation: (volume=length×width×depth×0.5236 mm$^3$). Data represent mean±S.E.

DRA9S Inhibits Growth of Prostate Cancer LNCaP Cells Xenografted in Balb c Nude Mice LNCaP cells (2×10$^6$ cells as a 50% suspension in Matrigel, Becton Dickinson, Bedford, Mass., in a final volume of 0.1 ml) were injected subcutaneously in the right flank of Balb c nude mice. After tumor formation (about 100 mm$^3$), nude mice were treated (iv) with vehicle control (0.1 ml normal saline), and DRA9S (40 mg/kg, 0.1 ml volume) everyday 5 days per week throughout the duration of the experiment. Tumor volume was calculated using the equation: (volume=length×width×depth×0.5236 mm$^3$). See, for example, FIG. 28. Data represent mean ±S.E.

Example 27

Figure 29:
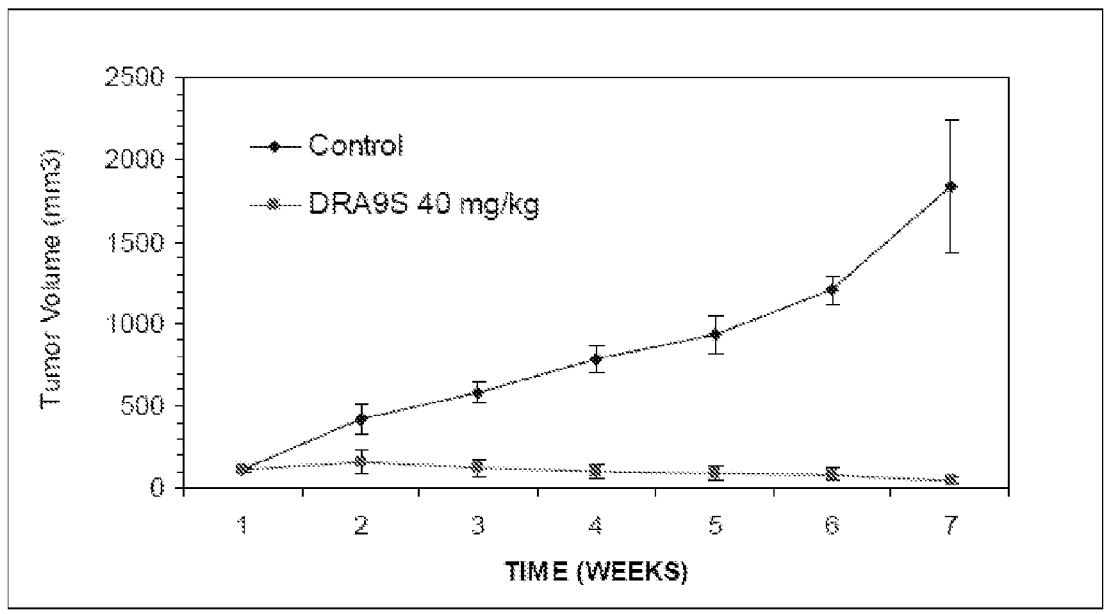
FIG. 29. DRA9S inhibits growth of prostate cancer PC-3 cells xenografted in Balb c nude mice. PC-3 cells ($1\times10^6$ cells, in a final volume of 0.1 ml PBS) were injected subcutaneously in the right flank of Balb c nude mice. After tumor formation (about 100 mm$^3$), nude mice were treated (iv) with vehicle control (0.1 ml normal saline), and DRA9S (40 mg/kg, 0.1 ml volume) everyday 5 days per week throughout the duration of the experiment. Tumor volume was calculated using the equation: (volume=length×width×depth×0.5236 mm$^3$). Data represent mean±S.E.

DRA9S Inhibits Growth of Prostate Cancer PC-3 Cells Xenografted in Balb c Nude Mice PC-3 cells (1×10$^6$ cells, in a final volume of 0.1 ml PBS) were injected subcutaneously in the right flank of Balb c nude mice. After tumor formation (about 100 mm$^3$), nude mice were treated (iv) with vehicle control (0.1 ml normal saline), and DRA9S (40 mg/kg, 0.1 ml volume) everyday 5 days per week throughout the duration of the experiment. Tumor volume was calculated using the equation: (volume=length× width×depth×0.5236 mm$^3$). See, for example, FIG. 29. Data represent mean ±S.E.

Example 28

Figure 30:
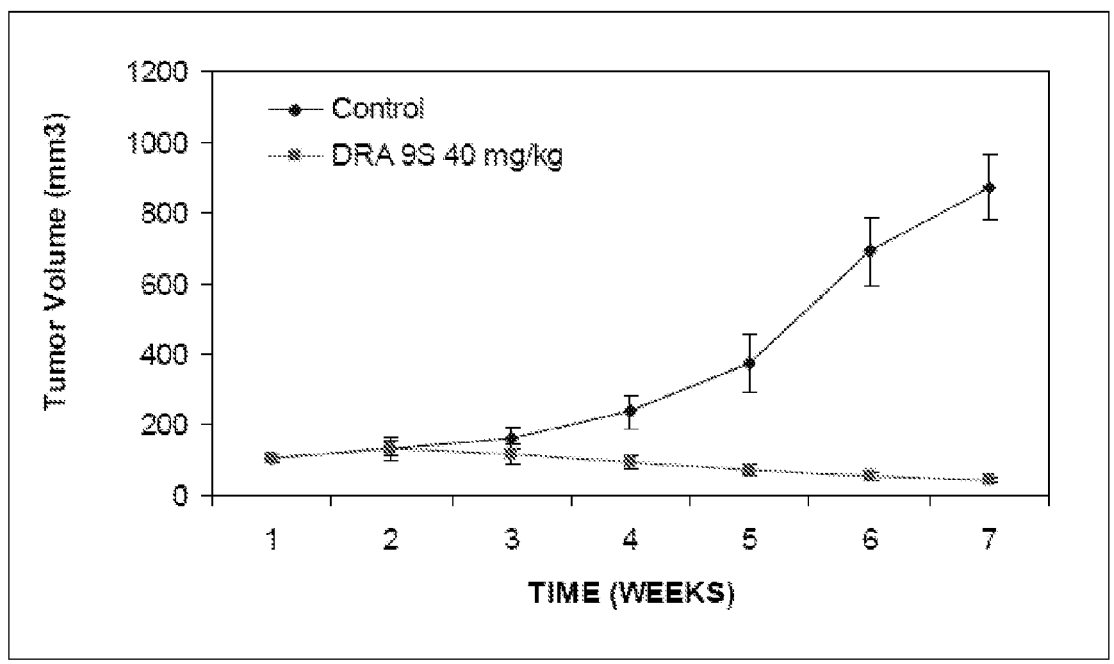
FIG. 30. DRA9S inhibits growth of breast cancer MDA-MB-468 cells xenografted in Balb c nude mice. MDA-MB-468 cells ($2\times10^6$ cells, in a final volume of 0.1 ml PBS) were injected subcutaneously in the right flank of Balb c nude mice. After tumor formation (about 100 mm$^3$), nude mice were treated (iv) with vehicle control (0.1 ml normal saline), and DRA9S (40 mg/kg, 0.1 ml volume) everyday 5 days per week throughout the duration of the experiment. Tumor volume was calculated using the equation: (volume=length×width×depth×0.5236 mm$^3$). Data represent mean±S.E.

DRA9S Inhibits Growth of Breast Cancer MDA-MB-468 Cells Xenografted in Balb c Nude Mice MDA-MB-468 cells (2×10$^6$ cells, in a final volume of 0.1 ml PBS) were injected subcutaneously in the right flank of Balb c nude mice. After tumor formation (about 100 mm$^3$), nude mice were treated (iv) with vehicle control (0.1 ml normal saline), and DRA9S (40 mg/kg, 0.1 ml volume) everyday 5 days per week throughout the duration of the experiment. Tumor volume was calculated using the equation: (volume=length×width×depth×0.5236 mm$^3$). See, for example, FIG. 30. Data represent mean ±S.E.

Example 29

Figure 31:
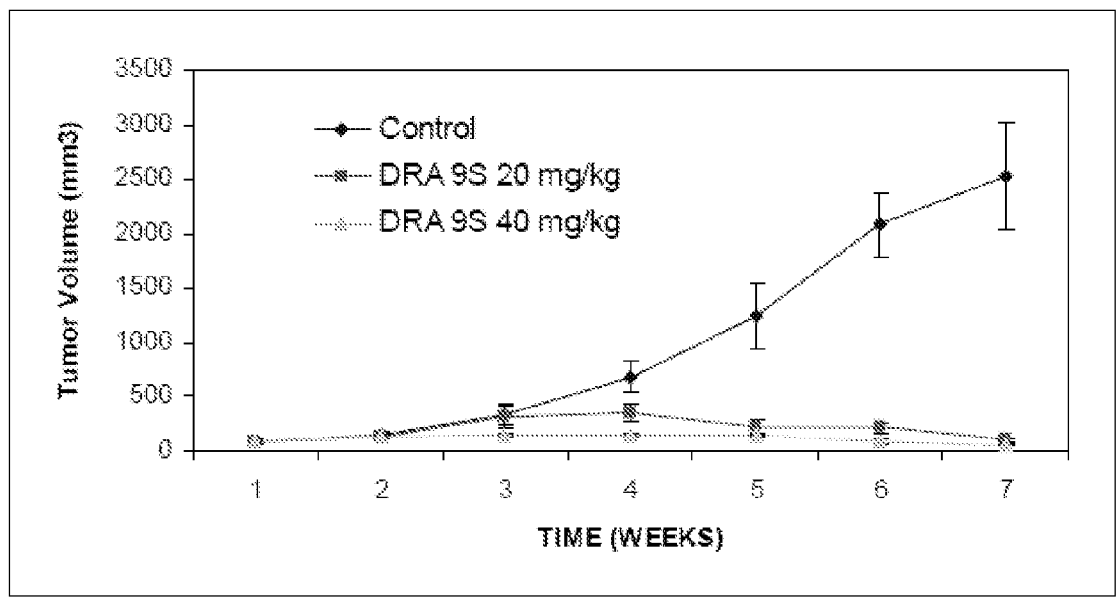
FIG. 31. DRA9S inhibits growth of pancreatic cancer AsPC-1 cells xenografted in Balb c nude mice. MDA-MB-468 cells ($2\times10^6$ cells, in a final volume of 0.1 ml PBS) were injected subcutaneously in the right flank of Balb c nude mice. After tumor formation (about 100 mm$^3$), nude mice were treated (iv) with vehicle control (0.1 ml normal saline), DRA9S (20 mg/kg, 0.1 ml volume), and DRA9S (40 mg/kg, 0.1 ml volume) everyday 5 days per week throughout the duration of the experiment. Tumor volume was calculated using the equation: (volume=length×width×depth×0.5236 mm$^3$). Data represent mean±S.E.

DRA9S Inhibits Growth of Pancreatic Cancer AsPC-1 Cells Xenografted in Balb c Nude Mice MDA-MB-468 cells (2×10$^6$ cells, in a final volume of 0.1 ml PBS) were injected subcutaneously in the right flank of Balb c nude mice. After tumor formation (about 100 mm$^3$), nude mice were treated (iv) with vehicle control (0.1 ml normal saline), DRA9S (20 mg/kg, 0.1 ml volume), and DRA9S (40 mg/kg, 0.1 ml volume) everyday 5 days per week throughout the duration of the experiment. Tumor volume was calculated using the equation: (volume=length×width× depth×0.5236 mm$^3$). See, for example, FIG. 31. Data represent mean ±S.E.

Example 30

Clinical Trials

This example is concerned with the development of human treatment protocols using the compounds of this invention alone or in combination with other anti-cancer drugs. DRAs will be of use in the clinical treatment of various cancers involving, for example, activation of caspase-8 to induce apoptosis in cancerous cells play a role. Such treatment will be particularly useful tools in anti-tumor therapy, for example, in treating patients with ovarian, breast, prostate, pancreatic, brain, colon, and lung cancers that are resistant to conventional chemotherapeutic regimens.

The various elements of conducting a clinical trial, including patient treatment and monitoring, will be known to those of skill in the art in light of the present disclosure. The following information is being presented as a general guideline for use in conducting clinical trials on DRAs.

Patients with advanced, metastatic breast, epithelial ovarian carcinoma, pancreatic, colon, or other cancers chosen for clinical study will typically be at high risk for developing the cancer, will have been treated previously for the cancer which is presently in remission, or will have failed to respond to at least one course of conventional therapy. In an exemplary clinical protocol, patients may undergo placement of a Tenckhoff catheter, or other suitable device, in the pleural or peritoneal cavity and undergo serial sampling of pleural/peritoneal effusion. Typically, one will wish to determine the absence of known loculation of the pleural or peritoneal cavity, creatinine levels that are below 2 mg/dl, and bilirubin levels that are below 2 mg/dl. The patient should exhibit a normal coagulation profile.

In regard to the DRAs and other anti-cancer drug administration, a Tenckhoff catheter, or alternative device may be placed in the pleural cavity or in the peritoneal cavity, unless such a device is already in place from prior surgery. A sample of pleural or peritoneal fluid can be obtained, so that baseline cellularity, cytology, LDH, and appropriate markers in the fluid (CEA, CA15-3, CA 125, PSA, p38 (phosphorylated and un-phosphorylated forms), and Akt (phosphorylated and un-phosphorylated forms) in the cells may be assessed and recorded.

In the same procedure, the DRAs may be administered alone or in combination with the other anti-cancer drug. The administration may be in the pleural/peritoneal cavity, directly into the tumor, or in a systemic manner. The starting dose may be 0.5 mg/kg body weight. Three patients may be treated at each dose level in the absence of grade>3 toxicity. Dose escalation may be done by 100% increments (0.5 mg, 1 mg, 2 mg, 4 mg) until drug related grade 2 toxicity is detected. Thereafter dose escalation may proceed by 25% increments. The administered dose may be fractionated equally into two infusions, separated by six hours if the combined endotoxin levels determined for the lot of the DRA and/or the lot of anti-cancer drug exceed 5 EU/kg for any given patient.

The DRAs and/or the other anti-cancer drug combination, may be administered over a short infusion time or at a steady rate of infusion over a 7 to 21 day period. The DRAs infusion may be administered alone or in combination with the anticancer drug and/or emodin like tyrosine kinase inhibitor. The infusion given at any dose level will be dependent upon the toxicity achieved after each. Hence, if Grade II toxicity was reached after any single infusion, or at a particular period of time for a steady rate infusion, further doses should be withheld or the steady rate infusion stopped unless toxicity improved. Increasing doses of the DRA alone or in combination with an anti-cancer drug will be administered to groups of patients until approximately 60% of patients show unacceptable Grade III or IV toxicity in any category. Doses that are ⅔ of this value could be defined as the safe dose.

Physical examination, tumor measurements, and laboratory tests should, of course, be performed before treatment and at intervals of about 3-4 weeks later. Laboratory studies should include CBC, differential and platelet count, urinalysis, SMA-12-100 (liver and renal function tests), coagulation profile, and any other appropriate chemistry studies to determine the extent of disease, or determine the cause of existing symptoms. Also appropriate biological markers in serum should be monitored e.g. CEA, CA 15-3, p38 (phosphorylated and non-phosphorylated forms) and Akt (phosphorylated and non-phosphorylated forms), p185, etc.

To monitor disease course and evaluate the anti-tumor responses, it is contemplated that the patients should be examined for appropriate tumor markers every 4 weeks, if initially abnormal, with twice weekly CBC, differential and platelet count for the 4 weeks; then, if no myelosuppression has been observed, weekly. If any patient has prolonged myelosuppression, a bone marrow examination is advised to rule out the possibility of tumor invasion of the marrow as the cause of pancytopenia. Coagulation profile shall be obtained every 4 weeks. An SMA-12-100 shall be performed weekly. Pleural/peritoneal effusion may be sampled 72 hours after the first dose, weekly thereafter for the first two courses, then every 4 weeks until progression or off study. Cellularity, cytology, LDH, and appropriate markers in the fluid (CEA, CA15-3, CA 125, ki67 and Tunel assay to measure apoptosis, Akt) and in the cells (Akt) may be assessed. When measurable disease is present, tumor measurements are to be recorded every 4 weeks. Appropriate radiological studies should be repeated every 8 weeks to evaluate tumor response. Spirometry and DLCO may be repeated 4 and 8 weeks after initiation of therapy and at the time study participation ends. An urinalysis may be performed every 4 weeks.

Clinical responses may be defined by acceptable measure. For example, a complete response may be defined by the disappearance of all measurable disease for at least a month. Whereas a partial response may be defined by a 50% or greater reduction of the sum of the products of perpendicular diameters of all evaluable tumor nodules or at least 1 month with no tumor sites showing enlargement. Similarly, a mixed response may be defined by a reduction of the product of perpendicular diameters of all measurable lesions by 50% or greater with progression in one or more sites.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, and those listed in the Appendix, to the extent that they provide exemplary procedural or other details supplementary to those set forth herein, are specifically incorporated herein by reference.

U.S. Pat. No. 4,683,195
U.S. Pat. No. 6,025,395
Alnemri et al., *Cell*, 87:171, 1996.
Ashkenazi and Dixit, *Science*, 281:1305-1308, 1998.
Ashkenazi et al., *Curr. Opin. Cell. Biol.*, 11:255-260, 1999.
Ashkenazi et al., *J. Clin. Invest.*, 104:155-162, 1999.
Ausubel et al., In: *Current Protocols in Molecular Biology*, John, Wiley & Sons, Inc, NY, 1994.
Butler et al., *Cancer Res.*, 5165-5170, 2000.
Butler et al., *Clin. Cancer Res.*, 7:962-970, 2001.
Cal et al., *Curr. Med. Chem. Anti-Cancer Agents*, 3:77-93, 2003.
Chen et al., *Oncogene*, 20:6073-6083, 2001.
Chinnaiyan et al., *Proc. Natl. Acad. Sci. USA*, 97:1754-1759, 2000.
Coffey et al., *Cancer Res.*, 61:3591-3594, 2001.
Coffey et al., *Med. Pediatr. Oncol.*, 35:577-581, 2000.
Cohen et al., *Anticancer Res.*, 22:1497-1504, 2002.
Cress and Seto, *J. Cell. Physiol.*, 184:1-16, 2000.
Cuello et al., *Cell Death Differ.*, doi: 10.1038/sj.cdd.4401387, 2004.
Culver et al., *Science*, 256(5063):1550-1552, 1992.
Deckert and Struhl, *Mol. Cell. Biol.*, 21:2726-2735, 2001.
Deeb et al., *Mol. Cancer. Ther.*, 2:95-103, 2003.
Degli-Esposti et al., *Immunity*, 7:813-820, 1997a.
Degli-Esposti et al., *J. Exp. Med.*, 186:1165-1170, 1997b.
Desagher and Martinou, *Trends Cell Biol.*, 10:369-377, 2000.
Droin et al., Mol. Cell Biol., 23(21):7638-7647, 2003.
Du et al., *Cell*, 102:33-42, 2000.
Emery et al., *J. Biol. Chem.*, 273:14363-14367, 1998.
French and Tschopp, *Cell Death Differ.*, 10:117-123, 2003.
French and Tschopp, *Nat. Med.*, 5:146-147, 1999.
Fulda and Debatin, *Cancer Res.*, 64:337-346. 2004.
Fulda and Debatin, *Drug Resist.*, 6:1-3, 2003.
Gait, In: *Oligonucleotide Synthesis: A Practical Approach*, IRL Press Oxford, United Kingdom, 1984.
Gibson et al., *Mol. Cell. Biol.*, 20:205-212, 2000.
Gliniak and Le, *Cancer Res.*, 59:6153-6158, 1999.
Glover, In: *DNA Cloning*, Vol. I and II, 1985.
Gong et al., *Cell Growth Differ.*, 10:491-502, 1999.
Gopee et al., *Toxicol. Sci.*, 78(2):204-214, 2004.
Gray and Teh, *Curr. Mol. Med.*, 1(4):401-429, 2001.
Green and Reed, *Science*, 281:1309-1312, 1998.
Green, *Cell*, 94:695-698, 1998.
Green, *Science*, 238:1246-1247, 1997.
Gregory et al., *Exp. Cell Res.*, 265:195-202, 2001.
Griffith et al., *J. Exp. Med.*, 189:1343-1354, 1999.
Grinberg et al., *J. Biol. Chem.*, 277(14):12237-12245, 2002.
Gross et al., *J. Biol. Chem.*, 274:1156-1163, 1999.
Gusman et al., *Carcinogenesis*, 22:1111-1117, 2001.
Hames and Higgins, In: *Nucleic acid hybridisation: a practical approach*, IRL, Oxford, UK, 1985.
He et al., *Oncogene*, 21:6032-6040, 2002.
Hegde et al., *J. Biol. Chem.*, 277:432-438, 2002.
Henderson and Brancolini, *Drug Resist.*, 6:247-256, 2003.
Hotta et al., *J. Orthop. Res.*, 21:949-957, 2003.
Hymowitz et al., *Mol. Cell.*, 4:563-571, 1999.
Igney and Krammer, *Nat. Rev. Cancer*, 2:277-288, 2002.

Kandasamy and Srivastava, *Cancer Res.*, 62:4929-4937, 2002.
Kandasamy et al., *Cancer Res.*, 63:1712-1721, 2003.
Kayagaki et al., *J. Exp. Med.*, 189:1451-1460, 1999b.
Kayagaki et al., *J. Immunol.*, 163:1906-1913, 1999a.
Keane et al., *Cancer Res.*, 59:734-741, 1999.
Keogh et al., *FEBS Lett.*, 471:93-98, 2000.
Khochbin et al., *Curr. Opin. Genet. Dev.*, 11:162-166, 2001.
Kim and Gupta, *Int. J. Oncol*, 16:1137-1139, 2000.
Kim et al., *Int. J. Oncol*, 18:187-194, 2001.
Kim et al., *Oncogene*, 18:2461-2470, 1999.
Kischkel et al., *J. Biol. Chem.*, 276:46639-46646, 2001.
Klein, *J. Urol*, 171:S50-S53, 2004.
Krammer, *Adv. Immunol.*, 71:163-210, 1999.
Krammer, *Toxicol. Lett.*, 102:131-137, 1998.
Kroemer et al., *Annu. Rev. Physiol*, 60:619-642, 1998.
LeBlanc and Ashkenazi, *Cell Death Differ.*, 10:66-75, 2003.
Lee et al., *FEBS Lett.*, 395:183-187, 1996.
Li et al., *Cell*, 94:491-501, 1998.
Luo et al., *Cell*, 94:481-490, 1998.
Mahlknecht and Hoelzer, Mol. Med., 6:623-644, 2000.
Marini and Belka, *Curr. Med. Chem. Anti-Cancer Agents*, 3:334-342, 2003.
Marini et al., *Radiother. Oncol*, 68:189-198, 2003.
Marks et al., *Curr. Opin. Oncol.*, 13:477,483, 2000b.
Marks et al., *J. Natl. Cancer Inst.*, 92:1210-1216, 2000.
Marks et al., *Nat. Rev. Cancer*, 1:194-202, 2001a.
Marsters et al., *Curr. Biol*, 7:1003-1006, 1997.
Mayer and Walker, In: *Immunochemical Methods in Cell and Molecular Biology*, Academic Press, 1988.
Medina et al., *Cancer Res.*, 57:3697-3707, 1997.
Neuzil et al., *Biochem. Biophys. Res. Commun.*, 314:186-191, 2004.
Ortiz et al., *Drug Resist.*, 5:162-175, 2002.
Pan et al., *FEBS Lett.*, 424:41-45, 1998.
Pan et al., *Science*, 276:111-113, 1977b.
Pan et al., *Science*, 277:815-818, 1997.
Park and Pezzuto, *Cancer Metastasis Rev.*, 21:231-255, 2002.
PCT Appln. WO/2079377
*Pharmaceutical Salts Properties, Selection and Use—A Handbook*, by C. G. Wermuth and P. H. Stahl, Verlag Helvetica Chimica Acta, 2002.
Pitti et al., *Cancer Metastasis Rev.*, 21:231-255, 1996.
Ratan et al., *Urol. Oncol.*, 7:223-227.2002.
Ray and Almasan, *Cancer Res.*, 63:4713-4723, 2003;
Rosato et al., *Mol Cancer Ther.*, 2:1273-1284, 2003.
Sambrook et al., In: *Molecular cloning: a laboratory manual*, 2$^{nd}$ Ed., Cold Spring Harbor Laboratory Press, Cold Spring Harbor, N.Y., 1989.
Schneider et al., *FEBS Lett.*, 416:329-334, 1997.
Screaton et al., *Curr. Biol.*, 7:693-696, 1997.
Shankar et al., *Int. J. Oncol.*, 24(5):1133-1140, 2004a.
Shankar et al., *Prostate*, 61(1):35-49, 2004b.
Sheridan et al., *Science*, 277:818-821, 1997.
Singh et al., *Cancer Res.*, 63:5390-5400, 2003.
Sinha and El-Bayoumy, *Curr. Cancer Drug Targets*, 4:13-28, 2004.
Smith & March, In: *March's Advanced Organic Chemistry: Reactions, Mechanisms, and Structure*, 6$^{th}$ Ed., John Wiley & Sons, NJ, 2007.
Srinivasula et al., *Mol Cell*, 1:949-957, 1998.
Srivastava, *Neoplasia*, 3:535-546, 2001.
Strejan et al., *Cell Immunol.*, 84(1):171-184, 1984.
Struhl, *Genes Dev.*, 12:599-606, 1998.
Suliman et al., *Oncogene*, 20:2122-2133, 2001.
Sun et al., *Cancer Res.*, 60:7149-7155, 2000a.
Sun et al., *Oncogene*, 19:4513-4522, 200b.
Susin et al., *Nature*, 397:441-446, 1999.
Suzuki et al., *Mol Cell*, 8:613-621, 2001.
Thomas and Hersey, *J. Immunol.*, 161:2195-2200, 1998.
Timmermann et al., *Cell. Mol. Life. Sci.*, 58:728-736, 2001.
Van Lint et al., *Gene Exp.*, 5:245-253, 1996.
Verhagen et al., *Cell*, 102:43-53, 2000.
Wajant et al., *Apoptosis*, 7:449-459, 2002.
Walczak et al., *EMBO J.*, 16:5386-5397, 1997.
Walczak et al., *Nat. Med.*, 5:157-163, 1999.
Wang et al., *Genes Dev.*, 10:2859-2869, 1996.
Wei et al., *Genes Dev.*, 14:2060-2071, 2000.
Weir and Blackwell, In: *Handbook Of Experimental Immunology*, Volumes I-IV, 1986.
Whanger, *Br. J. Nutr.*, 91:11-28, 2004.
Wiley et al., *Immunity*, 3:673-682, 1995.
Wolf and Green, *J. Biol. Chem.*, 274, 20049-20052, 1999.
Wu et al., *Nat. Genet.*, 17:141-143, 1997.
Zhang et al., *Biochem. Pharmacol.*, 66:1537-1545, 2003.
Zou et al., *Cell*, 90:405-413, 1997.

What is claimed is:

1. A method of treating breast cancer, leukemia, lymphoma, lung cancer, mesothelioma, pancreatic cancer or prostate cancer in an individual comprising administering to the individual a therapeutically effective amount of a compound having the formula:

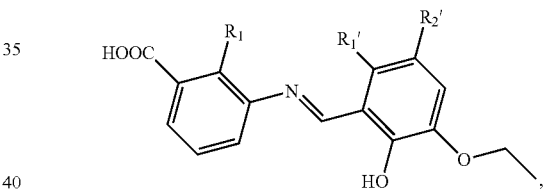

wherein:

$R_1'$ and $R_2'$ are each halo;

$R_1$ is —H or heteroatom-unsubstituted $C_1$-$C_3$-alkyl;

or the formula:

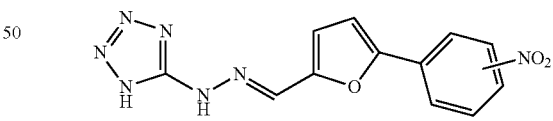

or a pharmaceutically acceptable salt of either formula.

2. The method of claim 1, wherein the compound is:

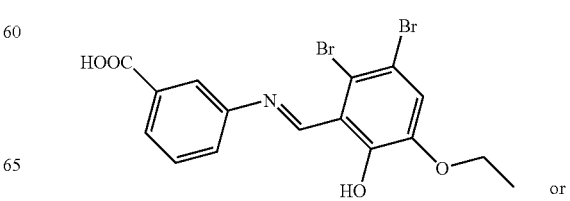

or

-continued

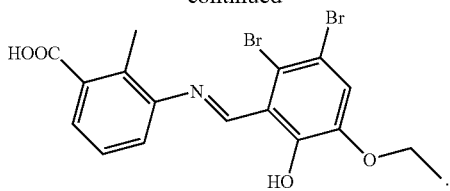

3. The method of claim 1, wherein the individual is a human.

4. The method of claim 1, wherein the compound is administered locally.

5. The method of claim 1, wherein the compound is administered systemically.

6. The method of claim 1, wherein the compound is administered by contacting a tumor cell during ex vivo purging.

7. The method of claim 4, wherein the compound is administered by direct intratumoral injection or by injection into tumor vasculature.

8. The method of claim 5, wherein the compound is administered intravenously, intra-arterially, intra-peritoneally, or orally.

* * * * *

UNITED STATES PATENT AND TRADEMARK OFFICE
CERTIFICATE OF CORRECTION

| | | |
|---|---|---|
| PATENT NO. | : 7,915,245 B2 | Page 1 of 1 |
| APPLICATION NO. | : 11/866162 | |
| DATED | : March 29, 2011 | |
| INVENTOR(S) | : Rakesh K. Srivastava et al. | |

It is certified that error appears in the above-identified patent and that said Letters Patent is hereby corrected as shown below:

In column 1, lines 9-12, delete paragraph and insert
--This invention was made with government support under U.S. Army Grants DAMD17-03-1-0242, X81XWH-04-1-0021, and PC060782 awarded by the Department of Defense. The government has certain rights in the invention.-- therefor.

Signed and Sealed this
Sixth Day of September, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,915,245 B2 | Page 1 of 1 |
| APPLICATION NO. | : 11/866162 | |
| DATED | : March 29, 2011 | |
| INVENTOR(S) | : Rakesh K. Srivastava et al. | |

It is certified that error appears in the above-identified patent and that said Letters Patent is hereby corrected as shown below:

In title page, item (73) Assignee, line 3, insert
--UNIVERSITY OF MARYLAND, BALTIMORE, A CONSTITUENT INSTITUTION OF THE UNIVERSITY SYSTEM OF MARYLAND, Baltimore, MD (US)--.

Signed and Sealed this
Eighteenth Day of October, 2011

David J. Kappos
*Director of the United States Patent and Trademark Office*